(12) United States Patent
Guay et al.

(10) Patent No.: US 12,060,387 B2
(45) Date of Patent: *Aug. 13, 2024

(54) POLYPEPTIDE-BASED SHUTTLE AGENTS FOR IMPROVING THE TRANSDUCTION EFFICIENCY OF POLYPEPTIDE CARGOS TO THE CYTOSOL OF TARGET EUKARYOTIC CELLS, USES THEREOF, METHODS AND KITS RELATING TO SAME

(71) Applicant: Feldan Bio Inc., Québec (CA)

(72) Inventors: David Guay, Québec (CA); Thomas Del'Guidice, Québec (CA); Jean-Pascal Lepetit-Stoffaes, Québec (CA)

(73) Assignee: Feldan Bio Inc., Quebec (CA)

( * ) Notice: Subject to any disclaimer, the term of this patent is extended or adjusted under 35 U.S.C. 154(b) by 1182 days.

This patent is subject to a terminal disclaimer.

(21) Appl. No.: 16/797,867

(22) Filed: Feb. 21, 2020

(65) Prior Publication Data

US 2020/0181202 A1    Jun. 11, 2020

Related U.S. Application Data

(63) Continuation of application No. 15/486,155, filed on Apr. 12, 2017, now Pat. No. 10,633,421, which is a continuation of application No. 15/094,365, filed on Apr. 8, 2016, now Pat. No. 9,738,687.

(60) Provisional application No. 62/246,892, filed on Oct. 27, 2015, provisional application No. 62/145,760, filed on Apr. 10, 2015.

(51) Int. Cl.
*C07K 14/00* (2006.01)
*C12N 15/90* (2006.01)

(52) U.S. Cl.
CPC ............ *C07K 14/001* (2013.01); *C07K 14/00* (2013.01); *C12N 15/907* (2013.01); *C07K 2319/01* (2013.01); *C07K 2319/10* (2013.01); *C07K 2319/21* (2013.01); *C12N 2501/60* (2013.01); *C12N 2501/998* (2013.01)

(58) Field of Classification Search
None
See application file for complete search history.

(56) References Cited

U.S. PATENT DOCUMENTS

| | | | |
|---|---|---|---|
| 7,579,318 | B2 | 8/2009 | Divita et al. |
| 8,242,081 | B2 | 8/2012 | Divita et al. |
| 9,738,687 | B2 | 8/2017 | Guay et al. |
| 9,982,267 | B2 | 5/2018 | Del Guidice |
| 10,633,421 | B2 | 4/2020 | Guay et al. |
| 11,629,170 | B2 * | 4/2023 | Del'Guidice ............ C07K 7/08 424/94.3 |
| 2003/0104622 | A1 | 6/2003 | Robbins et al. |
| 2007/0054401 | A1 | 3/2007 | Prochiantz et al. |
| 2015/0071903 | A1 | 3/2015 | Liu et al. |
| 2016/0298078 | A1 | 10/2016 | Guay et al. |
| 2018/0100158 | A1 | 4/2018 | Del'Guidice et al. |
| 2020/0270307 | A1 | 8/2020 | Del'Guidice et al. |
| 2022/0204561 | A1 | 6/2022 | Guay et al. |

FOREIGN PATENT DOCUMENTS

| | | |
|---|---|---|
| WO | WO-2015038662 A1 | 3/2015 |
| WO | WO-2015089462 A1 | 6/2015 |
| WO | WO-2016161516 A1 | 10/2016 |
| WO | WO-2017049407 A1 | 3/2017 |
| WO | WO-2017175072 A1 | 10/2017 |
| WO | WO-2018053632 A1 | 3/2018 |
| WO | WO-2018068135 A1 | 4/2018 |

OTHER PUBLICATIONS

Crombez et al.: A New Potent Secondary Amphipathic Cell-penetrating Peptide for siRNA Delivery Into Mammalian Cells. Molecular Therapy. 17(1): 95-103 (2009).
Del'Guidice et al.: Intrabody Delivery—The Feldan Shuttle Technology: A Peptide-Based Method to Deliver Antibodies. Drug Development & Delivery. 18(1):28-32 (2018).
Del'Guidice et al.: Membrane permeabilizing amphiphilic peptide delivers recombinant transcription factor and CRISPR-Cas9/Cpf1 ribonucleoproteins in hard-to-modify cells. PLOS One 13(4):e0195558. doi: 10.1371/journal.pone.0195558 (2018).
Deshayes et al.: Structural polymorphism of non-covalent peptide-based delivery systems: Highway to cellular uptake. Biochimica et Biophysica Acta 1798:2304-2314 (2010).
Ebina et al.: Transcription factor-mediated reprogramming toward hematopoietic stem cells. EMBO Journal. 34(6):694-709 (2015).
Erazo-Oliveras et al.: Improving the endosomal escape of cell-penetrating peptides and their cargos: strategies and challenges. Pharmaceuticals. 5(11):1177-1209 (2012).
Farkhani et al.: Cell penetrating peptides: efficient vectors for delivery of nanoparticles, nanocarriers, therapeutic and diagnostic molecules. Peptides. 57:78-94 (2014).
Firas et al.: Transcription factor-mediated reprogramming: epigenetics and therapeutic potential. Immunology and Cell Biology. 93(3):284-289 (2015).
Ford et al.: Protein transduction: an alternative to genetic intervention? Gene Ther. 8(1):1-4 (2001).
Fujita et al.: Applications of Engineered DNA-Binding Molecules Such as TAL Proteins and the CRISPR/Cas System in Biology Research. International Journal of Molecular Sciences. 16(10):23143-23164 (2015).

(Continued)

*Primary Examiner* — Nancy J Leith

(74) *Attorney, Agent, or Firm* — Wilson Sonsini Goodrich & Rosati

(57) ABSTRACT

The present description relates to synthetic peptides useful for increasing the transduction efficiency of polypeptide cargos to the cytosol of target eukaryotic cells. More specifically, the present description relates to synthetic peptides and polypeptide-based shuttle agents comprising an endosome leakage domain (ELD) operably linked to a cell penetrating domain (CPD), or an ELD operably linked to a histidine-rich domain and a CPD. Compositions, kits, methods and uses relating to same are also described.

19 Claims, 43 Drawing Sheets

Specification includes a Sequence Listing.

(56) References Cited

OTHER PUBLICATIONS

Hsu et al.: Development and applications of CRISPR-Cas9 for genome engineering. Cell 157(6):1262-1278 (2014).

Ilfeld et al.: The End of Postoperative Pain—A Fast-Approaching Possibility? And, if So, Will We Be Ready? Regional Anesthesia and Pain Medicine 34(2):85-87 (2009).

Iwasaki et al.: Cellular uptake and in vivo distribution of polyhistidine peptides. Journal of Controlled Release. 210:115-124 (2015).

Jinek et al.: Bacterial Immunity A Programmable Dual-RNA-Guided DNA Endonuclease in Adaptive. Science. 337(6096):816-821 (2012).

Kabouridis: Biological applications of protein transduction technology. Trends in Biotechnology. 21(11):498-503 (2003).

Kadkhodayan et al.: Generation of GFP Native Protein for Detection of Its Intracellular Uptake by Cell-Penetrating Peptides. Folia Biologica (Praha). 62, 103-109 (2016).

Keller et al.: Relationships between Cargo, Cell Penetrating Peptides and Cell Type for Uptake of Non-Covalent Complexes into Live Cells. Pharmaceuticals. 6: 184-203 (2013) doi:10.3390/ph6020184.

Keller et al.: Transduction of Proteins into Leishmania Tarentolae by Formation of Non-Covalent Complexes with Cell-Penetrating Peptides. Journal of Cellular Biochemistry. 115:243-252 (2014).

Krishnamurthy et al.: Engineered amphiphilic peptides enable delivery of proteins and CRISPR-associated nucleases to airway epithelia. Nature Communications. 0(1):4906. doi: 10.1038/s41467-019-12922-y (2019).

Kurzawa et al.: PEP and CADY-mediated delivery of fluorescent peptides and proteins into living cells. Biochimica et Biophysica Acta. 1798: 2274-2285 (2010).

Lee et al.: Activatable Cell Penetrating Peptide—Peptide Nucleic Acid Conjugate via Reduction of Azobenzene PEG Chains. J. Am. Chem. Soc. 136:12868-12871 (2014).

Li et al.: Delivery of intracellular-acting biologics in pro-apoptotic therapies. Current Pharmaceutical Design. 17(3):293-319 (2011).

Lin et al.: HLA-G expression in human ovrarian carcinoma counteracts NK cell function. Annals of Oncology. 18:1804-1809 (2007).

Morris et al.: A peptide carrier for the delivery of biologically active proteins into mammalian cells. Nat Biotechnol 19(12):1173-1176 (2001).

Mussbach et al.: Transduction of Peptides and Proteins Into Live Cells by Cell Penetrating Peptides. Journal of Cellular Biochemistry. 112: 3824-3833 (2011).

PCT/CA2020/050517 International Search Report and Written Opinion dated Jul. 17, 2020.

Ramsey et al.: Cell-Penetrating peptides transport therapeutics into cells. Pharmacology & Therapeutics. 154:78-86 (2015).

Regalado: Who owns the biggest biotech discover of the century?. MIT Technology Review. 4 pages (2014).

Sampson et al.: Exploiting CRISPR/Cas systems for biotechnology. Bioessays. 36(1):34-38 (2014).

Sato et al.: Peptide-membrane interactions and mechanisms of membrane destruction by amphipathic α-helical antimicrobial peptides. Biochimica et Biophysica Acta 1758:1245-1256 (2006).

Simeoni et al.: Insight into the mechanism of the peptide-based gene delivery system MPG: implications for delivery of siRNA into mammalian cells. Nucleic Acids Research, 31(11): 27170-2724 (2003).

Sun et al.: PTD4-apoptin protein therapy inhibits tumor growth in vivo. Int J cancer. 124(12):2973-2981 (2009).

Tansi et al.: Internalization of near-infrared fluorescently labeled activatable cell-penetrating peptide and of proteins into human fibrosarcoma cell line HT-1080. Journal of Cellular Biochemistry. (2015) doi: 10.1002/jcb.25075.

Thériault et al.: Differential modulation of Nav1.7 and Nav1.8 channels by antidepressant drugs. European Journal of Pharmacology. 764:395-403 (2015).

U.S. Appl. No. 16/341,681 Office Action dated Dec. 3, 2021.

U.S. Appl. No. 16/341,681 Restriction Requirement dated Jun. 3, 2021.

U.S. Appl. No. 62/474,827, filed Mar. 22, 2017.

WAN: An Overall Comparison of Small Molecules and Large Biologics in ADME Testing. ADMET & DMPK 4(1):1-22; doi: 10.5599/admet.4.1.276 (2016).

Aguila et al.: (2011). SALL4 is a robust stimulator for the expansion of hematopoietic stem cells. Blood 118(3): 576-585.

Akinci et al.: (2012). Reprogramming of pancreatic exocrine cells towards a beta (beta) cell character using Pdx1, Ngn3 and MafA. Biochem J, 442(3): 539-550.

Alford et al.: (2009). Toxicity of organic fluorophores used in molecular imaging: literature review. Mol Imaging. 8(6):341-54.

Amand et al.: (2012) Functionalization with C-terminal cysteine enhances transfection efficiency of cell-penetrating peptides through dimer formation. Biochem Biophys Res Commun,418(3): 469-474.

Andreu et al.: (1992) Shortened cecropin A-melittin hybrids. Significant size reduction retains potent antibiotic activity. FEBS Letters, 296:190-194.

Aoukaty, A. & Tan, R. (2005). Role for glycogen synthase kinase-3 in NK cell cytotoxicity and X-linked lymphoproliferative disease. J Immunol 174:4551-8.

Barrangou, R. and Luciano A. Marraffini (2014). CRISPR-Cas Systems: Prokaryotes Upgrade to Adaptive Immunity. Mod. Cell 54(2):234-244.

Bejarano, L. A. and C. Gonzalez (1999) Motif trap: A rapid method to clone motifs that can target proteins to defined subcellular localisations J Cell Sci, 112( Pt 23):4207-4211.

Bikard et al.: Programmable repression and activation of bacterial gene expression using an engineered CRISPR-Cas system. Nucleic Acids Res. 41:7429-7437 (2013).

Boman et al.: (1989) Antibacterial and antimalarial properties of peptides that are cecropin-melittin hybrids. FEBS letters, 259:103-106.

Braud et al.: (1998). HLA-E binds to natural killer cell receptors CD94/NKG2A, B and C. Nature 391:795-9.

Brock et al.: Efficient cell delivery mediated by lipid-specific endosomal escape of supercharged branched peptides; Traffic; 19:421-435 (2018).

Buganim et al.: (2014)The Developmental Potential of iPSCs Is Greatly Influenced by Reprogramming Factor Selection. Cell stem cell. 15: 295-309.

Burstein et al.: (2017), New CRISPR-Cas systems from uncultivated microbes. Nature. 542(7640):237-241.

Chan, C. K. and D. A. Jans (1999) Enhancement of polylysine-mediated transferrinfection by nuclear localization sequences: polylysine does not function as a nuclear localization sequence. Hum Gene Ther., 10(10):1695-1702.

Chan, C. K. and D. A. Jans (2001) Enhancement of MSH receptor- and GAL4-mediated gene transfer by switching the nuclear import pathway. Gene Ther 8(2):166-171.

Chang et al.: Cellular Internalization of Fluorescent Proteins via Arginine-rich Intracellular Delivery Peptide in Plant Cells; Plant Cell Physiol.; 46(3):482-488 (2005).

Cong et al.: Multiplex genome engineering using CRISPR/Cas systems. Science. 339.6121 (Feb. 15, 2013): 819-23. doi: 10.1126/science. 1231143. Epub Jan. 3, 2013.

Cooper et al.: (2001). The biology of human natural killer-cell subsets. Trends Immunol 22:633-640 (Abstract).

Cox et al.: Therapeutic genome editing: prospects and challenges. Nat Med 21:121-131 (2015).

De Kruijf et al.: (2010). HLA-E and HLA-G expression in classical HLA class I-negative tumors is of prognostic value for clinical outcome of early breast cancer patients. J Immunol 185:7452-9.

Delconte et al.: CIS is a potent checkpoint in NK cell-mediated tumor immunity. Nat Immunol, Jul. 2016; 17(7):816-24.

Denman et al.: (2012). Membrane-bound IL-21 promotes sustained ex vivo proliferation of human natural killer cells. PLoS One 7:e30264.

Dolfini et al.: (2012). The short isoform of NF-YA belongs to the embryonic stem cell transcription factor circuitry. Stem Cells, 30(11): 2450-2459.

Drin et al.: (2003) Studies on the internalization mechanism of cationic cell-penetrating peptides. J Biol Chem,278(33): 31192-31201.

(56) References Cited

OTHER PUBLICATIONS

Eisenberg et al.: (1982). The helical hydrophobic moment: a measure of the amphiphilicity of a helix. Nature 299:371-374. (Abstract only).
El-Andaloussi et al.: (2007). A novel cell-penetrating peptide, M918, for efficient delivery of proteins and peptide nucleic acids. Mol Ther, 15(10):1820-1826.
Elmquist et al.: (2001). VE-cadherin-derived cell-penetrating peptide, pVEC, with carrier functions. Exp Cell Res 269(2):237-244.
El-Sayed et al.: (2009) Delivery of macromolecules using arginine-rich cell-penetrating peptides: ways to overcome endosomal entrapment. AAPS J, 11(1):13-22.
Erazo-Oliveras et al.: Protein delivery into live cells by incubation with an endosomolytic agent. Nat. Methods 11, 861-867 (2014).
Fanara et al.: (2000). Quantitative analysis of nuclear localization signal (NLS)-importin alpha interaction through fluorescence depolarization. Evidence for auto-inhibitory regulation of NLS binding. J Biol Chem 275(28): 21218-21223.
Fasoli et al.: (2014) Mechanistic insight into CM18-Tat11 peptide membrane-perturbing action by whole-cell patch-clamp recording. Molecules. 19(7):9228-39.
Fawell et al.: (1994). Tat-mediated delivery of heterologous proteins into cells. Proc Natl Acad Sci U S A, 91(2): 664-668.
Fominaya et al.: (1998). A chimeric fusion protein containing transforming growth factor-alpha mediates gene transfer via binding to the EGF receptor. Gene Ther 5(4): 521-530.
Fominaya, J. and W. Wels (1996). Target cell-specific DNA transfer mediated by a chimeric multidomain protein. Novel non-viral gene delivery system. J Biol Chem 271(18): 10560-10568.
Fonoudi et al.: (2013). ISL1 protein transduction promotes cardiomyocyte differentiation from human embryonic stem cells. PLoS One 8(1): e55577.
Gao et al.: (2016) DNA-guided genome editing using the Natronobacterium gregoryi Argonaute. Nature Biotechnology 34:768-773.
Giguère et al.: (2015) Machine learning assisted design of highly active peptides for drug discovery. PLoS Comput Biol. 11(4):e1004074.
Gilbert et al.: (2013) CRISPR-mediated modular RNA-guided regulation of transcription in eukaryotes. Cell 154:442-451.
Gilmore, T. D. and H. M. Temin (1988). v-rel oncoproteins in the nucleus and in the cytoplasm transform chicken spleen cells. J Virol 62(3): 703-714.
Glover et al.: (2009). Multifunctional protein nanocarriers for targeted nuclear gene delivery in nondividing cells. FASEB J 23(9): 2996-3006.
Gomez-Cabrero et al.: Use of transduction proteins to target trabecular meshwork cells: outflow modulation by profilin I. Molecular Vision, 11:1071-1082, 2005.
Gordon et al.: (2012). The transcription factors T-bet and Eomes control key checkpoints of natural killer cell maturation. Immunity. 36(1): 55-67.
Gottschalk et al.: (1996). A novel DNA-peptide complex for efficient gene transfer and expression in mammalian cells. Gene Ther 3(5):448-457.
Gould et al.: (1989). A conserved tripeptide sorts proteins to peroxisomes. J Cell Biol 108(5): 1657-1664.
Green et al.: Autonomous functional domains of chemically synthesized human immunodeficiency virus tat trans-activator protein. Cell 55:1179-1188 (1988).
Grimes et al.: (1996). Endocytosis of activated TrkA: evidence that nerve growth factor induces formation of signaling endosomes. J Neurosci 16(24): 7950-7964.
Guo et al.: (2015). Predictive value of HLA-G and HLA-E in the prognosis of colorectal cancer patients. Cell Immunol 293:10-6.
Hallbrink et al.: (2001). Cargo delivery kinetics of cell-penetrating peptides. Biochim Biophys Acta 1515(2):101-109.
Herce, H. D. and A. E. Garcia (2007). Molecular dynamics simulations suggest a mechanism for translocation of the HIV-1 TAT peptide across lipid membranes. Proc Natl Acad Sci U S A, 104(52): 20805-20810.

Ho et al.: (2001). Synthetic protein transduction domains: enhanced transduction potential in vivo. *Cancer Research* 61: 474-477.
Horng et al.: (2007). NKG2D signaling is coupled to the interleukin 15 receptor signaling pathway. Nat Immunol 8:1345-52.
Hou et al.: Transdermal delivery of proteins mediated by non-covalently associated arginine-rich intracellular delivery peptides; Experimental Dermatology; 16:999-1006 (2007).
Shoya et al.: (1998). Two proline-rich nuclear localization signals in the amino- and carboxyl-terminal regions of the Borna disease virus phosphoprotein. J .Virol, 72(12): 9755-9762.
Hurt et al.: (1985). The first twelve amino acids (less than half of the pre-sequence) of an imported mitochondrial protein can direct mouse cytosolic dihydrofolate reductase into the yeast mitochondrial matrix. EMBO J, 4(8): 2061-2068.
Ichii et al.: (2004). Bcl6 acts as an amplifier for the generation and proliferative capacity of central memory CD8+ T cells. J Immunol 173(2): 883-891.
Irie et al.: (2000). Molecular cloning and characterization of Amida, a novel protein which interacts with a neuron-specific immediate early gene product arc, contains novel nuclear localization signals, and causes cell death in cultured cells. J Biol Chem 275(4): 2647-2653.
Ishigami et al.: (2015). Human leukocyte antigen (HLA)-E and HLA-F expression in gastric cancer. Anticancer Res 35:2279-85.
Kakudo et al.: (2004). Transferrin-modified liposomes equipped with a pH-sensitive fusogenic peptide: an artificial viral-like delivery system. Biochemistry. 43(19): 5618-5628.
Karniely, S. and O. Pines (2005). Single translation—dual destination: mechanisms of dual protein targeting in eukaryotes. EMBO Rep 6(5): 420-425.
Kato et al.: (1992). Max: functional domains and interaction with c-Myc. Genes Dev. 6(1): 81-92.
Kichler et al.: (2003). Histidine-rich amphipathic peptide antibiotics promote efficient delivery of DNA into mammalian cells. Proc Natl Acad Sci U S A, 100(4):1564-1568.
Kichler et al.: (2006). Cationic amphipathic histidine-rich peptides for gene delivery. Biochim Biophys Acta 1758(3): 301-307.
Kirwan, S. E. & Burshtyn, D. N. (2005). Killer cell Ig-like receptor-dependent signaling by Ig-like transcript 2 (ILT2/CD85j/LILRB1/LIR-1). J Immunol 175:5006-15.
Kleinschmidt, J. A. and A. Seiter (1988). Identification of domains involved in nuclear uptake and histone binding of protein N1 of Xenopus laevis. EMBO J, 7(6):1605-1614.
Kohler et al.: (2001). Adenoviral E1A protein nuclear import is preferentially mediated by importin alpha3 in vitro. Virology 289(2): 186-191.
Kwon et al.: (2010) A truncated HGP peptide sequence that retains endosomolytic activity and improves gene delivery efficiencies.Mol Pharm., 7(4):1260-1265.
Lamiable et al.: (2016). PEP-FOLD3: faster de novo structure prediction for linear peptides in solution and in complex. Nucleic Acids Res. 44(W1):W449-54.
Lanford et al.: (1986). Induction of nuclear transport with a synthetic peptide homologous to the SV40 T antigen transport signal. Cell 46(4): 575-582.
Lee et al.: Delivery of macromolecules into live cells by simple co-incubation with a peptide. Chembiochem., 11(3):325-330, 2010.
Levy et al.: Human leukocyte antigen-E protein is overexpressed in primary human colorectal cancer. Int J Oncol 32:633-41 (2008).
Li et al.: (2004). GALA: a designed synthetic pH-responsive amphipathic peptide with applications in drug and gene delivery. Adv Drug Deliv Rev, 56(7): 967-985.
Lin et al.: (2013). B lymphocyte-induced maturation protein 1 (BLIMP-1) attenuates autoimmune diabetes in NOD mice by suppressing Th1 and Th17 cells. Diabetologia 56(1):136-146.
Liou et al.: Protein transduction in human cells is enhanced by cell-penetrating peptides fused with an endosomolytic HA2 sequence; Peptides; 273-284 (2012).
Liu et al.: (2003). Systemic genetic transfer of p21WAF-1 and GM-CSF utilizing of a novel oligopeptide-based EGF receptor targeting polyplex. Cancer Gene Ther, 10(7): 529-539.
Liu et al.: (2014). E3 ubiquitin ligase Cbl-b in innate and adaptive immunity. Cell Cycle 13:1875-84.

(56) References Cited

OTHER PUBLICATIONS

Liu et al.: Cell-penetrating peptide-mediated delivery of TALEN proteins via bioconjugation for genome engineering. PLoS One 9(1):e85755, 2014.
Liu et al.: Intracellular delivery of quantum dots mediated by a histidine- and arginine-rich HR9 cell-penetrating peptide through the direct membrane translocation mechanism; Biomaterials; 32:3520-3537 (2011).
Lo et al.: An endosomolytic Tat peptide produced by incorporation of histidine and cysteine residues as a nonviral vector for DNA transfection. ScienceDriect, Biomaterials, 29:2408-2414, 2008.
Loeser et al.: (2007). Spontaneous tumor rejection by cbl-b-deficient CD8+ T cells. J Exp Med 204:879-91.
London, E. (1992). Diphtheria toxin: membrane interaction and membrane translocation. Biochim Biophys Acta 1113(1): 25-51.
Lord-Dufour et al.: (2009) Evidence for transcriptional regulation of the glucose-6-phosphate transporter by HIF-1alpha: Targeting G6PT with mumbaistatin analogs in hypoxic mesenchymal stromal cells. Stem cells, 27:489-497.
Lorieau et al.: (2010). The complete influenza hemagglutinin fusion domain adopts a tight helical hairpin arrangement at the lipid:water interface. Proc Natl Acad Sci U S A, 107(25): 11341-11346.
Lu et al.: (2007). Recombinant HoxB4 fusion proteins enhance hematopoietic differentiation of human embryonic stem cells. Stem Cells Dev 16(4): 547-559.
Luan et al.: (2015). Peptide amphiphiles with multifunctional fragments promoting cellular uptake and endosomal escape as efficient gene vectors.*J. Mater. Chem. B*, 3: 1068-1078.
Lutz-Nicoladoni et al.: (2015). Modulation of Immune Cell Functions by the E3 Ligase Cbl-b. Front Oncol 5:58.
Mack et al.: (1998). Aminooxypentane-RANTES induces CCR5 internalization but inhibits recycling: a novel inhibitory mechanism of HIV infectivity. J Exp Med, 187(8):1215-1224.
Maeng et al.: (2013). Effects of single nucleotide polymorphisms on treatment outcomes and toxicity in patients treated with sunitinib. Anticancer Res 33(10): 4619-4626.
Mahlum et al.: (2007). Engineering a noncarrier to a highly efficient carrier peptide for noncovalently delivering biologically active proteins into human cells. Anal Biochem. 365(2):215-221.
Makarova et al.: (2011) Unification of Cas protein families and a simple scenario for the origin and evolution of CRISPR-Cas systems. Biol Direct. 6:38.
Makkerh et al.: (1996). Comparative mutagenesis of nuclear localization signals reveals the importance of neutral and acidic amino acids. Curr Biol. 6(8): 1025-1027.
Martinez-Fong et al.: (1999). Neurotensin-SPDP-poly-L-lysine conjugate: a nonviral vector for targeted gene delivery to neural cells. Brain Res Mol Brain Res. 69(2): 249-262.
Matalon et al.: (2016). Dephosphorylation of the adaptor LAT and phospholipase C-gamma by SHP-1 inhibits natural killer cell cytotoxicity. Sci Signal 9:ra54.
Maurer, M. and E. von Stebut (2004). Macrophage inflammatory protein-1. Int J Biochem Cell Biol. 36(10): 1882-1886.
McKay et al.: (2002). Secretin-mediated gene delivery, a specific targeting mechanism with potential for treatment of biliary and pancreatic disease in cystic fibrosis. Mol Ther 5(4): 447-454.
Midoux et al.: (1998). Membrane permeabilization and efficient gene transfer by a peptide containing several histidines. Bioconjug Chem.9(2):260-267.
Milenkovic et al.: (2009). Identification of the signal directing Tim9 and Tim10 into the intermembrane space of mitochondria. Mol Biol Cell 20(10): 2530-2539.
Miyoshi et al.: (1994). [Structure and regulation of human thyroid-stimulating hormone (TSH) gene]. Nihon Rinsho 52(4):940-947.
Moede et al.: (1999). Identification of a nuclear localization signal, RRMKWKK, in the homeodomain transcription factor PDX-1. FEBS Lett 461(3): 229-234.
Montrose et al.: (2013). Xentry, a new class of cell-penetrating peptide uniquely equipped for delivery of drugs. Sci Rep 3: 1661.
Moreland et al.: (1987). Amino acid sequences that determine the nuclear localization of yeast histone 2B. Mol Cell Biol 7(11): 4048-4057.
Morris et al.: (2001). A peptide carrier for the delivery of biologically active proteins into mammalian cells. Nat Biotechnol 19(12): 1173-1176.
Morris et al.: (2004). Combination of a new generation of PNAs with a peptide-based carrier enables efficient targeting of cell cycle progression. Gene Ther 11(9): 757-764.
Nagahara et al.: Transduction of full-length TAT fusion proteins into mammalian cells: TAT-p27Kip1 induces cell migration; Nature Medicine; 4(12):1449-1452 (1998).
Nakanishi et al.: (2002). Interaction of the Vp3 nuclear localization signal with the importin alpha 2/beta heterodimer directs nuclear entry of infecting simian virus 40. J Virol, 76(18): 9368-9377.
O'Keefe, D. O. (1992). Characterization of a full-length, active-site mutant of diphtheria toxin. Arch Biochem Biophys 296(2): 678-684.
Paolino et al.: (2014). The E3 ligase Cbl-b and TAM receptors regulate cancer metastasis via natural killer cells. Nature 507:508-12.
Parameswaran et al.: (2016). Repression of GSK3 restores NK cell cytotoxicity in AML patients. Nat Commun 7:11154.
Parente et al.: (1990). Mechanism of leakage of phospholipid vesicle contents induced by the peptide GALA. Biochemistry, 29(37): 8720-8728.
Patel, P. & Woodgett, J. R. (2017). Glycogen Synthase Kinase 3: A Kinase for All Pathways? Curr Top Dev Biol 123:277-302.
Paul et al.: (1997). Gene transfer using a novel fusion protein, GAL4/invasin.Hum Gene Ther,8(10): 1253-1262.
PCT/IB2017/000512 International Search Report and Written Opinion dated Jul. 26, 2017.
Perez et al.: (1992). Antennapedia homeobox as a signal for the cellular internalization and nuclear addressing of a small exogenous peptide. J Cell Sci 102 (Pt 4): 717-722.
Pimenta et al.: (2000). Alpha1-antichymotrypsin and kallistatin hydrolysis by human cathepsin D.J Protein Chem, 19(5): 411-418.
Poli et al.: (2009). CD56bright natural killer (NK) cells: an important NK cell subset. Immunology 126:458-65.
Prieve, M. G. and M. L. Waterman (1999). Nuclear localization and formation of beta-catenin-lymphoid enhancer factor 1 complexes are not sufficient for activation of gene expression. Mol Cell Biol, 19(6): 4503-4515.
Rajagopalan, et al., (2007). Recombinant fusion proteins TAT-Mu, Mu and Mu-Mu mediate efficient non-viral gene delivery. J Gene Med, 9(4): 275-286.
Ramakrishna et al.: (2014) Gene disruption by cell-penetrating peptide-mediated delivery of Cas9 protein and guide RNA. Genome Research, 24:1020-1027.
Riddell et al.: (2014) Reprogramming committed murine blood cells to induced hematopoietic stem cells with defined factors. Cell, 157: 549-564.
Salomone et al.: (2012). A novel chimeric cell-penetrating peptide with membrane-disruptive properties for efficient endosomal escape. J Control Release, 163(3): 293-303.
Salomone et al.: (2013) In vitro efficient transfection by CM18-Tat11 hybrid peptide: a new tool for gene-delivery applications. PLoS One 8(7):e70108, 11 pages.
Salomone et al.: High-Yield nontoxic gene transfer through conjugation of the CM18-Tat11 chimeric peptide with nanosecond electric pulses. Molecular Pharmaceutics, 9 pages, 2014, available at: http://pubs.acs.org.
Schneider et al.: (1998).A novel peptide, Plaeidgielty, for the targeting of alpha9beta1-integrins.FEBS Lett , 429(3): 269-273.
Schreiber et al.: (1992). The human poly(ADP-ribose) polymerase nuclear localization signal is a bipartite element functionally separate from DNA binding and catalytic activity. EMBO J, 11(9): 3263-3269.
Schuster et al.: (1999). Multicomponent DNA carrier with a vesicular stomatitis virus G-peptide greatly enhances liver-targeted gene expression in mice. Bioconjug Chem, 10(6):1075-1083.
Scott et al.: (2010).Characterization and prediction of protein nucleolar localization sequences. Nucleic Acids Res, 38(21): 7388-7399.

(56) References Cited

OTHER PUBLICATIONS

Shaw et al.: (2008). Comparison of protein transduction domains in mediating cell delivery of a secreted CRE protein. Biochemistry, 47(4):1157-1166.
Shawe-Taylor and Cristianini (2004) Kernel methods for pattern analysis. Cambridge University Press, 12 pages.
Shen et al.: (2014) Improved PEP-FOLD approach for peptide and miniprotein structure prediction. J. Chem. Theor. Comput. 10:4745-4758.
Somasekaram et al.: (1999). Intracellular localization of human cytidine deaminase. Identification of a functional nuclear localization signal. J Biol Chem. 274(40): 28405-28412.
Stojanovski et al.: (2012). Mechanisms of protein sorting in mitochondria. Cold Spring Harbor Perspect Biol, 4(10):a011320, 18 pages.
Sudbeck, P. and G. Scherer (1997). Two independent nuclear localization signals are present in the DNA-binding high-mobility group domains of SRY and SOX9. J Biol Chem ., 272(44): 27848-27852.
Sung et al.: (2013).Efficient myogenic differentiation of human adipose-derived stem cells by the transduction of engineered MyoD protein. Biochem Biophys Res Commun, 437(1):156-161.
Takahashi et al.: Induction of pluripotent stem cells from mouse embryonic and adult fibroblast cultures by defined factors. Cell. Aug. 25, 2006;126(4):663-76. Epub Aug. 10, 2006.
Takeda et al.: (2006). NUP98-HOXA9 induces long-term proliferation and blocks differentiation of primary human CD34+ hematopoietic cells. Cancer Res., 66(13): 6628-6637.
Tan et al.: (2010). Increased levels of FoxA1 transcription factor in pluripotent P19 embryonal carcinoma cells stimulate neural differentiation. Stem Cells Dev., 19(9):1365-1374.
Tan et al.: (2012). Truncated peptides from melittin and its analog with high lytic activity at endosomal pH enhance branched polyethylenimine-mediated gene transfection. J Gene Med 14(4): 241-250.
Thévenet et al.: (2012) PEP-FOLD: an updated de novo structure prediction server for both linear and disulfide bonded cyclic peptides. Nucleic Acids Res. 40:W288-293.
Uherek et al.: (1998). A modular DNA carrier protein based on the structure of diphtheria toxin mediates target cell-specific gene delivery. J Biol Chem 273(15): 8835-8841.
U.S. Appl. No. 15/094,365 Applicant Initiated Interview Summary dated Jan. 11, 2017.
U.S. Appl. No. 15/094,365 Office Action dated Dec. 15, 2016.
U.S. Appl. No. 15/094,365 Restriction Requirement dated Aug. 2, 2016.
U.S. Appl. No. 15/486,155 Final Office Action dated Feb. 4, 2019.
U.S. Appl. No. 15/486,155 Final Office Action dated Sep. 25, 2019.
U.S. Appl. No. 15/486,155 Office Action dated Apr. 2, 2018.
U.S. Appl. No. 15/486,155 Office Action dated May 24, 2019.
U.S. Appl. No. 15/666,139 First Action Interview Office Action dated Feb. 2, 2018.
Varkouhi et al.: (2011). Endosomal escape pathways for delivery of biologicals. J Control Release 151(3): 220-228.
Veach et al.: (2004). Receptor/transporter-independent targeting of functional peptides across the plasma membrane. J Biol Chem., 279(12):11425-11431.
Vives et al.: (1997). A truncated HIV-1 Tat protein basic domain rapidly translocates through the plasma membrane and accumulates in the cell nucleus. J Biol Chem., 272(25): 16010-16017.

Wagstaff et al.: (2007). Histone-mediated transduction as an efficient means for gene delivery. Mol Ther., 15(4): 721-731.
Warr et al.: (2013). FOXO3A directs a protective autophagy program in haematopoietic stem cells. Nature 494(7437): 323-327.
Welch et al.: (1999). RanBP3 contains an unusual nuclear localization signal that is imported preferentially by importin-alpha3. Mol Cell Biol. 19(12):8400-8411.
Wiedenheft et al.: RNA-guided complex from a bacterial immune system enhances target recognition through seed sequence interactions. PNAS USA 108:10092-10097 (2011).
Witzel et al.: (2013). Androgen receptor expression is a predictive marker in chemotherapy-treated patients with endocrine receptor-positive primary breast cancers. J Cancer Res Clin Oncol., 139(5): 809-816.
Wu et al.: (2015). Rescuing lymphocytes from HLA-G immunosuppressive effects mediated by the tumor microenvironment. Oncotarget 6:37385-97.
Wu et al.: (1999). The quaking I-5 protein (QKI-5) has a novel nuclear localization signal and shuttles between the nucleus and the cytoplasm. J Biol Chem., 274(41): 29202-29210.
Wyman et al.: (1997). Design, synthesis, and characterization of a cationic peptide that binds to nucleic acids and permeabilizes bilayers. Biochemistry, 36(10): 3008-3017.
Ye et al.: (2007). Human leukocyte antigen G expression: as a significant prognostic indicator for patients with colorectal cancer. Mod Pathol 20:375-83.
Yie et al.: (2007). Expression of HLA-G is associated with prognosis in esophageal squamous cell carcinoma. Am J Clin Pathol 128:1002-1009.
Yie et al.: (2007). Expression of human leucocyte antigen G (HLA-G) is associated with prognosis in non-small cell lung cancer. Lung Cancer 58:267-74.
Yie et al.: (2007). Expression of human leukocyte antigen G (HLA-G) correlates with poor prognosis in gastric carcinoma. Ann Surg Oncol 14: 2721-2729.
Yu et al.: (1998). A constitutive nuclear localization signal from the second zinc-finger of orphan nuclear receptor TR2. J Endocrinol., 159(1):53-60.
Zetsche et al.: (2015). Cpf1 Is a Single RNA-Guided Endonuclease of a Class 2 CRISPR-Cas System. Cell. 25. pii: S0092-8674(15)01200-3[http://dx.doi.org/10.1016/j.cell.2015.09.038].
Zhen et al.: (2013). Impact of HLA-E gene polymorphism on HLA-E expression in tumor cells and prognosis in patients with stage III colorectal cancer. Med Oncol 30:482.
Zhou et al.: Generation of induced pluripotent stem cells using recombinant proteins. Cell Stem Cell 4(5):381-384 (2009).
Iwasaki et al.: Cellular uptake and in vivo distribution of polyhistidine peptides. J Control Release. 210:115-124 (2015).
Ain et al.: Effects of protein transduction domain (PTD) selection and position for improved intracellular delivery of PTD-Hsp27 fusion protein formulations. Arch. Pharm. Res. 39:1266-1274 (2016).
Cardarelli et al.: Quantitative Analysis of Tat Peptide Binding to Import Carriers Reveals Unconventional Nuclear Transport Properties. The Journal of Biological Chemistry. 286(14):12292-12299 (2011).
IL Patent Application No. IL265920 Office Action dated Jul. 25, 2022.
Salamone et al.: A novel chimeric cell-penetrating peptide with membrane disruptive properties for efficient endosomal escape. Journal of Controlled Release. 163(3):293-303 (2012).
U.S. Appl. No. 16/341,681 Final Office Action dated Jun. 15, 2022.

* cited by examiner

Fig. 18A
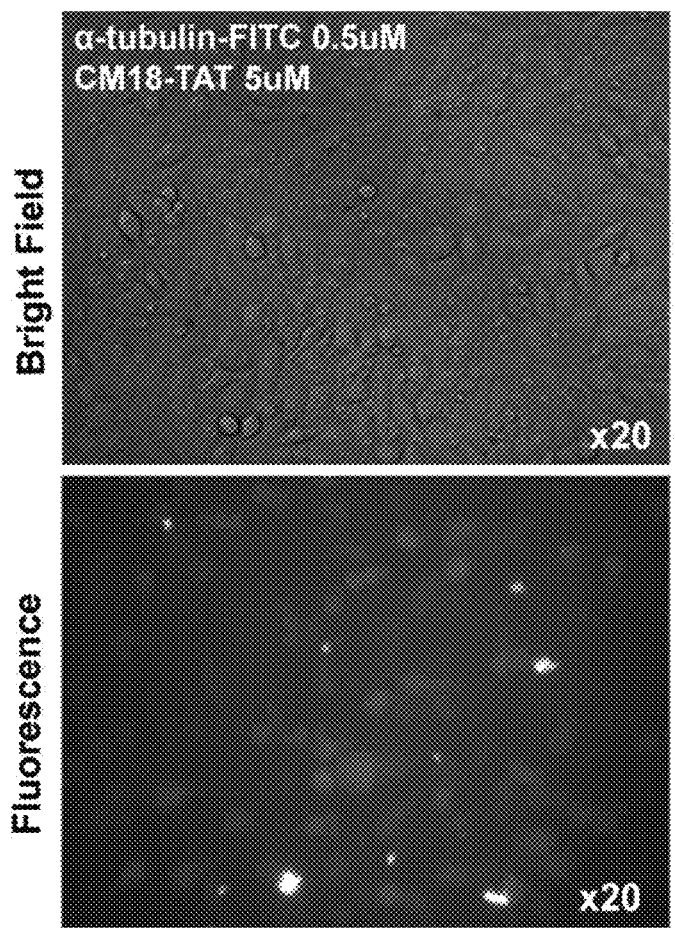
Fig. 18B
Fig. 18C
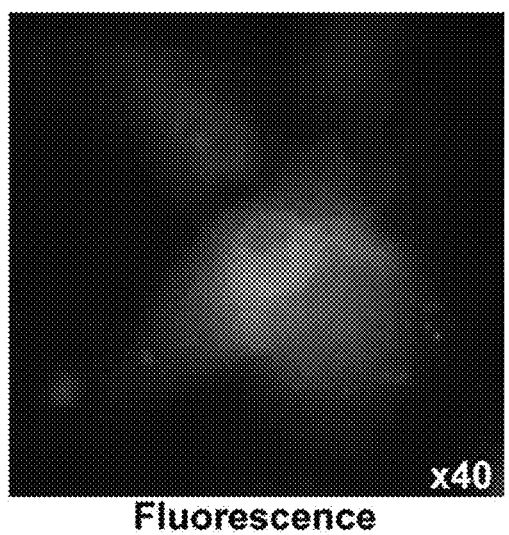

Fig. 24A
Fig. 24B
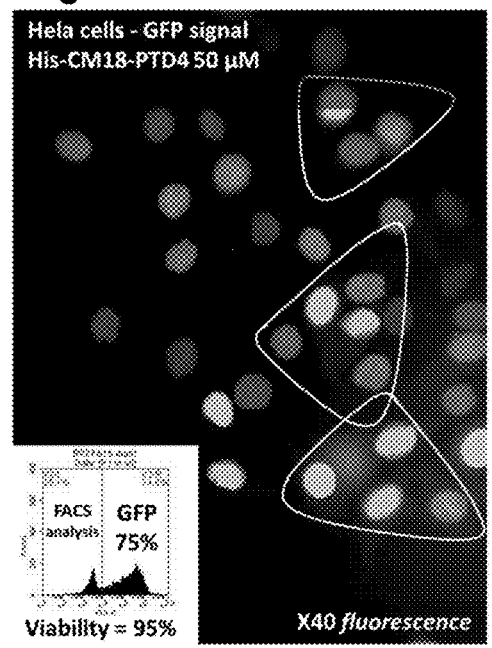
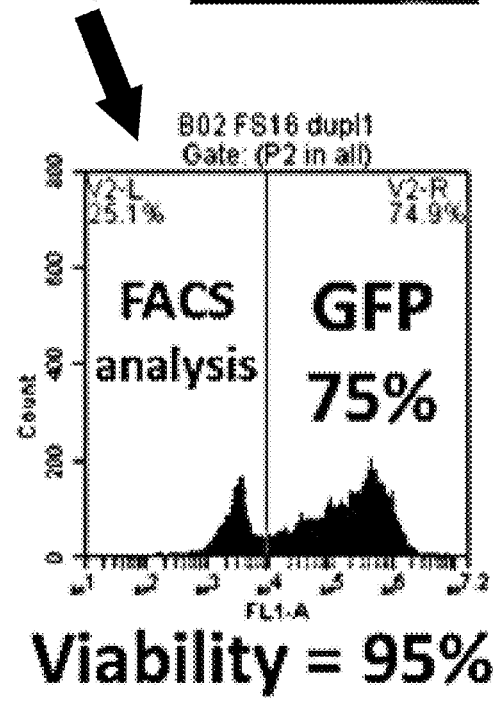

Fig. 25A
Fig. 25B
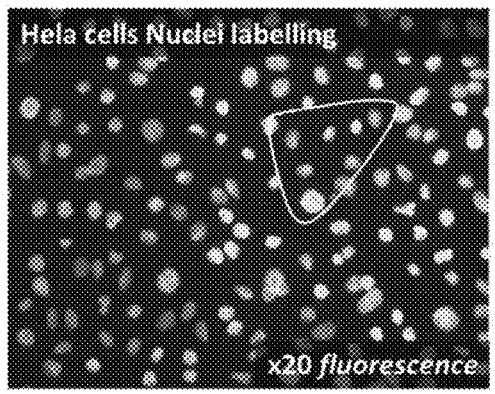
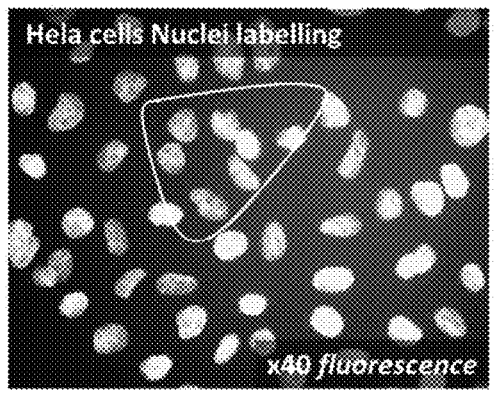
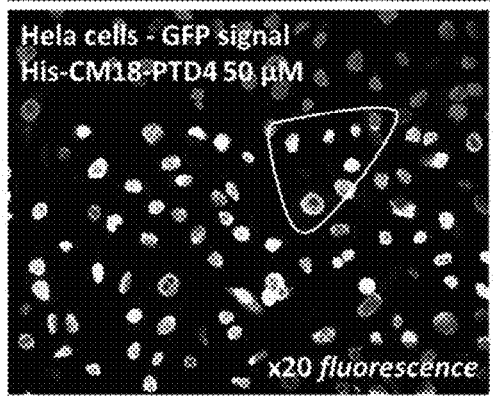
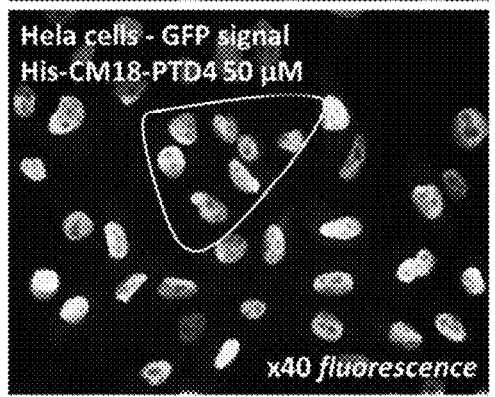
Fig. 26A
Fig. 26C
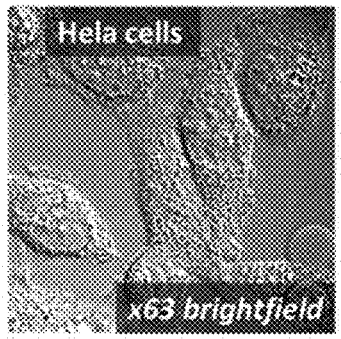
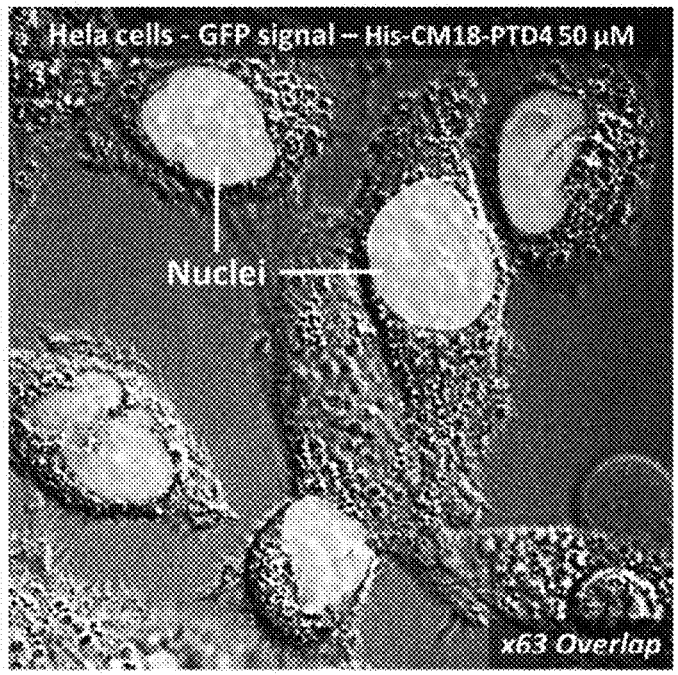
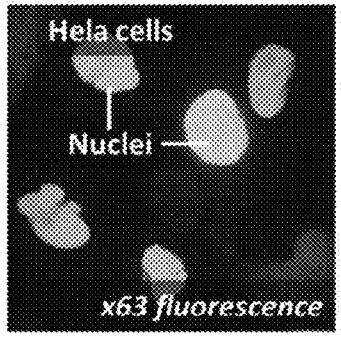
Fig. 26B Fig. 27A
Fig. 27B
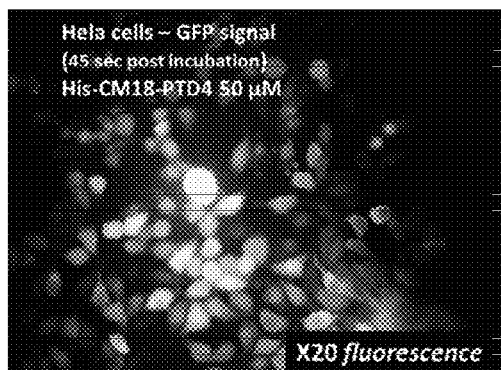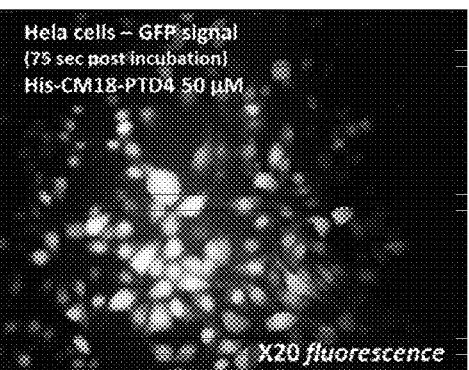
Fig. 27C
Fig. 27D Fig. 28A            Fig. 28B
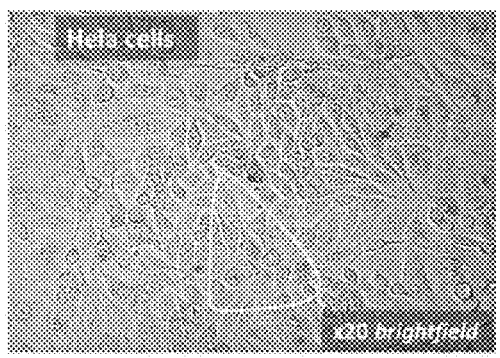 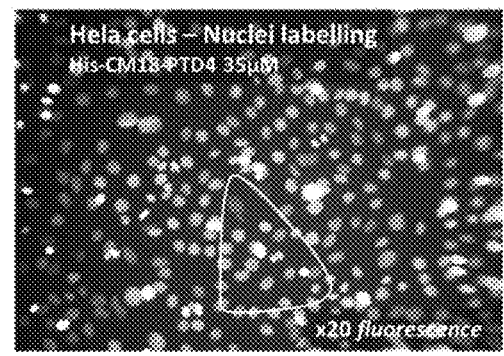
Fig. 28C            Fig. 28D

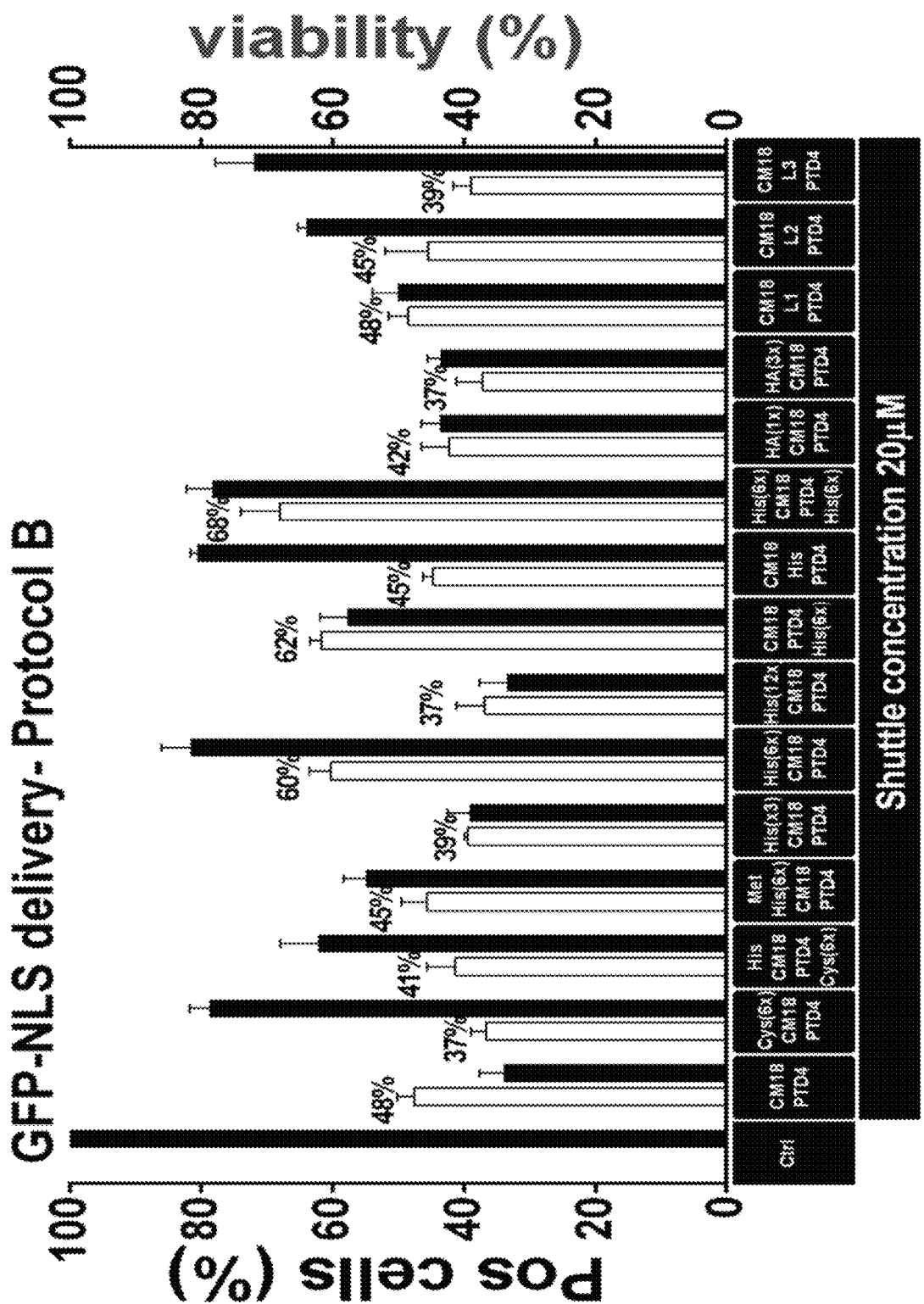

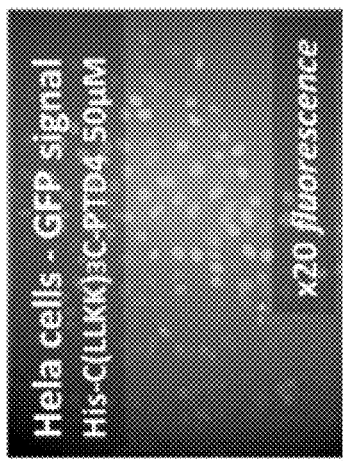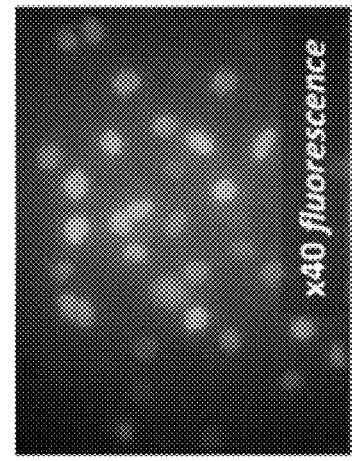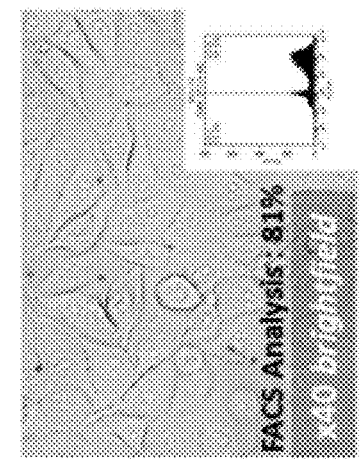
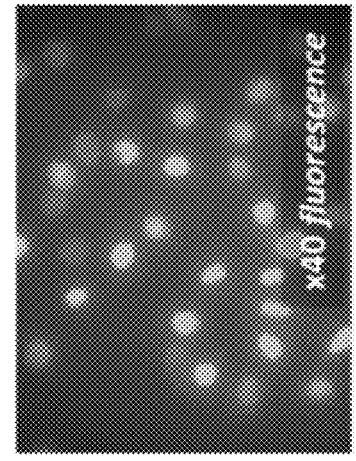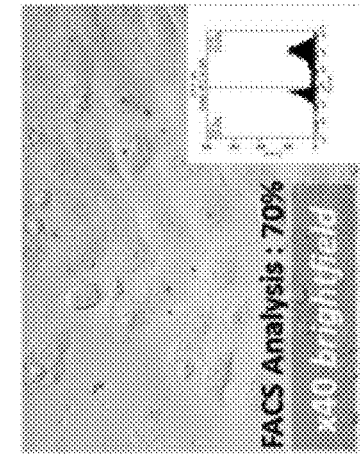
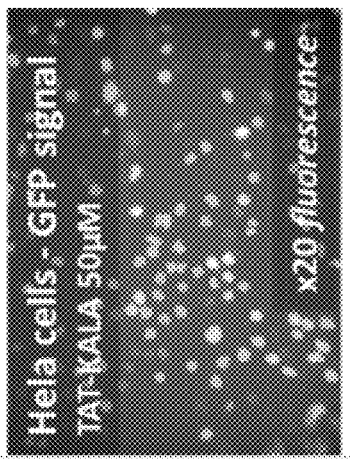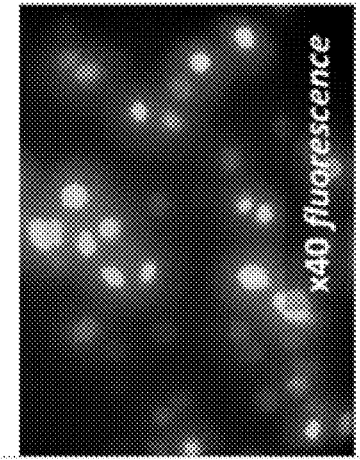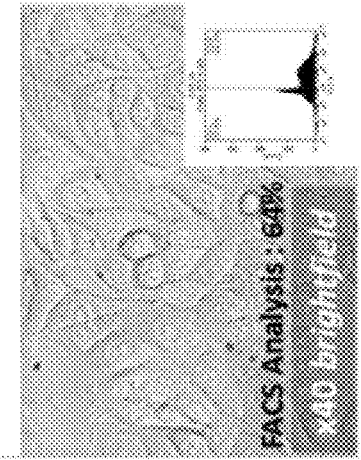
Fig. 30A, Fig. 30B, Fig. 30C Viability = 95%

Fig. 33A 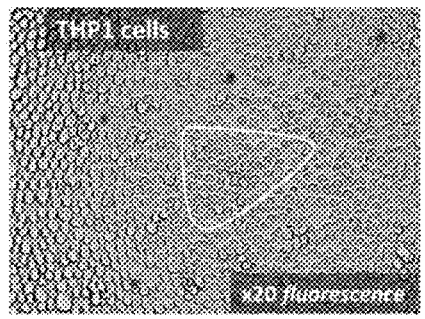 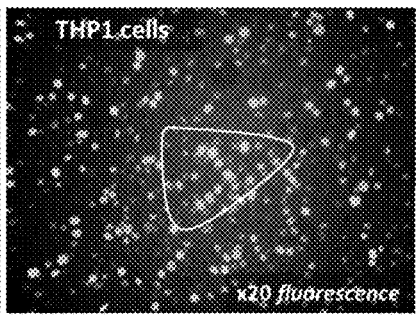 Fig. 33C
Fig. 33B 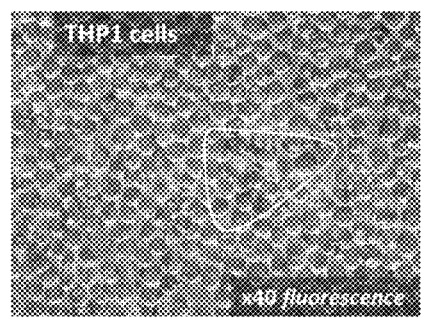 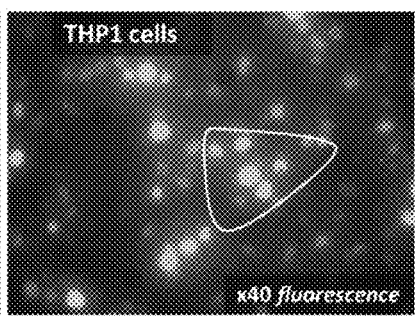 Fig. 33D

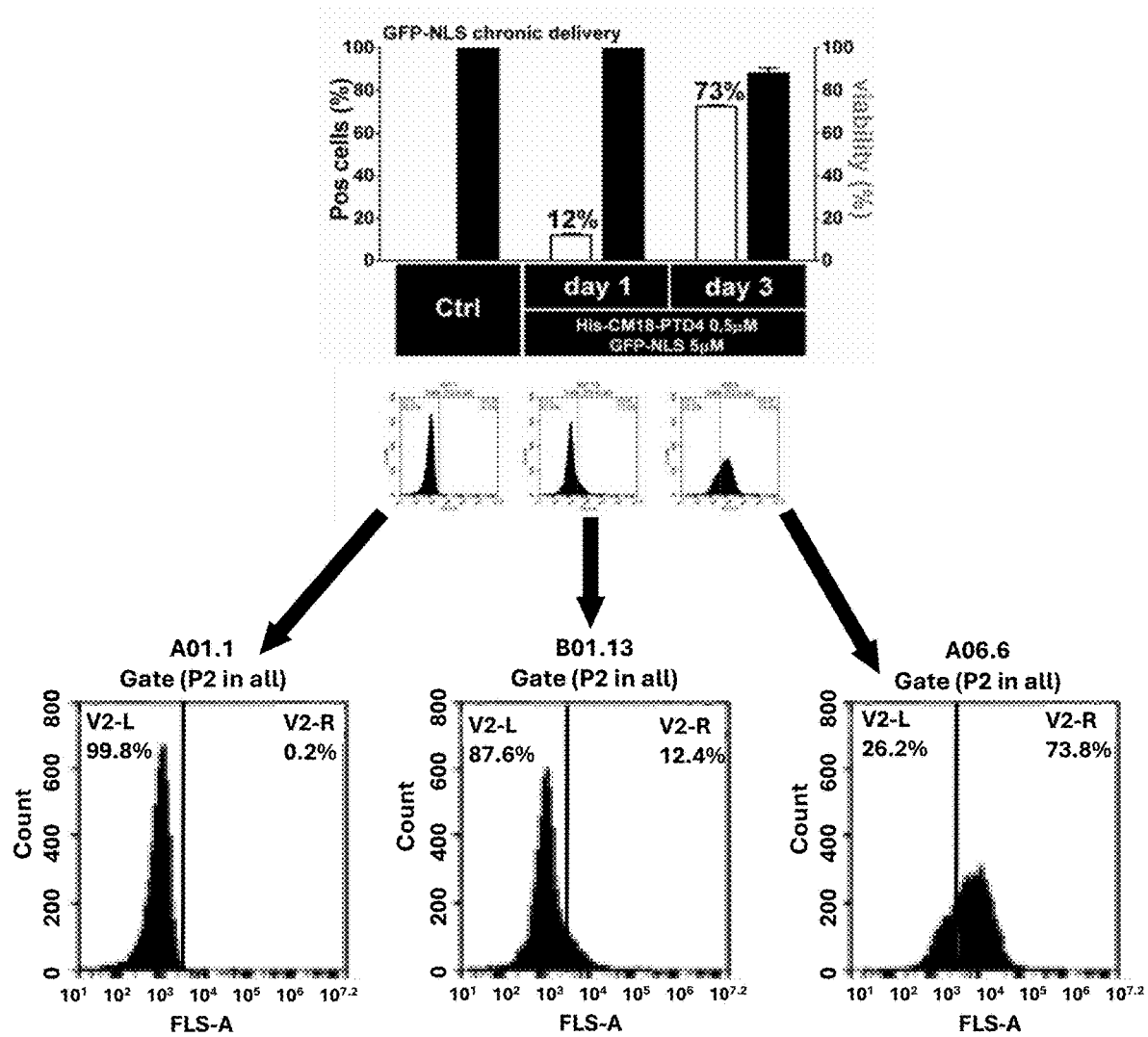

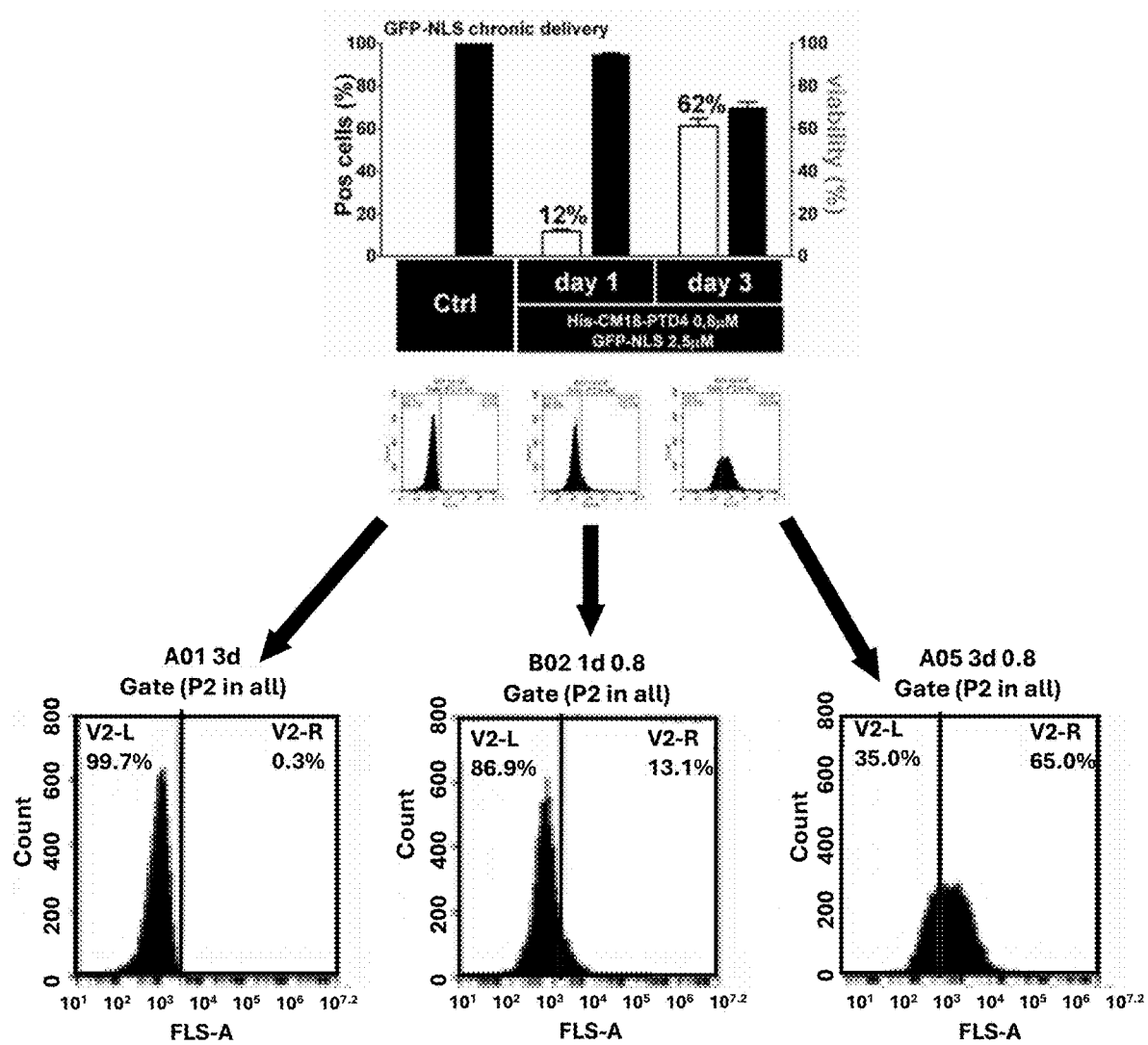

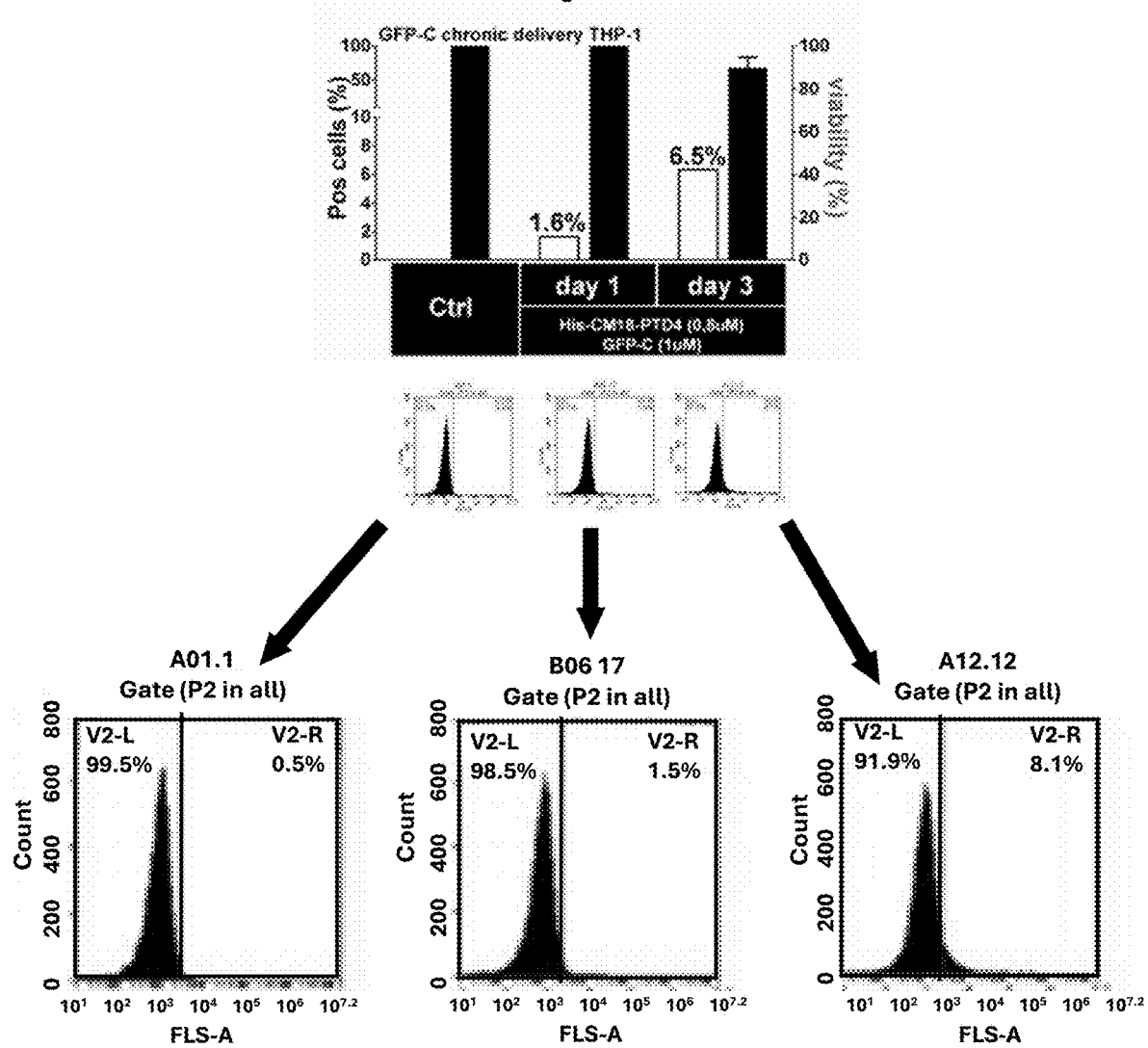

Fig. 36
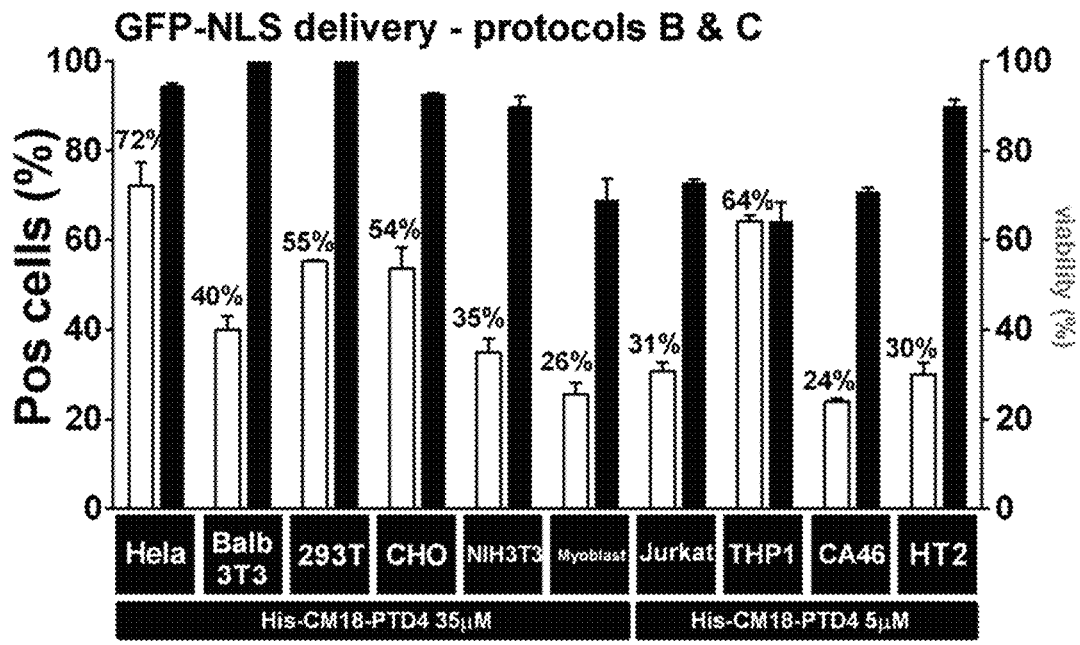
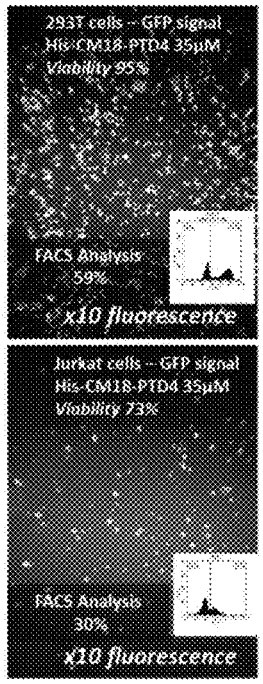 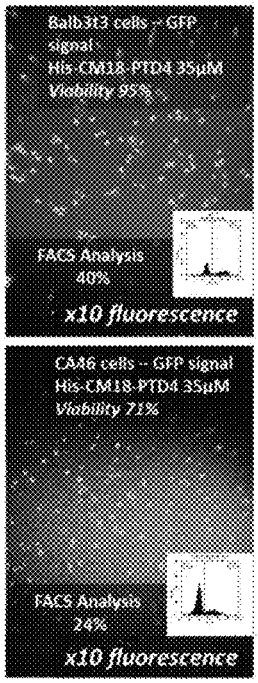 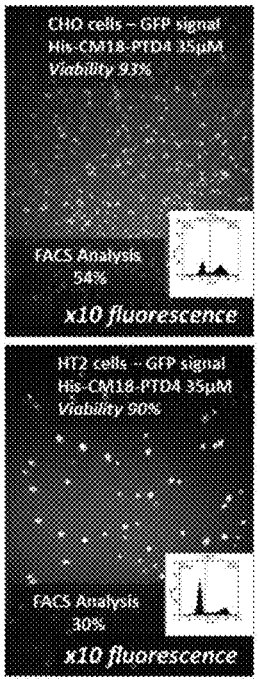 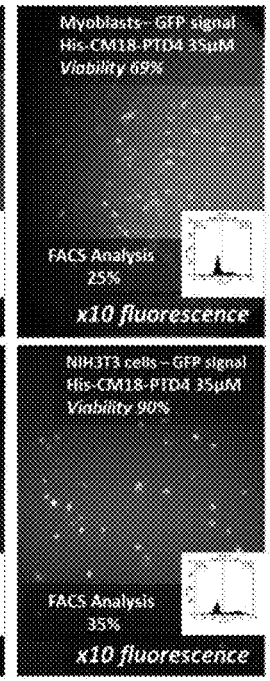
Fig. 37A    Fig. 37B    Fig. 37C    Fig. 37D
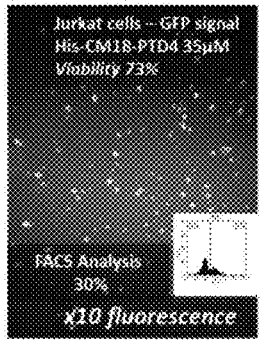 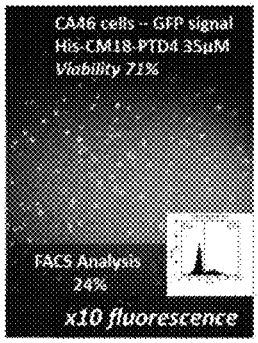 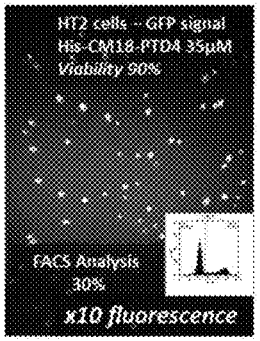 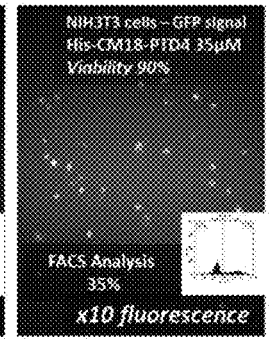
Fig. 37E    Fig. 37F    Fig. 37G    Fig. 37H Fig. 38A
Fig. 38B
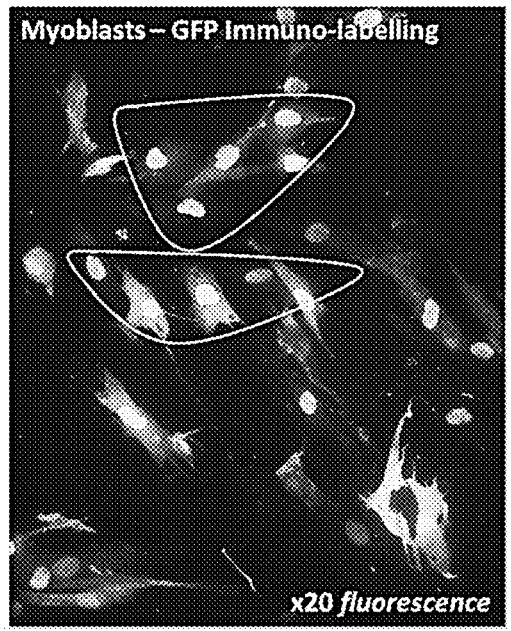
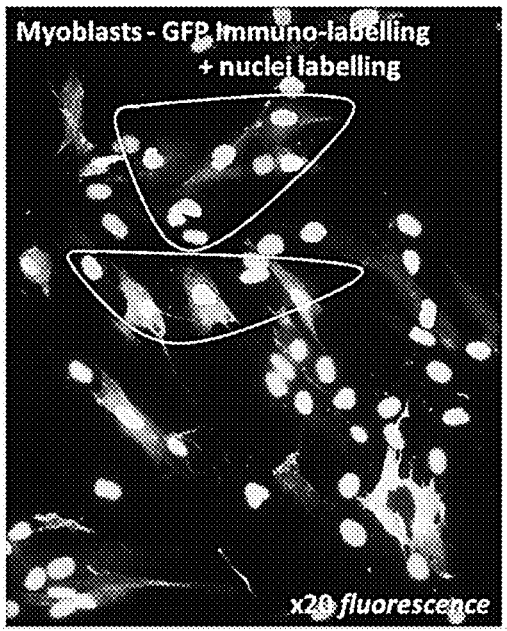
Fig. 39A
Fig. 39B
Fig. 39C
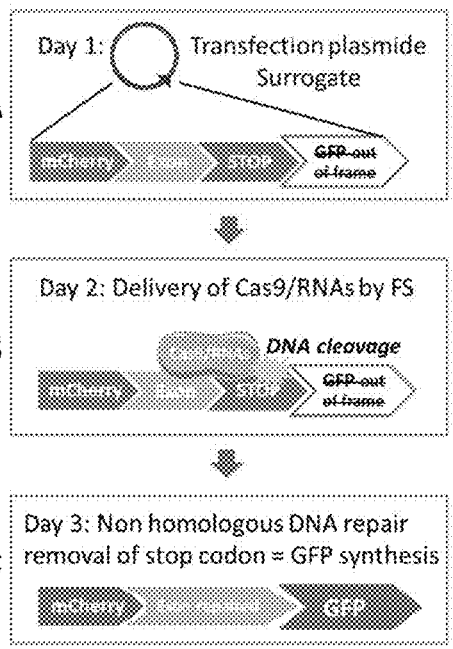
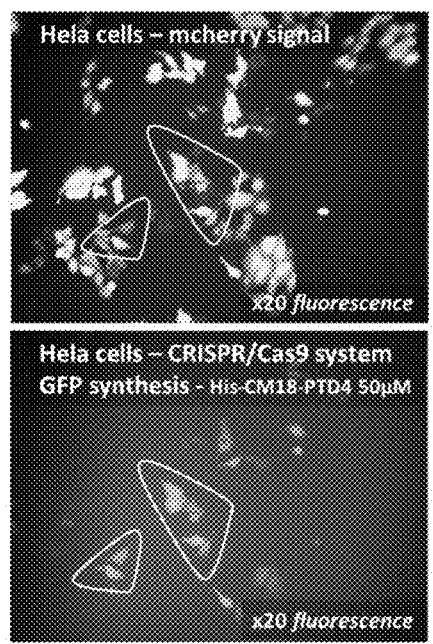
Fig. 39D
Fig. 39E

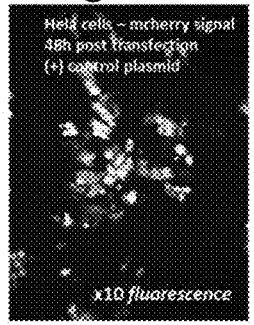 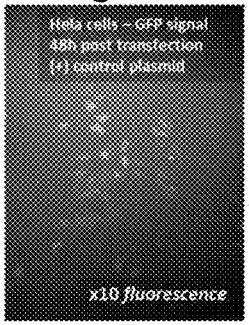 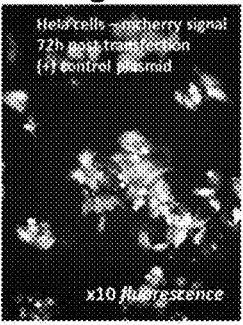 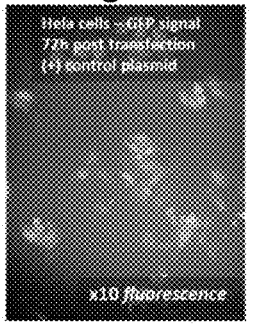
Fig. 40A  Fig. 40B  Fig. 40C  Fig. 40D
 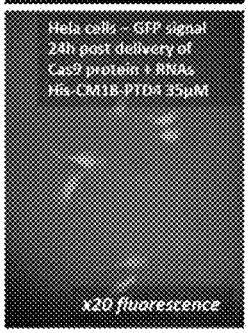 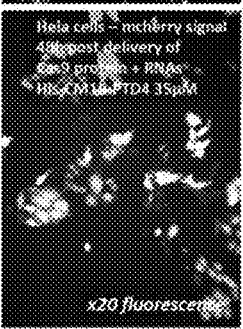 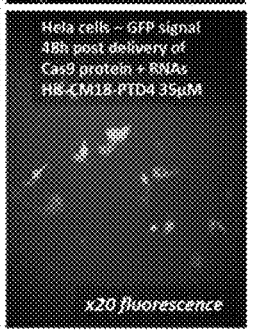
Fig. 40E  Fig. 40F  Fig. 40G  Fig. 40H
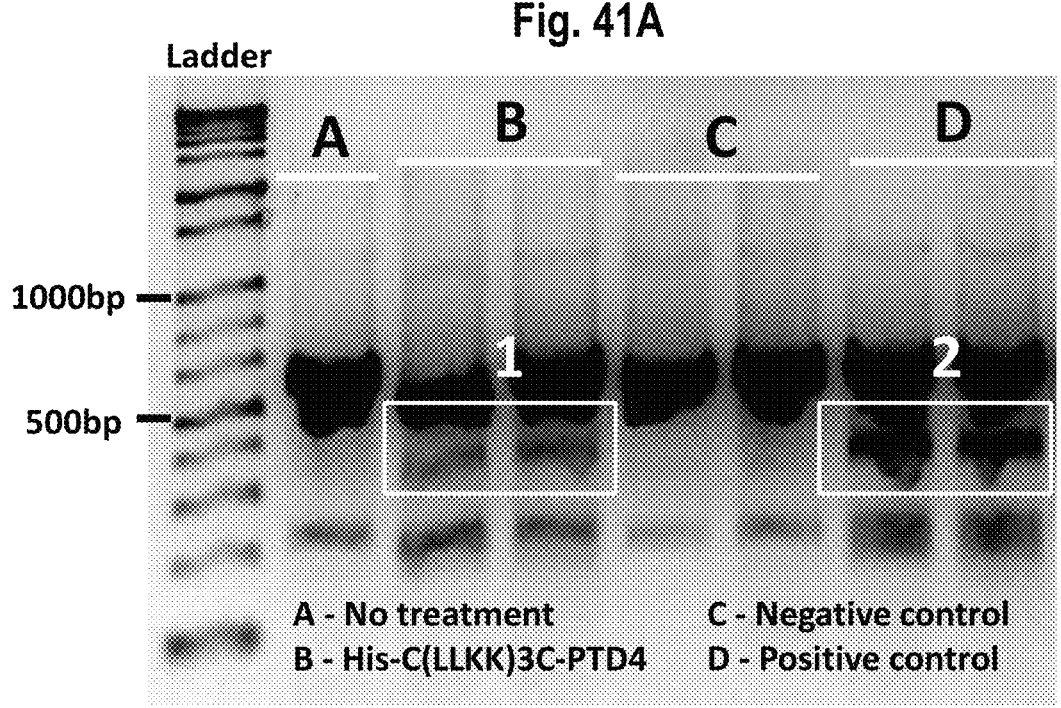
Fig. 41A
A - No treatment  C - Negative control
B - His-C(LLKK)3C-PTD4  D - Positive control Fig. 44
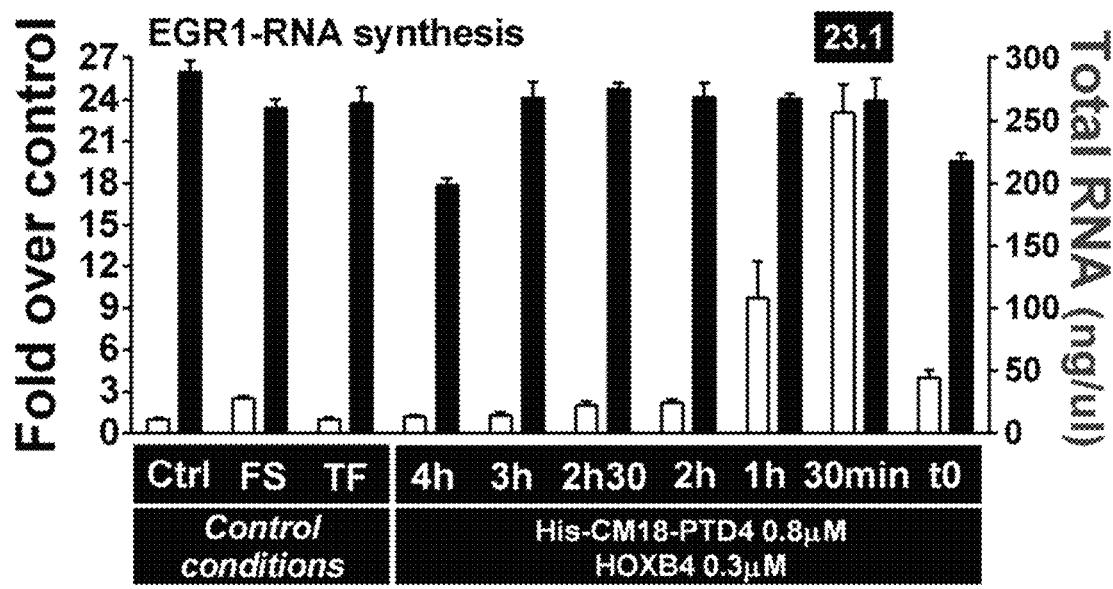
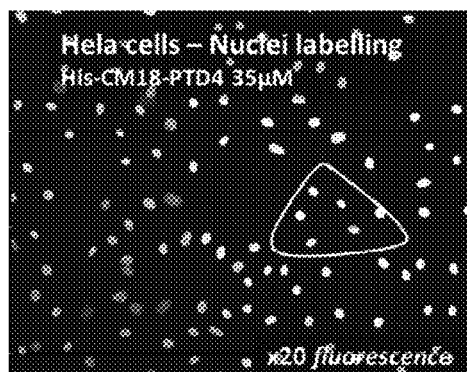
Fig. 45A
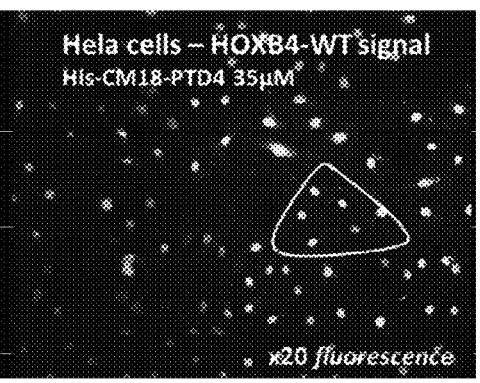
Fig. 45B
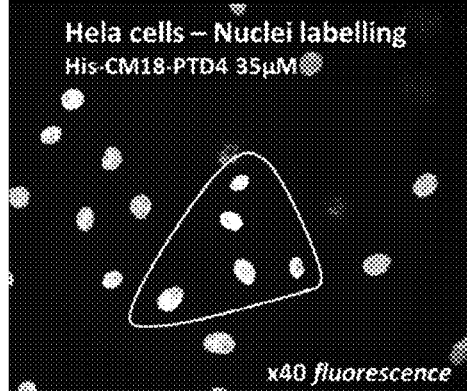
Fig. 45C
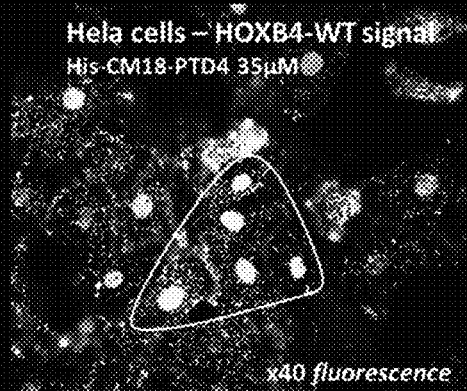
Fig. 45D

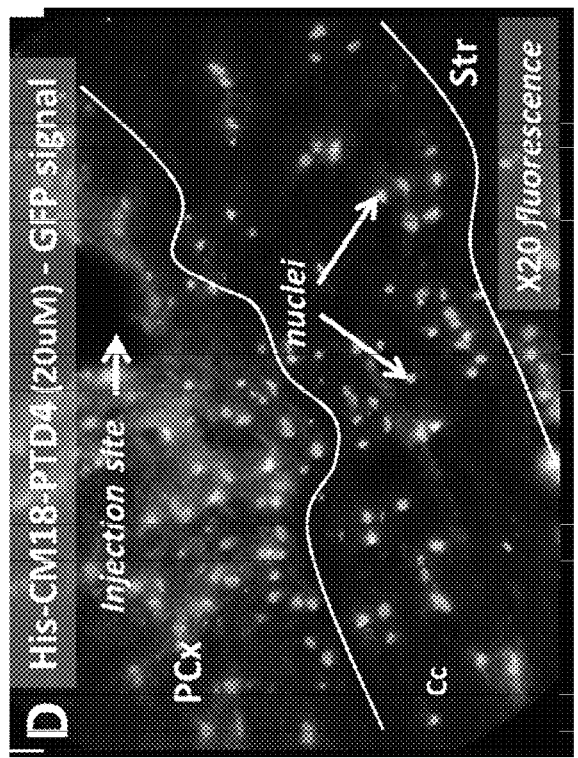
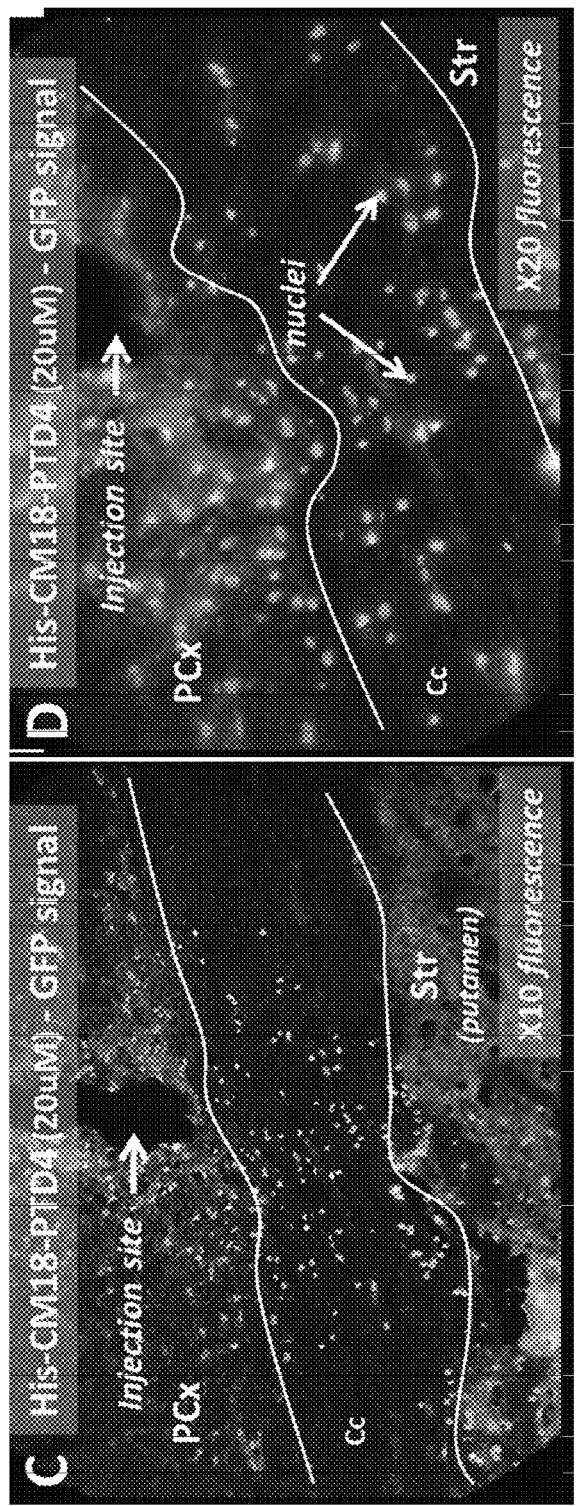
Fig. 48C
Fig. 48D

POLYPEPTIDE-BASED SHUTTLE AGENTS FOR IMPROVING THE TRANSDUCTION EFFICIENCY OF POLYPEPTIDE CARGOS TO THE CYTOSOL OF TARGET EUKARYOTIC CELLS, USES THEREOF, METHODS AND KITS RELATING TO SAME

CROSS REFERENCE TO RELATED APPLICATIONS

This application is a continuation of U.S. patent application Ser. No. 15/486,155, filed Apr. 12, 2017, which is a continuation of Ser. No. 15/094,365, filed Apr. 8, 2016, now U.S. Pat. No. 9,738,687, which claims priority under 35 U.S.C section 119 from Provisional Application Ser. No. 62/145,760, filed Apr. 10, 2015 and Provisional Application Ser. No. 62/246,892 filed Oct. 27, 2015, the disclosures of which are incorporated herein by reference in their entirety.

The present description relates to synthetic peptides useful for increasing the transduction efficiency of polypeptide cargos to the cytosol of target eukaryotic cells. More specifically, the present description relates to synthetic peptides and polypeptide-based shuttle agents comprising an endosome leakage domain (ELD) operably linked to a cell penetrating domain (CPD), or an ELD operably linked to a histidine-rich domain and a CPD.

SEQUENCE LISTING

The instant application contains a Sequence Listing which has been submitted electronically in ASCII format. Said ASCII copy, created Feb. 19, 2020, is named "49446703302_SL.txt" and is 28,256 bytes in size. The information in the electronic format of the Sequence Listing is incorporated by reference in its entirety.

BACKGROUND

Cell delivery technologies to transport large molecules inside eukaryotic cells have a wide range of applications, particularly in the biopharmaceutical industry. While some soluble chemical substances (e.g., small molecule drugs) may passively diffuse through the eukaryotic cell membrane, larger cargos (e.g., biologics, polynucleotides, and polypeptides) require the help of shuttle agents to reach their intracellular targets.

An area that would greatly benefit from advances in cell delivery technologies is the field of cell therapy, which has made enormous leaps over the last two decades. Deciphering the different growth factors and molecular cues that govern cell expansion, differentiation and reprogramming open the door to many therapeutic possibilities for the treatment of unmet medical needs. For example, induction of pluripotent stem cells directly from adult cells, direct cell conversion (trans-differentiation), and genome editing (Zinc finger nuclease, TALEN™ and CRISPR/Cas9 technologies) are examples of methods that have been developed to maximize the therapeutic value of cells for clinical applications. Presently, the production of cells with high therapeutic activity usually requires ex vivo manipulations, mainly achieved by viral transduction, raising important safety and economical concerns for human applications. The ability to directly deliver active proteins such as transcription factors or artificial nucleases, inside these cells, may advantageously circumvent the safety concerns and regulatory hurdles associated with more risky gene transfer methods.

In this regard, polypeptide-based transduction agents may be useful for introducing purified recombinant proteins directly into target cells, for example, to help bypass safety concerns regarding the introduction of foreign DNA. Lipid- or cationic polymer-based transduction agents exist, but introduce safety concerns regarding chemical toxicity and efficiency, which hamper their use in human therapy. Protein transduction approaches involving fusing a recombinant protein cargo directly to a cell-penetrating peptide (e.g., HIV transactivating protein TAT) require large amounts of the recombinant protein and often fail to deliver the cargo to the proper subcellular location, leading to massive endosomal trapping and eventual degradation. Several endosomal membrane disrupting peptides have been developed to try and facilitate the escape of endosomally-trapped cargos to the cytosol. However, many of these endosomolytic peptides are intended to alleviate endosomal entrapment of cargos that have already been delivered intracellularly, and do not by themselves aid in the initial step of shuttling the cargos intracellularly across the plasma membrane (Salomone et al., 2012; Salomone et al., 2013; Erazo-Oliveras et al., 2014; Fasoli et al., 2014). Thus, there is a need for improved shuttle agents capable of increasing the transduction efficiency of polypeptide cargos, and delivering the cargos to the cytosol of target eukaryotic cells.

The present description refers to a number of documents, the content of which is herein incorporated by reference in their entirety.

SUMMARY

The present description stems from the surprising discovery that synthetic peptides comprising an endosome leakage domain (ELD) operably linked to a cell penetrating domain (CPD) and optionally a histidine-rich domain, have the ability to increase the proportion of cells that can be transduced with a polypeptide cargo of interest, without the synthetic peptide being covalently bound to the polypeptide cargo. Following successful transduction, the synthetic peptides may facilitate the ability of endosomally-trapped polypeptide cargos to gain access to the cytosol, and optionally be targeted to various subcellular comparts (e.g., the nucleus).

Accordingly, the present description may additionally or alternatively relate to the following aspects:

(1) A synthetic peptide comprising an endosome leakage domain (ELD) operably linked to a cell penetrating domain (CPD), or an ELD operably linked to a histidine-rich domain and a CPD.

(2) A polypeptide-based shuttle agent comprising an endosome leakage domain (ELD) operably linked to a cell penetrating domain (CPD), or an ELD operably linked to a histidine-rich domain and a CPD, for use in increasing the transduction efficiency of an independent polypeptide cargo to the cytosol of a target eukaryotic cell.

(3) The synthetic peptide or polypeptide-based shuttle agent of (1) or (2), wherein the synthetic peptide or polypeptide-based shuttle agent: (a) comprises a minimum length of 20, 21, 22, 23, 24, 25, 26, 27, 28, 29, or 30 amino acid residues and a maximum length of 35, 40, 45, 50, 55, 65, 70, 75, 80, 85, 90, 95, 100, 105, 110, 115, 120, 125, 130, 135, 140, 145, or 150 amino acid residues; (b) has a predicted net charge of at least +6, +7, +8, +9, +10, +11, +12, +13, +14, or +15 at physiological pH; (c) is soluble in aqueous solution; or (d) any combination of (a) to (c).

(4) The synthetic peptide or polypeptide-based shuttle agent of any one of (1) to (3), wherein: (a) the ELD is or is from: an endosomolytic peptide; an antimicrobial peptide (AMP); a linear cationic alpha-helical antimicrobial peptide; a Cecropin-A/Melittin hybrid (CM series) peptide; pH-dependent membrane active peptide (PAMP); a peptide amphiphile; a peptide derived from the N terminus of the HA2 subunit of influenza hemagglutinin (HA); CM18; Diphtheria toxin T domain (DT); GALA; PEA; INF-7; LAH4; HGP; H5WYG; HA2; EB1; VSVG; *Pseudomonas* toxin; melittin; KALA; JST-1; C(LLKK)$_3$C; G(LLKK)$_3$G; or any combination thereof; (b) the CPD is or is from: a cell-penetrating peptide or the protein transduction domain from a cell-penetrating peptide; TAT; PTD4; Penetratin (Antennapedia); pVEC; M918; Pep-1; Pep-2; Xentry; arginine stretch; transportan; SynB1; SynB3; or any combination thereof; (c) the histidine-rich domain is a stretch of at least 3, at least 4, at least 5, or at least 6 amino acids comprising at least 50%, at least 55%, at least 60%, at least 65%, at least 70%, at least 75%, at least 80%, at least 85%, or at least 90% histidine residues; and/or comprises at least 2, at least 3, at least 4, at least 5, at least 6, at least 7, at least 8, or at least 9 consecutive histidine residues; or (d) any combination of (a) to (c).

(5) The synthetic peptide or polypeptide-based shuttle agent of any one of (1) to (4), wherein the synthetic peptide or polypeptide-based shuttle agent comprises: (a) an ELD comprising the amino acid sequence of any one of SEQ ID NOs: 1-15, 63, or 64, or a variant or fragment thereof having endosomolytic activity; (b) a CPD comprising the amino acid sequence of any one of SEQ ID NOs: 16-27 or 65, or a variant or fragment thereof having cell penetrating activity; (c) a histidine-rich domain having at least 2, at least 3, at least 4, at least 5, or at least 6 consecutive histidine residues; (d) of any combination of (a) to (c).

(6) The synthetic peptide or polypeptide-based shuttle agent of any one of (1) to (5), wherein the domains are operably linked via one or more linker domains.

(7) The synthetic peptide or polypeptide-based shuttle agent of any one of (1) to (6), wherein the synthetic peptide or polypeptide-based shuttle agent comprises at least two different types of CPDs and/or ELDs.

(8) The synthetic peptide or polypeptide-based shuttle agent of any one of (1) to (7), wherein the synthetic peptide or polypeptide-based shuttle agent comprises: (a) an ELD which is CM18, KALA, or C(LLKK)$_3$C having the amino acid sequence of SEQ ID NO: 1, 14, or 63, or a variant thereof having at least 85%, 90%, or 95% identity to SEQ ID NO: 1 and having endosomolytic activity; (b) a CPD which is TAT or PTD4 having the amino acid sequence of SEQ ID NO: 17 or 65, or a variant thereof having at least 85%, 90%, or 95% identity to SEQ ID NO: 17 or 65, and having cell penetrating activity; or Penetratin having the amino acid sequence of SEQ ID NO: 18, or a variant thereof having at least 85%, 90%, or 95% identity to SEQ ID NO: 18 and having cell penetrating activity; (c) a histidine-rich domain comprising at least 6 consecutive histidine residues; or (d) any combination of (a) to (c).

(9) The synthetic peptide or polypeptide-based shuttle agent of any one of (1) to (8), wherein the synthetic peptide or polypeptide-based shuttle agent comprises or consists of the amino acid sequence of any one of SEQ ID NOs: 57-59, 66-73, or 82-102, or a functional variant thereof having at least 85%, 90%, or 95% identity to any one of SEQ ID NOs: 57-59, 66-73, or 82-102.

(10) The synthetic peptide or polypeptide-based shuttle agent of any one of (1) to (9), wherein the synthetic peptide or polypeptide-based shuttle agent is non-toxic and/or is metabolizable.

(11) A composition comprising: (a) the synthetic peptide or polypeptide-based shuttle agent as defined in any one of (1) to (10), and a further independent synthetic peptide comprising a histidine-rich domain and a CPD; and/or (b) a cocktail of at least 2, at least 3, at least 4, or at least 5 different types of the synthetic peptides or polypeptide-based shuttle agents as defined in any one of (1) to (10).

(12) Use of the synthetic peptide, polypeptide-based shuttle agent, or composition as defined in any one of (1) to (11), for delivering an independent polypeptide cargo to the cytosol of a target eukaryotic cell.

(13) A method for increasing the transduction efficiency of a polypeptide cargo to the cytosol of a target eukaryotic cell, the method comprising contacting the target eukaryotic cell with the synthetic peptide, polypeptide-based shuttle agent, or composition as defined in any one of (1) to (11), and the polypeptide cargo.

(14) A kit for increasing the transduction efficiency of a polypeptide cargo to the cytosol of a target eukaryotic cell, the kit comprising the synthetic peptide, polypeptide-based shuttle agent, or composition as defined in any one of (1) to (11), and a suitable container.

(15) The synthetic peptide, polypeptide-based shuttle agent, composition, use, method or kit of any one of (1) to (14), for use in increasing the transduction efficiency of a polypeptide cargo to the cytosol of a target eukaryotic cell in the presence of serum.

(16) The synthetic peptide, polypeptide-based shuttle agent, composition, use, method or kit of any one of (2) to (15), wherein the polypeptide cargo: (a) comprises or lacks a CPD or a CPD as defined in (4)(b); (b) is a recombinant protein; (c) comprises a subcellular targeting domain; (d) is complexed with a DNA and/or RNA molecule; or (e) any combination of (a) to (d).

(17) The synthetic peptide, polypeptide-based shuttle agent, composition, use, method or kit of (16), wherein the subcellular targeting domain is: (a) a nuclear localization signal (NLS); (b) a nucleolar signal sequence; (c) a mitochondrial signal sequence; or (d) a peroxisome signal sequence.

(18) The synthetic peptide, polypeptide-based shuttle agent, composition, use, method or kit of (17), wherein: (a) the NLS is from: E1a, T-Ag, c-myc, T-Ag, op-T-NLS, Vp3, nucleoplasmin, histone 2B, Xenopus N1, PARP, PDX-1, QKI-5, HCDA, H2B, v-Rel, Amida, RanBP3, Pho4p, LEF-1, TCF-1, BDV-P, TR2, SOX9, or Max; (b) the nucleolar signal sequence is from BIRC5 or RECQL4; (c) the mitochondrial signal sequence is from Tim9 or Yeast cytochrome c oxidase subunit IV; or (d) the peroxisome signal sequence is from PTS1.

(19) The synthetic peptide, polypeptide-based shuttle agent, composition, use, method or kit of any one of (2) to (18), wherein the polypeptide cargo is a transcription factor, a nuclease, a cytokine, a hormone, a growth factor, or an antibody.

(20) The synthetic peptide, polypeptide-based shuttle agent, composition, use, method or kit of (19), wherein: (a) the transcription factor is: HOXB4, NUP98-

HOXA9, Oct3/4, Sox2, Sox9, Klf4, c-Myc, MyoD, Pdx1, Ngn3, MafA, Blimp-1, Eomes, T-bet, FOXO3A, NF-YA, SALL4, ISL1, FoxA1, Nanog, Esrrb, Lin28, HIF1-alpha, Hlf, Runx1t1, Pbx1, Lmo2, Zfp37, Prdm5, Bcl-6, or any combination thereof; and/or the nuclease is: an RNA-guided endonuclease, a CRISPR endonuclease, a type I CRISPR endonuclease, a type II CRISPR endonuclease, a type III CRISPR endonuclease, a type IV CRISPR endonuclease, a type V CRISPR endonuclease, a type VI CRISPR endonuclease, CRISPR associated protein 9 (Cas9), Cpf1, a zinc-finger nuclease (ZFN), a Transcription activator-like effector nucleases (TALENs), a homing endonuclease, a meganuclease, or any combination thereof.

(21) The synthetic peptide, polypeptide-based shuttle agent, composition, use, method or kit of any one of (1) to (20), for use in cell therapy, genome editing, adoptive cell transfer, and/or regenerative medicine.

(22) The shuttle agent, shuttle system, composition, use, method, or kit of any one of (2) to (21), wherein the target eukaryotic cell is a stem cell, a primary cell, an immune cell, a T cell, or a dendritic cell.

(23) A eukaryotic cell comprising the synthetic peptide or polypeptide-based shuttle agent as defined in any one of (1) to (10), or the composition of (11).

(24) The eukaryotic cell of (23), wherein said cell further comprises an independent polypeptide cargo delivered intracellularly by said synthetic peptide or polypeptide-based shuttle agent.

(25) A method for delivering an independent polypeptide cargo to the cytosol of a target eukaryotic cell, said method comprising contacting said target eukaryotic cell with the synthetic peptide or polypeptide-based shuttle agent as defined in any one of (1) to (10), or the composition of (11); and an independent polypeptide cargo to be delivered intracellularly by said synthetic peptide or polypeptide-based shuttle agent.

(26) The eukaryotic cell of (23) or (24), or the method of (25), wherein said independent polypeptide cargo is as defined in any one of (16) to (20).

(27) The eukaryotic cell of (24) or (26), or the method of (25) or (26), wherein said independent polypeptide cargo is as defined in any one of (16) to (20).

(28) The eukaryotic cell of (23), (24), (26) or (27), or the method of (25), (26), or (27), wherein said eukaryotic cell is an animal cell, a mammalian cell, a human cell, a stem cell, a primary cell, an immune cell, a T cell, or a dendritic cell.

In some aspects, the present description may relate to one or more of the following items:

1. A method for increasing the transduction efficiency of an independent polypeptide cargo to the cytosol of a target eukaryotic cell, said method comprising contacting said target eukaryotic cell with a synthetic peptide and said independent polypeptide cargo, wherein said synthetic peptide:
    (a) comprises an endosome leakage domain (ELD), or a variant or fragment thereof having endosomolytic activity, operably linked to a cell penetrating domain (CPD), wherein said ELD comprises the amino acid sequence of any one of SEQ ID NOs: 1-15, 63, or 64;
    (b) is not covalently bound to said independent polypeptide cargo;
    (c) has an overall length of between 20 and 100 amino acid residues;
    (d) has a net charge of at least +6 at physiological pH; and
    (e) is soluble in aqueous solution at physiological pH, wherein said CPD enables intracellular delivery of said synthetic peptide, and said ELD enables escape of endosomally trapped independent polypeptide cargo to the cytosol of the target eukaryotic cell.

2. The method of item 1, wherein said synthetic peptide has an overall length of between 20 and 70 amino acid residues.

3. The method of item 1, wherein said CPD comprises the amino acid sequence of any one of SEQ ID NOs: 16-27 or 65, or is a variant or fragment thereof having cell penetrating activity.

4. The method of item 1, wherein said synthetic peptide further comprises a histidine-rich domain consisting of a stretch of at least 6 amino acids comprising at least 50%, at least 55%, at least 60%, at least 65%, at least 70%, at least 75%, at least 80%, at least 85%, or at least 90% histidine residues; and/or comprises at least 2, at least 3, at least 4, at least 5, or at least 6 consecutive histidine residues.

5. The method of item 1, wherein said ELD variant or ELD fragment has at least 70%, at least 75%, at least 80%, at least 85%, at least 90%, or at least 95% sequence identity to any one of SEQ ID NOs: 1-15, 63, or 64.

6. The method of item 3, wherein said CPD variant or CPD fragment has at least 70%, at least 75%, at least 80%, at least 85%, at least 90%, or at least 95% sequence identity to any one of SEQ ID NOs: 16-27 or 65.

7. The method of item 1, wherein said ELD and CPD are operably linked via one or more linker domains.

8. The method of item 1, wherein said synthetic peptide is chemically synthesized without an N-terminal methionine residue.

9. The method of item 1, wherein the synthetic peptide comprises the amino acid sequence of any one of SEQ ID NOs: 57-59, 66-72, or 82-102, or a functional variant thereof having at least 70%, at least 85%, at least 90%, or at least 95% identity to any one of SEQ ID NOs: 57-59, 66-72, or 82-102.

10. The method of item 1, wherein said independent polypeptide cargo is a recombinant protein lacking a CPD.

11. The method of item 1, wherein said independent polypeptide cargo is a transcription factor, a nuclease, a cytokine, a hormone, a growth factor, or an antibody.

12. The method of item 11, wherein:
    (b) said transcription factor is: HOXB4, NUP98-HOXA9, Oct3/4, Sox2, Sox9, Klf4, c-Myc, MyoD, Pdx1, Ngn3, MafA, Blimp-1, Eomes, T-bet, FOXO3A, NF-YA, SALL4, ISL1, FoxA1, Nanog, Esrrb, Lin28, HIF1-alpha, Hlf, Runx1t1, Pbx1, Lmo2, Zfp37, Prdm5, Bcl-6, or any combination thereof; or
    (b) said nuclease is an RNA-guided endonuclease, a CRISPR endonuclease, a type I CRISPR endonuclease, a type II CRISPR endonuclease, a type III CRISPR endonuclease, a type IV CRISPR endonuclease, a type V CRISPR endonuclease, a type VI CRISPR endonuclease, CRISPR associated protein 9 (Cas9), Cpf1, a zinc-finger nuclease (ZFNs), a Transcription activator-like effector nucleases (TALENs), a homing endonuclease, or a meganuclease.

13. The method of item 11, wherein said nuclease is Cas9 or Cpf1.

14. The method of item 13, wherein said nuclease further comprises a guide RNA, a crRNA, a tracrRNA, or both a crRNA and a tracrRNA.
15. The method of item 1, wherein said independent polypeptide cargo comprises a nuclear localization signal or a further nuclear localization signal.
16. The method of item 15, wherein said independent polypeptide cargo is a transcription factor or a nuclease.
17. The method of item 16 wherein:
    (a) said transcription factor is: HOXB4, NUP98-HOXA9, Oct3/4, Sox2, Sox9, Klf4, c-Myc, MyoD, Pdx1, Ngn3, MafA, Blimp-1, Eomes, T-bet, FOXO3A, NF-YA, SALL4, ISL1, FoxA1, Nanog, Esrrb, Lin28, HIF1-alpha, Hlf, Runx1t1, Pbx1, Lmo2, Zfp37, Prdm5, Bcl-6, or any combination thereof; or
    (b) said nuclease is an RNA-guided endonuclease, a CRISPR endonuclease, a type I CRISPR endonuclease, a type II CRISPR endonuclease, a type III CRISPR endonuclease, a type IV CRISPR endonuclease, a type V CRISPR endonuclease, a type VI CRISPR endonuclease, CRISPR endonuclease, CRISPR associated protein 9 (Cas9), Cpf1, a zinc-finger nuclease (ZFNs), a Transcription activator-like effector nucleases (TALENs), a homing endonuclease, or a meganuclease.
18. The method of item 17, wherein said nuclease is Cas9 or Cpf1.
19. The method of item 18, wherein said nuclease further comprises a guide RNA.
20. The method of item 1, wherein said cell is stem cell, a primary cell, an immune cell, a T cell, or a dendritic cell.
21. A method for increasing the transduction efficiency of an independent polypeptide cargo to the cytosol of a target eukaryotic cell, said method comprising contacting said target eukaryotic cell with a synthetic peptide and said independent polypeptide cargo, wherein said synthetic peptide:
    (a) comprises an endosome leakage domain (ELD) operably linked to a cell penetrating domain (CPD), wherein said ELD is an endosomolytic peptide which is, or is derived from: a linear cationic alpha-helical antimicrobial peptide; a Cecropin-A/Melittin hybrid (CM series) peptide; pH-dependent membrane active peptide (PAMP); a peptide amphiphile; a peptide derived from the N terminus of the HA2 subunit of influenza hemagglutinin (HA); CM18; Diphtheria toxin T domain (DT); GALA; PEA; INF-7; LAH4; HGP; H5WYG; HA2; EB1; VSVG; *Pseudomonas* toxin; melittin; KALA; JST-1; C(LLKK)$_3$C; or G(LLKK)$_3$G;
    (b) is not covalently bound to said independent polypeptide cargo;
    (c) has an overall length of between 20 and 100 amino acid residues;
    (d) has a net charge of at least +6 at physiological pH; and
    (e) is soluble in aqueous solution at physiological pH, wherein said CPD enables intracellular delivery of said synthetic peptide, and said ELD enables escape of endosomally trapped independent polypeptide cargo to the cytosol of the target eukaryotic cell.
22. The method of item 21, wherein said CPD is, or is derived from: a cell-penetrating peptide or the protein transduction domain from a cell-penetrating peptide; TAT; PTD4; Penetratin (Antennapedia); pVEC; M918; Pep-1; Pep-2; Xentry; arginine stretch; transportan; SynB1; SynB3; or any combination thereof.
23. The method of item 21, wherein said synthetic peptide further comprises a histidine-rich domain consisting of a stretch of at least 3 amino acids comprising at least 50%, at least 55%, at least 60%, at least 65%, at least 70%, at least 75%, at least 80%, at least 85%, or at least 90% histidine residues; and/or comprises at least 2, at least 3, at least 4, at least 5, or at least 6 consecutive histidine residues.
24. The method of item 21, wherein said ELD and CPD are operably linked via one or more linker domains.
25. The method of item 21, wherein said independent polypeptide cargo is a transcription factor, a nuclease, a cytokine, a hormone, a growth factor, or an antibody.
26. The method of item 25, wherein said transcription factor is: HOXB4, NUP98-HOXA9, Oct3/4, Sox2, Klf4, c-Myc, MyoD, Pdx1, Ngn3, MafA, Blimp-1, Eomes, T-bet, FOXO3A, NF-YA, SALL4, ISL1, FoxA1, Nanog, Esrrb, Lin28, HIF1-alpha, Hlf, Runx1t1, Pbx1, Lmo2, Zfp37, Prdm5, Bcl-6, or any combination thereof.
27. The method of item 25, wherein said nuclease is an RNA-guided endonuclease, a CRISPR endonuclease, a type I CRISPR endonuclease, a type II CRISPR endonuclease, a type III CRISPR endonuclease, a type IV CRISPR endonuclease, a type V CRISPR endonuclease, a type VI CRISPR endonuclease, CRISPR associated protein 9 (Cas9), Cpf1, a zinc-finger nuclease (ZFNs), a Transcription activator-like effector nucleases (TALENs), a homing endonuclease, or a meganuclease.
28. The method of item 25, wherein said nuclease is Cas9 or Cpf1.
29. A method for increasing the transduction efficiency of an independent polypeptide cargo to the cytosol of a target eukaryotic cell, said method comprising contacting said target eukaryotic cell with a synthetic peptide and said independent polypeptide cargo which is not covalently bound to said synthetic peptide, wherein said synthetic peptide comprises an endosome leakage domain (ELD) operably linked to a cell penetrating domain, or an ELD operably linked to a CPD and a histidine-rich domain, wherein:
    (a) said ELD comprises the amino acid sequence of any one of SEQ ID NOs: 1-15, 63, or 64;
    (b) said CPD comprises the amino acid sequence of any one of SEQ ID NOs: 16-27 or 65; and
    (c) said histidine-rich domain comprises at least two consecutive histidine residues.
30. A method for delivering a CRISPR associated protein 9 (Cas9) to the nucleus of a target eukaryotic cell, said method comprising contacting said eukaryotic cell with a Cas9 recombinant protein comprising a nuclear localization signal, and a separate synthetic peptide shuttle agent less than 100 residues in length and comprising an endosome leakage domain (ELD) operably linked to a cell penetrating domain, or an ELD operably linked to a CPD and a histidine-rich domain, wherein:
    (a) said ELD comprises the amino acid sequence of any one of SEQ ID NOs: 1-15, 63, or 64;
    (b) said CPD comprises the amino acid sequence of any one of SEQ ID NOs: 16-27 or 65; and
    (c) said histidine-rich domain comprises at least two consecutive histidine residues.

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one" but it is also consistent with the meaning of "one or more", "at least one", and "one or more than one".

The term "about" is used to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used herein, "protein" or "polypeptide" means any peptide-linked chain of amino acids, which may or may not comprise any type of modification (e.g., post-translational modifications such as acetylation, phosphorylation, glycosylation, sulfatation, sumoylation, prenylation, ubiquitination, etc).

As used herein, the expression "is or is from" or "is from" comprises functional variants of a given protein domain (CPD or ELD), such as conservative amino acid substitutions, deletions, modifications, as well as variants or function derivatives, which do not abrogate the activity of the protein domain. Other objects, advantages and features of the present description will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1A shows the results of a fluorescence microscopy experiment, while FIG. 1B shows the results of a flow cytometry experiment.

FIGS. 18A-18C show the results of a transduction efficiency experiment in which the cargo protein, FITC-labeled anti-tubulin antibody (0.5 µM), was co-incubated with 5 µM of CM18-TAT-Cys (labeled "CM18-TAT"), prior to being exposed to HeLa cells. Functional antibody delivery was visualized by bright field (20×—FIG. 18A) and fluorescence microscopy (20×—FIG. 18B and 40×—FIG. 18C), in which fluorescent tubulin fibers in the cytoplasm were visualized.

FIG. 22A shows a comparison of GFP-NLS transduction efficiencies using different transduction protocols (Protocol A vs. B). FIG. 22B shows the effect of using different concentrations of the shuttle His-CM18-PTD4 when using Protocol B.

FIGS. 23A-23D, FIGS. 24A-24B, FIGS. 25A-25B and FIGS. 26A-26C are microscopy images showing the results of transduction experiments in which GFP-NLS (FIGS. 23A-23D, 24A, 24B, 25A-B and 26A-26C) cargo protein was intracellularly delivered with the shuttle His-CM18-PTD4 in HeLa cells. FIGS. 23D, 24A, 26A, and FIGS. 23A to 23C, 24B, 25A-B, 26B-C show the bright field and fluorescence images, respectively, of living cells. In FIG. 25A-25B, the cells were fixed, permeabilized and subjected to immuno-labelling with an anti-GFP antibody and a fluorescent secondary antibody. White triangle windows indicate examples of areas of co-labelling between nuclei (DAPI) and GFP-NLS signals. FIG. 26A-26C shows images captured by confocal microscopy.

FIGS. 27A-27D show microscopy images of a kinetic (time-course) transduction experiment in HeLa cells, where the fluorescence of GFP-NLS cargo protein was tracked after 45, 75, 100, and 120 seconds following intracellular delivery with the shuttle His-CM18-PTD4. The diffuse cytoplasmic fluorescence pattern observed after 45 seconds (FIG. 27A) gradually becomes a more concentrated nuclear pattern at 120 seconds (FIG. 27D).

FIGS. 28A-28D show microscopy images of co-delivery transduction experiment in which two cargo proteins (GFP-NLS and mCherry™-NLS) are simultaneously delivered intracellularly by the shuttle His-CM18-PTD4 in HeLa cells. Cells and fluorescent signals were visualized by (FIG. 28A) bright field and (FIGS. 28B-28D) fluorescence microscopy. White triangle windows indicate examples of areas of co-labelling between nuclei (DAPI) and GFP-NLS or mCherry™.

FIGS. 29A-29I show the results of GFP-NLS transduction efficiency experiments in HeLa cells using different shuttle agents or single-domain/control peptides. GFP-NLS transduction efficiency was evaluated by flow cytometry and the percentage of GFP fluorescent cells ("Pos cells (%)"), as well as corresponding cell viability data ("viability (%)") are shown in FIGS. 29A, 29B, 29D-29G, and 29I. In FIG. 29A and FIG. 29D-29F, cells were exposed to the cargo/shuttle agent for 10 seconds. In FIG. 29I, cells were exposed to the cargo/shuttle agent for 1 minute. In FIGS. 29B, 29C, 29G and 29H, cells were exposed to the cargo/shuttle agent for 1, 2, or 5 min. "Relative fluorescence intensity (FL1-A)" or "Signal intensity" corresponds to the mean of all fluorescence intensities from each cell with a GFP fluorescent signal after GFP-NLS fluorescent protein delivery with the shuttle agent. FIG. 29D shows the results of a control experiment in which only single-domain peptides (ELD or CDP) or the peptide His-PTD4 (His-CPD) were used for the GFP-NLS transduction, instead of the multi-domain shuttle agents.

FIG. 30A-30F shows microscopy images of HeLa cells transduced with GFP-NLS using the shuttle agent (FIG. 30A) TAT-KALA, (FIG. 30B) His-CM18-PTD4, (FIG. 30C) His-C(LLKK)₃C-PTD4, (FIG. 30D) PTD4-KALA, (FIG. 30E) EB1-PTD4, and (FIG. 30F) His-CM18-PTD4-His. The insets in the row of the lower pictures in FIGS. 30A-30F show the results of corresponding flow cytometry analyses, indicating the percentage of cells exhibiting GFP fluorescence.

FIG. 32D shows the results of corresponding flow cytometry analyses, indicating the percentage of cells exhibiting GFP fluorescence.

FIGS. 33A-33D show microscopy images of THP-1 cells transduced with GFP-NLS cargo protein using the shuttle His-CM18-PTD4. White triangle windows indicate examples of areas of co-labelling between cells (bright field; FIG. 33A-33B), and GFP-NLS fluorescence (FIG. 33C-33D).

In FIG. 34B, "Relative fluorescence intensity (FL1-A)" corresponds to the mean of all fluorescence intensities from each cell with a GFP fluorescent signal after GFP-NLS fluorescence protein delivery with the shuttle agent.

FIGS. 35A-35F show the results of transduction efficiency experiments in which THP-1 cells were exposed daily to GFP-NLS cargo in the presence of a shuttle agent for 2.5 hours. His-CM18-PTD4 was used in FIGS. 35A-35E, and His-C(LLKK)$_3$C-PTD4 was used in FIG. 35F. GFP-NLS transduction efficiency was determined by flow cytometry at Day 1 or Day 3, and the results are expressed as the percentage of GFP fluorescent cells ("Pos cells (%)"), as well as corresponding cell viability data ("viability (%)") in FIGS. 35A-35C and in FIG. 35F. FIG. 35D shows the metabolic activity index of the THP-1 cells after 1, 2, 4, and 24 h, and FIG. 35E shows the metabolic activity index of the THP-1 cells after 1 to 4 days, for cells exposed to the His-CM18-PTD4 shuttle.

FIG. 36 shows a comparison of the GFP-NLS transduction efficiencies in a plurality of different types of cells (e.g., adherent and suspension, as well as cell lines and primary cells) using the shuttle His-CM18-PTD4, as measured by flow cytometry. The results are expressed as the percentage of GFP fluorescent cells ("Pos cells (%)"), as well as corresponding cell viability data ("viability (%)").

FIGS. 37A-37H show fluorescence microscopy images of different types of cells transduced with GFP-NLS cargo using the shuttle His-CM18-PTD4. GFP fluorescence was visualized by fluorescence microscopy at a 10× magnification. The results of parallel flow cytometry experiments are also provided in the insets (viability and percentage of GFP-fluorescing cells).

FIGS. 38A-38B show fluorescence microscopy images of primary human myoblasts transduced with GFP-NLS using the shuttle His-CM18-PTD4. Cells were fixed and permeabilized prior to immuno-labelling GFP-NLS with an anti-GFP antibody and a fluorescent secondary antibody. Immuno-labelled GFP is shown in FIG. 38A, and this image is overlaid with nuclei (DAPI) labelling in FIG. 38B.

FIGS. 39A-39E show a schematic layout (FIGS. 39A, 39B and 39C) and sample fluorescence images (D and E) of a transfection plasmid surrogate assay used to evaluate the activity of intracellularly delivered CRISPR/Cas9-NLS complex. In FIG. 39A) At Day 1, cells are transfected with an expression plasmid encoding the fluorescent proteins mCherry™ and GFP, with a STOP codon separating their two open reading frames. Transfection of the cells with the expression plasmid results in only mCherry™ expression as shown in FIG. 39D. A CRISPR/Cas9-NLS complex, which has been designed/programmed to cleave the plasmid DNA at the STOP codon, is then delivered intracellularly to the transfected cells expressing mCherry™, resulting double-stranded cleavage of the plasmid DNA at the STOP codon as shown in FIG. 39B In a fraction of the cells, random non-homologous DNA repair of the cleaved plasmid occurs and results in removal of the STOP codon (FIG. 39C), and thus GFP expression and fluorescence (FIG. 39E). White triangle windows indicate examples of areas of co-labelling of mCherry™ and GFP fluorescence.

FIGS. 40A-40H show fluorescence microscopy images of HeLa cells expressing mCherry™ and GFP, indicating CRISPR/Cas9-NLS-mediated cleavage of plasmid surrogate DNA. In FIGS. 40A-40D, HeLa cells were co-transfected with three plasmids: the plasmid surrogate as described in the brief description of FIGS. 39A-39E, and two other expression plasmids encoding the Cas9-NLS protein and crRNA/tracrRNAs, respectively. CRISPR/Cas9-mediated cleavage of the plasmid surrogate at the STOP codon, and subsequent DNA repair by the cell, enables expression of GFP (FIGS. 40B and 40D) in addition to mCherry™ (FIGS. 40A and 40C). In FIGS. 40E and 40H, HeLa cells were transfected with the plasmid surrogate and then transduced with an active CRISPR/Cas9-NLS complex using the shuttle His-CM18-PTD4. CRISPR/Cas9-NLS-mediated cleavage of the plasmid surrogate at the STOP codon, and subsequent DNA repair by the cell, enables expression of GFP (FIGS. 40F and 40H) in addition to mCherry™ (FIGS. 40E and 40G).

FIG. 41A (Lanes A to D) shows the products of a DNA cleavage assay (T7E1 assay) separated by agarose gel electrophoresis, which is used to measure CRISPR/Cas9-mediated cleavage of cellular genomic DNA. HeLa cells were transduced with a CRISPR-Cas9-NLS complex programmed to cleave the PPIB gene. The presence of the cleavage product framed in white boxes 1 and 2, indicates cleavage of the PPIB gene by the CRISPR-Cas9-NLS complex, which was delivered intracellularly using the shuttle His-C(LLKK)$_3$C-PTD4 (FIG. 41A-lane B) or with a lipidic transfection agent used as a positive control (FIG. 41A-lane D). This cleavage product is absent in negative controls (FIG. 41A, Lanes A and C).

FIGS. 42-44 show the transcriptional activity of THP-1 cells that have been transduced with the transcription factor HOXB4 using different concentrations of the shuttle His-CM18-PTD4 and different cargo/shuttle exposure times. Successful intra-nuclear delivery of HOXB4 was determined by monitoring mRNA levels of a target gene by real-time PCR, and the results are normalized against those in the negative control (HOXB4 without shuttle agent) and expressed as "Fold over control" (left bars). Total cellular RNA (ng/µL) was quantified and used a marker for cell viability (right bars). "Ø" or "Ctrl" means "no treatment"; "TF" means "Transcription Factor alone"; "FS" means "shuttle alone".

FIGS. 45A-45D show fluorescence microscopy images of HeLa cells transduced with wild-type HOXB4 cargo using the shuttle His-CM18-PTD4. After a 30-minute incubation to allow transduced HOXB4-WT to accumulate in the nucleus, the cells were fixed, permeabilized and HOXB4-WT was labelled using a primary anti-HOXB4 monoclonal antibody and a fluorescent secondary antibody (FIGS. 45B and 45D). Nuclei were labelled with DAPI (FIGS. 45A and 45C). White triangle windows indicate examples of areas of co-labelling between nuclei and HOXB4—compare FIG. 45A vs 45B (×20 magnification), and FIG. 45C vs 45D (×40 magnification).

FIG. 46A shows the results with the shuttle agents: His-CM18-PTD4, His-CM18-PTD4-His, and His-C(LLKK)3C-PTD4 in HeLa cells. FIG. 46B shows the results with His-CM18-PTD4-His and His-CM18-L2-PTD4 in Jurkat cells. Negative controls (lane 4 in FIGS. 46A and 46B) show amplified HPTR DNA sequence after incubation of the cells with the CRISPR/Cas9 complex without the presence of the shuttle agent. Positive controls (lane 5 in FIGS. 46A and 46B) show the amplified HPTR DNA sequence after incubation of the cells with the Cas9/RNAs complex in presence of a commercial lipidic transfection agent.

FIGS. 48A-48D show in vivo GFP-NLS delivery in rat parietal cortex by His-CM18-PTD4. Briefly, GFP-NLS (20 µM) was injected in the parietal cortex of rat in presence of the shuttle agent His-CM18-PTD4 (20 µM) for 10 min. Dorso-ventral rat brain slices were collected and analysed by fluorescence microscopy at (FIG. 48A) 4×, (FIG. 48C) 10× and (FIG. 48D) 20× magnifications. The injection site is located in the deepest layers of the parietal cortex (PCx). In presence of the His-CM18-PTD4 shuttle agent, the GFP-NLS diffused in cell nuclei of the PCx, of the Corpus Callus (Cc) and of the striatum (Str) (white curves mark limitations between brains structures). FIG. 48B shows the stereotaxic coordinates of the injection site (black arrows) from the rat brain atlas of Franklin and Paxinos. The injection of GFP-NLS in presence of His-CM18-PTD4 was performed on the left part of the brain, and the negative control (injection of GFP-NLS alone), was done on the contralateral site. The black circle and connected black lines in FIG. 48B show the areas observed in the fluorescent pictures (FIGS. 48A, 48C and 48D).

SEQUENCE DESCRIPTIONS

TABLE A

Figure 1A:
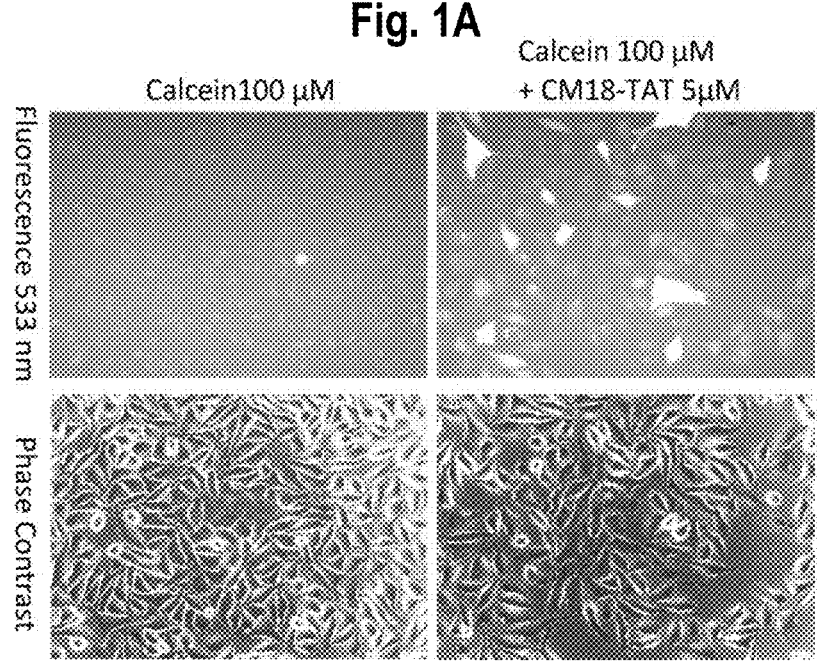
FIGS. 1A-1B show a typical result of a calcein endosomal escape assay in which HEK293A cells were loaded with the fluorescent dye calcein ("100 µM calcein"), and were then treated (or not) with a shuttle agent that facilitates endosomal escape of the calcein ("100 µM calcein+CM18-TAT 5 µM").

| SEQ ID NO: | Description |
| --- | --- |
| 1 | CM18 |
| 2 | Diphtheria toxin T domain (DT) |
| 3 | GALA |
| 4 | PEA |
| 5 | INF-7 |
| 6 | LAH4 |
| 7 | HGP |
| 8 | H5WYG |
| 9 | HA2 |
| 10 | EB1 |
| 11 | VSVG |
| 12 | *Pseudomonas* toxin |
| 13 | Melittin |
| 14 | KALA |
| 15 | JST-1 |
| 16 | SP |
| 17 | TAT |
| 18 | Penetratin (Antennapedia) |
| 19 | pVEC |
| 20 | M918 |
| 21 | Pep-1 |
| 22 | Pep-2 |
| 23 | Xentry |
| 24 | Arginine stretch |
| 25 | Transportan |
| 26 | SynB1 |
| 27 | SynB3 |
| 28 | E1a |
| 29 | SV40 T-Ag |
| 30 | c-myc |
| 31 | Op-T-NLS |
| 32 | Vp3 |
| 33 | Nucleoplasmin |
| 34 | Histone 2B NLS |
| 35 | Xenopus N1 |
| 36 | PARP |
| 37 | PDX-1 |
| 38 | QKI-5 |
| 39 | HCDA |
| 40 | H2B |
| 41 | v-Rel |
| 42 | Amida |
| 43 | RanBP3 |
| 44 | Pho4p |

TABLE A-continued

| SEQ ID NO: | Description |
| --- | --- |
| 45 | LEF-1 |
| 46 | TCF-1 |
| 47 | BDV-P |
| 48 | TR2 |
| 49 | SOX9 |
| 50 | Max |
| 51 | Mitochondrial signal sequence from Tim9 |
| 52 | Mitochondrial signal sequence from Yeast cytochrome c oxidase subunit IV |
| 53 | Mitochondrial signal sequence from 18S rRNA |
| 54 | Peroxisome signal sequence-PTS1 |
| 55 | Nucleolar signal sequence from BIRC5 |
| 56 | Nucleolar signal sequence from RECQL4 |
| 57 | CM18-TAT |
| 58 | CM18-Penetratin |
| 59 | His-CM18-TAT |
| 60 | GFP |
| 61 | TAT-GFP |
| 62 | GFP-NLS |
| 63 | C(LLKK)$_3$C |
| 64 | G(LLKK)$_3$G |
| 65 | PTD4 |
| 66 | TAT-CM18 |
| 67 | TAT-KALA |
| 68 | His-CM18-PTD4 |
| 69 | His-CM18-9Arg |
| 70 | His-CM18-Transportan |
| 71 | His-LAH4-PTD4 |
| 72 | His-C(LLKK)$_3$C-PTD4 |
| 73 | mCherry ™-NLS |
| 74 | Cas9-NLS |
| 75 | crRNA (Example 13.3) |
| 76 | tracrRNA (Example 13.3) |
| 77 | Feldan tracrRNA (Example 13.5, 13.6) |
| 78 | PPIB crRNA (Example 13.5) |
| 79 | Dharmacon tracrRNA (Example 13.5) |
| 80 | HOXB4-WT |
| 81 | His-PTD4 |
| 82 | PTD4-KALA |
| 83 | 9Arg-KALA |
| 84 | Pep1-KALA |
| 85 | Xentry-KALA |
| 86 | SynB3-KALA |
| 87 | VSVG-PTD4 |
| 88 | EB1-PTD4 |
| 89 | JST-PTD4 |
| 90 | CM18-PTD4 |
| 91 | 6Cys-CM18-PTD4 |
| 92 | CM18-L1-PTD4 |
| 93 | CM18-L2-PTD4 |
| 94 | CM18-L3-PTD4 |
| 95 | His-CM18-TAT |
| 96 | His-CM18-PTD4-6Cys |
| 97 | 3His-CM18-PTD4 |
| 98 | 12His-CM18-PTD4 |
| 99 | HA-CM18-PTD4 |
| 100 | 3HA-CM18-PTD4 |
| 101 | CM18-His-PTD4 |
| 102 | His-CM18-PTD4-His |
| 103 | HPRT crRNA (Example 13.6) |

DETAILED DESCRIPTION

The present description stems from the surprising discovery that multi-domain synthetic peptides comprising an endosome leakage domain (ELD) operably linked to a cell penetrating domain (CPD) can significantly increase the transduction efficiency of an independent polypeptide cargo to the cytosol of eukaryotic target cells. In contrast, this increase in transduction efficiency was not found using independent single-domain peptides containing only an ELD, or only a CPD used alone or together (i.e., in a mixture of separate single-domain peptides). Accordingly, in some aspects the present description relates to a polypeptide-based shuttle agent comprising an endosome leakage domain (ELD) operably linked to a cell penetrating domain (CPD), or an ELD operably linked to a histidine-rich domain and a CPD, for use in increasing the transduction efficiency of an independent polypeptide cargo to the cytosol of a target eukaryotic cell.

Synthetic Peptides and Polypeptide-Based Shuttle Agents

As used herein, the term "synthetic" used in expressions such as "synthetic peptide" or "synthetic polypeptide" is intended to refer to non-naturally occurring molecules that can be produced in vitro (e.g., synthesized chemically and/or produced using recombinant DNA technology). The purities of various synthetic preparations may be assessed by for example high-performance liquid chromatography analysis and mass spectroscopy. Chemical synthesis approaches may be advantageous over cellular expression systems (e.g., yeast or bacteria protein expression systems), as they may preclude the need for extensive recombinant protein purification steps (e.g., required for clinical use). In contrast, longer synthetic polypeptides may be more complicated and/or costly to produce via chemical synthesis approaches and such polypeptides may be more advantageously produced using cellular expression systems. In some embodiments, the peptides or shuttle agent of the present description may be chemically synthesized (e.g., solid- or liquid phase peptide synthesis), as opposed to expressed from a recombinant host cell. In some embodiments, the peptides or shuttle agent of the present description may lack an N-terminal methionine residue. A person of skill in the art may adapt a synthetic peptide or shuttle agent of the present description by using one or more modified amino acids (e.g., non-naturally-occurring amino acids), or by chemically modifying the synthetic peptide or shuttle agent of the present description, to suit particular needs of stability or other needs.

The expression "polypeptide-based" when used here in the context of a shuttle agent of the present description, is intended to distinguish the presently described shuttle agents from non-polypeptide or non-protein-based shuttle agents such as lipid- or cationic polymer-based transduction agents, which are often associated with increased cellular toxicity and may not be suitable for use in human therapy.

As used herein, the expression "increasing transduction efficiency" refers to the ability of a shuttle agent (e.g., a polypeptide-based shuttle agent of the present description) to improve the percentage or proportion of a population of target cells into which a cargo of interest (e.g., a polypeptide cargo) is delivered intracellularly across the plasma membrane. Immunofluorescence microscopy, flow cytometry, and other suitable methods may be used to assess cargo transduction efficiency. In some embodiments, a shuttle agent of the present description may enable a transduction efficiency of at least 25%, 30%, 35%, 40%, 45%, 50%, 55%, 60%, 65%, 70%, 75%, 80%, or 85%, for example as measure by immunofluorescence microscopy, flow cytometry, FACS, and other suitable methods. In some embodiments, a shuttle agent of the present description may enable one of the aforementioned transduction efficiencies together wish a cell viability of at least 25%, 30%, 35%, 40%, 45%, 50%, 55%, 60%, 65%, 70%, 75%, 80%, 85%, 90%, or 95%, for example as measure by the assay described in Example 3.3a, or by another suitable assay known in the art.

As used herein, the term "independent" is generally intended to refer to molecules or agents which are not covalently bound to one another. For example, the expression "independent polypeptide cargo" is intended to refer to a polypeptide cargo to be delivered intracellularly that is not covalently bound (e.g., not fused) to a shuttle agent of the present description. In some aspects, having shuttle agents that are independent of (not fused to) a polypeptide cargo may be advantageous by providing increased shuttle agent versatility—e.g., not being required to re-engineer a new fusion protein for different polypeptide cargoes, and/or being able to readily vary the ratio of shuttle agent to cargo (as opposed to being limited to a 1:1 ratio in the case of a fusion protein).

In addition to increasing target cell transduction efficiency, shuttle agents of the present description may facilitate the delivery of a cargo of interest (e.g., a polypeptide cargo) to the cytosol of target cells. In this regard, efficiently delivering an extracellular cargo to the cytosol of a target cell using approaches based on cell penetrating peptides can be challenging, as the cargo often becomes trapped in intracellular endosomes after crossing the plasma membrane, which may limit its intracellular availability and may result in its eventual metabolic degradation. For example, use of the protein transduction domain from the HIV-1 Tat protein has been reported to result in massive sequestration of the cargo into intracellular vesicles. In some aspects, shuttle agents of the present description may facilitate the ability of endosomally-trapped cargo to escape from the endosome and gain access to the cytoplasmic compartment. In this regard, the expression "to the cytosol" in the phrase "increasing the transduction efficiency of an independent polypeptide cargo to the cytosol," is intended to refer to the ability of shuttle agents of the present description to allow an intracellularly delivered cargo of interest to escape endosomal entrapment and gain access to the cytoplasmic compartment. After a cargo of interest has gained access to the cytosol, it may be subsequently targeted to various subcellular compartments (e.g., nucleus, nucleolus, mitochondria, peroxisome). In some embodiments, the expression "to the cytosol" is thus intended to encompass not only cytosolic delivery, but also delivery to other subcellular compartments that first require the cargo to gain access to the cytoplasmic compartment.

As used herein, a "domain" or "protein domain" generally refers to a part of a protein having a particular functionality or function. Some domains conserve their function when separated from the rest of the protein, and thus can be used in a modular fashion. By combining such domains from different proteins of viral, bacterial, or eukaryotic origin, it becomes possible in accordance with the present description to not only design multi-domain polypeptide-based shuttle agents that are able to deliver a cargo intracellularly, but also enable the cargo to escape endosomes and reach the cytoplasmic compartment.

The modular characteristic of many protein domains can provide flexibility in terms of their placement within the shuttle agents of the present description. However, some domains may perform better when engineered at certain positions of the shuttle agent (e.g., at the N- or C-terminal region, or therebetween). The position of the domain within its endogenous protein is sometimes an indicator of where the domain should be engineered within the shuttle agent, and of what type/length of linker should be used. Standard recombinant DNA techniques can be used by the skilled person to manipulate the placement and/or number of the domains within the shuttle agents of the present description in view of the present disclosure. Furthermore, assays disclosed herein, as well as others known in the art, can be used to assess the functionality of each of the domains within the context of the shuttle agents (e.g., their ability to facilitate cell penetration across the plasma membrane, endosome escape, and/or access to the cytosol). Standard methods can also be used to assess whether the domains of the shuttle agent affect the activity of the cargo to be delivered intracellularly. In this regard, the expression "operably linked" as used herein refers to the ability of the domains to carry out their intended function(s) (e.g., cell penetration, endosome escape, and/or subcellular targeting) within the context of the shuttle agents of the present description. For greater clarity, the expression "operably linked" is meant to define a functional connection between two or more domains without being limited to a particular order or distance between same.

In some embodiments, synthetic peptide or polypeptide-based shuttle agent of the present description may comprise a minimum length of 20, 21, 22, 23, 24, 25, 26, 27, 28, 29, or 30 amino acid residues and a maximum length of 35, 40, 45, 50, 55, 60, 65, 70, 75, 80, 85, 90, 95, 100, 105, 110, 115, 120, 125, 130, 135, 140, 145, or 150 amino acid residues. In some embodiments, shorter synthetic peptide or polypeptide-based shuttle agents are particularly advantageous because they may be more easily synthesized and purified by chemical synthesis approaches, which may be more suitable for clinical use (as opposed to recombinant proteins that must be purified from cellular expression systems). While numbers and ranges in the present description are often listed as multiples of 5, the present description should not be so limited. For example, the maximum length described herein should be understood as also encompassing a length of 36, 37, 38 . . . 51, 62, etc., in the present description, and that their non-listing herein is only for the sake of brevity. The same reasoning applies to the % of identities listed herein (e.g., 86%, 87% . . . 93% . . . ), the percentages of histidine residues, etc.

In some embodiments, synthetic peptide or polypeptide-based shuttle agent of the present description may comprise a predicted net charge of at least +5, +6, +7, at least +8, at least +9, at least +10, at least +11, at least +12, at least +13, at least +14, or at least +15 at physiological pH. These positive charges are generally conferred by the greater presence of positively-charged lysine and/or arginine residues, as opposed to negatively charged aspartate and/or glutamate residues.

In some embodiments, synthetic peptide or polypeptide-based shuttle agent of the present description may be soluble in aqueous solution (e.g., at physiological pH), which facilitates their use in for example cell culture media to delivery cargoes intracellularly to live cells.

In some embodiments, synthetic peptide or polypeptide-based shuttle agent of the present description may comprise or consist of the amino acid sequence of any one of SEQ ID NOs: 57-59, 66-72, or 82-102, or a functional variant thereof having at least 65%, 66%, 67%, 68%, 69%, 70%, 71%, 72%, 73%, 74%, 75%, 76%, 77%, 78%, 79%, 80%, 81% 82%, 83%, 84%, 85%, 86%, 87%, 88%, 89%, 90%, 91%, 92%, 93%, 94%, or 95% identity to any one of SEQ ID NOs: 57-59, 66-72, or 82-102.

In some embodiments, synthetic peptide or polypeptide-based shuttle agents of the present description may comprise oligomers (e.g., dimers, trimers, etc.) of a synthetic peptide or polypeptide-based shuttle agent as defined herein. Such oligomers may be constructed by covalently binding the same or different types of shuttle agent monomers (e.g., using disulfide bridges to link cysteine residues introduced into the monomer sequences).

In some embodiments, the synthetic peptide or polypeptide-based shuttle agent of the present description may comprise an N-terminal and/or a C-terminal cysteine residue.

Endosome Leakage Domains (ELDs)

In some aspects, synthetic peptide or polypeptide-based shuttle agents of the present description may comprise an endosome leakage domain (ELD) for facilitating endosome escape and access to the cytoplasmic compartment. As used herein, the expression "endosome leakage domain" refers to a sequence of amino acids which confers the ability of endosomally-trapped macromolecules to gain access to the cytoplasmic compartment. Without being bound by theory, endosome leakage domains are short sequences (often derived from viral or bacterial peptides), which are believed to induce destabilization of the endosomal membrane and liberation of the endosome contents into the cytoplasm. As used herein, the expression "endosomolytic peptide" is intended to refer to this general class of peptides having endosomal membrane-destabilizing properties. Accordingly, in some embodiments, synthetic peptide or polypeptide-based shuttle agents of the present description may comprise an ELD which is an endosomolytic peptide. The activity of such peptides may be assessed for example using the calcein endosome escape assays described in Example 2.

In some embodiments, the ELD may be a peptide that disrupts membranes at acidic pH, such as pH-dependent membrane active peptide (PMAP) or a pH-dependent lytic peptide. For example, the peptides GALA and INF-7 are amphiphilic peptides that form alpha helixes when a drop in pH modifies the charge of the amino acids which they contain. More particularly, without being bound by theory, it is suggested that ELDs such as GALA induce endosomal leakage by forming pores and flip-flop of membrane lipids following conformational change due to a decrease in pH (Kakudo, Chaki et al., 2004, Li, Nicol et al., 2004). In contrast, it is suggested that ELDs such as INF-7 induce endosomal leakage by accumulating in and destabilizing the endosomal membrane (El-Sayed, Futaki et al., 2009). Accordingly in the course of endosome maturation, the concomitant decline in pH causes a change in the conformation of the peptide and this destabilizes the endosome membrane leading to the liberation of the endosome contents. The same principle is thought to apply to the toxin A of *Pseudomonas* (Varkouhi, Scholte et al., 2011). Following a decline in pH, the conformation of the domain of translocation of the toxin changes, allowing its insertion into the endosome membrane where it forms pores (London 1992, O'Keefe 1992). This eventually favors endosome destabilization and translocation of the complex outside of the endosome. The above described ELDs are encompassed within the ELDs of the present description, as well as other mechanisms of endosome leakage whose mechanisms of action may be less well defined.

In some embodiments, the ELD may be an antimicrobial peptide (AMP) such as a linear cationic alpha-helical antimicrobial peptide (AMP). These peptides play a key role in the innate immune response due to their ability to strongly interact with bacterial membranes. Without being bound by theory, these peptides are thought to assume a disordered state in aqueous solution, but adopt an alpha-helical secondary structure in hydrophobic environments. The latter conformation thought to contribute to their typical concentration-dependent membrane-disrupting properties. When accumulated in endosomes at a certain concentrations, some antimicrobial peptides may induce endosomal leakage.

In some embodiments, the ELD may be an antimicrobial peptide (AMP) such as Cecropin-A/Melittin hybrid (CM series) peptide. Such peptides are thought to be among the smallest and most effective AMP-derived peptides with membrane-disrupting ability. Cecropins are a family of antimicrobial peptides with membrane-perturbing abilities against both Gram-positive and Gram-negative bacteria. Cecropin A (CA), the first identified antibacterial peptide, is composed of 37 amino acids with a linear structure. Melittin (M), a peptide of 26 amino acids, is a cell membrane lytic factor found in bee venom. Cecropin-melittin hybrid peptides have been shown to produce short efficient antibiotic peptides without cytotoxicity for eukaryotic cells (i.e., non-hemolytic), a desirable property in any antibacterial agent. These chimeric peptides were constructed from various combinations of the hydrophilic N-terminal domain of Cecropin A with the hydrophobic N-terminal domain of Melittin, and have been tested on bacterial model systems. Two 26-mers, CA(1-13)M(1-13) and CA(1-8) M(1-18) (Boman et al., 1989), have been shown to demonstrate a wider spectrum and improved potency of natural Cecropin A without the cytotoxic effects of melittin.

In an effort to produce shorter CM series peptides, the authors of Andreu et al., 1992 constructed hybrid peptides such as the 26-mer (CA(1-8)M(1-18)), and compared them with a 20-mer (CA(1-8)M(1-12)), a 18-mer (CA(1-8)M(1-10)) and six 15-mers ((CA(1-7)M(1-8), CA(1-7)M(2-9), CA(1-7)M(3-10), CA(1-7)M(4-11), CA(1-7)M(5-12), and CA(1-7)M(6-13)). The 20 and 18-mers maintained similar activity comparatively to CA(1-8)M(1-18). Among the six 15-mers, CA(1-7)M(1-8) showed low antibacterial activity, but the other five showed similar antibiotic potency compared to the 26-mer without hemolytic effect. Accordingly, in some embodiments, synthetic peptide or polypeptide-based shuttle agents of the present description may comprise an ELD which is or is from CM series peptide variants, such as those described above.

In some embodiments, the ELD may be the CM series peptide CM18 composed of residues 1-7 of Cecropin-A (KWKLFKKIGAVLKVLTTG) fused to residues 2-12 of Melittin (YGRKKRRQRRR), [C(1-7)M(2-12)]. When fused to the cell penetrating peptide TAT, CM18 was shown to independently cross the plasma membrane and destabilize the endosomal membrane, allowing some endosomally-trapped cargos to be released to the cytosol (Salomone et al., 2012). However, the use of a CM18-TAT11 peptide fused to a fluorophore (atto-633) in some of the author's experiments, raises uncertainty as to the contribution of the peptide versus the fluorophore, as the use of fluorophores themselves have been shown to contribute to endosomolysis— e.g., via photochemical disruption of the endosomal membrane (Erazo-Oliveras et al., 2014).

In some embodiments, the ELD may be CM18 having the amino acid sequence of SEQ ID NO: 1, or a variant thereof having at least 70%, 71%, 72%, 73%, 74%, 75%, 76%, 77%, 78%, 79%, 80%, 81%, 82%, 83%, 84%, 85%, 86%, 87%, 88%, 89%, 85%, 90%, 91%, 92%, 93%, 94%, or 95% identity to SEQ ID NO: 1 and having endosomolytic activity.

In some embodiments, the ELD may be a peptide derived from the N terminus of the HA2 subunit of influenza hemagglutinin (HA), which may also cause endosomal membrane destabilization when accumulated in the endosome.

In some embodiments, synthetic peptide or polypeptide-based shuttle agents of the present description may comprise an ELD which is or is from an ELD set forth in Table B, or a variant thereof having endosome escape activity and/or pH-dependent membrane disrupting activity.

TABLE B

Examples of endosome leakage domains

| Name | Amino acid sequence | SEQ ID NO: | Reference(s) |
|---|---|---|---|
| CM18 | KWKLFKKIGAVLKVLTTG | 1 | (Salomone, Cardarelli et al., 2012) |
| Diphtheria toxin T domain (DT) | VGSSLSCINLDWDVIRDKTKTKIE SLKEHGPIKNKMSESPNKTVSEEK AKQYLEEFHQTALEHPELSELKTV TGTNPVFAGANYAAWAVNVAQVID SETADNLEKTTAALSILPGIGSVM GIADGAVHHNTEEIVAQSIALSSL MVAQAIPLVGELVDIGFAAYNFVE SIINLFQVVHNSYNRPAYSPG | 2 | (Uherek, Fominaya et al., 1998, Glover, Ng et al., 2009) |
| GALA | WEAALAEALAEALAEHLAEALAEA LEALAA | 3 | (Parente, Nir et al., 1990) (Li, Nicol et al., 2004) |
| PEA | VLAGNPAKHDLDIKPTVISHRLHF PEGGSLAALTAHQACHLPLETFTR HRQPRGWEQLEQCGYPVQRLVALY LAARLSWNQVDQVIRNALASPGSG GDLGEAIREQPEQARLALT | 4 | (Fominaya and Wels 1996) |
| INF-7 | GLFEAIEGFIENGWEGMIDGWYGC | 5 | (El-Sayed, Futaki et al., 2009) |
| LAH4 | KKALLALALHHLAHLALHLALALK KA | 6 | (Kichler, Mason et al., 2006) Kichler et al., 2003 |
| HGP | LLGRRGWEVLKYWWNLLQYWSQEL | 7 | (Zhang, Cui et al., 2006) |
| H5WYG | GLFHAIAHFIHGGWHGLIHGWYG | 8 | (Midoux, Kichler et al., 1998) |
| HA2 | GLFGAIAGFIENGWEGMIDGWYG | 9 | (Lorieau, Louis et al., 2010) |
| EB1 | LIRLWSHLIHIWFQNRRLKWKKK | 10 | (Amand, Norden et al., 2012) |
| VSVG | KFTIVFPHNQKGNWKNVPSNYHYC P | 11 | (Schuster, Wu et al., 1999) |

TABLE B-continued

Examples of endosome leakage domains

| Name | Amino acid sequence | SEQ ID NO: | Reference(s) |
|---|---|---|---|
| Pseudomonas toxin | EGGSLAALTAHQACHLPLETFTRH RQPRGWEQLEQCGYPVQRLVALYL AARLSWNQVDQVIRNALASPGSGG DLGEAIREQPEQARLALTLAAAES ERFVRQGTGNDEAGAANAD | 12 | (Fominaya, Uherek et al., 1998) |
| Melittin | GIGAVLKVLTTGLPALISWIKRKR QQ | 13 | (Tan, Chen et al., 2012) |
| KALA | WEAKLAKALAKALAKHLAKALAKA LKACEA | 14 | (Wyman, Nicol et al., 1997) |
| JST-1 | GLFEALLELLESLWELLLEA | 15 | (Gottschalk, Sparrow et al., 1996) |
| C(LLKK)₃C | CLLKKLLKKLLKKC | 63 | (Luan et al., 2014) |
| G(LLKK)₃G | GLLKKLLKKLLKKG | 64 | (Luan et al., 2014) |

In some embodiments, shuttle agents of the present description may comprise one or more ELD or type of ELD. More particularly, they can comprise at least 2, at least 3, at least 4, at least 5, or more ELDs. In some embodiments, the shuttle agents can comprise between 1 and 10 ELDs, between 1 and 9 ELDs, between 1 and 8 ELDs, between 1 and 7 ELDs, between 1 and 6 ELDs, between 1 and 5 ELDs, between 1 and 4 ELDs, between 1 and 3 ELDs, etc.

In some embodiments, the order or placement of the ELD relative to the other domains (CPD, histidine-rich domains) within the shuttle agents of the present description may be varied provided the shuttling ability of the shuttle agent is retained.

In some embodiments, the ELD may be a variant or fragment of any one those listed in Table B, and having endosomolytic activity. In some embodiments, the ELD may comprise or consist of the amino acid sequence of any one of SEQ ID NOs: 1-15, 63, or 64, or a sequence which is at least 70%, 71%, 72%, 73%, 74%, 75%, 76%, 77%, 78%, 79%, 80%, 81%, 82%, 83%, 84%, 85%, 86%, 87%, 88%, 89%, 85%, 90%, 91%, 92%, 93%, 94%, or 95% identical to any one of SEQ ID NOs: 1-15, 63, or 64, and having endosomolytic activity.

Cell Penetration Domains (CPDs)

In some aspects, the shuttle agents of the present description may comprise a cell penetration domain (CPD). As used herein, the expression "cell penetration domain" refers to a sequence of amino acids which confers the ability of a macromolecule (e.g., peptide or protein) containing the CPD to be transduced into a cell.

In some embodiments, the CPD may be (or may be from) a cell-penetrating peptide or the protein transduction domain of a cell-penetrating peptide. Cell-penetrating peptides can serve as carriers to successfully deliver a variety of cargos intracellularly (e.g., polynucleotides, polypeptides, small molecule compounds or other macromolecules/compounds that are otherwise membrane-impermeable). Cell-penetrating peptides often include short peptides rich in basic amino acids that, once fused (or otherwise operably linked) to a macromolecule, mediate its internalization inside cells (Shaw, Catchpole et al., 2008). The first cell-penetrating peptide was identified by analyzing the cell penetration ability of the HIV-1 trans-activator of transcription (Tat) protein (Green and Loewenstein 1988, Vives, Brodin et al., 1997). This protein contains a short hydrophilic amino acid sequence, named "TAT", which promotes its insertion within the plasma membrane and the formation of pores. Since this discovery, many other cell-penetrating peptides have been described. In this regard, in some embodiments, the CPD can be a cell-penetrating peptide as listed in Table C, or a variant thereof having cell-penetrating activity.

TABLE C

Examples of cell-penetrating peptides

| Name | Amino acid sequence | SEQ ID NO: | Reference(s) |
| --- | --- | --- | --- |
| SP | AAVALLPAVLLALLAP | 16 | (Mahlum, Mandal et al., 2007) |
| TAT | YGRKKRRQRRR | 17 | (Green and Loewenstein 1988, Fawell, Seery et al., 1994, Vives, Brodin et al., 1997) |
| Penetratin (Antennapedia) | RQIKIWFQNRRMKWKK | 18 | (Perez, Joliot et al., 1992) |
| pVEC | LLIILRRRIRKQAHAHSK | 19 | (Elmquist, Lindgren et al., 2001) |
| M918 | MVTVLFRRLRIRRACGPPRVRV | 20 | (El-Andaloussi, Johansson et al., 2007) |
| Pep-1 | KETWWETWWTEWSQPKKKRKV | 21 | (Morris, Depollier et al., 2001) |
| Pep-2 | KETWFETWFTEWSQPKKKRKV | 22 | (Morris, Chaloin et al., 2004) |
| Xentry | LCLRPVG | 23 | (Montrose, Yang et al., 2013) |
| Arginine stretch | RRRRRRRR | 24 | (Zhou, Wu et al., 2009) |

TABLE C-continued

Examples of cell-penetrating peptides

| Name | Amino acid sequence | SEQ ID NO: | Reference(s) |
| --- | --- | --- | --- |
| Transportan | WTLNSAGYLLGKINLKALAALAKKIL | 25 | (Hallbrink, Floren et al., 2001) |
| SynB1 | RGGRLSYSRRRFSTSTGR | 26 | (Drin, Cottin et al., 2003) |
| SynB3 | RRLSYSRRRF | 27 | (Drin, Cottin et al., 2003) |
| PTD4 | YARAAARQARA | 65 | (Ho et al, 2001) |

Without being bound by theory, cell-penetrating peptides are thought to interact with the cell plasma membrane before crossing by pinocytosis or endocytosis. In the case of the TAT peptide, its hydrophilic nature and charge are thought to promote its insertion within the plasma membrane and the formation of a pore (Herce and Garcia 2007). Alpha helix motifs within hydrophobic peptides (such as SP) are also thought to form pores within plasma membranes (Veach, Liu et al., 2004).

In some embodiments, shuttle agents of the present description may comprise one or more CPD or type of CPD. More particularly, they may comprise at least 2, at least 3, at least 4, or at least 5 or more CPDs. In some embodiments, the shuttle agents can comprise between 1 and 10 CPDs, between 1 and 6 CPDs, between 1 and 5 CPDs, between 1 and 4 CPDs, between 1 and 3 CPDs, etc.

In some embodiments, the CPD may be TAT having the amino acid sequence of SEQ ID NO: 17, or a variant thereof having at least 70%, 71%, 72%, 73%, 74%, 75%, 76%, 77%, 78%, 79%, 80%, 81% 82%, 83%, 84%, 85%, 86%, 87%, 88%, 89%, 90%, 91%, 92%, 93%, 94%, or 95% identity to SEQ ID NO: 17 and having cell penetrating activity; or Penetratin having the amino acid sequence of SEQ ID NO: 18, or a variant thereof having at least 70%, 71%, 72%, 73%, 74%, 75%, 76%, 77%, 78%, 79%, 80%, 81% 82%, 83%, 84%, 85%, 86%, 87%, 88%, 89%, 85%, 86%, 87%, 88%, 89%, 90%, 91%, 92%, 93%, 94%, or 95% identity to SEQ ID NO: 18 and having cell penetrating activity.

In some embodiments, the CPD may be PTD4 having the amino acid sequence of SEQ ID NO: 65, or a variant thereof having at least 70%, 71%, 72%, 73%, 74%, 75%, 76%, 77%, 78%, 79%, 80%, 81% 82%, 83%, 84%, 85%, 86%, 87%, 88%, 89%, 90%, 91%, 92%, 93%, 94%, or 95% identity to SEQ ID NO: 65.

In some embodiments, the order or placement of the CPD relative to the other domains (ELD, histidine-rich domains) within the shuttle agents of the present description may be varied provided the shuttling ability of the shuttle agent is retained.

In some embodiments, the CPD may be a variant or fragment of any one those listed in Table C, and having cell penetrating activity. In some embodiments, the CPD may comprise or consist of the amino acid sequence of any one of SEQ ID NOs: 16-27 or 65, or a sequence which is at least 70%, 71%, 72%, 73%, 74%, 75%, 76%, 77%, 78%, 79%, 80%, 81%, 82%, 83%, 84%, 85%, 86%, 87%, 88%, 89%, 85%, 90%, 91%, 92%, 93%, 94%, or 95% identical to any one of SEQ ID NOs: 16-27 or 65, and having cell penetrating activity.

Histidine-Rich Domains

In some aspects, the shuttle agents of the present description may comprise a histidine-rich domain. In other embodiments, the shuttle agents of the present description may be combined/used together with a further independent synthetic peptide comprising or consisting essentially of a histidine-rich domain and a CPD (e.g., but lacking an ELD). This latter approach may provide the added advantage of allowing the concentration of the histidine-rich domain to be varied or controlled independently from the concentration of the ELD and the CPD contained in the shuttle agent. Without being bound by theory, the histidine-rich domain may act as a proton sponge in the endosome, providing another mechanism of endosomal membrane destabilization.

In some embodiments, the histidine-rich domain may be a stretch of at least 2, at least 3, at least 4, at least 5, or at least 6 amino acids comprising at least 30%, at least 35%, at least 40%, at least 45%, at least 50%, at least 55%, at least 60%, at least 65%, at least 70%, at least 75%, at least 80%, at least 85%, or at least 90% histidine residues. In some embodiments, the histidine-rich domain may comprise at least 2, at least 3, at least 4 at least 5, at least 6, at least 7, at least 8, or at least 9 consecutive histidine residues. Without being bound by theory, the histidine-rich domain in the shuttle agent may act as a proton sponge in the endosome through protonation of their imidazole groups under acidic conditions of the endosomes, providing another mechanism of endosomal membrane destabilization and thus further facilitating the ability of endosomally-trapped cargos to gain access to the cytosol. In some embodiments, the histidine-rich domain may be located at the N or C terminus of the synthetic peptide or shuttle agent. In some embodiments, the histidine-rich domain may be located N-terminal or C terminal to the CPD and/or ELD.

In some embodiments, the order or placement of the histidine-rich domain relative to the other domains (CPD, ELD) within the shuttle agents of the present description may be varied provided the shuttling ability of the shuttle agent is retained. In some embodiments, the shuttle agents of the present description may comprise more than one histidine-rich domain (e.g., histidine-rich domains at the amino and carboxyl termini).

Linkers

In some embodiments, suitable linkers (e.g., flexible polypeptide linkers) can be used to operably connect the domains (CPDs, ELDs, or histidine-rich domains) to one another within the context of synthetic peptides and shuttle agents of the present description. In some embodiments, linkers may be formed by adding sequences of small hydrophobic amino acids without rotatory potential (such as glycine) and polar serine residues that confer stability and flexibility. Linkers may be soft and allow the domains of the shuttle agents to move. In some embodiments, prolines may be avoided since they can add significant conformational rigidity. In some embodiments, the linkers may be serine/glycine-rich linkers (e.g., GGS, GGSGGGS (SEQ ID NO: 104) GGSGGGSGGGS (SEQ ID NO: 105), or the like). In some embodiments, the use shuttle agents comprising a suitable linker may be advantageous for delivering an independent polypeptide cargo to suspension cells, rather than to adherent cells.

Cargos

In some aspects, the synthetic peptide or polypeptide-based shuttle agent of the present description may be useful for delivering an independent cargo (e.g., a polypeptide cargo) to the cytosol of a target eukaryotic cell. In some embodiments, the polypeptide cargo may be fused to one or more CPDs to further facilitate intracellular delivery. In some embodiments, the CPD fused to the polypeptide cargo may be the same or different from the CPD of the shuttle agent of the present description. Such fusion proteins may be constructed using standard recombinant technology. In some embodiments, the independent polypeptide cargo may be fused, complexed with, or covalently bound to a second biologically active cargo (e.g., a biologically active polypeptide or compound). Alternatively or simultaneously, the polypeptide cargo may comprise a subcellular targeting domain.

In some embodiments, the polypeptide cargo must be delivered to the nucleus for it to carry out its intended biological effect. One such example is when the cargo is a polypeptide intended for nuclear delivery (e.g., a transcription factor). In this regard, studies on the mechanisms of translocation of viral DNA have led to the identification of nuclear localization signals (NLSs). The NLS sequences are recognized by proteins (importins a and B), which act as transporters and mediators of translocation across the nuclear envelope. NLSs are generally enriched in charged amino acids such as arginine, histidine, and lysine, conferring a positive charge which is partially responsible for their recognition by importins. Accordingly, in some embodiments, the polypeptide cargo may comprise an NLS for facilitating nuclear delivery, such as one or more of the NLSs as listed in Table D, or a variant thereof having nuclear targeting activity. Of course, it is understood that, in certain embodiments, the polypeptide cargo may comprise its natural NLS.

TABLE D

Nuclear localization signals

| Name | Amino acid sequence | SEQ ID NO: | Reference(s) |
|---|---|---|---|
| Ela | KRPRP | 28 | (Kohler, Gorlich et al., 2001) |
| SV40 T-Ag | PKKKRKV | 29 | (Lanford, Kanda et al., 1986) |
| c-myc | PAAKRVKLD | 30 | (Makkerh, Dingwall et al., 1996) |
| Op-T-NLS | SSDDEATADSQHAAPP KKKRKV | 31 | (Chan and Jam 1999) |
| Vp3 | KKKRK | 32 | (Nakanishi, Shum et al., 2002) |
| Nucleoplasmin | KRPAATKKAGQAKKKK | 33 | (Fanara, Hodel et al., 2000) |

TABLE D-continued

Nuclear localization signals

| Name | Amino acid sequence | SEQ ID NO: | Reference(s) |
|---|---|---|---|
| Histone 2B NLS | DGKKRKRSRK | 34 | (Moreland, Langevin et al., 1987) |
| Xenopus N1 | VRKKRKTEEESPLKDK DAKKSKQE | 35 | (Kleinschmidt and Seiter 1988) |
| PARP | KRKGDEVDGVDECAKK SKK | 36 | (Schreiber, Molinete et al., 1992) |
| PDX-1 | RRMKWKK | 37 | (Moede, Leibiger et al., 1999) |
| QKI-5 | RVHPYQR | 38 | (Wu, Zhou et al., 1999) |
| HCDA | KRPACTLKPECVQQLL VCSQEAKK | 39 | (Somasekaram, Jarmuz et al., 1999) |
| H2B | GKKRSKA | 40 | (Moreland, Langevin et al., 1987) |
| v-Rel | KAKRQR | 41 | (Gilmore and Temin 1988) |
| Amida | RKRRR | 42 | (Irie, Yamagata et al., 2000) |
| RanBP3 | PPVKRERTS | 43 | (Welch, Franke et al., 1999) |
| Pho4p | PYLNKRKGKP | 44 | (Welch, Franke et al., 1999) |
| LEF-1 | KKKKRKREK | 45 | (Prieve and Waterman 1999) |
| TCF-1 | KKKRRSREK | 46 | (Prieve and Waterman 1999) |
| BDV-P | PRPRKIPR | 47 | (Shoya, Kobayashi et al., 1998) |
| TR2 | KDCVINKHHRNRCQYC RLQR | 48 | (Yu, Lee et al., 1998) |
| SOX9 | PRRRK | 49 | (Sudbeck and Scherer 1997) |
| Max | PQSRKKLR | 50 | (Kato, Lee et al., 1992) |

Once delivered to the cytoplasm, recombinant proteins are exposed to protein trafficking system of eukaryotic cells. Indeed, all proteins are synthetized in the cell's cytoplasm and are then redistributed to their final subcellular localization by a system of transport based on small amino acid sequences recognized by shuttle proteins (Karniely and Pines 2005, Stojanovski, Bohnert et al., 2012). In addition to NLSs, other localization sequences can mediate subcellular targeting to various organelles following intracellular delivery of the polypeptide cargos of the present description. Accordingly, in some embodiments, polypeptide cargos of the present description may comprise a subcellular localization signal for facilitating delivery of the shuttle agent and cargo to specific organelles, such as one or more of the sequences as listed in Table E, or a variant thereof having corresponding subcellular targeting activity.

TABLE E

Subcellular localization signals

| Name | Amino acid sequence | SEQ ID NO: | Reference(s) |
|---|---|---|---|
| Mitochondrial signal sequence from Tim9 | NLVERCFTD | 51 | (Milenkovic, Ramming et al., 2009) |
| Mitochondrial signal sequence from Yeast cytochrome c oxidase subunit IV | MLSLRQSIRFFK | 52 | (Hurt, Pesold-Hurt et al., 1985) |
| Mitochondrial signal sequence from 18S rRNA | MLISRCKWSRFPGNQR | 53 | (Bejarano and Gonzalez 1999) |
| Peroxisome signal sequence-PTS1 | SKL | 54 | (Gould, Keller et al., 1989) |
| Nucleolar signal sequence from BIRC5 | MQRKPTIRRKNLRLRRK | 55 | (Scott, Boisvert et al., 2010) |

TABLE E-continued

Subcellular localization signals

| Name | Amino acid sequence | SEQ ID NO: | Reference(s) |
|---|---|---|---|
| Nucleolar signal sequence from RECQL4 | KQAWKQKWRKK | 56 | (Scott, Boisvert et al., 2010) |

In some embodiments, the cargo can be a biologically active compound such as a biologically active (recombinant) polypeptide (e.g., a transcription factor, a cytokine, or a nuclease) intended for intracellular delivery. As used herein, the expression "biologically active" refers to the ability of a compound to mediate a structural, regulatory, and/or biochemical function when introduced in a target cell.

In some embodiments, the cargo may be a recombinant polypeptide intended for nuclear delivery, such as a transcription factor. In some embodiments, the transcription factor can be HOXB4 (Lu, Feng et al., 2007), NUP98-HOXA9 (Takeda, Goolsby et al., 2006), Oct3/4, Sox2, Sox9, Klf4, c-Myc (Takahashi and Yamanaka 2006), MyoD (Sung, Mun et al., 2013), Pdx1, Ngn3 and MafA (Akinci, Banga et al., 2012), Blimp-1 (Lin, Chou et al., 2013), Eomes, T-bet (Gordon, Chaix et al., 2012), FOXO3A (Warr, Binnewies et al., 2013), NF-YA (Dolfini, Minuzzo et al., 2012), SALL4 (Aguila, Liao et al., 2011), ISL1 (Fonoudi, Yeganeh et al., 2013), FoxA1 (Tan, Xie et al., 2010), Nanog, Esrrb, Lin28 (Buganim et al., 2014), HIF1-alpha (Lord-Dufour et al., 2009), Hlf, Runx1t1, Pbx1, Lmo2, Zfp37, Prdm5 (Riddell et al., 2014), or Bcl-6 (Ichii, Sakamoto et al., 2004).

In some embodiments, the cargo may be a recombinant polypeptide intended for nuclear delivery, such as a nuclease useful for genome editing technologies. In some embodiments, the nuclease may be an RNA-guided endonuclease, a CRISPR endonuclease, a type I CRISPR endonuclease, a type II CRISPR endonuclease, a type III CRISPR endonuclease, a type IV CRISPR endonuclease, a type V CRISPR endonuclease, a type VI CRISPR endonuclease CRISPR associated protein 9 (Cas9), Cpf1 (Zetsche et al., 2015), a zinc-finger nuclease (ZFN), a Transcription activator-like effector nuclease (TALEN) (Cox et al., 2015), a homing endonuclease, a meganuclease, or any combination thereof. Other nucleases not explicitly mentioned here may nevertheless be encompassed in the present description. In some embodiments, the nuclease may be fused to a nuclear localization signal (e.g., Cas9-NLS; Cpf1-NLS; ZFN-NLS; TALEN-NLS). In some embodiments, the nuclease may be complexed with a nucleic acid (e.g., one or more guide RNAs, a crRNA, a tracrRNAs, or both a crRNA and a tracrRNA). In some embodiments, the nuclease may possess DNA or RNA-binding activity, but may lack the ability to cleave DNA.

In some embodiments, the shuttle agents of the present description may be used for intracellular delivery (e.g., nuclear delivery) of one or more CRISPR endonucleases, for example one or more of the CRISPR endonucleases described below.

Type I and its subtypes A, B, C, D, E, F and I, including their respective Cas1, Cas2, Cas3, Cas4, Cas6, Cas7 and Cas8 proteins, and the signature homologs and subunits of these Cas proteins including Cse1, Cse2, Cas7, Cas5, and Cas6e subunits in E. coli (type I-E) and Csy1, Csy2, Csy3, and Cas6f in Pseudomonas aeruginosa (type I-F) (Wiedenheft et al., 2011; Makarova et al, 2011). Type II and its subtypes A, B, C, including their respective Cas1, Cas2 and Cas9 proteins, and the signature homologs and subunits of these Cas proteins including Csn complexes (Makarova et al, 2011). Type III and its subtypes A, B and MTH326-like module, including their respective Cas1, Cas2, Cas6 and Cas10 proteins, and the signature homologs and subunits of these Cas proteins including Csm and CMR complexes (Makarova et al, 2011). Type IV represents the Csf3 family of Cas proteins. Members of this family show up near CRISPR repeats in Acidithiobacillus ferrooxidans ATCC 23270, Azoarcus sp. (strain EbN1), and Rhodoferax ferrireducens (strain DSM 15236/ATCC BAA-621/T118). In the latter two species, the CRISPR/Cas locus is found on a plasmid. Type V and it subtypes have only recently been discovered and include Cpf1, C2c1, and C2c3. Type VI includes the enzyme C2c2, which reported shares little homology to known sequences.

In some embodiments, the shuttle agents of the present description may be used in conjunction with one or more of the nucleases, endonucleases, RNA-guided endonuclease, CRISPR endonuclease described above, for a variety of applications, such as those described herein. CRISPR systems interact with their respective nucleic acids, such as DNA binding, RNA binding, helicase, and nuclease motifs (Marakova et al, 2011; Barrangou & Marraffini, 2014). CRISPR systems may be used for different genome editing applications including:
  a Cas-mediated genome editing method conducting to non-homologous end-joining (NHEJ) and/or Homologous-directed recombination (HDR) (Cong et al, 2013);
  a catalytically dead Cas (dCas) that can repress and/or activate transcription initiation when bound to promoter sequences, to one or several gRNA(s) and to a RNA polymerase with or without a complex formation with others protein partners (Bikard et al, 2013);
  a catalytically dead Cas (dCas) that can also be fused to different functional proteins domains as a method to bring enzymatic activities at specific sites of the genome including transcription repression, transcription activation, chromatin remodeling, fluorescent reporter, histone modification, recombinase system acetylation, methylation, ubiquitylation, phosphorylation, sumoylation, ribosylation and citrullination (Gilbert et al, 2013).

The person of ordinary skill in the art will understand that the present shuttle agents, although exemplified with Cas9 in the present examples, may be used with other nucleases as described herein. Thus, nucleases such as Cpf1, Cas9, and variants of such nucleases or others, are encompassed by the present description. It should be understood that, in one aspect, the present description may broadly cover any cargo having nuclease activity, such an RNA-guided endonuclease, or variants thereof (e.g., those that can bind to DNA or RNA, but have lost their nuclease activity; or those that have been fused to a transcription factor).

In some embodiments, the polypeptide cargo may be a cytokine such as a chemokine, an interferon, an interleukin, a lymphokine, or a tumour necrosis factor. In some embodiments, the polypeptide cargo may be a hormone or growth factor. In some embodiments, the cargo may be an antibody (e.g., a labelled antibody). In some embodiments, the cargo can be a detectable label (fluorescent polypeptide or reporter enzyme) that is intended for intracellular delivery, for example, for research and/or diagnostic purposes.

In some embodiments, the cargo may be a globular protein or a fibrous protein. In some embodiments, the cargo may have a molecule weight of any one of about 5, 10, 15, 20, 25, 30, 35, 40, 45, to 50 to about 150, 200, 250, 300, 350, 400, 450, 500 kDa or more. In some embodiments, the cargo may have a molecule weight of between about 20 to 200 kDa.

Non-Toxic, Metabolizable Synthetic Peptides and Shuttle Agents

In some embodiments, synthetic peptides and shuttle agents of the present description may be non-toxic to the intended target eukaryotic cells at concentrations up to 50 µM, 45 µM, 40 µM, 35 µM, 30 µM, 25 µM, 20 µM, 15 µM, 10 µM, 9 µM, 8 µM, 7 µM, 6 µM, 5 µM, 4 µM, 3 µM, 2 µM, 1 µM, 0.5 µMm 0.1 µM, or 0.05 µM. Cellular toxicity of shuttle agents of the present description may be measured using any suitable method. Furthermore, transduction protocols may be adapted (e.g., concentrations of shuttle and/or cargo used, shuttle/cargo exposure times, exposure in the presence or absence of serum), to reduce or minimize toxicity of the shuttle agents, and/or to improve/maximize transfection efficiency.

In some embodiments, synthetic peptides and shuttle agents of the present description may be readily metabolizable by intended target eukaryotic cells. For example, the synthetic peptides and shuttle agents may consist entirely or essentially of peptides or polypeptides, for which the target eukaryotic cells possess the cellular machinery to metabolize/degrade. Indeed, the intracellular half-life of the synthetic peptides and polypeptide-based shuttle agents of the present description is expected to be much lower than the half-life of foreign organic compounds such as fluorophores. However, fluorophores can be toxic and must be investigated before they can be safely used clinically (Alford et al., 2009). In some embodiments, synthetic peptides and shuttle agents of the present description may be suitable for clinical use. In some embodiments, the synthetic peptides and shuttle agents of the present description may avoid the use of domains or compounds for which toxicity is uncertain or has not been ruled out.

Cocktails

In some embodiments, the present description relates to a composition comprising a cocktail of at least 2, at least 3, at least 4, or at least 5 different types of the synthetic peptides or polypeptide-based shuttle agents as defined herein. In some embodiments, combining different types of synthetic peptides or polypeptide-based shuttle agents (e.g., different shuttle agents comprising different types of CPDs) may provide increased versatility for delivering different polypeptide cargos intracellularly. Furthermore, without being bound by theory, combining lower concentrations of different types of shuttle agents may help reduce cellular toxicity associated with using a single type of shuttle agent (e.g., at higher concentrations).

Methods, Kits, Uses and Cells

In some embodiments, the present description relates to a method for increasing the transduction efficiency of a polypeptide cargo to the cytosol of a target eukaryotic cell. The method may comprise contacting the target eukaryotic cell with the synthetic peptide, polypeptide-based shuttle agent, or composition as defined herein, and the polypeptide cargo. In some embodiments, the synthetic peptide, polypeptide-based shuttle agent, or composition may be pre-incubated with the polypeptide cargo to form a mixture, prior to exposing the target eukaryotic cell to that mixture. In some embodiments, the type of CPD may be selected based on the amino acid sequence of the polypeptide cargo to be delivered intracellularly. In other embodiments, the type of CPD and ELD may be selected to take into account the amino acid sequence of the polypeptide cargo to be delivered intracellularly, the type of cell, the type of tissue, etc.

In some embodiments, the method may comprise multiple treatments of the target cells with the synthetic peptide, polypeptide-based shuttle agent, or composition (e.g., 1, 2, 3, 4 or more times per day, and/or on a pre-determined schedule). In such cases, lower concentrations of the synthetic peptide, polypeptide-based shuttle agent, or composition may be advisable (e.g., for reduced toxicity). In some embodiments, the cells may be suspension cells or adherent cells. In some embodiments, the person of skill in the art will be able to adapt the teachings of the present description using different combinations of shuttles, domains, uses and methods to suit particular needs of delivering a polypeptide cargo to particular cells with a desired viability.

In some embodiments, the methods of the present description may apply to methods of delivering a polypeptide cargo intracellularly to a cell in vivo. Such methods may be accomplished by parenteral administration or direct injection into a tissue, organ, or system.

In some embodiments, the synthetic peptide, polypeptide-based shuttle agent, or composition, and the polypeptide cargo may be exposed to the target cell in the presence or absence of serum. In some embodiments, the method may be suitable for clinical or therapeutic use.

In some embodiments, the present description relates to a kit for increasing the transduction efficiency of a polypeptide cargo to the cytosol of a target eukaryotic cell. The kit may comprise the synthetic peptide, polypeptide-based shuttle agent, or composition as defined herein, and a suitable container.

In some embodiments, the target eukaryotic cells may be an animal cell, a mammalian cell, or a human cell. In some embodiments, the target eukaryotic cells may be a stem cell (e.g., embryonic stem cells, pluripotent stem cells, induced pluripotent stem cells, neural stem cells, mesenchymal stem cells, hematopoietic stem cells, peripheral blood stem cells), primary cells (e.g., myoblasts, fibroblasts), or an immune cell (e.g., T cells, dendritic cells, antigen presenting cells). In some embodiments, the present description relates to an isolated cell comprising a synthetic peptide or polypeptide-based shuttle agent as defined herein. In some embodiments, the cell may be a protein-induced pluripotent stem cell. It will be understood that cells that are often resistant or not amenable to protein transduction may be interesting candidates for the synthetic peptides or polypeptide-based shuttle agents of the present description.

Other objects, advantages and features of the present description will become more apparent upon reading of the following non-restrictive description of specific embodiments thereof, given by way of example only with reference to the accompanying drawings.

EXAMPLES

Example 1

Materials and Methods
1.1 Materials

All chemicals were purchased from Sigma-Aldrich (St. Louis, Mo, USA or Oakville, ON, Canada) or equivalent grade from BioShop Canada Inc. (Mississauga, ON, Canada) or VWR (Ville Mont-Royal, QC, Canada), unless otherwise noted.

1.2 Reagents

TABLE 1.1

| Reagents | | |
|---|---|---|
| RPMI 1640 media | Sigma-Aldrich | Oakville, ON, Canada |
| DMEM | Sigma-Aldrich | Oakville, ON, Canada |
| Fetal bovine serum (FBS) | NorthBio | Toronto, ON, Canada |
| L-glutamine-Penicillin-Streptomycin | Sigma-Aldrich | Oakville, ON, Canada |
| Trypsin-EDTA solution | Sigma-Aldrich | Oakville, ON, Canada |
| pEGFP-C1 | CLONTECH Laboratories | Palo Alto, CA, USA |
| FITC-Antibody α-tubulin | Abcam ab64503 | Cambridge, MA, USA |
| ITS | Invitrogen/41400-045 | Burlington, ON, Canada |
| FGF 2 | Feldan Bio/1D-07-017 | Quebec, QC, Canada |
| Dexamethasone | Sigma-Aldrich/D8893 | Oakville, ON, Canada |
| Bovine serum albumin (BSA) | Sigma-Aldrich/A-1933 | Oakville, ON, Canada |
| MB1 media | GE Healthcare HyClone | Logan, Utah, USA |
| Calcein | Sigma-Aldrich/C0875 | Oakville, ON, Canada |
| HisTrap ™ FF column | GE Healthcare | Baie d'Urfe, QC, Canada |
| Q Sepharose ™ | GE Healthcare | Baie d'Urfe, QC, Canada |
| SP Sepharose ™ | GE Healthcare | Baie d'Urfe, QC, Canada |
| Amicon Ultra centrifugal filters | EMD Millipore | Etobicoke, ON Canada |
| Label IT ® Cy ®5 kit | Minis Bio LLC | Madison, WI, USA |
| Calf serum | NorthBio | Toronto, ON, Canada |
| beta-mercaptoethanol | Sigma-Aldrich | Oakville, ON, Canada |
| IL-2 | Feldan Bio/rhIL-2 Research | Quebec, QC, Canada |
| Rezazurine sodium salt | Sigma-Aldrich/R7017-1G | Oakville, ON, Canada |
| Anti-HOXB4 monoclonal antibody | Novus Bio #NBP2-37257 | Oakville, ON, Canada |
| Alexa ™-594 Anti-Mouse | Abcam #150116 | Toronto, ON, Canada |
| Fluoroshield ™ with DAPI | Sigma #F6057 | Oakville, ON, Canada |
| GFP Monoclonal antibody | Feldan Bio #A017 | Quebec, QC, Canada |
| Phusion ™ High-Fidelity DNA polymerase | (NEB #M0530S) | Whitby, ON, Canada |
| Edit-R ™ Synthetic crRNA Positive Controls | (Dharmacon #U-007000-05) | Ottawa, ON, Canada |
| T7 Endonuclease I | (NEB, Cat #M0302S) | Whitby, ON, Canada |
| FastFect ™ transfection reagent | (Feldan Bio # 9K-010-0001) | Quebec, QC, Canada |

1.3 Cell Lines

HeLa, HEK293A, HEK293T, THP-1, CHO, NIH3T3, CA46, Balb3T3 and HT2 cells were obtained from American Type Culture Collection (Manassas, VA, USA) and cultured following the manufacturer's instructions. Myoblasts are primary human cells kindly provided by Professor J. P. Tremblay (Université Laval, Quebec, Canada).

TABLE 1.2

| Cell lines and culture conditions | | | | | |
|---|---|---|---|---|---|
| HeLa (adherent cells) | Human cervical carcinoma cells | ATCC ™ CCL-2 | DMEM | 10% FBS | L-glutamine 2 mM Penicillin 100 units Streptomycin 100 µg/mL |
| HEK 293A (adherent cells) | Human embryonic Epithelial kidney cells | ATCC ™ CRL-1573 | DMEM | 10% FBS | L-glutamine 2 mM Penicillin 100 units Streptomycin 100 µg/mL |
| HEK 293T (adherent cells) | Human embryonic Epithelial kidney cells | ATCC ™ CRL-3216 | DMEM | 10% FBS | L-glutamine 2 mM Penicillin 100 units Streptomycin 100 µg/mL |
| THP-1 (suspension cells) | Acute monocytic leukemia | ATCC ™ TIB202 | RPMI 1640 | 10% FBS | 2- mercaptoethanol 0.05 mM L-glutamine 2 mM Penicillin 100 units Streptomycin 100 µg/mL |
| Myoblasts (primary adherent cells) | Human (13 months) myoblasts | Kindly provided by Professor J P Tremblay | MB1 | 15% FBS | ITS 1×, FGF 2 10 ng/mL, Dexamethasone 0.39 µg/mL, BSA 0.5 mg/mL, MB1 85% |
| CHO (adherent cells) | Chinese hamster ovary cells | ATCC ™ CCL-61 | DMEM | 10% FBS | L-glutamine 2 mM Penicillin 100 units Streptomycin 100 µg/mL |

TABLE 1.2-continued

| | | | Cell lines and culture conditions | | | |
|---|---|---|---|---|---|---|
| NIH3T3 (adherent cells) | Fibroblasts | ATCC ™ CRL-1658 | DMEM | 10% Calf serum | L-glutamine 2 mM Penicillin 100 units Streptomycin 100 µg/mL | |
| HT2 (suspension cells) | T lymphocytes | ATCC ™ CRL-1841 | RPMI 1640 | 10% FBS | 200 IU/mL IL-2 β-mercaptoethanol 0.05 mM L-glutamine 2 mM Penicillin 100 units Streptomycin 100 µg/mL | |
| CA46 (suspension cells) | *Homo sapiens* Burkitt's lymphoma | ATCC ™ CRL-1648 | RPMI 1640 | 20% FBS | L-glutamine 2 mM Penicillin 100 units Streptomycin 100 µg/mL | |
| Balb3T3 (adherent cells) | Fibroblasts | ATCC ™ CCL-163 | DMEM | 10% Calf serum | L-glutamine 2 mM Penicillin 100 units Streptomycin 100 µg/mL | |
| Jurkat (suspension cells) | Human T cells | ATCC ™ TIB-152 | RPMI 1640 | 10% FBS | L-glutamine 2 mM Penicillin 100 units Streptomycin 100 µg/mL | |

FBS: Fetal bovine serum 1.4 Protein Purification

Fusion proteins were expressed in bacteria (*E. coli* BL21DE3) under standard conditions using an isopropyl β-D-1-thiogalactopyranoside (IPTG) inducible vector containing a T5 promoter. Culture media contained 24 g yeast extract, 12 g tryptone, 4 mL glycerol, 2.3 g $KH_2PO_4$, and 12.5 g $K_2HPO_4$ per liter. Bacterial broth was incubated at 37° C. under agitation with appropriate antibiotic (e.g., ampicillin). Expression was induced at optical density (600 nm) between 0.5 and 0.6 with a final concentration of 1 mM IPTG for 3 hours at 30° C. Bacteria were recuperated following centrifugation at 5000 RPM and bacterial pellets were stored at −20° C.

Bacterial pellets were resuspended in Tris buffer (Tris 25 mM pH 7.5, NaCl 100 mM, imidazole 5 mM) with phenylmethylsulfonyl fluoride (PMSF) 1 mM, and lysed by passing 3 times through the homogenizer Panda 2K™ at 1000 bar. The solution was centrifuged at 15000 RPM, 4° C. for 30 minutes. Supernatants were collected and filtered with a 0.22 µM filtration device.

Solubilized proteins were loaded, using a FPLC (AKTA Explorer 100R), on HisTrap™ FF column previously equilibrated with 5 column volumes (CV) of Tris buffer. The column was washed with 30 column volumes (CV) of Tris buffer supplemented with 0.1% Triton X-114 followed with 30 CV of Tris buffer with imidazole 40 mM. Proteins were eluted with 5 CV of Tris buffer with 350 mM Imidazole and collected. Collected fractions corresponding to specific proteins were determined by standard denaturing SDS-PAGE.

Purified proteins were diluted in Tris 20 mM at the desired pH according to the protein's pI and loaded on an appropriate ion exchange column (Q Sepharose™ or SP Sepharose™) previously equilibrated with 5 CV of Tris 20 mM, NaCl 30 mM. The column was washed with 10 CV of Tris 20 mM, NaCl 30 mM and proteins were eluted with a NaCl gradient until 1 M on 15 CV. Collected fractions corresponding to specific proteins were determined by standard denaturing SDS-PAGE. Purified proteins were then washed and concentrated in PBS 1× on Amicon Ultra™ centrifugal filters 10,000 MWCO. Protein concentration was evaluated using a standard Bradford assay.

1.5 Synthetic Peptides and Shuttle Agents

All peptides used in this study were purchased from GLBiochem (Shanghai, China) and their purities were confirmed by high-performance liquid chromatography analysis and mass spectroscopy. In some cases, chimeric peptides were synthesized to contain a C-terminal cysteine residue to allow the preparation of peptide dimers. These dimeric peptides were directly synthetized with a disulfide bridge between the C-terminal cysteines of two monomers. The amino acid sequences and characteristics of each of the synthetic peptides and shuttle agents tested in the present examples are summarized in Table 1.3.

TABLE 1.3

| | | Synthetic peptides and shuttle agents tested | | | | | |
|---|---|---|---|---|---|---|---|
| ELD | CM18 | KWKLFKKIGAVLKVLTTG [1] [SEQ ID NO: 1] | 18 | 2.03 | 10.60 | 5+/0− | 0.350 |
| | C(LLKK)₃C | CLLKKLLKKLLKKC [63] [SEQ ID NO: 63] | 14 | 1.69 | 10.05 | 6+/0− | 0.314 |
| | LAH4 | KKALLALALHHLAHLALHL ALALKKA [6] [SEQ ID NO: 6] | 26 | 2.78 | 10.48 | 4+/0− | 0.923 |
| | KALA | WEAKLAKALAKALAKHLA KALAKALKACEA [14] [SEQ ID NO: 14] | 30 | 3.13 | 9.9 | 7+/2− | 0.283 |
| CPD | TAT-cys | YGRKKRRQRRRC [SEQ ID NO: 17] | 12 | 1.66 | 12.01 | 8+/0− | −3.125 |
| | Penetratin-cys | RQIKIWFQNRRMKWKKC [SEQ ID NO: 18] | 17 | 2.35 | 11.75 | 7+/0− | −1.482 |

TABLE 1.3-continued

Synthetic peptides and shuttle agents tested

| | | | | | | | |
|---|---|---|---|---|---|---|---|
| | PTD4 | YARAAARQARA [SEQ ID NO: 65] | 11 | 1.2 | 11.72 | 3+/0- | -0.682 |
| His-PTD4 | His-PTD4 | HHHHHHYARAAARQARA [SEQ ID NO: 81] | 17 | 2.03 | 11.71 | 3+/0- | -1.57 |
| CPD-ELD | TAT-CM18 | YGRKKRRQRRRCKWKLFK KIGAVLKVLTTG [SEQ ID NO: 66] | 30 | 3.68 | 12.02 | 13+/0- | -1.041 |
| | TAT-KALA | YGRKKRRQRRRCWEAKLA KALAKALAKHLAKALAKAL KACEA [SEQ ID NO: 67] | 42 | 4.67 | 11.46 | 15+/2- | -0.768 |
| | PTD4-KALA | YARAAARQARAWEAKLAK ALAKALAKHLAKALAKALK ACEA [SEQ ID NO: 82] | 41 | 4.32 | 10.46 | 10+/2- | 0.024 |
| | 9Arg-KALA | RRRRRRRRRWEAKLAKALA KALAKHLAKALAKALKACE A [SEQ ID NO: 83] | 39 | 4.54 | 12.11 | 16+/2- | -0.821 |
| | Pep1-KALA | KETWWETWWTEWSQPKKK RKVWEAKLAKALAKALAK HLAKALAKALKCEA [SEQ ID NO: 84] | 51 | 5.62 | 10.01 | 13+/5- | -0.673 |
| | Xentry-KALA | LCLRPVGWEAKLAKALAKA LAKHLAKALAKALKACEA [SEQ ID NO: 85] | 37 | 3.87 | 9.93 | 8+/2- | 0.441 |
| | SynB3-KALA | RRLSYSRRRFWEAKLAKAL AKALAKHLAKALAKALKA CEA [SEQ ID NO: 86] | 40 | 4.51 | 11.12 | 12+/2- | -0.258 |
| ELD-CPD | CM18-TAT-Cys | KWKLFKKIGAVLKVLTTGY GRKKRRQRRRC [SEQ ID NO: 57] | 30 | 3.67 | 12.02 | 13+/0- | -1.04 |
| | CM18-Penetratin-Cys | KWKLFKKIGAVLKVLTTGR QIKIWFQNRRMKWKKC [SEQ ID NO: 58] | 35 | 4.36 | 11.36 | 12+/0- | -0.54 |
| | dCM18-TAT-Cys | KWKLFKKIGAVLKVLTTGY GRKKRRQRRRC [SEQ ID NO: 57] | 60 | 7.34 | 12.16 | 26+/0- | -1.04 |
| | (CM18-TAT-cys dimer) | KWKLFKKIGAVLKVLTTGY GRKKRRQRRRC [SEQ ID NO: 57] | | | | | |
| | dCM18-Penetratin-Cys | KWKLFKKIGAVLKVLTTGR QIKIWFQNRRMKWKKC [SEQ ID NO: 58] | 70 | 8.72 | 12.05 | 24+/0- | -0.54 |
| | (CM18-Penetratin-Cys dimer) | KWKLFKKIGAVLKVLTTGR QIKIWFQNRRMKWKKC [SEQ ID NO: 58] | | | | | |
| | VSVG-PTD4 | KFTIVFPHNQKGNWKNVPS NYHYCPYARAAARQARA [SEQ ID NO: 87] | 36 | 4.2 | 10.3 | 6+/0- | -0.89 |
| | EB1-PTD4 | LIRLWSHLIHIWFQNRRLKW KKKYARAAARQARA [SEQ ID NO: 88] | 34 | 4.29 | 12.31 | 10+/0- | -0.647 |
| | JST-PTD4 | GLFEALLELLESLWELLLEA YARAAARQARA [SEQ ID NO: 89] | 31 | 3.49 | 4.65 | 5+/3- | 0.435 |
| | CM18-PTD4 | KWKLFKKIGAVLKVLTTGY ARAAARQARA [SEQ ID NO: 90] | 29 | 3.217 | 11.76 | 8+/0- | -0.041 |

TABLE 1.3-continued

Synthetic peptides and shuttle agents tested

| | | | | | | | |
|---|---|---|---|---|---|---|---|
| | 6Cys-CM18-PTD4 | CCCCCCKWKLFKKIGAVLK VLTTGYARAAARQARA [SEQ ID NO: 91] | 35 | 3.835 | 9.7 | 8+/0− | 0.394 |
| | CM18-L1-PTD4 | KWKLFKKIGAVLKVLTTGG GSYARAAARQARA [SEQ ID NO: 92] | 32 | 3.42 | 11.76 | 8+/0− | −0.087 |
| | CM18-L2-PTD4 | KWKLFKKIGAVLKVLTTGG GSGGGSYARAAARQARA [SEQ ID NO: 93] | 36 | 3.68 | 11.76 | 8+/0− | −0.133 |
| | CM18-L3-PTD4 | KWKLFKKIGAVLKVLTTGG GSGGGSGGGSYARAAARQ ARA [SEQ ID NO: 94] | 41 | 3.99 | 11.76 | 8+/0 | −0.176 |
| His-ELD-CPD | Met-His-CM18-TAT-Cys | MHHHHHHKWKLFKKIGAV LKVLTTGYGRKKRRQRRRC [SEQ ID NO: 59*] | 37 | 4.63 | 12.02 | 13+/0− | −1.311 |
| | His-CM18-TAT | HHHHHHKWKLFKKIGAVLK VLTTGYGRKKRRQRRR [SEQ ID NO: 95] | 35 | 4.4 | 12.31 | 13+/0− | −1.208 |
| | His-CM18-PTD4 | HHHHHHKWKLFKKIGAVLK VLTTGYARAAARQARA [SEQ ID NO: 68] | 35 | 4.039 | 11.76 | 8+/0− | −0.583 |
| | His-CM18-PTD4-6Cys | HHHHHHKWKLFKKIGAVLK VLTTGYARAAARQARACCC CCC [SEQ ID NO: 96*] | 41 | 4.659 | 9.7 | 8+/0− | −0.132 |
| | His-CM18-9Arg | HHHHHHKWKLFKKIGAVLK VLTTGRRRRRRRRR [SEQ ID NO: 69] | 33 | 4.26 | 12.91 | 14+/0− | −1.618 |
| | His-CM18-Transportan | HHHHHHKWKLFKKIGAVLK VLTTGGWTLNSAGYLLKIN LKALAALAKKIL [SEQ ID NO: 70] | 50 | 5.62 | 10.6 | 9+/0− | 0.092 |
| | His-LAH4-PTD4 | HHHHHHKKALLALALHHLA HLALHLALALKKAYARAAA RQARA [SEQ ID NO: 71] | 43 | 4.78 | 11.75 | 7+/0− | −0.63 |
| | His-C(LLKK)₃C-PTD4 | HHHHHHCLLKKLLKKLLKK CYARAAARQARA [SEQ ID NO: 72] | 31 | 3.56 | 11.21 | 9+/0− | −0.827 |
| | 3His-CM18-PTD4 | HHHKWKLFKKIGAVLKVLT TGYARAAARQARA [SEQ ID NO: 97] | 32 | 3.63 | 11.76 | 8+/0− | −0.338 |
| | 12His-CM18-PTD4 | HHHHHHHHHHHHKWKLFK KIGAVLKVLTTGYARAAAR QARA [SEQ ID NO: 98] | 41 | 4.86 | 11.76 | 8+/0− | −0.966 |
| | HA-CM18-PTD4 | HHHAHHHKWKLFKKIGAVL KVLTTGYARAAARQARA [SEQ ID NO: 99] | 36 | 4.11 | 11.76 | 8+/0− | −0.517 |
| | 3HA-CM18-PTD4 | HAHHAEIHAHKWKLFKKIG AVLKVLTTGYARAAARQAR A [SEQ ID NO: 100] | 38 | 4.25 | 11.76 | 8+/0− | −0.395 |
| ELD-His-CPD | CM18-His-PTD4 | KWKLFKKIGAVLKVLTTGH HHHHYARAAARQARA [SEQ ID NO: 101] | 35 | 4.04 | 11.76 | 8+/0− | −0.583 |
| His-ELD-CPD-His | His-CM18-PTD4-His | HHHHHHKWKLFKKIGAVLK VLTTGYARAAARQARAHH HHHH [SEQ ID NO: 102] | 41 | 4.86 | 11.76 | 8+/0− | −0.966 |

Results computed using the ProtParam™ online tool available from ExPASy™ Bioinformatics Resource Portal (www.expasy.org)
MW: Molecular weight
pI: Isoelectric point
Charge: Total number of positively (+) and negatively (−) charged residues

Example 2

Peptide Shuttle Agents Facilitate Escape of Endosomally-Trapped Calcein

2.1 Endosome Escape Assays

Microscopy-based and flow cytometry-based fluorescence assays were developed to study endosome leakage and to determine whether the addition of the shuttle agents facilitates endosome leakage of the polypeptide cargo.

2.1.1 Endosomal Leakage Visualization by Microscopy

Calcein is a membrane-impermeable fluorescent molecule that is readily internalized by cells when administered to the extracellular medium. Its fluorescence is pH-dependent and calcein self-quenches at higher concentrations. Once internalized, calcein becomes sequestered at high concentrations in cell endosomes and can be visualized by fluorescence microscopy as a punctate pattern. Following endosomal leakage, calcein is released to the cell cytoplasm and this release can be visualized by fluorescence microscopy as a diffuse pattern.

One day before the calcein assay was performed, mammalian cells (e.g., HeLa, HEK293A, or myoblasts) in exponential growth phase were harvested and plated in a 24-well plate (80,000 cells per well). The cells were allowed to attach by incubating overnight in appropriate growth media, as described in Example 1. The next day, the media was removed and replaced with 300 μL of fresh media without FBS containing 62.5 μg/mL (100 μM) of calcein, except for HEK293A (250 μg/mL, 400 μM). At the same time, the shuttle agent(s) to be tested was added at a predetermined concentration. The plate was incubated at 37° C. for 30 minutes. The cells were washed with 1×PBS (37° C.) and fresh media containing FBS was added. The plate was incubated at 37° C. for 2.5 hours. The cells were washed three times and were visualized by phase contrast and fluorescence microscopy (IX81™, Olympus).

A typical result is shown in FIG. 1A, in which untreated HEK293A cells loaded with calcein ("100 μM calcein") show a low intensity, punctate fluorescent pattern when visualized by fluorescence microscopy (upper left panel in FIG. 1A). In contrast, HeLa cells treated with a shuttle agent that facilitates endosomal escape of calcein ("100 μM calcein+CM18-TAT 5 μM") show a higher intensity, more diffuse fluorescence pattern in a greater proportion of cells (upper right panel in FIG. 1A).

2.1.2 Endosomal Leakage Quantification by Flow Cytometry

In addition to microscopy, flow cytometry allows a more quantitative analysis of the endosomal leakage as the fluorescence intensity signal increases once the calcein is released in the cytoplasm. Calcein fluorescence is optimal at physiological pH (e.g., in the cytosol), as compared to the acidic environment of the endosome.

One day before the calcein assay was performed, mammalian cells (e.g., HeLa, HEK293, or myoblasts) in exponential growth phase were harvested and plated in a 96-well plate (20,000 cells per well). The cells were allowed to attach by incubating overnight in appropriate growth media, as described in Example 1. The next day, the media in wells was removed and replaced with 50 μL of fresh media without serum containing 62.5 μg/mL (100 μM) of calcein, except for HEK293A (250 μg/mL, 400 μM). At the same time, the shuttle agent(s) to be tested was added at a predetermined concentration. The plate was incubated at 37° C. for 30 minutes. The cells were washed with 1×PBS (37° C.) and fresh media containing 5-10% serum was added. The plate was incubated at 37° C. for 2.5 hours. The cells were washed with 1×PBS and detached using trypsinization. Trypsinization was stopped by addition of appropriate growth media, and calcein fluorescence was quantified using flow cytometry (Accuri C6, Becton, Dickinson and Company (BD)).

Untreated calcein-loaded cells were used as a control to distinguish cells having a baseline of fluorescence due to endosomally-trapped calcein from cells having increased fluorescence due to release of calcein from endosomes. Fluorescence signal means ("mean counts") were analyzed for endosomal escape quantification. In some cases, the "Mean Factor" was calculated, which corresponds to the fold-increase of the mean counts relative to control (untreated calcein-loaded cells). Also, the events scanned by flow cytometry corresponding to cells (size and granularity) were analyzed. The cellular mortality was monitored with the percentage of cells in the total events scanned. When it became lower than the control, it was considered that the number of cellular debris was increasing due to toxicity and the assay was discarded.

Figure 1B:
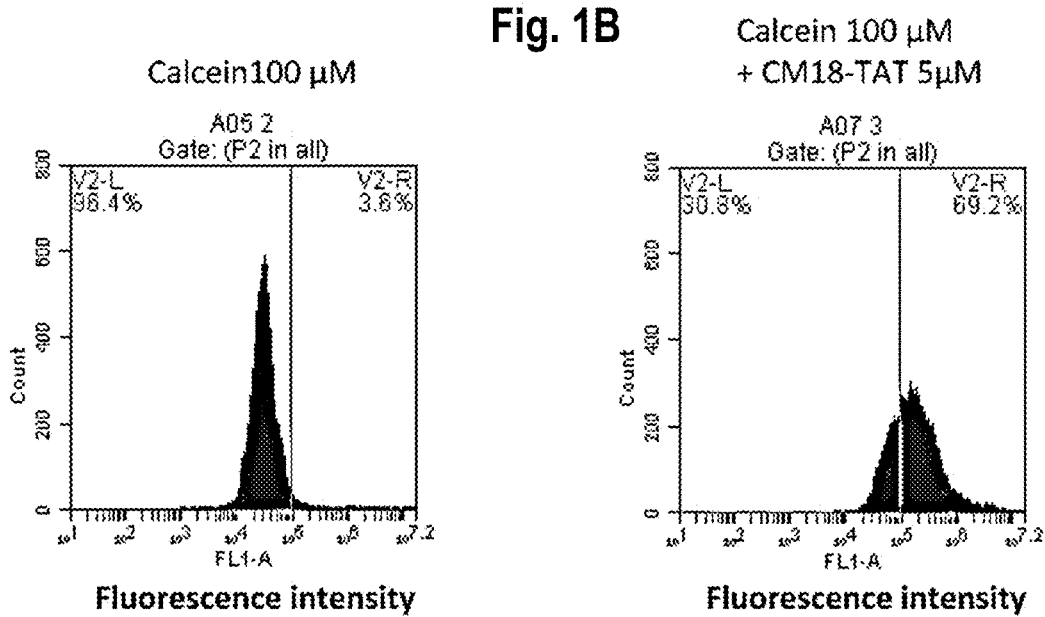

A typical result is shown in FIG. 1B, in which an increase in fluorescence intensity (right-shift) is observed for calcein-loaded HeLa cells treated with a shuttle agent that facilitates endosomal escape ("Calcein 100 μM+CM18-TAT 5 μM", right panel in FIG. 1B), as compared to untreated calcein-loaded HeLa cells ("Calcein 100 μM", left panel in FIG. 1B). The increase in calcein fluorescence is caused by the increase in pH associated with the release of calcein from the endosome (acidic) to the cytoplasm (physiological).

2.2 Results from Endosome Escape Assays

2.2.1 HeLa Cells

HeLa cells were cultured and tested in the endosomal escape assays as described in Example 2.1. The results of flow cytometry analyses are summarized below. In each case, the flow cytometry results were also confirmed by fluorescence microscopy (data not shown).

TABLE 2.1

CM18-Penetratin-Cys v. Controls in HeLa cells

| Domains | Peptide | Cells | Concentration (μM) | Mean Counts (±St. Dev.; n = 3) | Mean Factor |
|---|---|---|---|---|---|
| — | No peptide | HeLa | 0 | 55 359 ± 6844 | 1.0 |
| ELD | CM18 | HeLa | 5 | 46 564 ± 9618 | 0.8 |
| CPD | TAT-Cys | HeLa | 5 | 74 961 ± 9337 | 1.3 |
|  | Penetratin-Cys | HeLa | 5 | 59 551 ± 7119 | 1.1 |
| ELD + | CM18 + TAT-Cys | HeLa | 5 + 5 | 64 333 ± 6198 | 1.2 |
| CPD | CM18 + Penetratin-Cys | HeLa | 5 + 5 | 40 976 ± 8167 | 0.7 |
| ELD – CPD | CM18-Penetratin-Cys | HeLa | 5 | 262 066 ± 28 146 | 4.7 |

TABLE 2.2

CM18-TAT-Cys v. Control in HeLa cells

| Domains | Peptide | Cells | Concentration (μM) | Mean counts (n = 3) | Stand. dev. | Mean Factor |
|---|---|---|---|---|---|---|
| — | No peptide | HeLa | 0 | 53 369 | 4192 | 1.0 |
| ELD-CPD | CM18-TAT-Cys | HeLa | 5 | 306 572 | 46 564 | 5.7 |

The results in Tables 2.1 and 2.2 show that treating calcein-loaded HeLa cells with the shuttle agents CM18-Penetratin-Cys and CM18-TAT-Cys (having the domain structure ELD-CPD) results in increased mean cellular calcein fluorescence intensity, as compared to untreated control cells or cells treated with single-domain peptides used alone (CM18, TAT-Cys, Penetratin-Cys) or together (CM18+TAT-Cys, CM18+Penetratin-Cys). These results suggest that CM18-Penetratin-Cys and CM18-TAT-Cys facilitate escape of endosomally-trapped calcein, but that single domain peptides (used alone or together) do not.

TABLE 2.3

Figure 2:
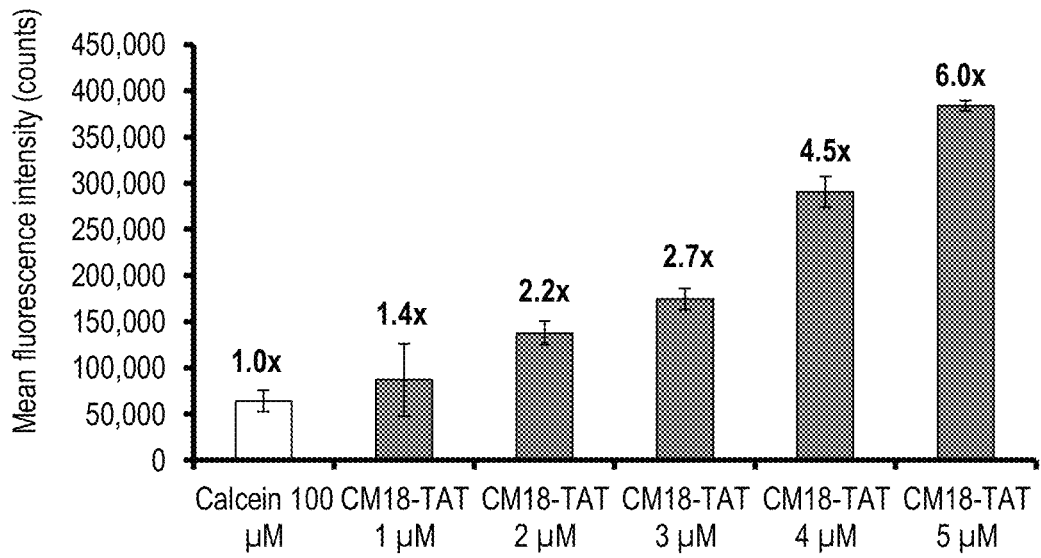
FIG. 2 shows the results of a calcein endosomal escape flow cytometry assay in which HeLa cells were loaded with calcein ("calcein 100 µM"), and were then treated with increasing concentrations of the shuttle agent CM18-TAT-Cys (labeled "CM18-TAT").

Dose response of CM18-TAT-Cys in HeLa cells, data from FIG. 2

| Domains | Peptide | Cells | Concentration (µM) | Mean counts (n = 3) | Stand. dev. | Mean Factor |
|---|---|---|---|---|---|---|
| — | No peptide ("calcein 100 µM") | HeLa | 0 | 63 872 | 11 587 | 1.0 |
| ELD-CPD | CM18-TAT-Cys | HeLa | 1 | 86 919 | 39 165 | 1.4 |
| | CM18-TAT-Cys | HeLa | 2 | 137 887 | 13 119 | 2.2 |
| | CM18-TAT-Cys | HeLa | 3 | 174 327 | 11 519 | 2.7 |
| | CM18-TAT-Cys | HeLa | 4 | 290 548 | 16 593 | 4.5 |
| | CM18-TAT-Cys | HeLa | 5 | 383 685 | 5578 | 6.0 |

TABLE 2.4

Dose response of CM18-TAT-Cys in HeLa cells

| Domains | Peptide | Cells | Concentration (µM) | Mean counts (n = 3) | Stand. dev. | Mean Factor |
|---|---|---|---|---|---|---|
| — | No peptide | HeLa | 0 | 81 013 | 14 213 | 1.0 |
| ELD-CPD | CM18-TAT-Cys | HeLa | 3 | 170 652 | 63 848 | 2.1 |
| | CM18-TAT-Cys | HeLa | 4 | 251 799 | 33 880 | 3.1 |
| | CM18-TAT-Cys | HeLa | 5 | 335 324 | 10 651 | 4.1 |

TABLE 2.5

Figure 3:
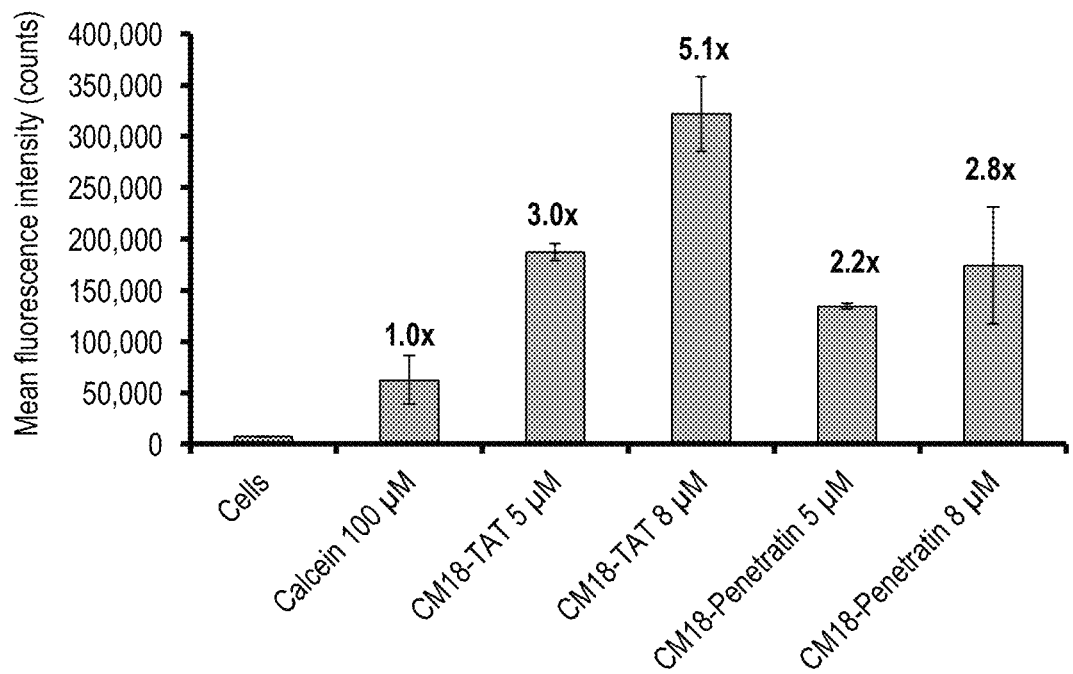
FIGS. 3 and 4 show the results of calcein endosomal escape flow cytometry assays in which HeLa cells (FIG. 3) or primary myoblasts (FIG. 4) were loaded with calcein ("calcein 100 µM"), and were then treated with 5 µM or 8 µM of the shuttle agents CM18-TAT-Cys or CM18-Penetratin-Cys (labeled "CM18-TAT" and "CM18-Penetratin", respectively).

Dose response of CM18-TAT-Cys and CM18-Penetratin-Cys in HeLa cells, data from FIG. 3

| Domains | Peptide | Cells | Concentration (µM) | Mean counts (n = 3) | Stand. dev. | Mean Factor |
|---|---|---|---|---|---|---|
| — | No peptide | HeLa | 0 | 62 503 | 23 752 | 1.0 |
| ELD-CPD | CM18-TAT-Cys | HeLa | 5 | 187 180 | 8593 | 3.0 |
| | CM18-TAT-Cys | HeLa | 8 | 321 873 | 36 512 | 5.1 |
| | CM18-Penetratin-Cys | HeLa | 5 | 134 506 | 2992 | 2.2 |
| | CM18-Penetratin-Cys | HeLa | 8 | 174 233 | 56 922 | 2.8 |

The results in Tables 2.3 (FIG. 2), 2.4, and 2.5 (FIG. 3) suggest that CM18-TAT-Cys and CM18-Penetratin-Cys facilitate escape of endosomally-trapped calcein in HeLa cells in a dose-dependent manner. In some cases, concentrations of CM18-TAT-Cys or CM18-Penetratin-Cys above 10 µM were associated with an increase in cell toxicity in HeLa cells.

TABLE 2.6

Dimers v. monomers of CM18-TAT-Cys and CM18-Penetratin-Cys in HeLa cells

| Domains | Peptide | Cells | Concentration (µM) | Mean counts (n = 4) | Stand. dev. | Mean Factor |
|---|---|---|---|---|---|---|
| — | No peptide | HeLa | 0 | 60 239 | 9860 | 1.0 |
| ELD-CPD | CM18-TAT-Cys | HeLa | 4 | 128 461 | 25 742 | 2.1 |
| | CM18-Penetratin-Cys | HeLa | 4 | 116 873 | 3543 | 1.9 |
| ELD-CPD dimer | dCM18-TAT-Cys | HeLa | 2 | 79 380 | 4297 | 1.3 |
| | dCM18-Penetratin-Cys | HeLa | 2 | 128 363 | 8754 | 2.1 |

TABLE 2.7

Monomers v. dimers of CM18-TAT-Cys and CM18-Penetratin-Cys in HeLa cells

| Domains | Peptide | Cells | Concentration (µM) | Mean counts (n = 3) | Stand. dev. | Mean Factor |
|---|---|---|---|---|---|---|
| — | No peptide | HeLa | 0 | 55 834 | 1336 | 1.0 |
| ELD-CPD | CM18-TAT-Cys | HeLa | 4 | 159 042 | 16 867 | 2.8 |
| ELD-CPD dimer | dCM18-TAT-Cys | HeLa | 2 | 174 274 | 9 553 | 3.1 |

The results in Table 2.6 and 2.7 suggest that shuttle peptide dimers (which are molecules comprising more than one ELD and CPD) are able to facilitate calcein endosomal escape levels that are comparable to the corresponding monomers.

2.2.3 HEK293A Cells

To examine the effects of the shuttle agents on a different cell line, HEK293A cells were cultured and tested in the endosomal escape assays as described in Example 2.1. The results of flow cytometry analyses are summarized below in Table 2.8 and in FIG. 1B.

TABLE 2.8

CM18-TAT-Cys in HEK293A cells

| Domains | Peptide | Cells | Concentration (µM) | Mean counts (n = 2) | Stand. dev. | Mean Factor |
|---|---|---|---|---|---|---|
| — | No peptide | HEK293A | 0 | 165 819 | 7693 | 1.0 |
| ELD-CPD | CM18-TAT-Cys | HEK293A | 0.5 | 196 182 | 17 224 | 1.2 |
| | CM18-TAT-Cys | HEK293A | 5 | 629 783 | 1424 | 3.8 |

The results in Table 2.8 and in FIG. 1B show that treating calcein-loaded HEK293A cells with the shuttle agent CM18-TAT-Cys results in increased mean cellular calcein fluorescence intensity, as compared to untreated control cells.

2.2.2 Myoblasts

To examine the effects of the shuttle agents on primary cells, primary myoblast cells were cultured and tested in the endosomal escape assays as described in Example 2.1. The results of flow cytometry analyses are summarized below in Tables 2.9 and 2.10, and in FIG. 4. In each case, the flow cytometry results were also confirmed by fluorescence microscopy.

TABLE 2.9

Figure 4:
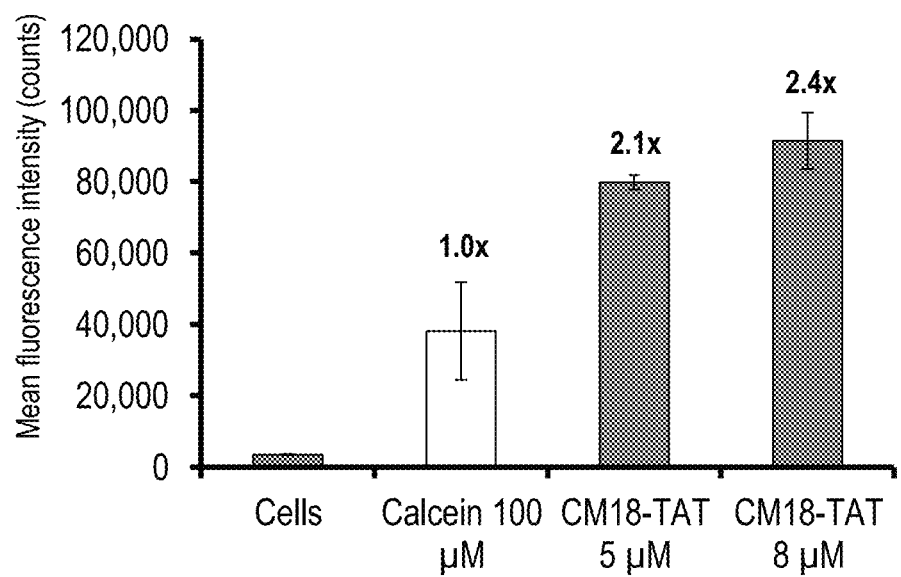

Dose response of CM18-TAT-Cys in primary myoblasts, data from FIG. 4

| Domains | Peptide | Cells | Peptide Conc. (µM) | Mean counts (n = 3) | Stand. dev. | Mean Factor |
|---|---|---|---|---|---|---|
| — | No peptide; no calcein ("Cells") | Myoblasts | 0 | 863 | 61 | n/a |
| — | No peptide ("Calcein 100 µM") | Myoblasts | 0 | 38 111 | 13 715 | 1.0 |
| ELD-CPD | CM18-TAT-Cys | Myoblasts | 5 | 79 826 | 12 050 | 2.1 |
| | CM18-TAT-Cys | Myoblasts | 8 | 91 421 | 10 846 | 2.4 |

TABLE 2.10

Dose response of CM18-TAT-Cys in primary myoblasts

| Domains | Peptide | Cells | Peptide Conc. (µM) | Mean counts (n = 3) | Stand. dev. | Mean Factor |
|---|---|---|---|---|---|---|
| — | No peptide | Myoblasts | 0 | 31 071 | 21 075 | 1.0 |
| ELD-CPD | CM18-TAT-Cys | Myoblasts | 5 | 91 618 | 10 535 | 2.9 |
| | CM18-TAT-Cys | Myoblasts | 7.5 | 95 289 | 11 266 | 3.1 |

The results in Table 2.9 (shown graphically in FIG. 4) and Table 2.10 suggest that CM18-TAT-Cys facilitates escape of endosomally-trapped calcein in a dose-dependent manner in primary myoblasts. Concentrations of CM18-TAT-Cys above 10 µM were associated with an increase in cell toxicity in myoblast cells, as for HeLa cells.

TABLE 2.11

Monomers v. dimers CM18-TAT-Cys and CM18-Penetratin-Cys in primary myoblasts

| Domains | Peptide | Cells | Concentration (µM) | Mean counts | Stand. dev. | Mean Factor |
|---|---|---|---|---|---|---|
| — | No peptide | Myoblasts | 0 | 30 175 | 4687 | 1.0 |
| ELD-CPD | CM18-TAT-Cys | Myoblasts | 5 | 88 686 | 19 481 | 2.9 |
| ELD-CPD dimer | dCM18-TAT-Cys | Myoblasts | 2.5 | 64 864 | 1264 | 2.1 |
| ELD-CPD | CM18-Penetratin-Cys | Myoblasts | 5 | 65 636 | 3288 | 2.2 |
| ELD-CPD dimer | dCM18-Penetratin-Cys | Myoblasts | 2.5 | 71 547 | 10 975 | 2.4 |

The results in Table 2.11 suggest that shuttle peptide dimers are able to facilitate calcein endosomal escape levels that are comparable to the corresponding monomers in primary myoblasts.

Example 3

Peptide Shuttle Agents Increase GFP Transduction Efficiency 3.1 Protein Transduction Assay One day before the transduction assay was performed, mammalian cells (e.g., HEK293, CHO, HeLa, THP-1, and myoblasts) in exponential growth phase were harvested and plated in a 96-well plate (20,000 cells per well). The cells were incubated overnight in appropriate growth media containing FBS (see Example 1). The next day, in separate sterile 1.5 mL tubes, cargo protein at 0.5 to 10 µM (GFP, TAT-GFP, GFP-NLS, or FITC-labeled anti-tubulin antibody) was pre-mixed (pre-incubated) for 10 min at 37° C. with shuttle agents (0.5 to 5 µM) in 50 µL of fresh medium without serum (unless otherwise specified). GFP, GFP-NLS and TAT-GFP are recombinant proteins developed and produced by Feldan (see Example 3.4 below). FITC-labeled anti-tubulin antibody was purchased from Abcam (ab64503). The media in wells was removed and the cells were washed three times with freshly prepared phosphate buffered saline (PBS) previously warmed at 37° C. The cells were incubated with the cargo protein/shuttle agent mixture at 37° C. for 5 or 60 min. After the incubation, the cells were quickly washed three times with freshly prepared PBS and/or heparin (0.5 mg/mL) previously warmed at 37° C. The washes with heparin were required for human THP-1 blood cells to avoid undesired cell membrane-bound protein background in subsequent analyses (microscopy and flow cytometry). The cells were finally incubated in 50 µL of fresh medium with serum at 37° C. before analysis.

3.2 Fluorescence Microscopy Analysis

The delivery of fluorescent protein cargo in cytosolic and nuclear cell compartments was observed with an Olympus IX70™ microscope (Japan) equipped with a fluorescence lamp (Model U-LH100HGAPO) and different filters. The Olympus filter U-MF2™ (C54942-Exc495/Em510) was used to observe GFP and FITC-labeled antibody fluorescent signals. The Olympus filter HQ-TR™ (V-N41004-Exc555-60/Em645-75) was used to observe mCherry™ and GFP antibody fluorescent signals. The Olympus filter U-MWU2™ (Exc330/Em385) was used to observe DAPI or Blue Hoechst fluorescent signals. The cells incubated in 50 µL of fresh medium were directly observed by microscopy (Bright-field and fluorescence) at different power fields (4× to 40×). The cells were observed using a CoolSNAP-PRO™ camera (Series A02D874021) and images were acquired using the Image-Proplus™ software.

3.2a Cell Immuno-Labelling

Adherent cells were plated on a sterile glass strip at 1.5×10⁵ cells per well in a 24-plate well and incubated overnight at 37° C. For fixation, cells were incubated in 500 µL per well of formaldehyde (3.7% v/v) for 15 minutes at room temperature, and washed 3 times for 5 minutes with PBS. For permeabilization, cells were incubated in 500 µL per well of Triton X-100 (0.2%) for 10 minutes at room temperature, and washed 3 times for 5 minutes with PBS. For blocking, cells were incubated in 500 µL per well of PBS containing 1% BSA (PBS/BSA) for 60 minutes at room temperature. Primary mouse monoclonal antibody was diluted PBS/BSA (1%). Cells were incubated in 30 µL of primary antibody overnight at 4° C. Cells were washed 3 times for 5 minutes with PBS. Secondary antibody was diluted in PBS/BSA (1%) and cells were incubated in 250 μL of secondary antibody 30 minutes at room temperature in the dark. Cells were washed 3 times for 5 minutes with PBS. Glass strips containing the cells were mounted on microscope glass slides with 10 μL of the mounting medium Fluoroshield™ with DAPI.

3.3 Flow Cytometry Analysis:

The fluorescence of GFP was quantified using flow cytometry (Accuri C6, Becton, Dickinson and Company (BD)). Untreated cells were used to establish a baseline in order to quantify the increased fluorescence due to the internalization of the fluorescent protein in treated cells. The percentage of cells with a fluorescence signal above the maximum fluorescence of untreated cells, "mean %" or "Pos cells (%)", is used to identify positive fluorescent cells. "Relative fluorescence intensity (FL1-A)" corresponds to the mean of all fluorescence intensities from each cell with a fluorescent signal after fluorescent protein delivery with the shuttle agent. Also, the events scanned by flow cytometry corresponding to cells (size and granularity) were analyzed. The cellular toxicity (% cell viability) was monitored comparing the percentage of cells in the total events scanned of treated cells comparatively to untreated cells.

3.3a Viability Analysis

The viability of cells was assessed with a rezazurine test. Rezazurine is a sodium salt colorant that is converted from blue to pink by mitochondrial enzymes in metabolically active cells. This colorimetric conversion, which only occurs in viable cells, can be measured by spectroscopy analysis in order to quantify the percentage of viable cells. The stock solution of rezazurine was prepared in water at 1 mg/100 mL and stored at 4° C. 25 μL of the stock solution was added to each well of a 96-well plate, and cells were incubated at 37° C. for one hour before spectrometry analysis. The incubation time used for the rezazurine enzymatic reaction depended on the quantity of cells and the volume of medium used in the wells.

3.4 Construction and Amino Acid Sequence of GFP

The GFP-encoding gene was cloned in a T5 bacterial expression vector to express a GFP protein containing a 6× histidine tag and a serine/glycine rich linker in the N-terminal end, and a serine/glycine rich linker and a stop codon (−) at the C-terminal end. Recombinant GFP protein was purified as described in Example 1.4. The sequence of the GFP construct was:

[SEQ ID NO: 60]
MHHHHHHGGGGSGGGGSGGGSGGA*STGTGIR*MVSKGEELFTGVVPILVELDGDV

NGHKFSVSGEGEGDATYGKLTLKFICTTGKLPVPWPTLVTTLTYGVQCFS

RYPDHMKQHDFFKSAMPEGYVQERTIFFKDDGNYKTRAEVKFEGDTLVNR

IELKGIDFKEDGNILGHKLEYNYNSHNVYIMADKQKNGIKVNFKIRHNIE

DGSVQLADHYQQNTPIGDGPVLLPDNHYLSTQSALSKDPNEKRDHMVLLE

Figure 5:
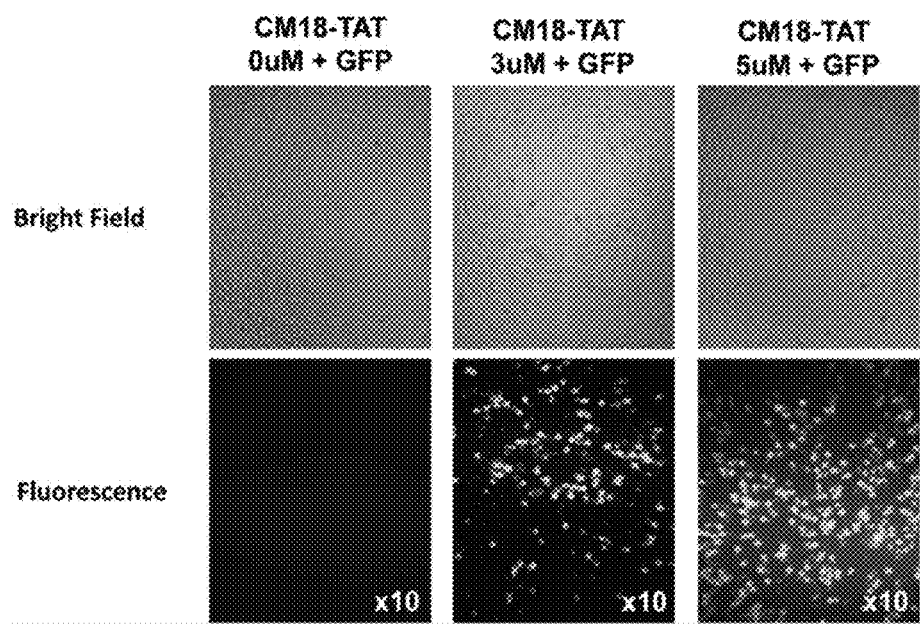
FIG. 5 shows the results of a GFP transduction experiment visualized by fluorescence microscopy in which a GFP cargo protein was co-incubated with 0, 3 or 5 µM of CM18-TAT-Cys (labeled "CM18-TAT"), and then exposed to HeLa cells. The cells were observed by bright field (upper pictures in FIG. 5) and fluorescence microscopy (lower pictures in FIG. 5).

FVTAAGITLGMDELYKGGSGGGSGGGSGWIRASSGGREIS-
(MW = 31.46 kDa; pI = 26.19)
Serine/glycine rich linkers are in bold
GFP sequence is underlined 3.5 GFP Transduction by CM18-TAT-Cys in HeLa Cells: Fluorescence Microscopy HeLa cells were cultured and tested in the protein transduction assay described in Example 3.1. Briefly, GFP recombinant protein was co-incubated with 0, 3 or 5 μM of CM18-TAT, and then exposed to HeLa cells for 1 hour. The cells were observed by bright field and fluorescence microscopy as described in Example 3.2. The results presented in FIG. 5 show that GFP was delivered intracellularly to HeLa cells in the presence of the shuttle agent CM18-TAT.

3.6 GFP Transduction by Shuttle Agents in HeLa Cells: Dose Responses (CM18-TAT-Cys, dCM18-TAT-Cys, GFP) and Cell Viability HeLa cells were cultured and tested in the protein transduction assay described in Examples 3.1-3.3. Briefly, GFP recombinant protein was co-incubated with different concentrations of CM18-TAT-Cys or dimerized CM18-TAT-Cys (dCM18-TAT-Cys), and then exposed to HeLa cells for 1 hour. The results are shown in Table 3.1 and FIGS. 6A-6B.

TABLE 3.1

Figure 6A:
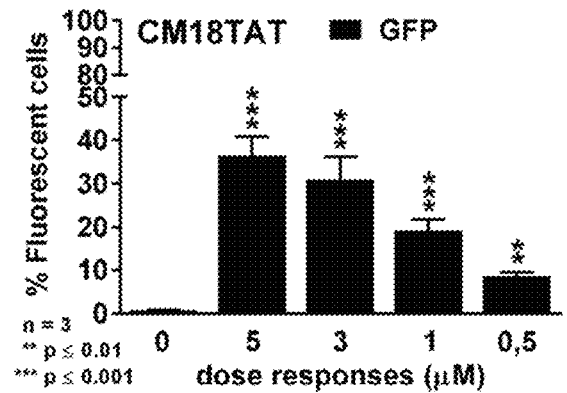
FIGS. 6A-6B show the results of a GFP transduction efficiency experiment in which GFP cargo protein (10 µM) was co-incubated with different concentrations of CM18-TAT-Cys (labeled "CM18-TAT"), prior to being exposed to HeLa cells. Cells were evaluated by flow cytometry and the percentage of fluorescent (GFP-positive) cell is shown in FIG. 6A, and corresponding cell toxicity data is shown in FIG. 6B.
Figure 6B:
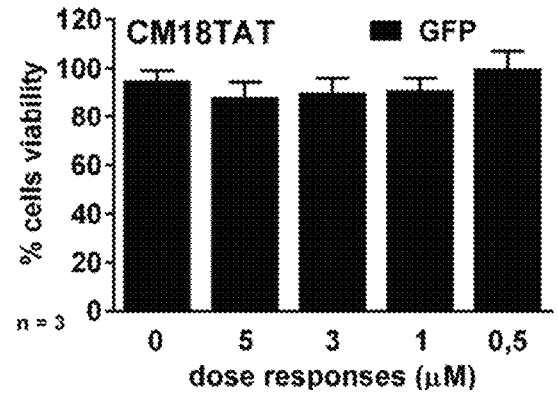

Dose response (CM18-TAT) and cell viability, data from FIGS. 6A and 6B

| | | | FIG. 6A | | FIG. 6B |
|---|---|---|---|---|---|
| Shuttle | Cells | Concentration (μM) | Mean (%) (n = 3) | Standard deviation | Cell viability (%) (±St. Dev.; n = 3) |
| CM18-TAT-Cys | HeLa | 0 | 0.69 | 0.12 | 95 ± 4 |
| | HeLa | 0.5 | 8.67 | 0.96 | 88.4 ± 6 |
| | HeLa | 1 | 20.03 | 2.55 | 90 ± 6 |
| | HeLa | 3 | 31.06 | 5.28 | 91 ± 5 |
| | HeLa | 5 | 36.91 | 4.33 | 90 ± 7 |

Table 3.1 and FIG. 6A show the results of flow cytometry analysis of the fluorescence intensity of HeLa cells transduced with GFP (5 μM) without or with 5, 3, 1, and 0.5 μM of CM18-TAT-Cys. Corresponding cellular toxicity data are presented in Table 3.1 and in FIG. 6B. These results suggest that the shuttle agent CM18-TAT-Cys increases the transduction efficiency of GFP in a dose-dependent manner.

TABLE 3.2

Figure 7A:
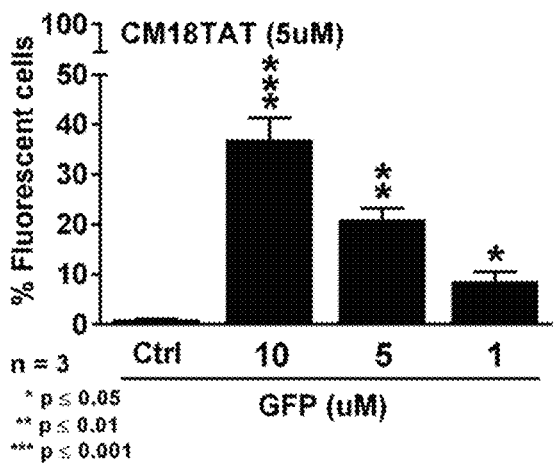
FIGS. 7A-7B show the results of a GFP transduction efficiency experiment in which different concentrations of GFP cargo protein (10, 5 or 1 µM) were co-incubated with either 5 µM of CM18-TAT-Cys (FIG. 7A, labeled "CM18TAT"), or 2.5 µM of dCM18-TAT-Cys (FIG. 7B, labeled "dCM18TAT"), prior to being exposed to HeLa cells. Cells were evaluated by flow cytometry and the percentages of fluorescent (GFP-positive) cells are shown.
Figure 7B:
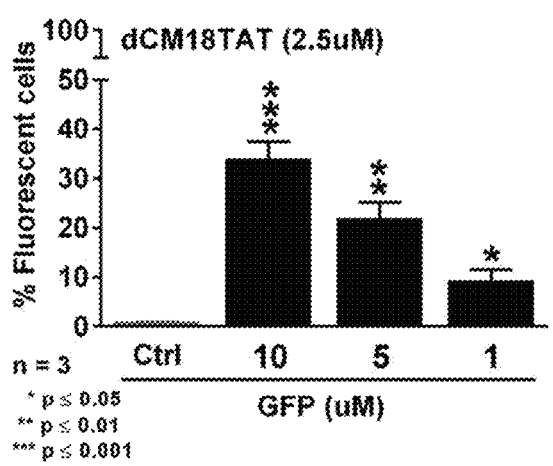

Dose response (GFP), data from FIGS. 7A and 7B

| Shuttle | Cells | Conc. of shuttle agent (μM) | Conc. of GFP (μM) | Mean (%) (n = 3) | Standard deviation |
|---|---|---|---|---|---|
| Control | HeLa | 0 | 10 | 0.93 | 0.08 |
| CM18-TAT-Cys | HeLa | 5 | 10 | 37.1 | 4.29 |
| | HeLa | 5 | 5 | 21.1 | 2.19 |
| | HeLa | 5 | 1 | 8.56 | 1.91 |
| Control | HeLa | 0 | 10 | 0.91 | 0.09 |
| dCM18-TAT-Cys | HeLa | 2.5 | 10 | 34.2 | 3.42 |
| | HeLa | 2.5 | 5 | 22.2 | 3.17 |
| | HeLa | 2.5 | 1 | 9.38 | 2.11 |

Table 3.2 and FIGS. 7A-7B show the results of flow cytometry analysis of the fluorescence intensity of HeLa cells transduced with different concentrations of GFP (1 to 10 μM) without or with 5 μM of CM18-TAT-Cys (FIG. 7A) or 2.5 μM dCM18-TAT-Cys (FIG. 7B).

3.7 GFP Transduction in HeLa Cells: Dose Responses of CM18-TAT-Cys and CM18-Penetratin-Cys, and Dimers Thereof.

HeLa cells were cultured and tested in the protein transduction assay described in Example 3.1. Briefly, GFP recombinant protein (5 μM) was co-incubated with different concentrations and combinations of CM18-TAT-Cys, CM18-Penetratin-Cys, and dimers of each (dCM18-TAT-Cys, dCM18-Penetratin-Cys), and then exposed to HeLa cells for 1 hour. The cells were subjected to flow cytometry analysis as described in Example 3.3. The results are shown in Table 3.3 and FIG. 8, as well as in Table 3.4 and FIG. 9.

TABLE 3.3

Figure 8:
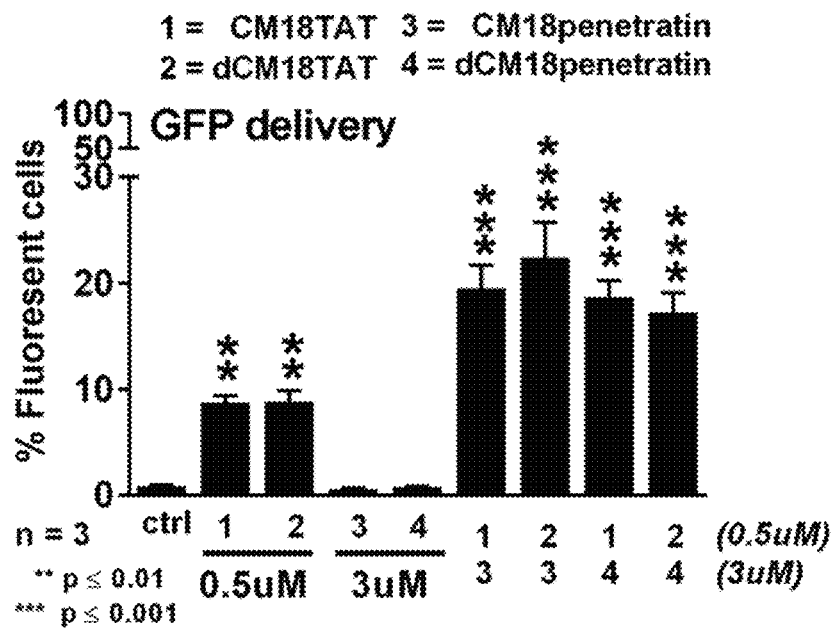
FIGS. 8 and 9 show the results of GFP transduction efficiency experiments in which GFP cargo protein (10 µM) was co-incubated with different concentrations and combinations of CM18-TAT-Cys (labeled "CM18TAT"), CM18-Penetratin-Cys (labeled "CM18penetratin"), and dimers of each (dCM18-TAT-Cys (labeled "dCM18TAT"), dCM18-Penetratin-Cys (labeled "dCM18penetratin"), prior to being exposed to HeLa cells. Cells were evaluated by flow cytometry and the percentages of fluorescent (GFP-positive) cells are shown.

Data in FIG. 8

| No. in FIG. 8 | Shuttle agent | Cells | Concentration (µM) | Mean (%) (n = 3) | Standard deviation |
|---|---|---|---|---|---|
| Control ("ctrl") | No shuttle | HeLa | 0 | 0.43 | 0.08 |
| 1 | CM18-TAT-Cys | HeLa | 0.5 | 8.75 | 0.63 |
| 2 | dCM18-TAT-Cys | HeLa | 0.5 | 8.86 | 1.03 |
| 3 | CM18-Penetratin-Cys | HeLa | 3 | 0.59 | 0.11 |
| 4 | dCM18-Penetratin-Cys | HeLa | 3 | 0.73 | 0.08 |
| 1 + 3 | CM18-TAT-Cys + CM18-Penetratin-Cys | HeLa | 0.5 3 | 19.52 | 2.18 |
| 2 + 3 | dCM18-TAT-Cys + CM18-Penetratin-Cys | HeLa | 0.5 3 | 22.44 | 3.29 |
| 1 + 4 | CM18-TAT-Cys + dCM18-Penetratin-Cys | HeLa | 0.5 3 | 18.73 | 1.55 |
| 2 + 4 | dCM18-TAT-Cys + dCM18-Penetratin-Cys | HeLa | 0.5 3 | 17.19 | 1.93 |

The results in Table 3.3 and FIG. 8 show that the transduction efficiency of GFP is increased in HeLa cells using the shuttle agents CM18-TAT-Cys and dCM18-TAT-Cys (see bars "1" and "2" in FIG. 8). Although no GFP intracellular delivery was observed using CM18-Penetratin-Cys or dCM18-Penetratin-Cys alone (see bars "3" or "4" in FIG. 8), combination of CM18-TAT-Cys with CM18-Penetratin-Cys (monomer or dimer) improved GFP protein delivery (see four right-most bars in FIG. 8).

TABLE 3.4

Figure 9:
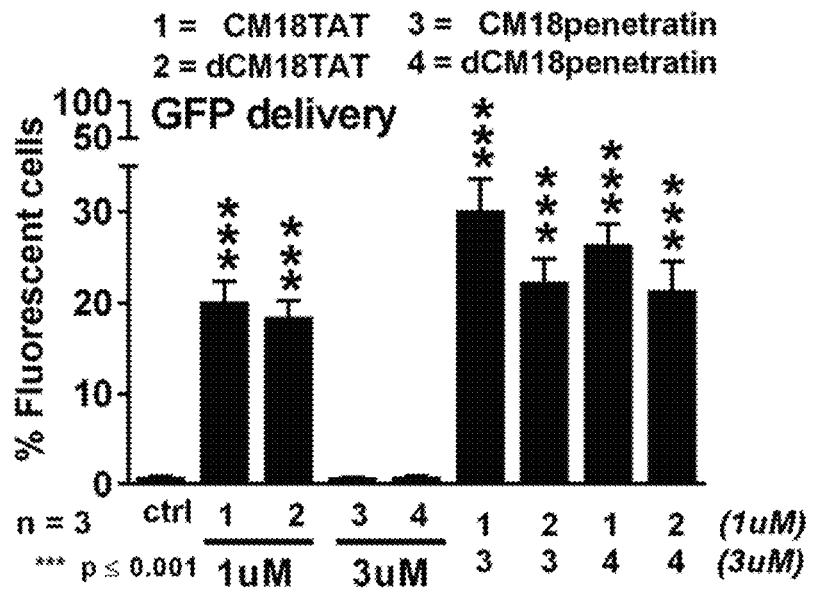

Data in FIG. 9

| No. in FIG. 9 | Shuttle | Cells | Concentration (µM) | Mean (%) (n = 3) | Standard deviation |
|---|---|---|---|---|---|
| Control ("ctrl") | No shuttle | HeLa | 0 | 0.51 | 0.07 |
| 1 | CM18-TAT-Cys | HeLa | 1 | 20.19 | 2.19 |
| 2 | dCM18-TAT-Cys | HeLa | 1 | 18.43 | 1.89 |
| 3 | CM18-Penetratin-Cys | HeLa | 3 | 0.81 | 0.07 |
| 4 | dCM18-Penetratin-Cys | HeLa | 3 | 0.92 | 0.08 |
| 1 + 3 | CM18-TAT-Cys + CM18-Penetratin-Cys | HeLa | 1 3 | 30.19 | 3.44 |
| 2 + 3 | dCM18-TAT-Cys + CM18-Penetratin-Cys | HeLa | 1 3 | 22.36 | 2.46 |
| 1 + 4 | CM18-TAT-Cys + dCM18-Penetratin-Cys | HeLa | 1 3 | 26.47 | 2.25 |
| 2 + 4 | dCM18-TAT-Cys + dCM18-Penetratin-Cys | HeLa | 1 3 | 21.44 | 3.11 |

The results in Table 3.4 and FIG. 9 show that the transduction efficiency of GFP is increased in HeLa cells using the shuttle agents CM18-TAT-Cys and dCM18-TAT-Cys (see bars "1" and "2" in FIG. 9). Although no GFP intracellular delivery was observed using CM18-Penetratin-Cys or dCM18-Penetratin-Cys alone (see bars "3" or "4" in FIG. 9), combination of CM18-TAT-Cys with CM18-Penetratin-Cys (monomer or dimer) improved GFP protein delivery (see four right-most bars in FIG. 9).

3.8 GFP Transduction by Shuttle Agents in HeLa Cells: Controls

HeLa cells were cultured and tested in the protein transduction assay described in Example 3.1. Briefly, GFP recombinant protein (5 µM) was co-incubated with 5 µM of each of the following peptide(s): TAT-Cys; CM18; Penetratin-Cys; TAT-Cys+CM18; Penetratin-Cys+CM18; and CM18-TAT-Cys, and then exposed to HeLa cells for 1 hour. GFP fluorescence was visualized by bright field and fluorescence microscopy. The microscopy results (data not shown) showed that GFP was successfully delivered intracellularly using CM18-TAT-Cys. However, GFP was not successfully delivered intracellularly using single-domain peptides used alone (CM18, TAT-Cys, Penetratin-Cys) or together (CM18+TAT-Cys, CM18+Penetratin-Cys). These results are consistent with those presented in Tables 2.1 and 2.2 with respect to the calcein endosome escape assays.

Example 4

Peptide Shuttle Agents Increase TAT-GFP Transduction Efficiency

The experiments in Example 3 showed the ability of shuttle agents to deliver GFP intracellularly. The experiments presented in this example show that the shuttle agents can also increase the intracellular delivery of a GFP cargo protein that is fused to a CPD (TAT-GFP).

4.1 Construction and Amino Acid Sequence of TAT-GFP

Construction was performed as described in Example 3.4, except that a TAT sequence was cloned between the 6× histidine tag and the GFP sequences. The 6× histidine tag, TAT, GFP and a stop codon (−) are separated by serine/glycine rich linkers. The recombinant TAT-GFP protein was purified as described in Example 1.4. The sequence of the TAT-GFP construct was:

[SEQ ID NO: 61]
MHHHHHHGGGGSGGGGSGGASTGTGRKKRRQRRRPPQGGGGSGGGGSGGG

TGIRMVSKGEELFTGVVPILVELDGDVNGHKFSVSGEGEGDATYGKLTLK

FICTTGKLPVPWPTLVTTLTYGVQCFSRYPDHMKQHDFFKSAMPEGYVQE

RTIFFKDDGNYKTRAEVKFEGDTLVNRIELKGIDFKEDGNILGHKLEYNY

NSHNVYIMADKQKNGIKVNFKIRHNIEDGSVQLADHYQQNTPIGDGPVLL

PDNHYLSTQSALSKDPNEKRDHMVLLEFVTAAGITLGMDELYKGGSGGGS

Figure 10:
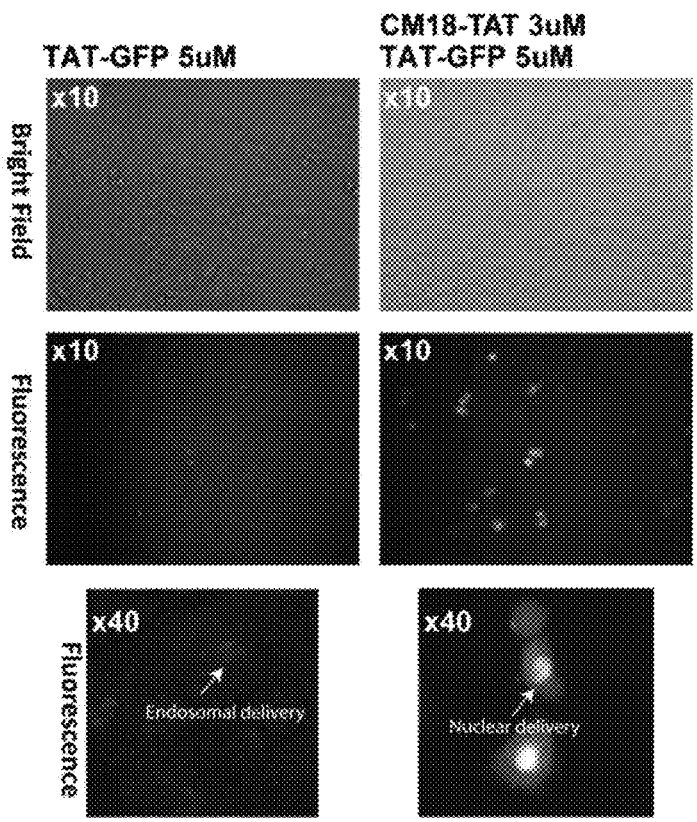
FIG. 10 shows typical results of a TAT-GFP transduction experiment in which TAT-GFP cargo protein (5 µM) was co-incubated with 3 µM of CM18-TAT-Cys (labeled "CM18-TAT"), prior to being exposed to HeLa cells. Cells and GFP fluorescence were visualized by bright field and fluorescence microscopy at 10× and 40× magnifications. Arrows indicate the endosome delivery of TAT-GFP in the absence of CM18-TAT-Cys, as well as its nuclear delivery in the presence of CM18-TAT-Cys.

GGGSGWIRASSGGREIS-
(MW = 34.06 kDa; pI = 8.36)
TAT sequence is underlined
Serine/glycine rich linkers are in bold 4.2 TAT-GFP Transduction by CM18-TAT-Cys in HeLa Cells: Visualisation by Fluorescence Microscopy HeLa cells were cultured and tested in the protein transduction assay described in Example 3.1. Briefly, TAT-GFP recombinant protein (5 µM) was co-incubated with 3 µM of CM18-TAT-Cys and then exposed to HeLa cells for 1 hour. Cells and GFP fluorescence were visualized by bright field and fluorescence microscopy (as described in Example 3.2) at 10× and 40× magnifications, and sample results are shown in FIG. 10. The microscopy results revealed that in the absence of CM18-TAT-Cys, TAT-GFP shows a low intensity, endosomal distribution as reported in the literature. In contrast, TAT-GFP is delivered to the cytoplasm and to the nucleus in the presence of the shuttle agent CM18-TAT-Cys. Without being bound by theory, the TAT peptide itself may act as a nuclear localization signal (NLS), explaining the nuclear localization of TAT-GFP. These results show that CM18-TAT-Cys is able to increase TAT-GFP transduction efficiency and allow endosomally-trapped TAT-GFP to gain access to the cytoplasmic and nuclear compartments.

4.3 TAT-GFP Transduction by CM18-TAT-Cys in HeLa Cells: Dose Responses and Viability of Cells Transduced HeLa cells were cultured and tested in the protein transduction assay described in Example 3.1. Briefly, TAT-GFP- Cys recombinant protein (5 μM) was co-incubated with different concentrations of CM18-TAT-Cys (0, 0.5, 1, 3, or 5 μM) and then exposed to HeLa cells for 1 hour. The cells were subjected to flow cytometry analysis as described in Example 3.3. Results are shown in Table 4.1 and FIG. 11A. Corresponding cellular toxicity data are presented in FIG. 11B.

TABLE 4.3

Figure 11A:
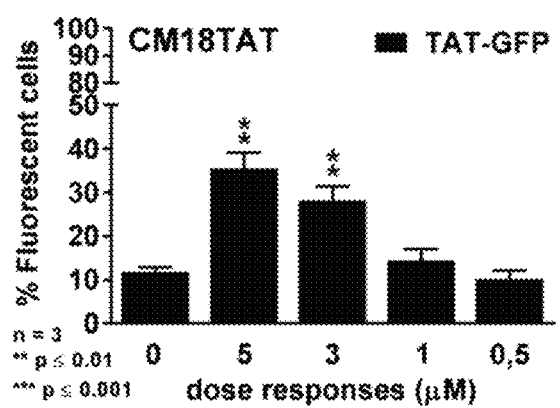
FIGS. 11A-11B show the results of a TAT-GFP transduction efficiency experiment in which TAT-GFP cargo protein (5 µM) was co-incubated with different concentrations of CM18-TAT-Cys (labeled "CM18TAT"), prior to being exposed to HeLa cells. Cells were evaluated by flow cytometry and the percentage of fluorescent (GFP-positive) cell is shown in FIG. 11A, and corresponding cell toxicity data is shown in FIG. 11B.
Figure 11B:
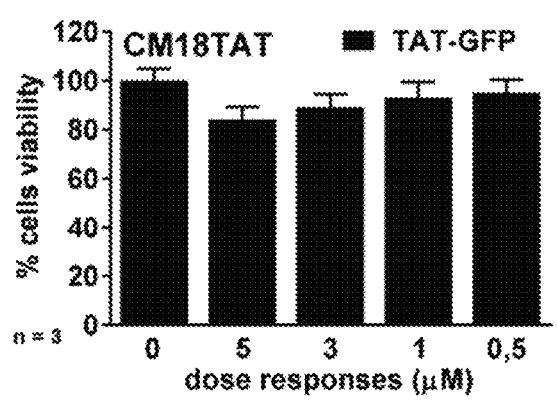

Data from FIG. 11A and 11B

| | | | FIG. 11A | | FIG. 11B |
|---|---|---|---|---|---|
| Shuttle agent | Cells | Concentration (μM) | Mean (%) (n = 3) | Standard deviation | Cell viability (%) (±St. Dev.; n = 3) |
| CM18-TAT-Cys | HeLa | 0 | 11.79[1] | 1.16 | 100 |
| | HeLa | 0.5 | 10.19 | 1.94 | 84.36 ± 5 |
| | HeLa | 1 | 14.46 | 2.59 | 89.26 ± 5.26 |
| | HeLa | 3 | 28.12 | 3.27 | 93.18 ± 6.28 |
| | HeLa | 5 | 35.5[2] | 3.59 | 95.14 ± 5.28 |

[1] The fluorescence was mostly endosomal, as confinned by fluorescence microscopy.
[2] Fluorescence was more diffuse and also nuclear, as confirmed by fluorescence microscopy.

Example 5

Peptide Shuttle Agents Increase GFP-NLS Transduction Efficiency and Nuclear Localization The experiments in Examples 3 and 4 showed the ability of shuttle agents to deliver GFP and TAT-GFP intracellularly. The experiments presented in this example show that the shuttle agents can facilitate nuclear delivery of a GFP protein cargo fused to a nuclear localization signal (NLS).

5.1 Construction and Amino Acid Sequence of GFP-NLS

Construction was performed as described in Example 3.4, except that an optimized NLS sequence was cloned between the GFP sequence and the stop codon (−). The NLS sequence is separated from the GFP sequence and the stop codon by two serine/glycine rich linkers. The recombinant GFP-NLS protein was purified as described in Example 1.4. The sequence of the GFP-NLS construct was:

[SEQ ID NO: 62]
MHHHHHHGGGGSGGGGSGGASTGIRMVSKGEELFTGVVPILVELDGDVNG

HKFSVSGEGEGDATYGKLTLKFICTTGKLPVPWPTLVTTLTYGVQCFSRY

PDHMKQHDFFKSAMPEGYVQERTIFFKDDGNYKTRAEVKFEGDTLVNRIE

LKGIDFKEDGNILGHKLEYNYNSHNVYIMADKQKNGIKVNFKIRHNIEDG

SVQLADHYQQNTPIGDGPVLLPDNHYLSTQSALSKDPNEKRDHMVLLEFV

TAAGITLGMDELYKGGSGGGSGGGSGWIRASSGGRSSDDEATADSQHAAP

Figure 12:
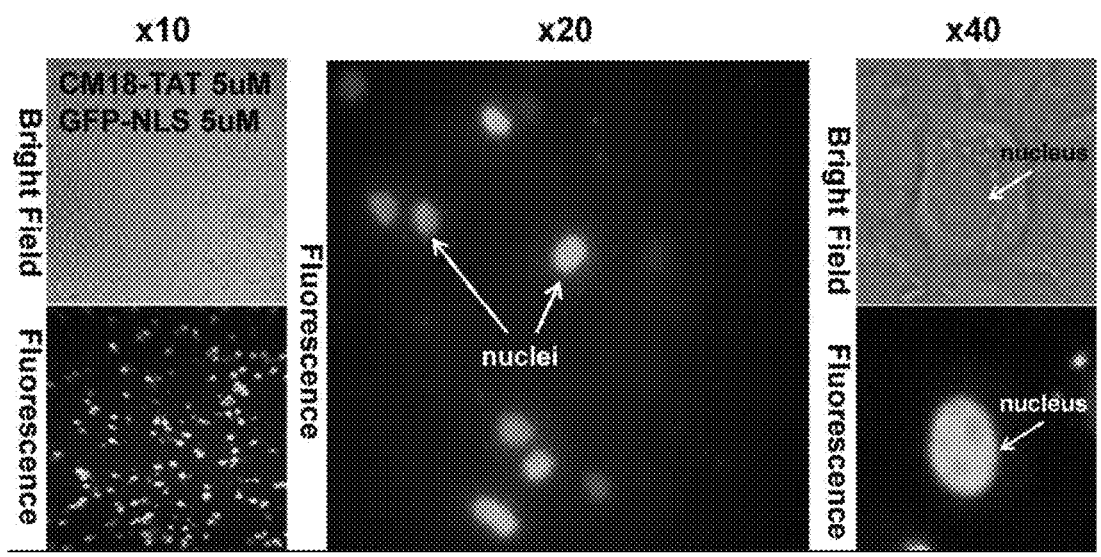
FIG. 12 shows typical results of a GFP-NLS transduction experiment in which GFP-NLS cargo protein (5 µM) was co-incubated with 5 µM of CM18-TAT-Cys (labeled "CM18-TAT"), prior to being exposed to HeLa cells for 5 minutes. Cells and GFP fluorescence were visualized by bright field and fluorescence microscopy at 10×, 20×, and 40× magnifications. Arrows indicate areas of nuclear delivery of GFP-NLS.

PKKKRKVGGSGGGSGGGSGGGRGTEIS-
(MW = 34.85 kDa; pI = 6.46)
NLS sequence is underlined
Serine/glycine rich linkers are in bold 5.2 Nuclear delivery of GFP-NLS by CM18-TAT-Cys in HeLa cells in 5 minutes: Visualisation by Fluorescence Microscopy HeLa cells were cultured and tested in the protein transduction assay described in Example 3.1. Briefly, GFP-NLS recombinant protein (5 μM) was co-incubated with 5 μM of CM18-TAT-Cys, and then exposed to HeLa cells. GFP fluorescence was visualized by bright field and fluorescence microscopy after 5 minutes (as described in Example 3.2) at 10×, 20× and 40× magnifications, and sample results are shown in FIG. 12. The microscopy results revealed that GFP-NLS is efficiently delivered to the nucleus in the presence of the shuttle agent CM18-TAT-Cys, after only 5 minutes of incubation.

5.3 GFP-NLS Transduction by CM18-TAT-Cys in HeLa Cells: Dose Responses and Viability of Cells Transduced HeLa cells were cultured and tested in the protein transduction assay described in Example 3.1. GFP-NLS recombinant protein (5 μM) was co-incubated with 0, 0.5, 1, 3, or 5 μM of CM18-TAT-Cys, and then exposed to HeLa cells for 1 hour. The cells were subjected to flow cytometry analysis as described in Example 3.3. Results are shown in Table 5.1 and FIG. 13A. Corresponding cellular toxicity data are presented in FIG. 13B.

TABLE 5.1

Figure 13A:
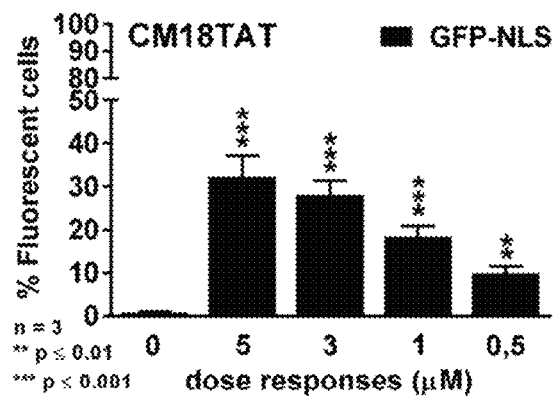
FIGS. 13A-13B show the results of a GFP-NLS transduction efficiency experiment in which GFP-NLS cargo protein (5 µM) was co-incubated with different concentrations of CM18-TAT-Cys (labeled "CM18TAT"), prior to being exposed to HeLa cells. Cells were evaluated by flow cytometry and the percentage of fluorescent (GFP-positive) cell is shown in FIG. 13A, and corresponding cell toxicity data is shown in FIG. 13B.
Figure 13B:
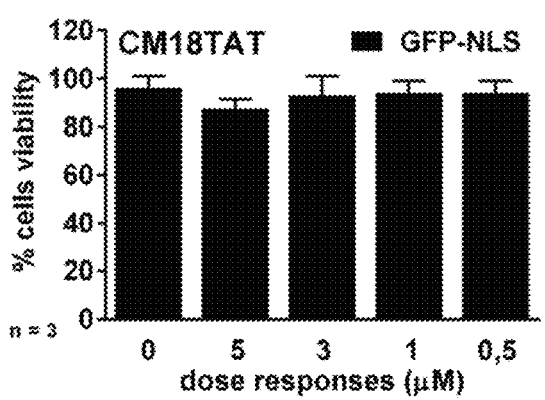

Data from FIG. 13A and 13B

| | | | FIG. 13A | | FIG. 13B |
|---|---|---|---|---|---|
| Shuttle agent | Cells | Concentration (μM) | Mean (%) (n = 3) | Standard deviation | Cell viability (%) (±St. Dev.; n = 3) |
| CM18-TAT-Cys | HeLa | 0 | 0.90 | 0.12 | 100 |
| | HeLa | 0.5 | 9.81 | 1.63 | 87.6 ± 4 |
| | HeLa | 1 | 18.42 | 2.47 | 93 ± 8 |
| | HeLa | 3 | 28.09 | 3.24 | 94 ± 5 |
| | HeLa | 5 | 32.26 | 4.79 | 93 ± 4 |

These results show that CM18-TAT-Cys is able to increase GFP-NLS transduction efficiency in HeLa cells in a dose-dependent manner.

5.4 GFP-NLS Transduction by CM18-TAT-Cys, CM18-Penetratin-Cys, and Dimers thereof in HeLa Cells HeLa cells were cultured and tested in the protein transduction assay described in Example 3.1. GFP-NLS recombinant protein (5 μM) was co-incubated with different concentrations and combinations of CM18-TAT-Cys, CM18-Penetratin-Cys, and dimers of each (dCM18-TAT-Cys, dCM18-Penetratin-Cys), and then exposed to HeLa cells for 1 hour. The cells were subjected to flow cytometry analysis as described in Example 3.3. The results are shown in Tables 5.2 and 5.3, and in FIGS. 14 and 15.

TABLE 5.2

Figure 14:
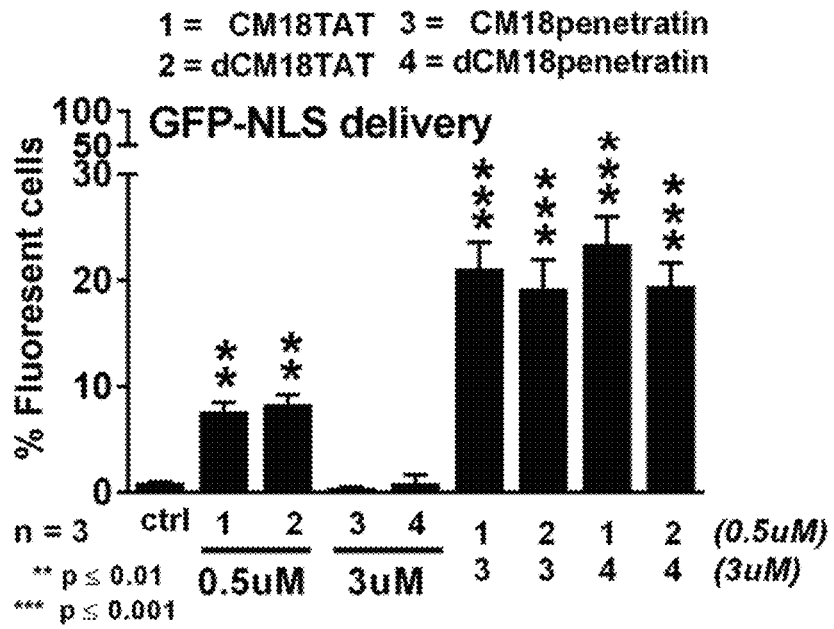
FIGS. 14 and 15 show the results of GFP-NLS transduction efficiency experiments in which GFP-NLS cargo protein (5 µM) was co-incubated with different concentrations and combinations of CM18-TAT (labeled "CM18TAT"), CM18-Penetratin (labeled "CM18penetratin"), and dimers of each (dCM18-TAT-Cys, dCM18-Penetratin-Cys; labeled "dCM18TAT" and "dCM18penetratin", respectively), prior to being exposed to HeLa cells. Cells were evaluated by flow cytometry and the percentages of fluorescent (GFP-positive) cells are shown.

Data in FIG. 14

| No. in FIG. 14 | Shuttle agent | Cells | Concentration (μM) | Mean (%) (n = 3) | Standard deviation |
|---|---|---|---|---|---|
| ctrl | No shuttle | HeLa | 0 | 0.41 | 0.10 |
| 1 | CM18-TAT-Cys | HeLa | 0.5 | 7.64 | 0.85 |
| 2 | dCM18-TAT-Cys | HeLa | 0.5 | 8.29 | 0.91 |
| 3 | CM18-Penetratin-Cys | HeLa | 3 | 0.43 | 0.08 |
| 4 | dCM18-Penetratin-Cys | HeLa | 3 | 0.85 | 0.07 |
| 1 + 3 | CM18-TAT-Cys + CM18-Penetratin-Cys | HeLa | 0.5 3 | 21.1 | 2.47 |
| 2 + 3 | dCM18-TAT-Cys + CM18-Penetratin-Cys | HeLa | 0.5 3 | 19.22 | 2.73 |
| 1 + 4 | CM18-TAT-Cys + dCM18-Penetratin-Cys | HeLa | 0.5 3 | 23.44 | 2.51 |
| 2 + 4 | dCM18-TAT-Cys + dCM18-Penetratin-Cys | HeLa | 0.5 3 | 19.47 | 2.16 |

TABLE 5.3

Figure 15:
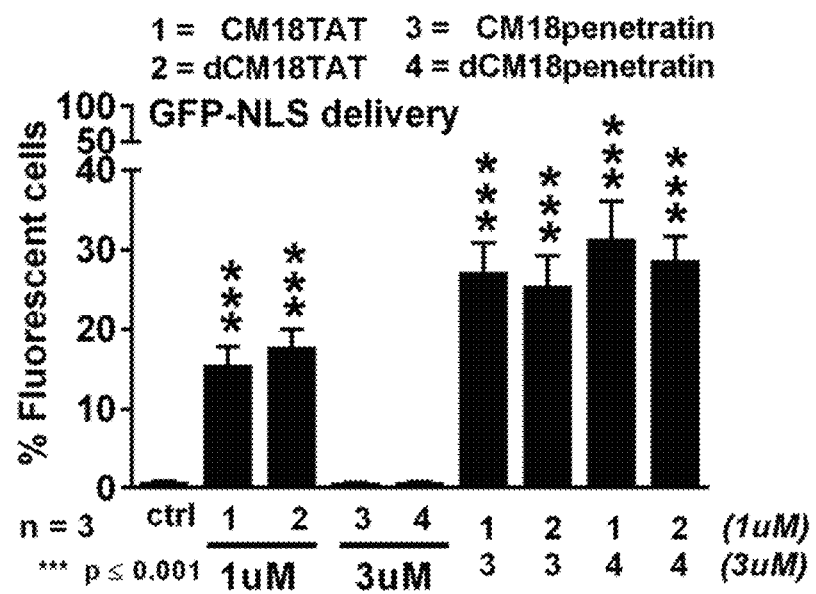

Data in FIG. 15

| No. in FIG. 15 | Shuttle agent | Cells | Concentration (μM) | Mean (%) (n = 3) | Standard deviation |
|---|---|---|---|---|---|
| ctrl | No shuttle | HeLa | 0 | 0.44 | 0.12 |
| 1 | CM18-TAT-Cys | HeLa | 1 | 15.56 | 2.24 |
| 2 | dCM18-TAT-Cys | HeLa | 1 | 17.83 | 2.13 |
| 3 | CM18-Penetratin-Cys | HeLa | 3 | 0.68 | 0.05 |
| 4 | dCM18-Penetratin-Cys | HeLa | 3 | 0.84 | 0.07 |
| 1 + 3 | CM18-TAT-Cys + CM18-Penetratin-Cys | HeLa | 1 3 | 27.26 | 3.61 |
| 2 + 3 | dCM18-TAT-Cys + CM18-Penetratin-Cys | HeLa | 1 3 | 25.47 | 3.77 |
| 1 + 4 | CM18-TAT-Cys + dCM18-Penetratin-Cys | HeLa | 1 3 | 31.47 | 4.59 |
| 2 + 4 | dCM18-TAT-Cys + dCM18-Penetratin-Cys | HeLa | 1 3 | 28.74 | 2.93 |

The results in Tables 5.2 and 5.3 and FIGS. 14 and 15 show that the transduction efficiency of GFP-NLS is increased in HeLa cells using the shuttle agents CM18-TAT-Cys and dCM18-TAT-Cys (see bars "1" and "2" in FIGS. 14 and 15). Although no GFP-NLS intracellular delivery was observed using CM18-Penetratin-Cys or dCM18-Penetratin-Cys alone (see bars "3" and "4" in FIGS. 14 and 15), combination of CM18-TAT-Cys with CM18-Penetratin-Cys (monomer or dimer) improved GFP-NLS intracellular delivery (see four right-most bars in FIGS. 14 and 15).

5.5 GFP-NLS Transduction by Shuttle Agents in HeLa Cells: 5 min v. 1 h Incubation; with or without FBS HeLa cells were cultured and tested in the protein transduction assay described in Example 3.1. GFP-NLS recombinant protein (5 μM) was co-incubated with either CM18-TAT-Cys (3.5 μM) alone or with dCM18-Penetratin-Cys (1 μM). Cells were incubated for 5 minutes or 1 hour in plain DMEM media ("DMEM") or DMEM media containing 10% FBS ("FBS"), before being subjected to flow cytometry analysis as described in Example 3.3. The results are shown in Table 5.4, and in FIG. 16. Cells that were not treated with shuttle agent or GFP-NLS ("ctrl"), and cells that were treated with GFP-NLS without shuttle agent ("GFP-NLS 5 μM") were used as controls.

TABLE 5.4

Figure 16:
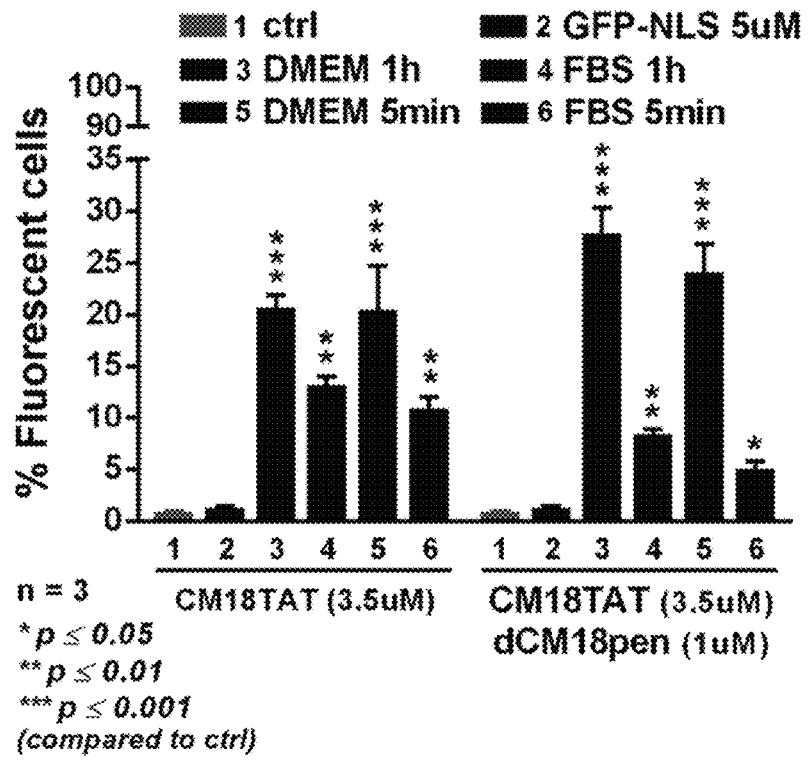
FIG. 16 shows the results of a GFP-NLS transduction efficiency experiment in which GFP-NLS cargo protein (5 µM) was co-incubated with either CM18-TAT-Cys (3.5 µM, labeled "CM18TAT") alone or with dCM18-Penetratin-Cys (1 µM, labeled "dCM18pen") for 5 minutes or 1 hour in plain DMEM media ("DMEM") or DMEM media containing 10% FBS ("FBS"), before being subjected to flow cytometry analysis. The percentages of fluorescent (GFP-positive) cells are shown. Cells that were not treated with shuttle agent or GFP-NLS ("ctrl"), and cells that were treated with GFP-NLS without shuttle agent ("GFP-NLS 5 µM") were used as controls.

Data in FIG. 16

| Shuttle | No. in FIG. 16 | Cells | Medium | Incubation time | Shuttle Conc. (μM) | Mean (%) (n = 3) | Standard deviation |
|---|---|---|---|---|---|---|---|
| No shuttle (Ctrl) | 1 | HeLa | DMEM | 1 h | 0 | 0.59 | 0.09 |
| GFP-NLS alone | 2 | HeLa | DMEM | 1 h | 0 | 1.19 | 0.31 |
| CM18-TAT-Cys | 3 | HeLa | DMEM | 1 h | 3.5 | 20.69 | 1.19 |
| | 4 | HeLa | FBS | 1 h | 3.5 | 13.20 | 0.82 |
| CM18-TAT-Cys | 5 | HeLa | DMEM | 5 min | 3.5 | 20.45 | 4.26 |
| | 6 | HeLa | FBS | 5 min | 3.5 | 10.83 | 1.25 |
| No shuttle (Ctrl) | 1 | HeLa | DMEM | 1 h | 0 | 0.53 | 0.11 |
| GFP-NLS alone | 2 | HeLa | DMEM | 1 h | 0 | 1.25 | 0.40 |
| CM18-TAT-Cys + dCM18-Penetratin-Cys | 3 | HeLa | DMEM | 1 h | 3.5 1 | 27.90 | 2.42 |
| | 4 | HeLa | FBS | 1 h | 3.5 1 | 8.35 | 0.46 |
| CM18-TAT-Cys + dCM18-Penetratin-Cys | 5 | HeLa | DMEM | 5 min | 3.5 1 | 24.10 | 2.76 |
| | 6 | HeLa | FBS | 5 min | 3.5 1 | 5.02 | 0.72 |

The results in Table 5.4 and FIG. 16 show that the addition of even a relatively low amount of the dimer dCM18-Penetratin-Cys (1 μM; "dCM18pen") to the CM18-TAT-Cys monomer improved GFP-NLS transduction efficiency. Interestingly, intracellular GFP-NLS delivery was achieved in as little as 5 minutes of incubation, and delivery was still achievable (although reduced) in the presence of FBS.

5.6 GFP-NLS Transduction by Shuttle Agents in THP-1 Suspension Cells

The ability of the shuttle agents to deliver GFP-NLS intracellularly was tested in THP-1 cells, which is an acute monocytic leukemia cell line that grows in suspension. THP-1 cells were cultured (see Example 1) and tested in the protein transduction assay described in Example 3.1. GFP-NLS recombinant protein (5 μM) was co-incubated with or without 1 μM CM18-TAT-Cys, and exposed to the THP-1 cells for 5 minutes, before being subjected to flow cytometry analysis as described in Example 3.3. The results are shown in Table 5.5 and in FIG. 17A. Corresponding cellular toxicity data are presented in FIG. 17B.

TABLE 5.5

Figure 17A:
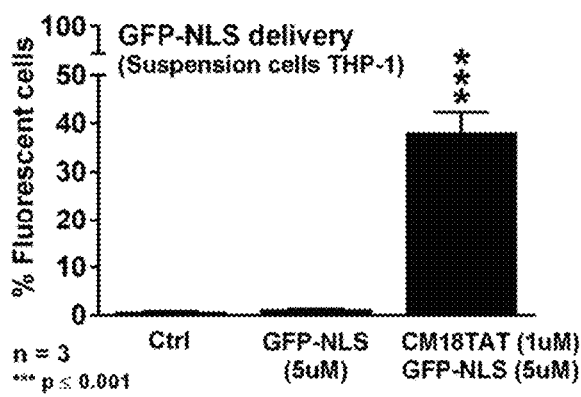
FIGS. 17A-17B show the results of a GFP-NLS transduction efficiency experiment in which GFP-NLS cargo protein (5 µM) was co-incubated with or without 1 µM CM18-TAT-Cys (labeled "CM18TAT"), prior to being exposed to THP-1 cells. Cells were evaluated by flow cytometry and the percentage of fluorescent (GFP-positive) cells is shown in FIG. 17A, and corresponding cell toxicity data is shown in FIG. 17B.
Figure 17B:
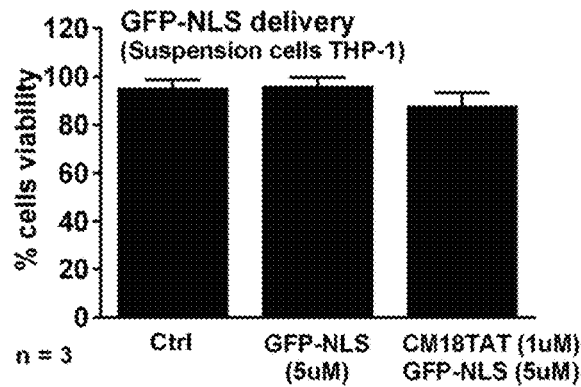

Data in FIG. 17A and 17B

| | | | FIG. 17A | | FIG. 17B Cell viability |
|---|---|---|---|---|---|
| Shuttle | Cells | Shuttle Conc. (μM) | Mean (%) (n = 3) | Standard deviation | (%) (±St. Dev.; n = 3) |
| No shuttle (Ctrl) | THP-1 | 0 | 1.23 | 0.16 | 95 ± 4 |
| GFP-NLS alone | | 0 | 2.49 | 0.37 | 96 ± 3 |
| CM18-TAT-Cys | | 1 | 38.1 | 4.16 | 85 ± 6 |

The results in Table 5.5 and FIG. 17A-17B demonstrate the ability of the shuttle agents to deliver protein cargo intracellularly to a human monocytic cell line grown in suspension.

Example 6

Peptide Shuttle Agents Increase Transduction Efficiency of an FITC-Labeled Anti-Tubulin Antibody The experiments in Examples 3-5 showed the ability of shuttle agents to increase the transduction efficiency of GFP, TAT-GFP, and GFP-NLS. The experiments presented in this example show that the shuttle agents can also deliver a larger protein cargo: an FITC-labeled anti-tubulin antibody. The FITC-labeled anti-tubulin antibody was purchased from (Abcam, ab64503) and has an estimated molecular weight of 150 KDa. The delivery and microscopy protocols are described in Example 3.

6.1 Transduction of a Functional Antibody by CM18-TAT-Cys in HeLa Cells: Visualization by Microscopy FITC-labeled anti-tubulin antibody (0.5 µM) was co-incubated with 5 µM of CM18-TAT-Cys and exposed to HeLa cells for 1 hour. Antibody delivery was visualized by bright field (20×) and fluorescence microscopy (20× and 40×). As shown in FIG. 18, fluorescent tubulin fibers in the cytoplasm were visualized, demonstrating the functionality of the antibody inside the cell.

6.2 Transduction of a Functional Antibody by CM18-TAT-Cys, CM18-Penetratin-Cys, and Dimers in HeLa Cells: Flow Cytometry HeLa cells were cultured and tested in the protein transduction assay described in Example 3.1. FITC-labeled anti-tubulin antibody (0.5 µM) was co-incubated with 3.5 µM of CM18-TAT-Cys, CM18-Penetratin-Cys or dCM18-Penetratin-Cys, or a combination of 3.5 µM of CM18-TAT-Cys and 0.5 µM of dCM18-Penetratin-Cys, and exposed to HeLa cells for 1 hour. The cells were subjected to flow cytometry analysis as described in Example 3.3. Results are shown in Table 6.1 and FIG. 19A. Corresponding cellular toxicity data are presented in FIG. 19B.

TABLE 6.1

Figure 19A:
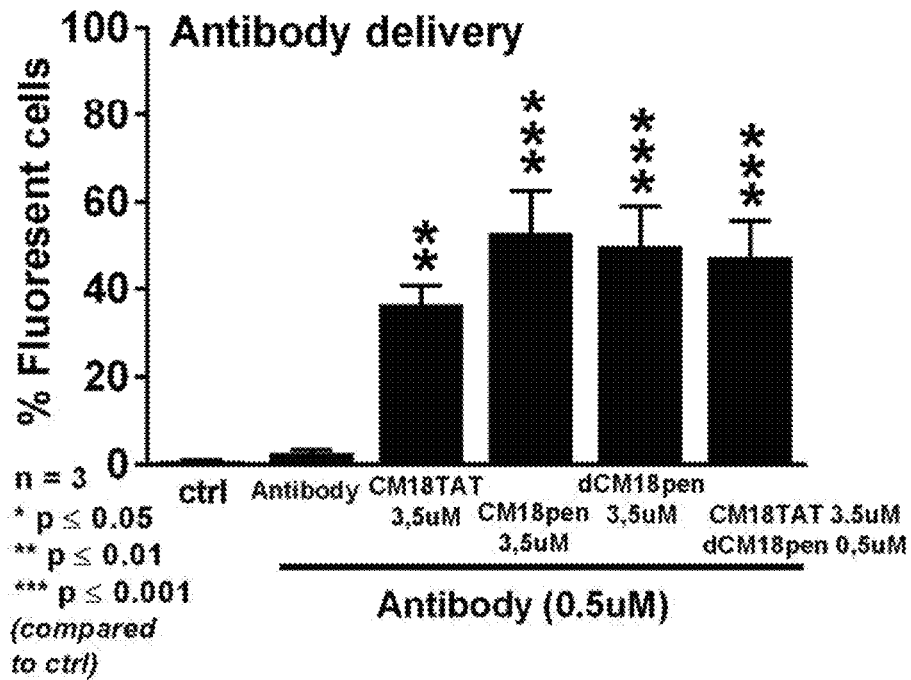
FIGS. 19A-19B show the results of an FITC-labeled anti-tubulin antibody transduction efficiency experiment in which the antibody cargo protein (0.5 µM) was co-incubated with 3.5 µM of CM18-TAT-Cys (labeled "CM18TAT"), CM18-Penetratin-Cys (labeled "CM18pen") or dCM18-Penetratin-Cys (labeled "dCM18pen"), or a combination of 3.5 µM of CM18-TAT-Cys and 0.5 µM of dCM18-Penetratin-Cys, prior to being exposed to HeLa cells. Cells were evaluated by flow cytometry and the percentage of fluorescent (FITC-positive) cell is shown in FIG. 19A, and corresponding cell toxicity data is shown in FIG. 19B.
Figure 19B:
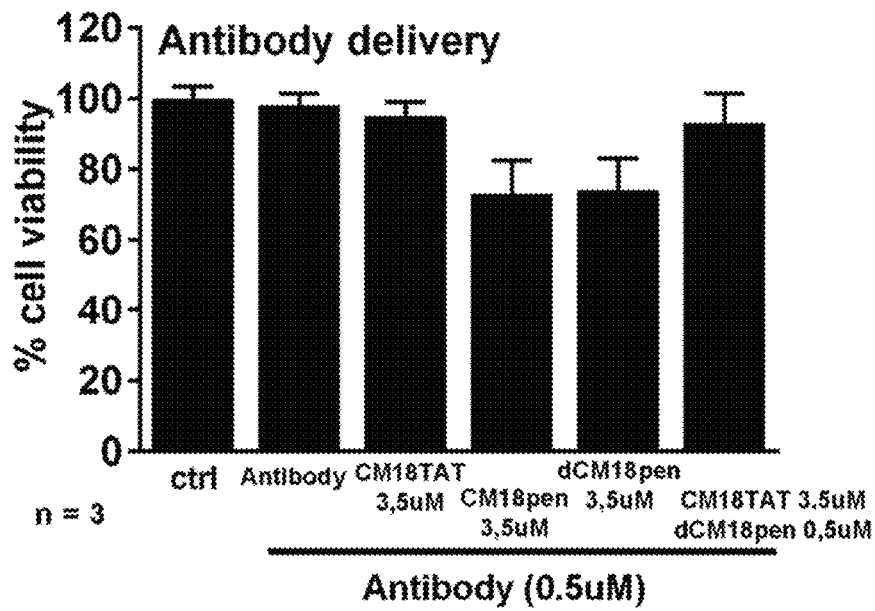

Data from FIG. 19A and 19B

| Domains | Shuttle agent | Cells | Shuttle Conc. (µM) | FIG.19A Mean (%) (n = 3) | Standard deviation | FIG.19B Cell viability (%) (± St. Dev.; n = 3) |
|---|---|---|---|---|---|---|
| — | No shuttle ("Ctrl") | HeLa | 0 | 0.9 | 0.06 | 98 ± 1.0 |
| — | Antibody alone ("antibody") | HeLa | 0 | 2.66 | 0.61 | 96 ± 3.4 |
| ELD-CPD | CM18-TAT-Cys | HeLa | 3.5 | 36.56 | 4.06 | 95 ± 4.06 |
| | CM18-Penetratin-Cys | HeLa | 3.5 | 53.05 | 9.5 | 73 ± 9.5 |
| ELD-CPD dimer | dCM18-Penetratin-Cys | HeLa | 3.5 | 50.23 | 9.12 | 74 ± 9.0 |
| ELD-CPD + ELD-CPD dimer | CM18-TAT-Cys + dCM18-Penetratin-Cys | HeLa | 3.5 0.5 | 47.19 | 8.5 | 93 ± 8.5 |

The results in Table 6.1 and FIGS. 18A-18C and 19A-19B show that both CM18-TAT-Cys and CM18-Penetratin-Cys facilitate intracellular delivery of an FITC-labeled anti-tubulin antibody. In contrast to the results with GFP, TAT-GFP, and GFP-NLS in Examples 3-5, CM18-Penetratin-Cys was able to deliver the antibody cargo intracellularly when used alone (without CM18-TAT-Cys). However, combination of CM18-TAT-Cys and dCM18-Penetratin-Cys allowed for higher intracellular delivery as compared with CM18-TAT-Cys alone, and with less cell toxicity as compared to CM18-Penetratin-Cys and dCM18-Penetratin-Cys (see FIGS. 19A and 19B).

Example 7

CM18-TAT-Cys Enables Intracellular Plasmid DNA Delivery but Poor Plasmid Expression The ability of the CM18-TAT-Cys shuttle agent to deliver plasmid DNA intracellularly was tested in this example on HEK293A cells using a plasmid encoding GFP.

7.1 Transfection Assay in HEK293A Cells

One day before the transfection assay was performed, mammalian cells (HEK293A) in exponential growth phase were harvested and plated in a 24-well plate (50,000 cells per well). The cells were incubated overnight in appropriate growth media containing FBS. The next day, in separate sterile 1.5 mL tubes, pEGFP labeled with a Cy5™ fluorochrome was mixed for 10 min at 37° C. with CM18-TAT-Cys (0.05, 0.5, or 5 µM) in fresh PBS at a final 100 µL volume. The media in wells was removed and the cells were quickly washed three times with PBS and 500 µL of warm media without FBS was added. The pEGFP and CM18-TAT-Cys solution was added to the cells and incubated at 37° C. for 4 hours. After the incubation, cells were washed with PBS and fresh media containing FBS was added. Cells were incubated at 37° C. before being subjected to flow cytometry analysis as described in Example 3.

7.2 Plasmid DNA Delivery with CM18-TAT-Cys

Plasmid DNA (pEGFP) was labeled with a Cy5™ dye following the manufacturer's instructions (Mirus Bio LLC). Cy5™ Moiety did not influence transfection efficiency when compared to unlabelled plasmid using standard transfection protocol (data not shown). Flow cytometry analysis allowed quantification of Cy5™ emission, corresponding to DNA intracellular delivery, and GFP emission, corresponding to successful nuclear delivery, DNA transcription and protein expression. The results are shown in Table 7.1 and in FIG. 20.

TABLE 7.1

Figure 20:
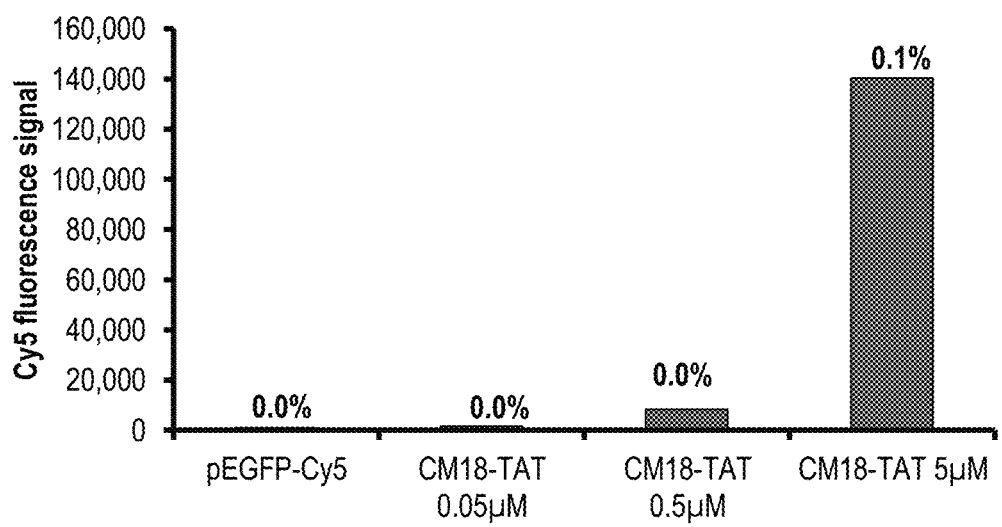
FIG. 20 shows the results of DNA transfection efficiency experiment in which plasmid DNA (pEGFP) was labeled with a Cy5™ dye was co-incubated with 0, 0.05, 0.5, or 5 µM of CM18-TAT-Cys (labeled "CM18-TAT"), prior to being exposed to HEK293A cells. Flow cytometry analysis allowed quantification of Cy5™ emission (corresponding to DNA intracellular delivery; y-axis) and GFP emission (corresponding to successful nuclear delivery of DNA; percentage indicated above each bar).

Data from FIG. 20

| | | Cy5 ™ fluorescence | | GFP expression | |
|---|---|---|---|---|---|
| Sample | DNA (ng) | Mean Cy5 ™ signal (n = 3) | Standard deviation | Mean (% of cells with GFP signal; n = 3) | Standard deviation |
| pEGFP-Cy5 alone | 500 | 914 | 0 | 0.0% | n/a |
| CM18-TAT-Cys, 0.05 µM | 500 | 1450 | 120 | 0.0% | n/a |
| CM18-TAT-Cys, 0.5 µM | 500 | 8362 | 294 | 0.0% | n/a |
| CM18-TAT-Cys, 5 µM | 500 | 140 497 | 3977 | 0.1% | n/a |

The results shown in Table 7.1 and in FIG. 20 show that CM18-TAT-Cys was able to increase the intracellular delivery the plasmid DNA when used at 0.05, 0.5 and 5 µM concentrations, as compared to cell incubated with DNA alone ("pEGFP-Cy5"). However, no expression of GFP was detected in the cells, which suggests that very little of the plasmid DNA gained access to the cytoplasmic compartment, allowing nuclear localization. Without being bound by theory, it is possible that the plasmid DNA was massively sequestered in endosomes, preventing escape to the cytoplasmic compartment. Salomone et al., 2013 reported the use of a CM18-TAT11 hybrid peptide to deliver plasmid DNA intracellularly. They used the luciferase enzyme reporter assay to assess transfection efficiency, which may not be ideal for quantifying the efficiency of cytoplasmic/nuclear delivery, as the proportion of plasmid DNA that is successfully released from endosomes and delivered to the nucleus may be overestimated due to the potent activity of the luciferase enzyme. In this regard, the authors of Salomone et al., 2013 even noted that the expression of luciferase occurs together with a massive entrapment of (naked) DNA molecules into vesicles, which is consistent with the results shown in Table 7.1 and in FIG. 20.

Example 8

Addition of a Histidine-Rich Domain to Shuttle Agents Further Improves GFP-NLS Transduction Efficiency
8.1 GFP-NLS Transduction by His-CM18-TAT-Cys in HeLa Cells: Visualization by Microscopy GFP-NLS (5 µM; see Example 5) was co-incubated with 5 µM of CM18-TAT-Cys or His-CM18-TAT and exposed to HeLa cells for 1 hour. Nuclear fluorescence of intracellularly delivered GFP-NLS was confirmed by fluorescence microscopy (data not shown), indicating successful delivery of GFP-NLS to the nucleus.
8.2 GFP-NLS Transduction by His-CM18-TAT in HeLa Cells: Flow Cytometry HeLa cells were cultured and tested in the protein transduction assay described in Example 3.1. GFP-NLS (5 µM) was co-incubated with 0, 1, 3, or 5 µM of CM18-TAT-Cys or His-CM18-TAT, and exposed to HeLa cells for 1 hour. The cells were subjected to flow cytometry analysis as described in Example 3.3. Results are shown in Table 8.1 and FIG. 21A. Corresponding cellular toxicity data are presented in FIG. 21B.

TABLE 8.1

Figure 21A:
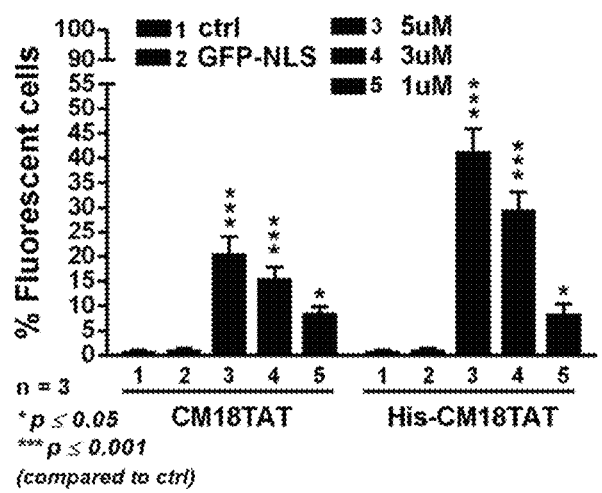
FIGS. 21A-21B show the results of a GFP-NLS transduction efficiency experiment in which the GFP-NLS cargo protein (5 µM) was co-incubated with 1, 3, or 5 µM of CM18-TAT-Cys (labeled "CM18TAT"), of His-CM18-TAT (labeled "His-CM18TAT"), prior to being exposed to HeLa cells. Cells were evaluated by flow cytometry and the percentage of fluorescent (GFP-positive) cell is shown in FIG. 21A, and corresponding cell toxicity data is shown in FIG. 21B.
Figure 21B:
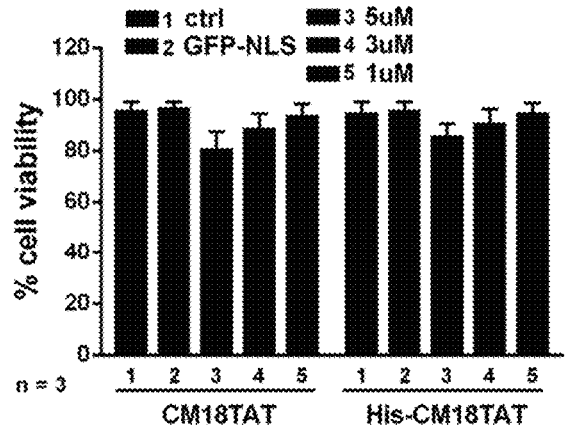

Data from FIG. 21A and 21B

| | | | FIG. 21A | | FIG. 21B |
|---|---|---|---|---|---|
| Shuttle agent | Cells | Shuttle Conc. (µM) | Mean (%) cell with GFP signal (n = 3) | Standard deviation | Cell viability (%) (±St. Dev.; n = 3) |
| Ctrl (no shuttle, no GFP-NLS) | HeLa | 0 | 0.63 | 0.10 | 96 ± 3.17 |
| GFP-NLS alone | | 0 | 0.93 | 0.26 | 97 ± 2.05 |
| | | 5 | 20.54 | 3.51 | 81 ± 6.34 |
| CM18-TAT-Cys | | 3 | 15.66 | 2.18 | 89 ± 5.37 |
| | | 1 | 8.64 | 1.11 | 94 ± 4.28 |
| Ctrl (no shuttle, no GFP-NLS) | HeLa | 0 | 0.51 | 0.28 | 95 ± 4.19 |
| GFP-NLS alone | | 0 | 1.07 | 0.42 | 96 ± 3.16 |
| | | 5 | 41.38 | 4.59 | 86 ± 4.59 |
| His-CM18-TAT | | 3 | 29.58 | 3.61 | 91 ± 5.18 |
| | | 1 | 8.45 | 1.83 | 95 ± 3.55 |

Strikingly, the results in Table 8.1 and in FIG. 21A-21B show that His-CM18-TAT was able to increase GFP-NLS protein transduction efficiency by about 2-fold at 3 µM and 5 µM concentrations, as compared to CM18-TAT-Cys. These results suggest that adding a histidine-rich domain to a shuttle agent comprising an ELD and CPD, may significantly increase its polypeptide cargo transduction efficiency. Alternatively or in parallel, combining the shuttle agents with a further independent synthetic peptide containing a histidine-rich domain fused to a CPD (but lacking an ELD) may provide a similar advantage for protein transduction, with the added advantage of allowing the concentration of the histidine-rich domain to be varied or controlled independently from the concentration of the shuttle agent. Without being bound by theory, the histidine-rich domain may act as a proton sponge in the endosome, providing another mechanism of endosomal membrane destabilization.

Example 9

His-CM18-PTD4 Increases Transduction Efficiency and Nuclear Delivery of GFP-NLS, mCherry™-NLS and FITC-Labeled Anti-Tubulin Antibody
9.1 Protein Transduction Protocols
Protocol A: Protein Transduction Assay for Delivery in Cell Culture Medium One day before the transduction assay was performed, cells in exponential growth phase were harvested and plated in a 96-well plate (20,000 cells per well). The cells were incubated overnight in appropriate growth media containing FBS (see Example 1). The next day, in separate sterile 1.5-mL tubes, cargo protein at the desired concentration was pre-mixed (pre-incubated) for 10 min at 37° C. with the desired concentration of shuttle agents in 50 µL of fresh serum-free medium (unless otherwise specified). The media in wells was removed and the cells were washed one to three times (depending on the type of cells used) with PBS previously warmed at 37° C. The cells were incubated with the cargo protein/shuttle agent mixture at 37° C. for the desired length of time. After the incubation, the cells were washed three times with PBS and/or heparin (0.5 mg/mL) previously warmed at 37° C. The washes with heparin were used for human THP-1 blood cells to avoid undesired cell membrane-bound protein background in subsequent analyses (microscopy and flow cytometry). The cells were finally incubated in 50 µL of fresh medium with serum at 37° C. before analysis.
Protocol B: Protein Transduction Assay for Adherent Cells in PBS One day before the transduction assay was performed, cells in exponential growth phase were harvested and plated in a 96-well plate (20,000 cells per well). The cells were incubated overnight in appropriate growth media containing serum (see Example 1). The next day, in separate sterile 1.5-mL tubes, shuttle agents were diluted in sterile distilled water at room temperature (if the cargo is or comprised a nucleic acid, nuclease-free water was used). Cargo protein (s) were then added to the shuttle agents and, if necessary, sterile PBS was added to obtain the desired concentrations of shuttle agent and cargo in a sufficient final volume to cover the cells (e.g., 10 to 100 µL per well for a 96-well plate). The shuttle agent/cargo mixture was then immediately used for experiments. At least three controls were included for each experiment, including: (1) shuttle agent alone (e.g., at highest concentration tested); (2) cargo alone; and (3) without any cargo or shuttle agent. The media in wells was removed, cells were washed once with PBS previously warmed at 37° C., and the shuttle agent/cargo mixture was then added to cover all cells for the desired length of time. The shuttle agent/cargo mixture in wells was removed, the cells were washed once with PBS, and fresh complete medium was added. Before analysis, the cells were washed once with PBS and fresh complete medium was added.
Protocol C: Protein Transduction Assay for Suspension Cells in PBS One day before the transduction assay was performed, suspension cells in exponential growth phase were harvested and plated in a 96-well plate (20,000 cells per well). The cells were incubated overnight in appropriate growth media containing serum (see Example 1). The next day, in separate sterile 1.5-mL tubes, shuttle agents were diluted in sterile distilled water at room temperature (if the cargo is or comprised a nucleic acid, nuclease-free water was used). Cargo protein(s) were then added to the shuttle agents and, if necessary, sterile PBS or cell culture medium (serum-free) was added to obtain the desired concentrations of shuttle agent and cargo in a sufficient final volume to resuspend the cells (e.g., 10 to 100 μL per well in a 96-well plate). The shuttle agent/cargo mixture was then immediately used for experiments. At least three controls were included for each experiment, including: (1) shuttle agent alone (e.g., at highest concentration tested); (2) cargo alone; and (3) without any cargo or shuttle agent. The cells were centrifuged for 2 minutes at 400 g, the medium was then removed and the cells were resuspended in PBS previously warmed at 37° C. The cells were centrifuged again 2 minutes at 400 g, the PBS removed, and the cells were resuspended in the shuttle agent/cargo mixture. After the desired incubation time, 100 μL of complete medium was added directly on the cells. Cells were centrifuged for 2 minutes at 400 g and the medium was removed. The pellet was resuspended and washed in 200 μL of PBS previously warmed at 37° C. After another centrifugation, the PBS was removed and the cells were resuspended in 100 μL of complete medium. The last two steps were repeated one time before analysis.

Figure 22A:
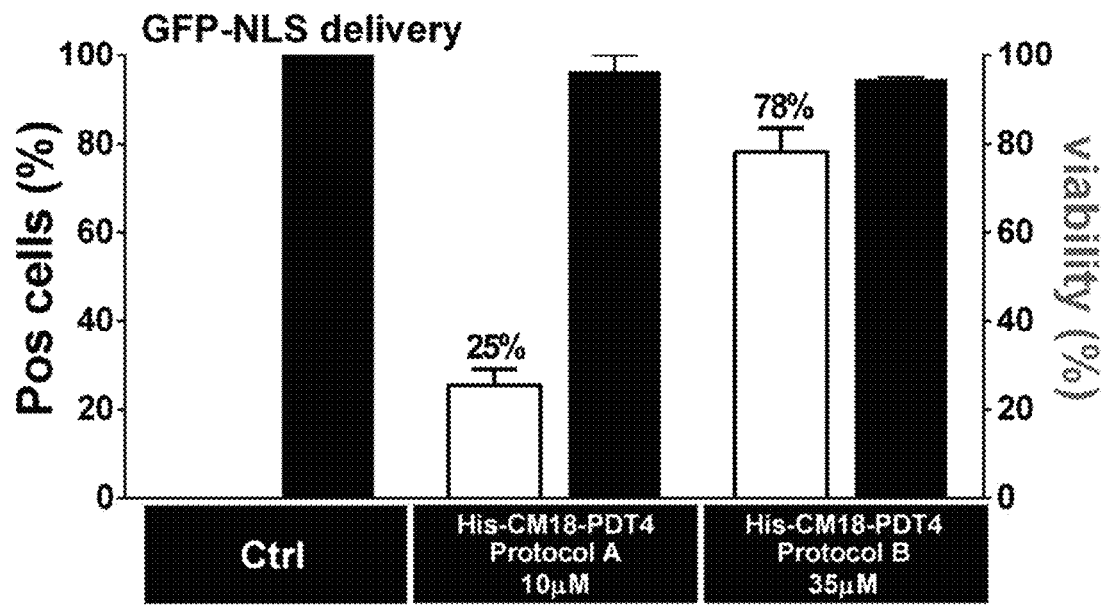
FIGS. 22A-22B show the results of a transduction efficiency experiment in which GFP-NLS cargo protein was intracellularly delivered using the shuttle His-CM18-PTD4 in HeLa cells. GFP-NLS transduction efficiency was evaluated by flow cytometry and the percentage of GFP fluorescent cells ("Pos cells (%)"), as well as corresponding cell viability data ("viability (%)") are shown.

9.2 GFP-NLS Transduction by His-CM18-PTD4 in HeLa Cells using Protocol A or B: Flow Cytometry To compare the effects of different protocols on shuttle agent transduction efficiency, HeLa cells were cultured and tested in the protein transduction assays using Protocol A or B as described in Example 9.1. Briefly, GFP-NLS recombinant protein (5 μM; see Example 5.1) was co-incubated with 10 μM of His-CM18-PTD4 and exposed to HeLa cells for 1 hour using Protocol A, or was co-incubated with 35 μM of His-CM18-PTD4 and exposed to HeLa cells for 10 seconds using Protocol B. The cells were subjected to flow cytometry analysis as described in Example 3.3. Results are shown in Table 9.1 and FIG. 22A. ("Pos cells (%)" is the percentage of cells emanating a GFP signal).

TABLE 9.1

Comparison of Protein Transduction Protocols A and B: Data from FIG. 22A

| Protocol | Shuttle | Cells | Conc. of shuttle (μM) | Conc. of GFP-NLS (μM) | Mean % cells with GFP signal (± St. Dev.; n = 3) | Cell viability (%) (± St. Dev.; n = 3) |
|---|---|---|---|---|---|---|
| B | None ("Ctrl") | HeLa | 0 | 5 | 0.53 ± 0.07 | 100 |
| A | His-CM18-PTD4 | HeLa | 10 | 5 | 25.4 ± 3.6 | 96.4 ± 2.7 |
| B | His-CM18-PTD4 | HeLa | 35 | 5 | 78.3 ± 5.3 | 94.6 ± 0.4 |

The above results show that higher protein transduction efficiency for the cargo GFP-NLS using the shuttle agent His-CM18-PTD4 was obtained using Protocol B, as compared to Protocol A.

Figure 22B:
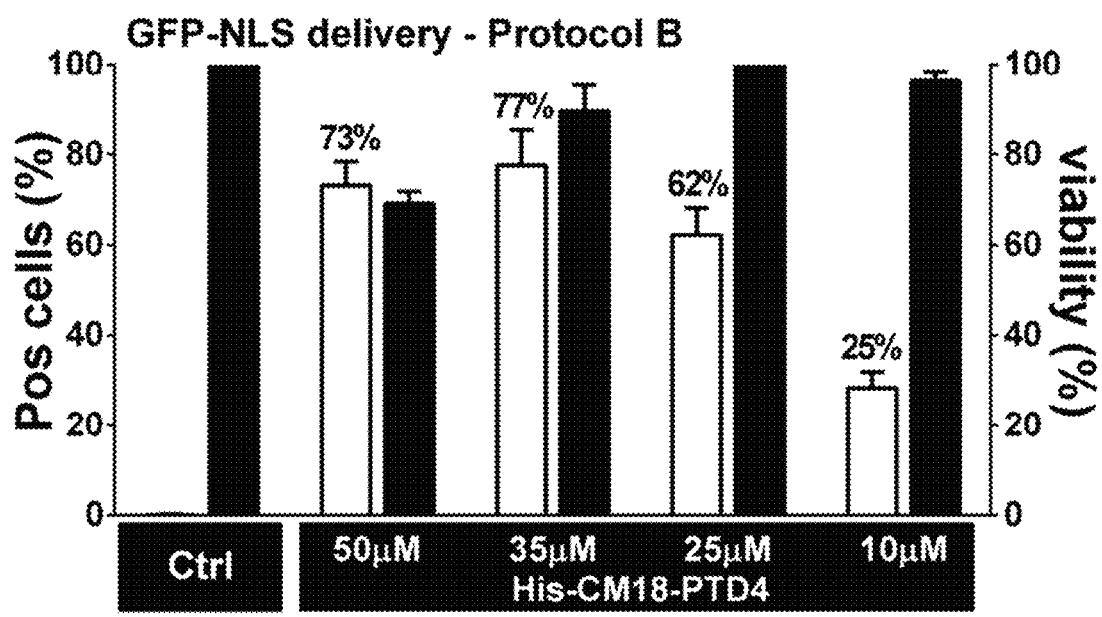

9.3 GFP-NLS Transduction by His-CM18-PTD4 in HeLa Cells using Protocol B: Flow Cytometry A dose response experiment was performed to evaluate the effect of His-CM18-PTD4 concentration on protein transduction efficiency. HeLa cells were cultured and tested in the protein transduction assay described in Protocol B of Example 9.1. Briefly, GFP-NLS recombinant protein (5 μM; see Example 5.1) was co-incubated with 0, 50, 35, 25, or 10 μM of His-CM18-PTD4, and then exposed to HeLa cells for 10 seconds. The cells were subjected to flow cytometry analysis as described in Example 3.3. Results are shown in Table 9.2 and FIG. 22B.

TABLE 9.2

Dose response of shuttle agent using Protocol B: Data from FIG. 22B

| Protocol | Shuttle | Cells | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|---|
| B | None ("Ctrl") | HeLa | 0 | 5 | 0.13 ± 0.1 | 100 ± 0 |
| | His-CM18-PTD4 | | 50 | 5 | 73.2 ± 5.2 | 69.2 ± 2.7 |
| | | | 35 | 5 | 77.7 ± 7.8 | 79.6 ± 5.9 |
| | | | 25 | 5 | 62.1 ± 6.1 | 95.3 ± 3.7 |
| | | | 10 | 5 | 25.3 ± 3.6 | 96.3 ± 2.3 |

The above results show that His-CM18-PTD4 is able to increase GFP-NLS transduction efficiency in HeLa cells in a dose-dependent manner.

9.4 GFP-NLS Transduction by His-CM18-PTD4 in HeLa Cells using Protocol B: Visualization by Microscopy GFP-NLS recombinant protein (5 μM; see Example 5.1) was co-incubated with 35 μM of His-CM18-PTD4, and then exposed to HeLa cells for 10 seconds using Protocol B as described in Example 9.1. The cells were then subjected to fluorescence microscopy analysis as described in Examples 3.2 and 3.2a.

For the sample results shown in FIGS. 23A-23D and 24A-24B, GFP fluorescence of the HeLa cells was immediately visualized by bright field and fluorescence microscopy at 4×, 20× and 40× magnifications after the final washing step.

Figure 23A:
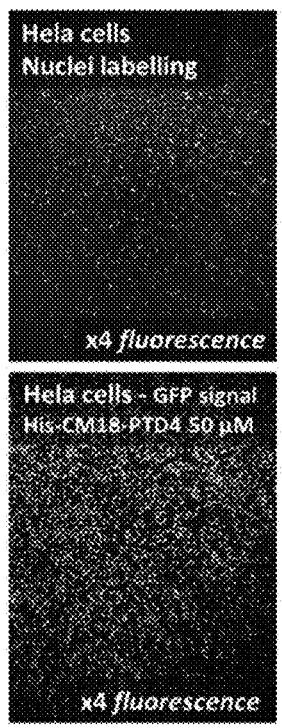
Figure 23B:
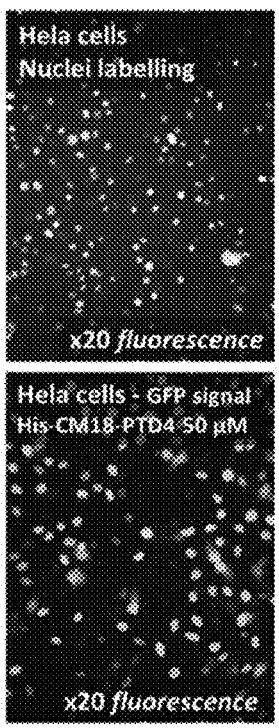
Figure 23C:
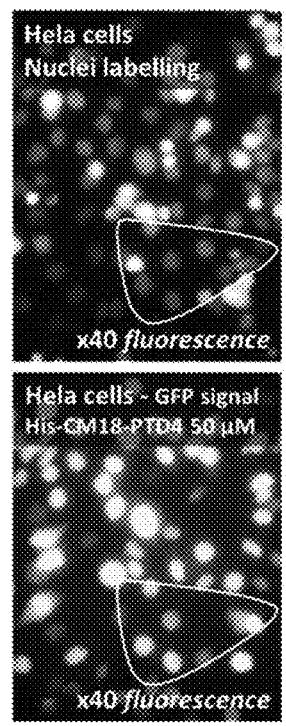
Figure 23D:
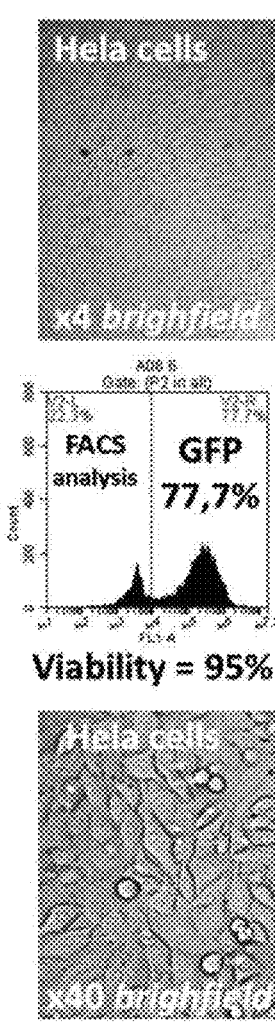

In FIGS. 23A-23D, the upper panels in FIGS. 23A, 23B and 23C show nuclei labelling (DAPI) at 4×, 20× and 40× magnifications, respectively, while the lower respective panels show corresponding GFP-NLS fluorescence. In FIG. 23C, white triangle windows indicate examples of areas of co-labelling between nuclei (DAPI) and GFP-NLS signals. In FIG. 23D, the upper and bottom panels show sample bright field images of the HeLa cells, and the middle panel shows the results of a corresponding FACS analysis (performed as described in Example 3.3), which indicates the percentage of cells in a 96-plate with a GFP signal. No significant GFP fluorescence was observed in negative control samples (i.e., cells exposed to GFP-NLS without any shuttle agent; data not shown).

FIGS. 24A-24B shows bright field (FIG. 24A) and fluorescent images (FIG. 24B). The inset in FIG. 24B shows the results of a corresponding FACS analysis (performed as described in Example 3.3), which indicates the percentage of cells in a 96-plate well with a GFP signal. No significant GFP fluorescence was observed in negative control samples (i.e., cells exposed to GFP-NLS without any shuttle agent; data not shown).

For the sample results shown in FIGS. 25A-25B, the HeLa cells were fixed, permeabilized and subjected to immuno-labelling as described in Example 3.2a before visualization by fluorescence microscopy as described in Example 3.2. GFP-NLS was labelled using a primary mouse monoclonal anti-GFP antibody (Feldan, #A017) and a secondary goat anti-mouse Alexa™-594 antibody (Abcam #150116). The upper panels in FIGS. 25A-25B show nuclei labelling (DAPI), and the lower respective panels show corresponding labelling for GFP-NLS. FIGS. 25A and 25B show sample images at 20× and 40× magnifications, respectively. White triangle windows indicate examples of areas of co-labelling between nuclei and GFP-NLS. No significant GFP-NLS labelling was observed in negative control samples (i.e., cells exposed to GFP-NLS without any shuttle agent; data not shown).

FIG. 26A-26C shows sample images captured with confocal microscopy at 63× magnification of living cells. FIG. 26A shows a bright field image, while FIG. 26B shows the corresponding fluorescent GFP-NLS. FIG. 26C is an overlay between the images in FIGS. 26A and 26B. No significant GFP-NLS fluorescence was observed in negative control samples (i.e., cells exposed to GFP-NLS without any shuttle agent; data not shown).

9.4a FTIC-Labeled Anti-Tubulin Antibody Transduction by His-CM18-PTD4 in HeLa Cells using Protocol B: Visualization by Microscopy FITC-labeled anti tubulin antibody (0.5 µM; Abcam, ab64503) was co-incubated with 50 µM of His-CM18-PTD4, and then exposed to HeLa cells for 10 seconds using Protocol B as described in Example 9.1. The cells were then subjected to fluorescence microscopy analysis as described in Examples 3.2 and 3.2a, wherein the FITC fluorescence of the anti-tubulin antibody in the HeLa cells was immediately visualized by bright field and fluorescence microscopy at 20× magnification after the final washing step. No significant FITC fluorescence was observed in negative control samples (i.e., cells exposed to the FITC-labeled anti-tubulin antibody without any shuttle agent; data not shown).

Overall, the results in Examples 9.4 and 9.4a show that GFP-NLS and FITC-labeled anti-tubulin antibody cargos are successfully transduced and delivered to the nucleus and/or the cytosol of HeLa cells in the presence of the shuttle agent His-CM18-PTD4.

9.5 GFP-NLS Kinetic Transduction by His-CM18-PTD4 in HeLa Cells: Visualization by Microscopy GFP-NLS recombinant protein (5 µM; see Example 5.1) was co-incubated with 50 µM of His-CM18-PTD4, and then exposed to HeLa cells for 10 seconds using Protocol B as described in Example 9.1. After a washing step, the GFP fluorescence of the HeLa cells was immediately visualized by fluorescence microscopy (Example 3.2) at 20× magnification after different intervals of time. Typical results are shown in FIGS. 27A to 27D, in which fluorescence microscopy images were captured after 45, 75, 100, and 120 seconds (see FIGS. 27A, 27B, 27C and 27D, respectively).

As shown in FIG. 27A, diffuse cellular GFP fluorescence was generally observed after 45 seconds, with areas of lower GFP fluorescence in the nucleus in many cells. These results suggest predominantly cytoplasmic and low nuclear distribution of the GPF-NLS delivered intracellularly via the shuttle agent after 45 seconds. FIGS. 27B to 27D show the gradual redistribution of GFP fluorescence to the cell nuclei at 75 seconds (FIG. 27B), 100 seconds (FIG. 27C), and 120 seconds (FIG. 27D) following exposure to the His-CM18-PTD4 shuttle agent and GFP-NLS cargo. No significant cellular GFP fluorescence was observed in negative control samples (i.e., cells exposed to GFP-NLS without any shuttle agent; data not shown).

The results in Example 9.5 show that GFP-NLS is successfully delivered to the nucleus of HeLa cells in the presence of the shuttle agent His-CM18-PTD4 by 2 minutes.

9.6 GFP-NLS and mCherry™-NLS Co-Transduction by His-CM18-PTD4 in HeLa Cells: Visualization by Microscopy mCherry™-NLS recombinant protein was constructed, expressed and purified from a bacterial expression system as described in Example 1.4. The sequence of the mCherry™-NLS recombinant protein was:

[SEQ ID NO: 73]
MHHHHHHGGGGSGGGGSGGASTGIRMVSKCEEDNMAIIKEFMRFKVHME

GSVNGHEFEIEGEGEGRPYEGTQTAKLKVTKGGPLPFAWDILSPQFMYGS

KAYVKHPADIPDYLKLSFPEGFKWERVMNFEDGGVVTVTQDSSLQDGEFI

YKVKLRGTNFPSDGQVMQKKTMGWEASSERMYPEDGALKGEIKQRLKLKD

GGHYDAEVKTTYKAKKPVQLPGAYNVNIKLDITSHNEDYTIVEQYERAEG

RHSTGGMDELYKGGSGGGSGGGSGWIRASSGGR<u>SSDDEATADSQHAAPPK</u>

<u>KKRKV</u>GGSGGGSGGGSGGGRGTEIS
(MW = 34.71 kDa; pI = 6.68)
NLS sequence is underlined
Serine/glycine rich linkers are in bold GFP-NLS recombinant protein (5 µM; see Example 5.1) and mCherry™-NLS recombinant protein (5 µM) were co-incubated together with 35 µM of His-CM18-PTD4, and then exposed to HeLa cells for 10 seconds using Protocol B as described in Example 9.1. After washing steps, the cells were immediately visualized by bright field and fluorescence microscopy at 20× magnifications as described in Example 3.2. Sample results are shown in FIG. 28A-28D, in which corresponding images showing bright field (FIG. 28A), DAPI fluorescence (FIG. 28B), GFP-NLS fluorescence (FIG. 28C), and mCherry™-NLS fluorescence (FIG. 28D) are shown. White triangle windows indicate examples of areas of co-labelling between GFP-NLS and mCherry™ fluorescence signals in cell nuclei. No significant cellular GFP or mCherry™ fluorescence was observed in negative control samples (i.e., cells exposed to GFP-NLS or mCherry™ without any shuttle agent; data not shown).

These results show that GFP-NLS and mCherry™-NLS are successfully delivered together to the nucleus in HeLa cells in the presence of the shuttle agent His-CM18-PTD4.

9.7 GFP-NLS Transduction by His-CM18-PTD4 in THP-1 Suspension Cells: Flow Cytometry The ability of the His-CM18-PTD4 to deliver GFP-NLS in the nuclei of suspension cells was tested using THP-1 cells. THP-1 cells were cultured and tested in the protein transduction assays using Protocols A and C as described in Example 9.1. GFP-NLS (5 µM; see Example 5.1) was co-incubated with 1 µM of His-CM18-PTD4 and exposed to THP-1 cells for 1 hour (Protocol A), or was co-incubated with 5 µM of His-CM18-PTD4 and exposed to THP-1 cells for 15 seconds (Protocol C). The cells were subjected to flow cytometry analysis as described in Example 3.3. Results are shown in Table 9.3 and in FIG. 31.

TABLE 9.3

Figure 31:
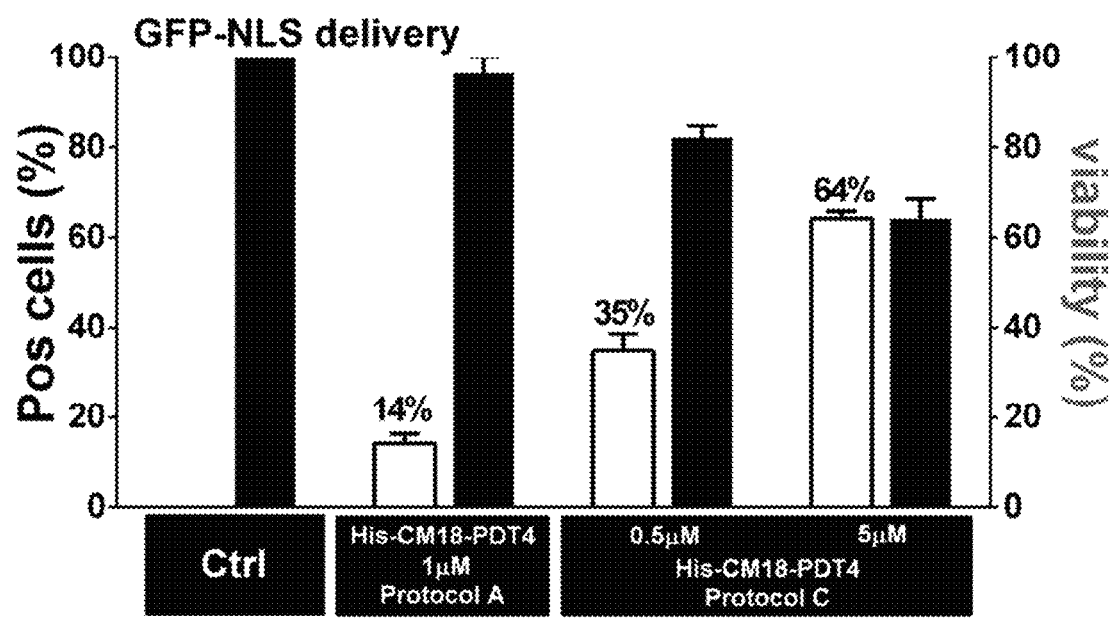
FIG. 31 shows the results of a transduction efficiency experiment in which GFP-NLS cargo protein was intracellularly delivered using the shuttle His-CM18-PTD4 in THP-1 cells using different Protocols (Protocol A vs C). GFP-NLS transduction efficiency was evaluated by flow cytometry and the percentage of GFP fluorescent cells ("Pos cells (%)"), as well as corresponding cell viability data ("viability (%)") are shown. "Ctrl" corresponds to THP-1 cells exposed to GFP-NLS cargo protein in the absence of a shuttle agent.

Data from FIG. 31

| Protocol | Shuttle | Cells | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|---|
| C | No shuttle ("Ctrl") | THP-1 | 0 | 5 | 0.2 ± 0.03 | 99.1 ± 0.7 |
| A | His-CM18-PTD4 | | 1 | 5 | 14.2 ± 2.2 | 96.9 ± 3.6 |
| C | His-CM18-PTD4 | | 0.5 | 5 | 34.9 ± 3.8 | 82.1 ± 2.7 |
| | | | 5 | 5 | 64.1 ± 1.6 | 64.0 ± 4.1 |

9.8 GFP-NLS Transduction by His-CM18-PTD4 in THP-1 Cells: Visualization by Microscopy GFP-NLS recombinant protein (5 μM; see Example 5.1) was co-incubated with 5 μM of His-CM18-PTD4, and then exposed to THP-1 cells for 15 seconds using Protocol C as described in Example 9.1. The cells were subjected to microscopy visualization as described in Example 3.2.

Figure 32A:
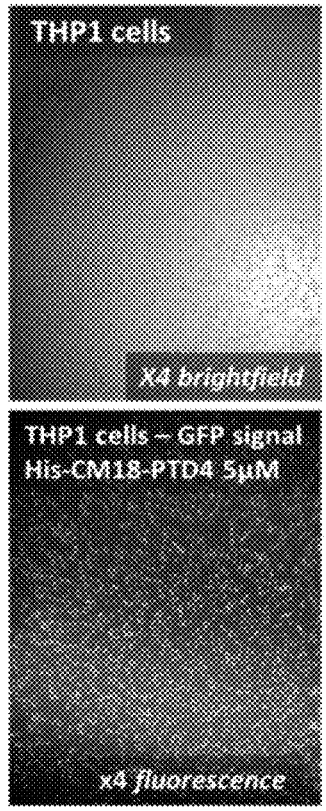
FIGS. 32A-32D show microscopy images of THP-1 cells transduced with GFP-NLS cargo protein using the shuttle His-CM18-PTD4. Images captured under at 4×, 10× and 40× magnifications are shown in FIGS. 32A-32C, respectively. White triangle windows in FIG. 32C indicate examples of areas of co-labelling between cells (bright field) and GFP-NLS fluorescence.
Figure 32B:
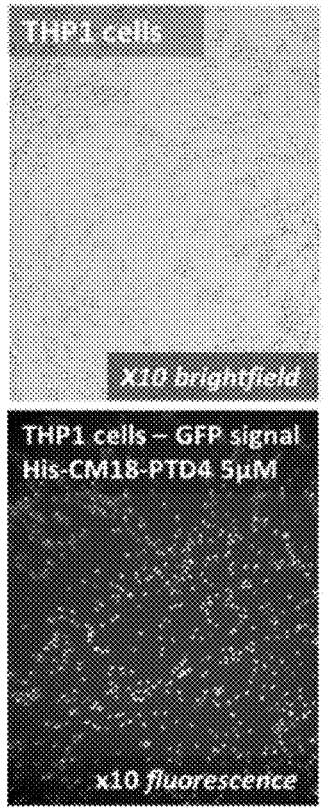
Figure 32C:
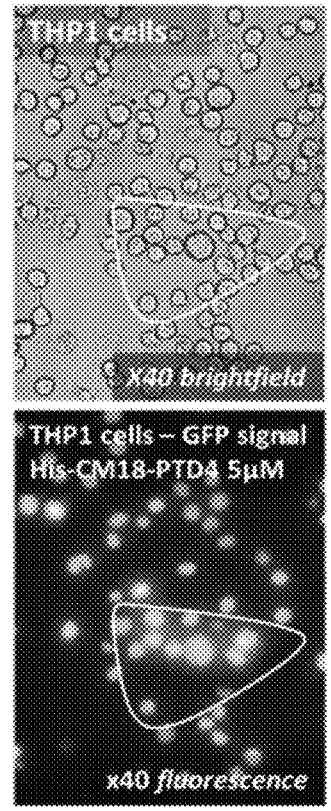
Figure 32D:
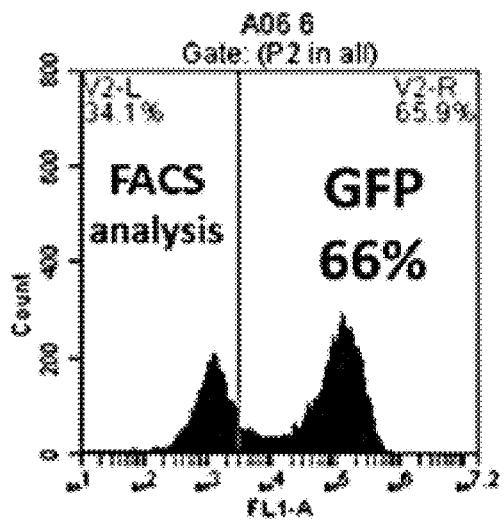
Figure 33E:
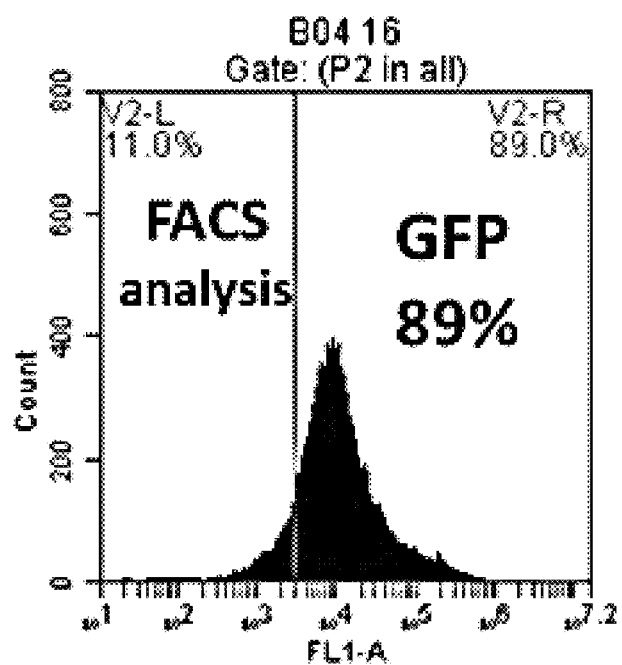
FIG. 33E shows FACS analysis of GFP-positive cells.

For the sample results shown in FIG. 32A-32D, GFP fluorescence of the HeLa cells was immediately visualized by bright field (upper panels in FIGS. 32A-32C) and fluorescence (lower panels in FIGS. 32A-32C) microscopy at 4×, 10× and 40× magnifications (FIGS. 32A-32C, respectively) after the final washing step. White triangle windows in FIG. 32C indicate examples of areas of co-labelling between bright field and fluorescence images. FIG. 32D shows typical results of a corresponding FACS analysis (performed as described in Example 3.3), which indicates the percentage of cells in a 96-plate well with a GFP signal. Additional results are shown in FIG. 33A-33D, in which FIGS. 33A and 33B show bright field images, and FIGS. 33C and 33D show corresponding fluorescence images. White triangle windows indicate examples of areas of co-labelling between FIGS. 33A and 33C, as well as FIGS. 33B and 33D. The right-most panel shows typical results of a corresponding FACS analysis (performed as described in Example 3.3), which indicates the percentage of cells in a 96-plate well with a GFP signal.

No significant cellular GFP fluorescence was observed in negative control samples (i.e., cells exposed to GFP-NLS without any shuttle agent; data not shown).

The results in this example show that GFP-NLS is successfully delivered intracellularly in THP-1 cells in the presence of the shuttle agent His-CM18-PTD4.

Example 10

Different Multi-Domain Shuttle Agents, but not Single-Domain Peptides, Successfully Transduce GFP-NLS in HeLa and THP-1 Cells 10.1 GFP-NLS Transduction by Different Shuttle Agents in HeLa cells: Flow Cytometry HeLa cells were cultured and tested in the protein transduction assays using Protocol B as described in Example 9.1. Briefly, GFP-NLS recombinant protein (5 μM; see Example 5.1) was co-incubated with 50 μM of different shuttle agents and exposed to the HeLa cells for 10 seconds. The cells were subjected to flow cytometry analysis as described in Example 3.3. Results are shown in Table 10.1 and FIG. 29A. "Pos cells (%)" is the mean percentages of all cells that emanate a GFP signal. The negative control ("Ctrl") corresponds to cells that were incubated with GFP-NLS recombinant protein (5 μM) without any shuttle agent.

TABLE 10.1

Figure 29A:
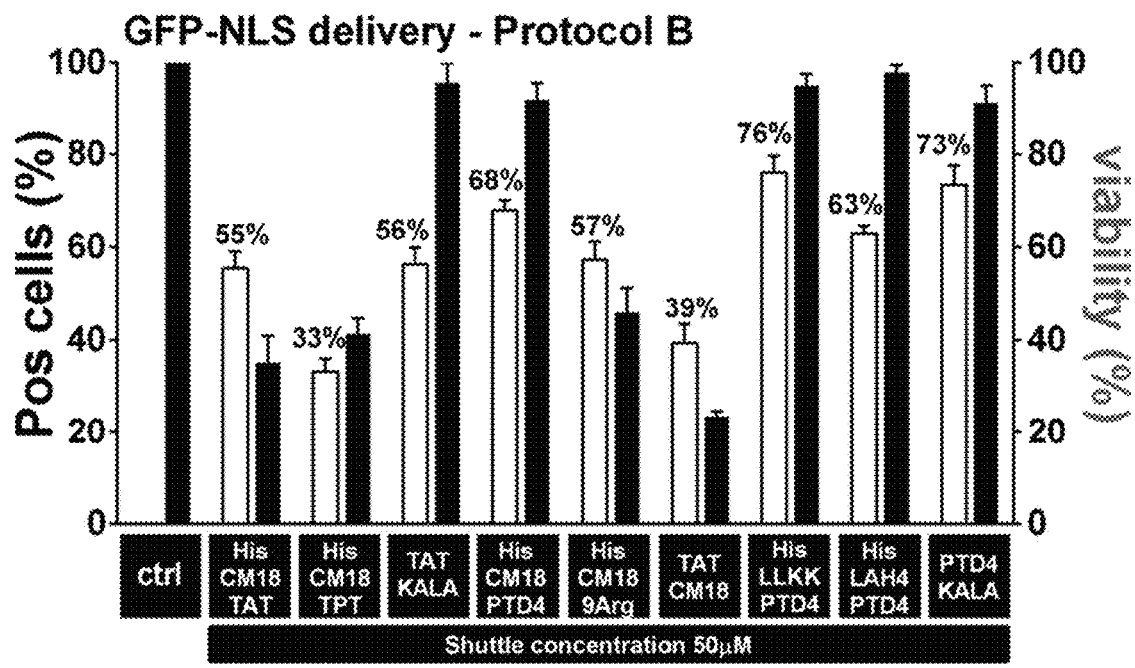

Data from FIG. 29A

| Protocol | Shuttle agent | Cells | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|---|
| B | No shuttle ("ctrl") | HeLa | 0 | 5 | 0 | 100 |
| | His-CM18-TAT | HeLa | 50 | | 55.5 ± 3.6 | 35.2 ± 5.7 |
| | His-CM18-Transportan (TPT) | HeLa | | | 33.2 ± 2.8 | 41.3 ± 3.3 |
| | TAT-KALA | HeLa | | | 56.3 ± 3.6 | 95.6 ± 4.3 |
| | His-CM18-PTD4 | HeLa | | | 68 ± 2.2 | 92 ± 3.6 |
| | His-CM18-9Arg | HeLa | | | 57.2 ± 3.9 | 45.8 ± 5.4 |
| | TAT-CM18 | HeLa | | | 39.4 ± 3.9 | 23.5 ± 1.1 |
| | His-C(LLKK)₃C-PTD4 | HeLa | | | 76 ± 3.8 | 95 ± 2.7 |
| | His-LAH4-PTD4 | HeLa | | | 63 ± 1.64 | 98 ± 1.5 |
| | PTD4-KALA | HeLa | | | 73.4 ± 4.12 | 91.4 ± 3.67 |

10.2 GFP-NLS Transduction by Different Shuttle Agents with Varying Incubation Times in HeLa Cells: Flow Cytometry HeLa cells were cultured and tested in the protein transduction assays using Protocol B as described in Example 9.1. Briefly, GFP-NLS recombinant protein (5 μM; see Example 5.1) was co-incubated with 10 μM of TAT-KALA, His-CM18-PTD4, or His-C(LLKK)₃C-PTD4 for 1, 2, or 5 minutes. After the final washing step, the cells were subjected to flow cytometry analysis as described in Example 3.3. Results are shown in Table 10.2 and FIG. 29B. "Pos cells (%)" is the mean percentages of all cells that emanate a GFP signal. The negative control ("Ctrl") corresponds to cells that were incubated with GFP-NLS recombinant protein (5 μM) without any shuttle agent.

TABLE 10.2

Figure 29B:
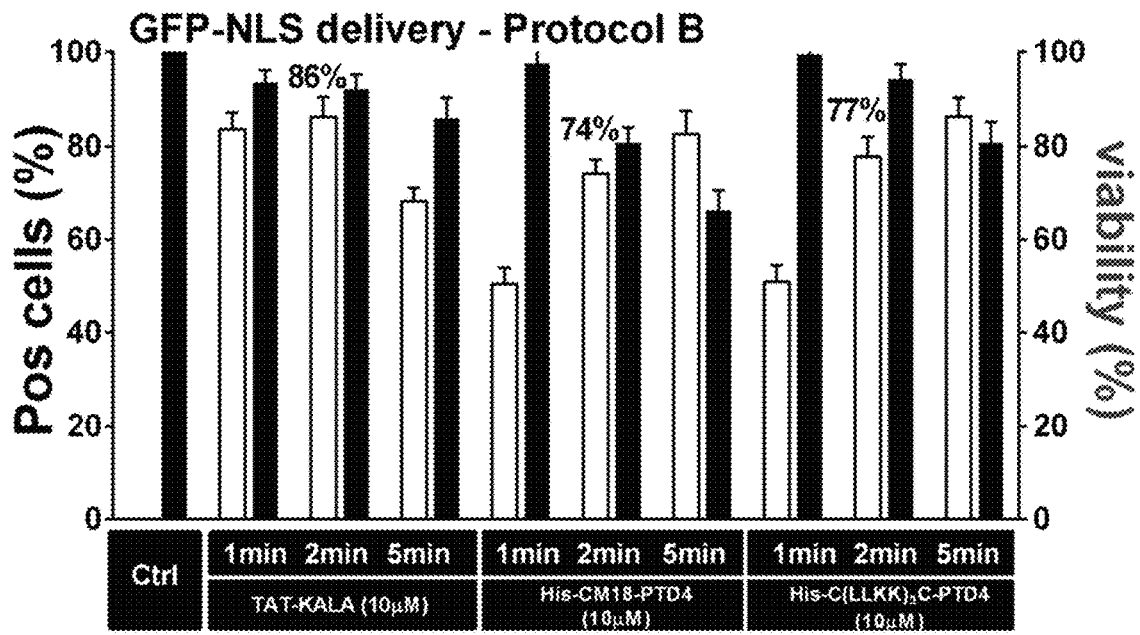

Data from FIG. 29B

| Protocol | Shuttle agent | Cells | Conc. of shuttle (μM) | Incubation time | Mean % cells with GFP signal (±St. Dev.; n = 3) | Cell viability (%) (±St. Dev.; n = 3) |
|---|---|---|---|---|---|---|
| — | No shuttle ("Ctrl") | HeLa | 0 | 5 min. | 0 ± n/a | 97.5 ± 1.7 |
| B | TAT-KALA | HeLa | 10 | 1 min. | 83.7 ± 3.5 | 93.5 ± 2.7 |
|  |  |  |  | 2 min. | 86.2 ± 4.3 | 92.1 ± 3.1 |
|  |  |  |  | 5 min. | 68.1 ± 3.0 | 86 ± 4.4 |
|  | His-CM18-PTD4 | HeLa | 10 | 1 min. | 50.6 ± 3.5 | 97.6 ± 2.7 |
|  |  |  |  | 2 min. | 74 ± 3.3 | 80.9 ± 3.2 |
|  |  |  |  | 5 min. | 82.7 ± 5.0 | 66.2 ± 4.4 |
|  | His-C(LLKK)$_3$C-PTD4 | HeLa | 10 | 1 min. | 51.1 ± 3.5 | 99.5 ± 2.7 |
|  |  |  |  | 2 min. | 77.8 ± 4.3 | 94.3 ± 3.2 |
|  |  |  |  | 5 min. | 86.4 ± 4.0 | 80.8 ± 4.4 |

10.3 GFP-NLS Transduction by TAT-KALA, His-CM18-PTD4 and His-C(LLKK)$_3$C-PTD4 with Varying Incubation Times in HeLa Cells: Flow Cytometry HeLa cells were cultured and tested in the protein transduction assays using Protocol C as described in Example 9.1. Briefly, GFP-NLS recombinant protein (5 μM; see Example 5.1) was co-incubated with 5 μM of TAT-KALA, His-CM18-PTD4, or His-C(LLKK)$_3$C-PTD4 for 1, 2, or 5 minutes. After the final washing step, the cells were subjected to flow cytometry analysis as described in Example 3.3. Results are shown in Table 10.3 and FIG. 29C. The negative control ("Ctrl") corresponds to cells that were incubated with GFP-NLS recombinant protein (5 μM) without any shuttle agent.

TABLE 10.3

Figure 29C:
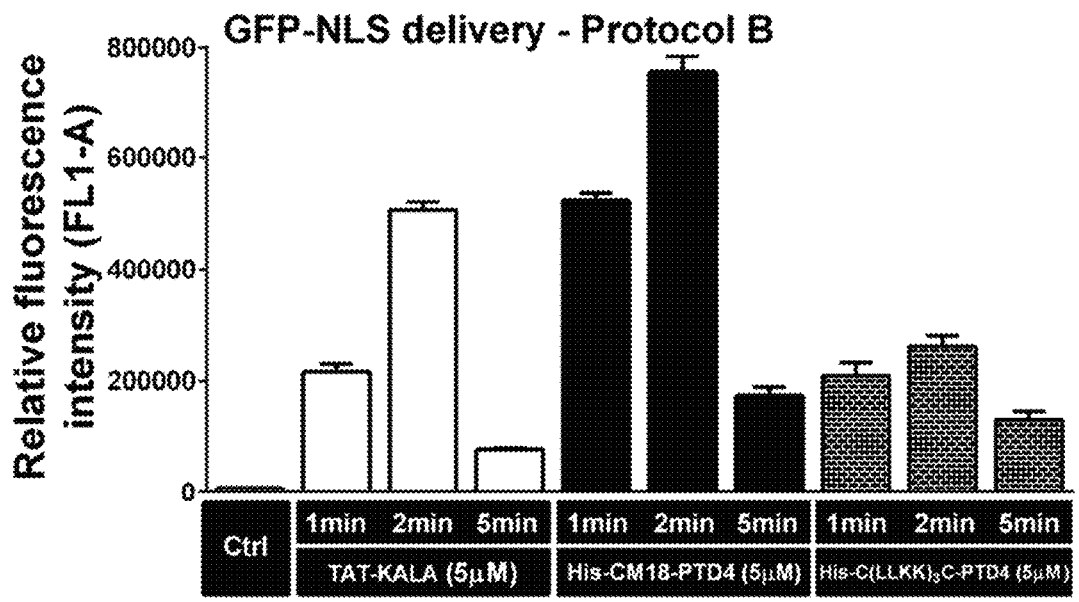

Data from FIG. 29C

| Protocol | Shuttle agent | Cells | Conc. of shuttle (μM) | Incubation time | Relative fluorescence intensity (FL1-A) (n = 3) | St. Dev. |
|---|---|---|---|---|---|---|
|  | No shuttle ("Ctrl") |  | 0 | 5 min. | 8903 | 501 |
| C | TAT-KALA | HeLa | 10 | 1 min. | 216 367 | 13 863.48 |
|  |  |  |  | 2 min. | 506 158 | 14 536.28 |
|  |  |  |  | 5 min. | 78 010 | 2 463.96 |
|  | His-CM18-PTD4 | HeLa | 10 | 1 min. | 524 151 | 12 366.48 |
|  |  |  |  | 2 min. | 755 624 | 26 933.16 |
|  |  |  |  | 5 min. | 173 930 | 15 567.33 |
|  | His-C(LLKK)$_3$C-PTD4 | HeLa | 10 | 1 min. | 208 968 | 23 669.19 |
|  |  |  |  | 2 min. | 262 411.5 | 19 836.84 |
|  |  |  |  | 5 min. | 129 890 | 16 693.29 |

10.4 GFP-NLS Transduction by Different Shuttle Agents in HeLa Cells: Flow Cytometry HeLa cells were cultured and tested in the protein transduction assays using Protocol B as described in Example 9.1. Briefly, GFP-NLS recombinant protein (5 μM; see Example 5.1) was co-incubated with 50 μM of different shuttle agents (see Table 1.3 for amino acid sequences and properties) and exposed to the HeLa cells for 10 seconds. The cells were subjected to flow cytometry analysis as described in Example 3.3. Results are shown in Tables 10.3a & 10.3b and FIGS. 29E & 29F. "Pos cells (%)" is the mean percentages of all cells that emanate a GFP signal. The negative control ("Ctrl") corresponds to cells that were incubated with GFP-NLS recombinant protein (5 μM) without any shuttle agent.

TABLE 10.3a

Figure 29D:
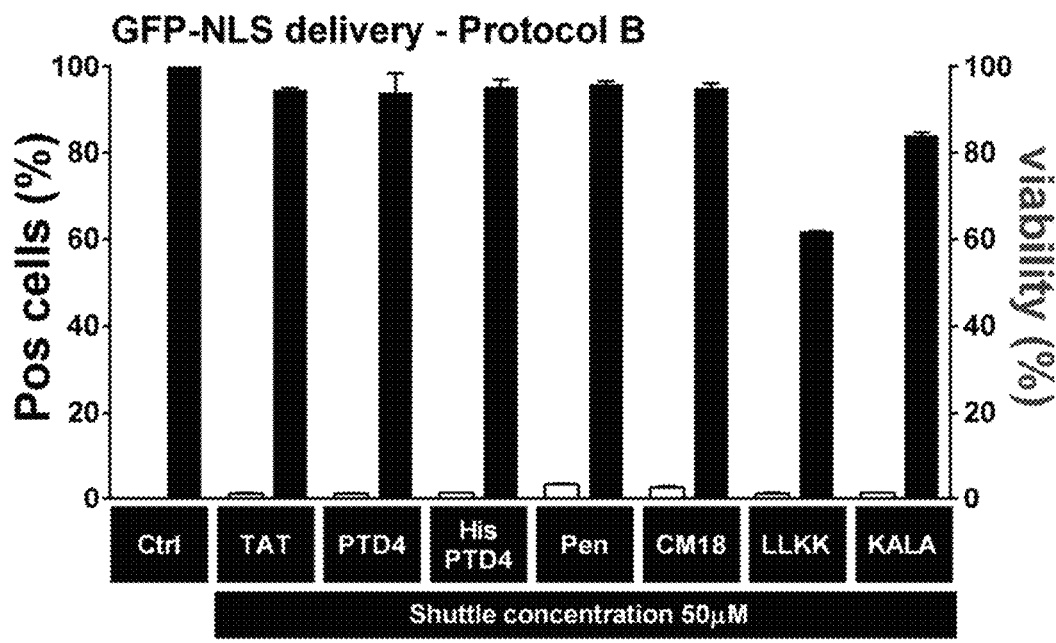
Figure 29E:
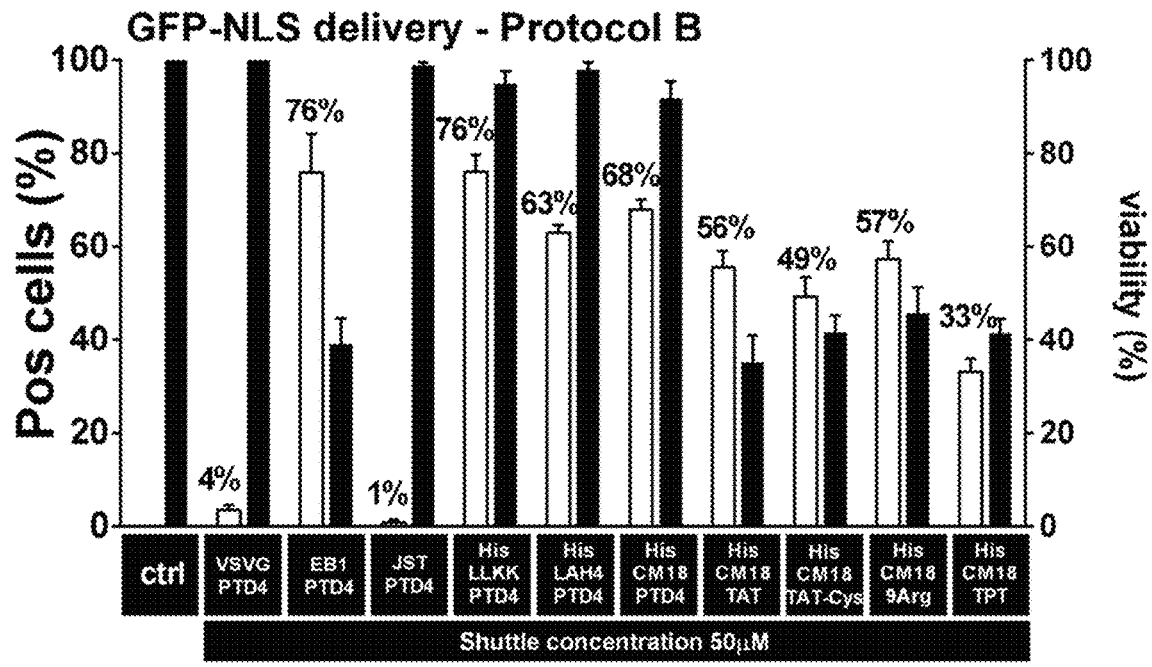

Data from FIG. 29E

| Domain structure | Shuttle agent | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|
| — | No shuttle ("Ctrl") | 0 | 5 | 0 | 100 |
| ELD-CPD | VSVG-PTD4 | 50 | 5 | 3.5 ± 1.1 | 100 |
|  | EB1-PTD4 |  |  | 75.8 ± 8.26 | 39 ± 5.6 |
|  | JST-PTD4 |  |  | 0.84 ± 0.69 | 98.9 ± 0.57 |

TABLE 10.3a-continued

Data from FIG. 29E

| Domain structure | Shuttle agent | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|
| His-ELD-CPD | His-C(LLKK)$_3$C-PTD4 | 50 | 5 | 76 ± 3.8 | 95 ± 2.7 |
|  | His-LAH4-PTD4 |  |  | 63 ± 1.64 | 98 ± 1.5 |
|  | His-CM18-PTD4 |  |  | 68 ± 2.2 | 92 ± 3.6 |
|  | His-CM18-TAT |  |  | 55.5 ± 3.6 | 35.2 ± 5.7 |
|  | His-CM18-TAT-Cys* |  |  | 49.3 ± 4.1 | 41.4 ± 3.91 |

TABLE 10.3a-continued

Data from FIG. 29E

| Domain structure | Shuttle agent | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|
| | His-CM18-9Arg | | | 57.2 ± 3.93 | 45.8 ± 3.53 |
| | His-CM18-Transportan (TPT) | | | 33.2 ± 2.82 | 41.3 ± 3.29 |

*Not shown in FIG. 29E

TABLE 10.3b

Figure 29F:
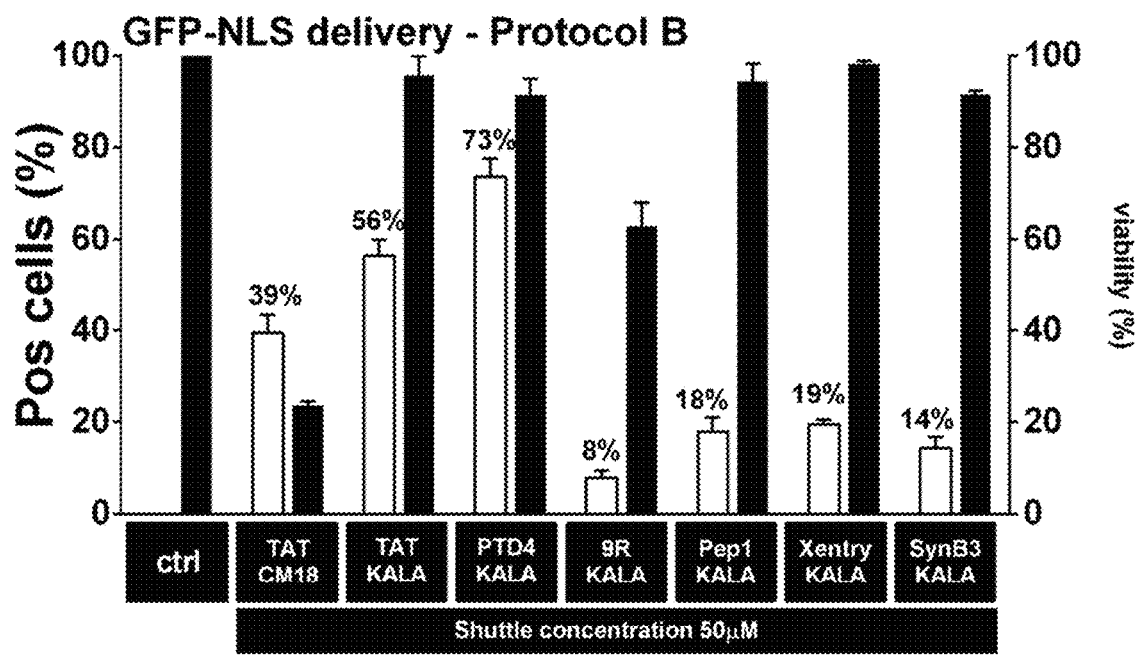

Data from FIG. 29F

| Domain structure | Shuttle agent | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|
| — | No shuttle ("Ctrl") | 0 | 5 | 0 | 100 |
| CPD-ELD | TAT-CM18 | 50 | 5 | 39.4 ± 3.9 | 23.5 ± 1.1 |
| | TAT-KALA | | | 56.3 ± 3.6 | 95.6 ± 4.3 |
| | PTD4-KALA | | | 73.4 ± 4.12 | 91.4 ± 3.67 |
| | 9Arg-KALA | | | 7.8 ± 1.53 | 62.8 ± 5.11 |
| | Pep1-KALA | | | 17.2 ± 3.07 | 94.7 ± 3.77 |
| | Xentry-KALA | | | 19.4 ± 1.01 | 98.3 ± 0.64 |
| | SynB3-KALA | | | 14.3 ± 2.37 | 91.1 ± 0.82 |

HeLa cells were cultured and tested in the protein transduction assays using Protocol B as described in Example 9.1. Briefly, GFP-NLS recombinant protein (5 μM; see Example 5.1) was co-incubated with 10 μM of TAT-KALA, His-CM18-PTD4, or His-C(LLKK)$_3$C-PTD4 for 1, 2, or 5 minutes. After the final washing step, the cells were subjected to flow cytometry analysis as described in Example 3.3. Results are shown in Tables 10.3c & 10.3b and FIGS. 29G and 29H. "Pos cells (%)" is the mean percentages of all cells that emanate a GFP signal. The negative control ("Ctrl") corresponds to cells that were incubated with GFP-NLS recombinant protein (5 μM) without any shuttle agent.

TABLE 10.3c

Figure 29G:
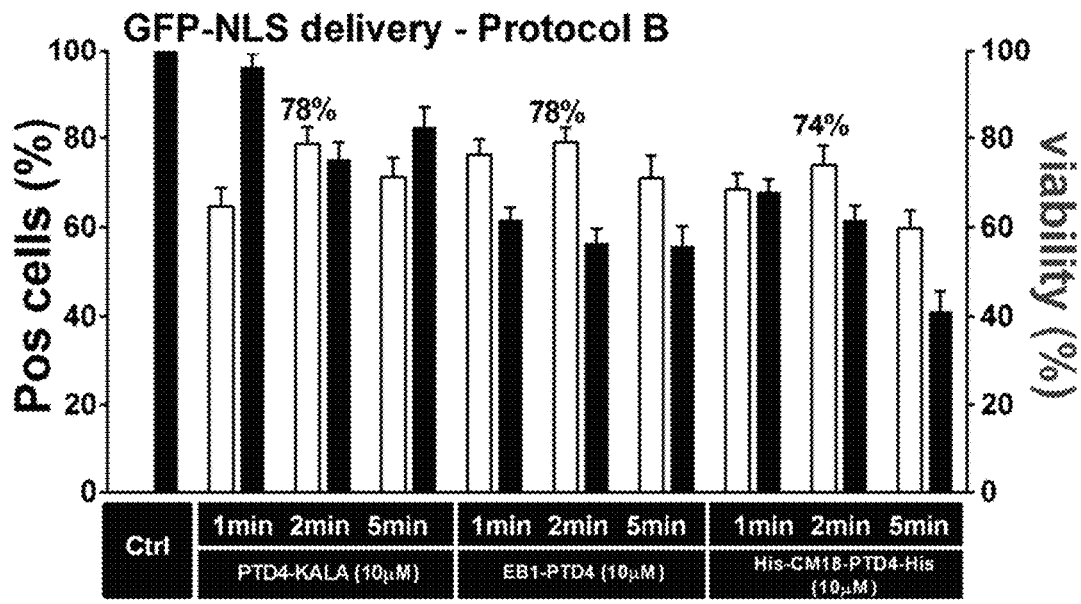

Data from FIG. 29G

| Domain structure | Shuttle agent | Conc. of shuttle (μM) | Conc. of GFP-NLS (μM) | Incubation time (min) | Mean % cells with GFP signal (±St. Dev.; n = 3) | Cell viability (%) (±St. Dev.; n = 3) |
|---|---|---|---|---|---|---|
| — | No shuttle ("Ctrl") | 0 | 5 | 5 | 0 ± n/a | 98.3 ± 0.9 |
| CPD-ELD | PTD4-KALA | 10 | 5 | 1 | 64.6 ± 4.3 | 96.2 ± 3.0 |
| | | | | 2 | 78.8 ± 3.6 | 75.3 ± 3.8 |
| | | | | 5 | 71.4 ± 4.2 | 82.4 ± 4.7 |
| ELD-CPD | EB1-PTD4 | 10 | 5 | 1 | 76.3 ± 3.5 | 61.7 ± 2.7 |
| | | | | 2 | 79.0 ± 3.3 | 56.6 ± 3.2 |
| | | | | 5 | 71.1 ± 5.0 | 55.8 ± 4.4 |
| His-ELD-CPD-His | His-CM18-PTD4-His | 10 | 5 | 1 | 68.6 ± 3.5 | 68.1 ± 2.7 |
| | | | | 2 | 74.1 ± 4.3 | 61.6 ± 3.2 |
| | | | | 5 | 59.8 ± 4.0 | 41.2 ± 4.4 |

TABLE 10.3d

Figure 29H:
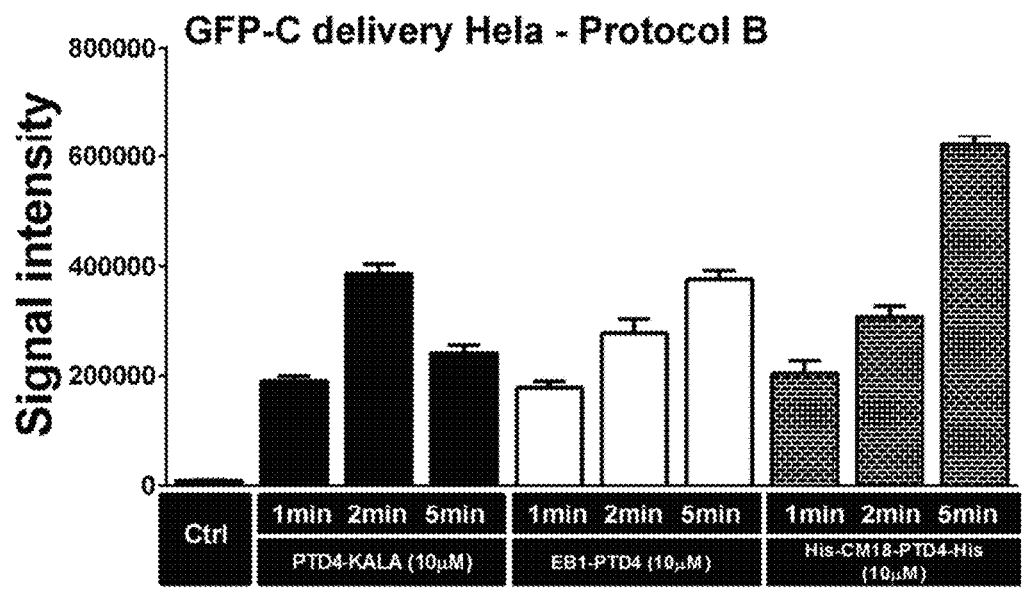

Data from FIG. 29H

| Domain structure | Shuttle agent | Conc. of shuttle (μM) | Conc. of GFP-NLS (μM) | Incubation time (min) | Relative Fluorescence Intensity (FL1-A) (±St. Dev.; n = 3) |
|---|---|---|---|---|---|
| — | No shuttle ("Ctrl") | 0 | 5 | 5 | 8903 ± 501.37 |
| CPD-EED | PTD4-KALA | 10 | 5 | 1 | 190 287 ± 9445 |
| | | | | 2 | 386 480 ± 17 229 |
| | | | | 5 | 241 230 ± 14 229 |
| ELD-CPD | EB1-PTD4 | 10 | 5 | 1 | 178 000 ± 11 934 |
| | | | | 2 | 277 476 ± 25 319 |
| | | | | 5 | 376 555 ± 16 075 |
| His-ELD-CPD-His | His-CM18-PTD4-His | 10 | 5 | 1 | 204 338 ± 22 673 |
| | | | | 2 | 307 329 ± 19 618 |
| | | | | 5 | 619 964 ± 17 411 |

The shuttle agent CM18-PTD4 was used as a model to demonstrate the modular nature of the individual protein domains, as well as their ability to be modified. More particularly, the presence or absence of: an N-terminal cysteine residue ("Cys"); different flexible linkers between the ELD and CPD domains ("L1": GGS; "L2": GGSGGGS (SEQ ID NO: 104); and "L3": GGSGGGSGGGS (SEQ ID NO: 105)) and different lengths, positions, and variants to histidine-rich domains; were studied.

HeLa cells were cultured and tested in the protein transduction assays using Protocol B as described in Example 9.1. Briefly, GFP-NLS recombinant protein (5 μM; see Example 5.1) was co-incubated with 20 μM of different shuttle peptide variants (see Table 1.3 for amino acid sequences and properties) of the shuttle agent His-CM18-PTD4 for 1 minute. After the final washing step, the cells were subjected to flow cytometry analysis as described in Example 3.3. Results are shown in Table 10.3e and FIG. 29I. "Pos cells (%)" is the mean percentages of all cells that emanate a GFP signal. The negative control ("Ctrl") corresponds to cells that were incubated with GFP-NLS recombinant protein (5 μM) without any shuttle agent.

TABLE 10.3e

Data from FIG. 29I

| Domain structure | Shuttle agent | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|
| — | No shuttle ("Ctrl") | 0 | 5 | 0 | 99.6 ± 0.12 |
| ELD-CPD | CM18-PTD4 | 20 | 5 | 47.6 ± 2.6 | 33.9 ± 3.7 |
|  | Cys-CM18-PTD4 |  |  | 36.6 ± 2.3 | 78.7 ± 3.1 |
|  | CM18-L1-PTD4 |  |  | 48.5 ± 3.0 | 50.1 ± 3.8 |
|  | CM18-L2-PTD4 |  |  | 45.5 ± 6.5 | 64.0 ± 1.3 |
|  | CM18-L3-PTD4 |  |  | 39.0 ± 2.7 | 71.9 ± 6.0 |
| His-ELD-CPD | His-CM18-PTD4 | 20 | 5 | 60.3 ± 3.2 | 81.6 ± 4.5 |
|  | His-CM18-PTD4-6Cys |  |  | 41.3 ± 4.28 | 62 ± 5.76 |
|  | Met-His-CM18-PTD4-Cys |  |  | 45.6 ± 3.88 | 54.9 ± 3.45 |
|  | 3His-CM18-PTD4 |  |  | 39.4 ± 0.5 | 39.2 ± 3.3 |
|  | 12His-CM18-PTD4 |  |  | 36.9 ± 4.3 | 33.4 ± 4.3 |
|  | HA-CM18-PTD4 |  |  | 42.3 ± 4.2 | 68.3 ± 4.1 |
|  | 3HA-CM18-PTD4 |  |  | 37.2 ± 3.9 | 43.6 ± 2.8 |
| ELD-His-CPD | CM18-His-PTD4 | 20 | 5 | 61.7 ± 1.8 | 57.7 ± 4.2 |
| His-ELD-CPD-His | His-CM18-PTD4-His | 20 | 5 | 68.0 ± 6.0 | 78.6 ± 1.1 |

These results show that variations in a given shuttle (e.g., CM18-PTD4) may be used to modulate the degree of transduction efficiency and cell viability of the given shuttle. More particularly, the addition of an N-terminal cysteine residue to CM18-PTD4 (see Cys-CM18-PTD4), decreased GFP-NLS transduction efficiency by 11% (from 47.6% to 36.6%), but increased cell viability from 33.9% to 78.7%. Introduction of flexible linker domains (L1, L2, and L3) of different lengths between the CM18 and PTD4 domains did not result in a dramatic loss of transduction efficiency, but increased cell viability (see CM18-L1-PTD4, CM18-L2-PTD4, and CM18-L3-PTD4). Finally, variations to the amino acid sequences and/or positions of the histidine-rich domain(s) did not result in a complete loss of transduction efficiency and cell viability of His-CM18-PTD4 (see 3His-CM18-PTD4, 12His-CM18-PTD4, HA-CM18-PTD4, 3HA-CM18-PTD4, CM18-His-PTD4, and His-CM18-PTD4-His). Of note, adding a second histidine-rich domain at the C terminus of His-CM18-PTD4 (i.e., His-CM18-PTD4-His) increased transduction efficiency from 60% to 68% with similar cell viability.

10.5 Lack of GFP-NLS Transduction by Single-Domain Peptides or a His-CPD Peptide in HeLa Cells: Flow Cytometry HeLa cells were cultured and tested in the protein transduction assays using Protocol B as described in Example 9.1. Briefly, GFP-NLS recombinant protein (5 μM; see Example 5.1) was co-incubated with 50 μM of different single-domain peptides (TAT; PTD4; Penetratin; CM18; C(LLKK)$_3$C; KALA) or the two-domain peptide His-PTD4 (lacking an ELD), and exposed to the HeLa cells for 10 seconds. After the final washing step, the cells were subjected to flow cytometry analysis as described in Example 3.3. Results are shown in Table 10.4 and FIG. 29D. "Pos cells (%)" is the mean percentages of all cells that emanate a GFP signal. The negative control ("Ctrl") corresponds to cells that were incubated with GFP-NLS recombinant protein (5 μM) without any single-domain peptide or shuttle agent.

TABLE 10.4

Data from FIG. 29D

| Protocol | Domain | Single-domain peptide | Cells | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|---|---|
| B | — | No peptide ("Ctrl") | HeLa | 0 | 5 | 0.1 ± 0.02 | 98.3 ± 0.59 |
|  | CPD | TAT | HeLa | 50 | 5 | 1.1 ± 0.27 | 94.6 ± 0.44 |
|  |  | PTD4 |  |  |  | 1.1 ± 0.06 | 94 ± 4.5 |
|  |  | Penetratin (Pen) |  |  |  | 3.6 ± 0.1 | 96 ± 0.6 |
|  | ELD | CM18 | HeLa | 50 | 5 | 2.9 ± 0.2 | 95 ± 1.2 |
|  |  | C(LLKK)$_3$C |  |  |  | 1.1 ± 0.57 | 61.8 ± 0.1 |
|  |  | KALA |  |  |  | 1.4 ± 0.13 | 84 ± 0.7 |
|  | His-CPD | His-PTD4 | HeLa | 50 | 5 | 1.04 ± 0.12 | 96.5 ± 0.28 |

These results show that the single-domain peptides TAT, PTD4, Penetratin, CM18, C(LLKK)$_3$C, KALA, or the two-domain peptide His-PTD4 (lacking an ELD), are not able to successfully transduce GFP-NLS in HeLa cells.

10.6 GFP-NLS transduction by TAT-KALA, His-CM18-PTD4, His-C(LLKK)$_3$C-PTD4, PTD4-KALA, EB1-PTD4, and His-CM18-PTD4-His in HeLa Cells: Visualization by Microscopy GFP-NLS recombinant protein (5 μM; see Example 5.1) was co-incubated with 50 μM of shuttle agent, and then exposed to HeLa cells for 10 seconds using Protocol B as described in Example 9.1. The cells were visualized by microscopy as described in Example 3.2, after an incubation time of 2 minutes.

Figure 30D:
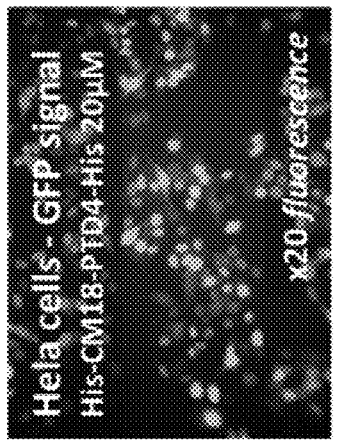
Figure 30D:
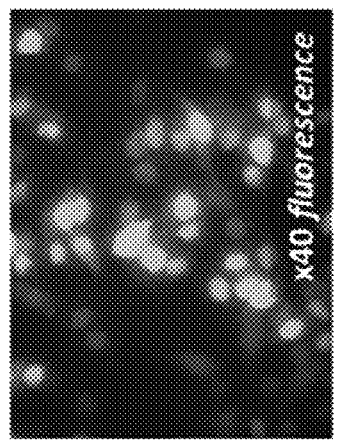
Figure 30D:
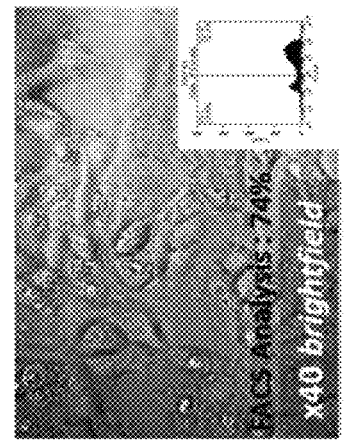
Figure 30E:
Figure 30E:
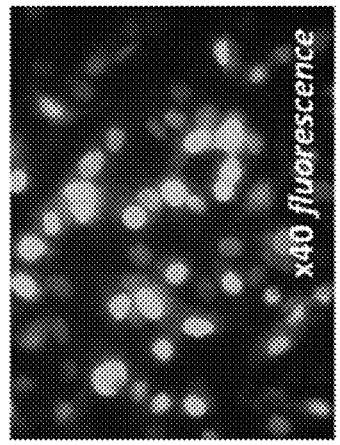
Figure 30E:
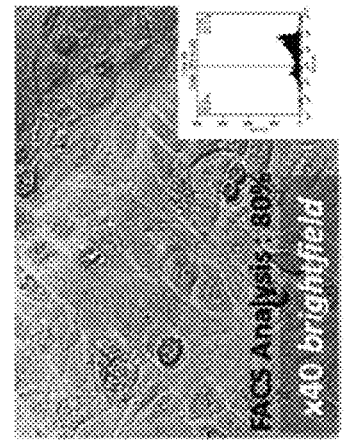
Figure 30F:
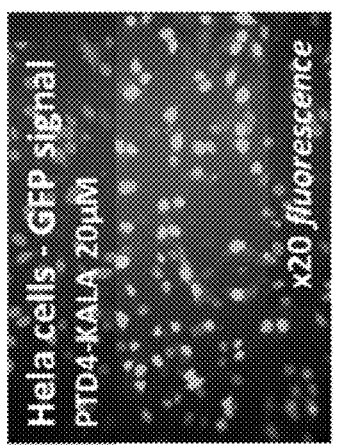
Figure 30F:
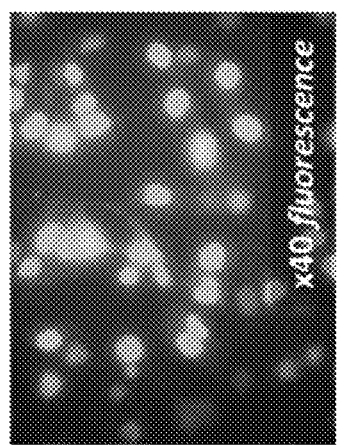
Figure 30F:
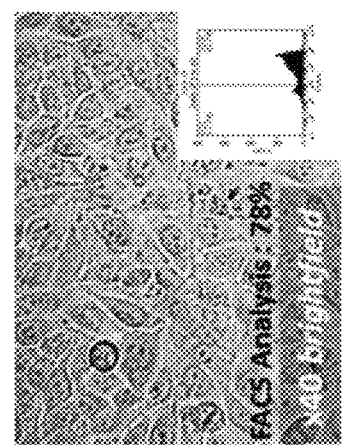

For the sample results shown in FIGS. 30A-30F, GFP fluorescence of the HeLa cells was immediately visualized by bright field (bottom row panels in FIGS. 30A-30F) and fluorescence (upper and middle row panels in FIGS. 30A-30F) microscopy at 20× or 40× magnifications after the final washing step. The results with the shuttle agents TAT- KALA, His-CM18-PTD4, and His-C(LLKK)$_3$C-PTD4 are shown in FIGS. 30A, 30B and 30C, respectively. The results with the shuttle agents PTD4-KALA, EB1-PTD4, and His-CM18-PTD4-His are shown in FIGS. 30D, 30E and 30F, respectively. The insets in the bottom row panels in FIGS. 30A-30F show the results of corresponding FACS analyses (performed as described in Example 3.3), which indicates the percentage of cells in a 96-plate well with a GFP signal. No significant cellular GFP fluorescence was observed in negative control samples (i.e., cells exposed to GFP-NLS without any shuttle agent; data not shown).

10.7 GFP-NLS Transduction by TAT-KALA, His-CM18-PTD4 and His-C(LLKK)$_3$C-PTD4 with Varying Incubation Times in THP-1 Cells: Flow Cytometry THP-1 cells were cultured and tested in the protein transduction assays using Protocol C as described in Example 9.1. Briefly, GFP-NLS recombinant protein (5 µM; see Example 5.1) was co-incubated with 1 µM of TAT-KALA, His-CM18-PTD4, or His-C(LLKK)3C-PTD4 for 15, 30, 60, or 120 seconds. After the final washing step, the cells were subjected to flow cytometry analysis as described in Example 3.3. The mean percentages of cells emanating a GFP signal ("Pos cells (%)") are shown in Table 10.5 and in FIG. 34A. The mean fluorescence intensity is shown in Table 10.6 and FIG. 34B. The negative control ("Ctrl") corresponds to cells that were incubated with GFP-NLS recombinant protein (5 µM) without any shuttle agent.

TABLE 10.4

Figure 34A:
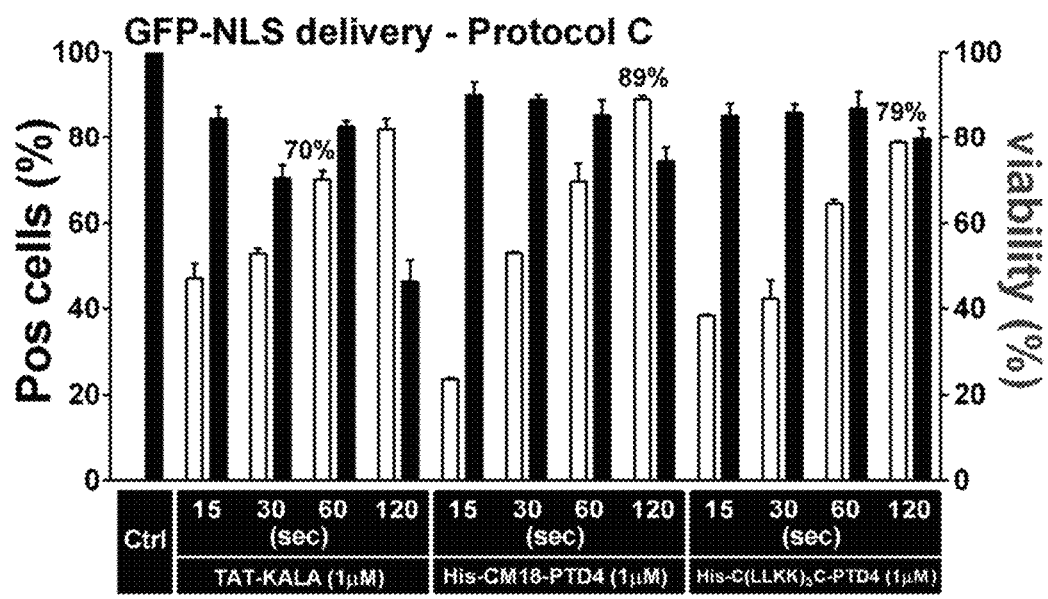
FIGS. 34A-34B show the results of GFP-NLS transduction efficiency experiments in THP-1 cells using the shuttle TAT-KALA, His-CM18-PTD4, or His-C(LLKK)$_3$C-PTD4. The cargo protein/shuttle agents were exposed to the THP-1 cells for 15, 30, 60 or 120 seconds. GFP-NLS transduction efficiency was evaluated by flow cytometry and the percentage of GFP fluorescent cells ("Pos cells (%)"), as well as corresponding cell viability data ("viability (%)") are shown in FIG. 34A.

Data from FIG. 34A

| Protocol | Shuttle agent | Cells | Conc. of shuttle (µM) | Conc. of GFP-NLS (µM) | Incubation time (sec.) | Mean % cells with (%) GFP signal (±St. Dev.; n = 3) | Cell viability (±St. Dev.; n = 3) |
|---|---|---|---|---|---|---|---|
| C | No shuttle ("Ctrl") | THP-1 | 0 | 5 | 120 | 1.12 ± 0.27 | 97.3 ± 1.55 |
|   | TAT-KALA | THP-1 | 1 | 5 | 15 | 47 ± 3.5 | 84.6 ± 2.7 |
|   |   |   |   |   | 30 | 52.9 ± 1.3 | 70.3 ± 3.2 |
|   |   |   |   |   | 60 | 70.1 ± 2.0 | 82.7 ± 1.4 |
|   |   |   |   |   | 120 | 82.1 ± 2.5 | 46.3 ± 4.9 |
|   | His-CM18-PTD4 | THP-1 | 1 | 5 | 15 | 23.7 ± 0.2 | 90 ± 3.0 |
|   |   |   |   |   | 30 | 53 ± 0.3 | 89 ± 1.1 |
|   |   |   |   |   | 60 | 69.6 ± 4.2 | 85.3 ± 3.6 |
|   |   |   |   |   | 120 | 89 ± 0.8 | 74.3 ± 3.2 |
|   | His-C(LLKK)$_3$C-PTD4 | THP-1 | 1 | 5 | 15 | 38.4 ± 0.3 | 85.2 ± 2.8 |
|   |   |   |   |   | 30 | 42.3 ± 4.2 | 86 ± 2.0 |
|   |   |   |   |   | 60 | 64.5 ± 1.0 | 86.9 ± 3.8 |
|   |   |   |   |   | 120 | 78.7 ± 0.3 | 79.6 ± 2.8 |

TABLE 10.5

Figure 34B:
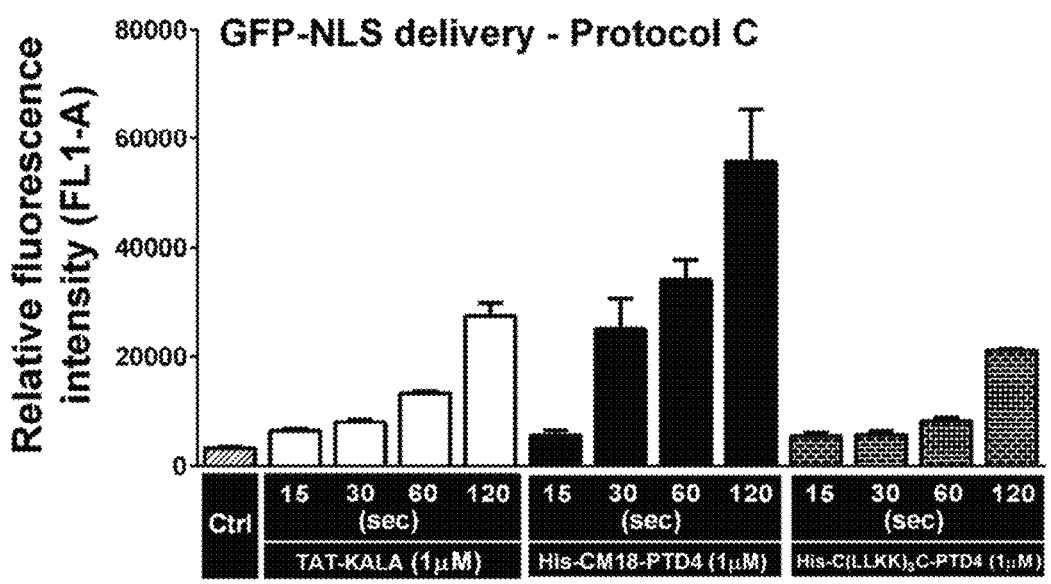

Data from FIG. 34B

| Protocol | Shuttle agent | Cells | Conc. of shuttle (µM) | Incubation time (sec.) | Relative fluorescence intensity (FL1-A) (n = 3) | Standard Deviation |
|---|---|---|---|---|---|---|
| C | No shuttle ("Ctrl") | THP-1 | 0 | 120 | 217 | 23.09 |
|   | TAT-KALA | THP-1 | 1 | 15 | 6 455.12 | 333.48 |
|   |   |   |   | 30 | 8 106.81 | 436.28 |
|   |   |   |   | 60 | 13 286.2 | 463.96 |
|   |   |   |   | 120 | 27 464.92 | 2 366.48 |
|   | His-CM18-PTD4 | THP-1 | 1 | 15 | 5 605.45 | 933.16 |
|   |   |   |   | 30 | 25 076.41 | 5 567.33 |
|   |   |   |   | 60 | 34 046.94 | 3 669.19 |
|   |   |   |   | 120 | 55 613.48 | 9 836.84 |
|   | His-C(LLKK)$_3$C-PTD4 | THP-1 | 1 | 15 | 5 475.12 | 693.29 |
|   |   |   |   | 30 | 5 755.8 | 635.18 |
|   |   |   |   | 60 | 8 267.38 | 733.29 |
|   |   |   |   | 120 | 21 165.06 | 209.37 |

Example 11

Repeated Daily Treatments with Low Concentrations of Shuttle Agent in the Presence of Serum Results in GFP-NLS Transduction in THP-1 Cells 11.1 GFP-NLS Transduction with His-CM18-PTD4 or His-C(LLKK)3C-PTD4 in THP-1 Cells: Flow Cytometry THP-1 cells were cultured and tested in the protein transduction assay using Protocol A as described in Example 9.1, but with the following modifications. GFP-NLS recombinant protein (5, 2.5, or 1 μM; see Example 5.1) was co-incubated with 0.5 or 0.8 μM of His-CM18-PTD4, or with 0.8 μM of His-C(LLKK)$_3$C-PTD4, and then exposed to THP-1 cells each day for 150 min in the presence of cell culture medium containing serum. Cells were washed and subjected to flow cytometry analysis as described in Example 3.3 after 1 or 3 days of repeated exposure to the shuttle agent/cargo. The results are shown in Table 11.1 and in FIGS. 35A, 35B, 35C and 35F. The negative control ("Ctrl") corresponds to cells that were incubated with GFP-NLS recombinant protein (5 μM) without any shuttle agent.

TABLE 11.1

Data from FIGS. 35A, 35B, 35C and 35F

| FIG. | Shuttle agent | Cells | Conc. of shuttle (μM) | Conc. of GFP-NLS (μM) | Exposure to shuttle/cargo (days) | Mean % cells with GFP signal (±St. Dev.; n = 3) | Cell viability (%) (±St. Dev.; n = 3) |
|---|---|---|---|---|---|---|---|
| 35A | No shuttle (Ctrl) | THP-1 | 0 | 5 | 0 | 0.15 ± 0.04 | 98.7 ± 0.1 |
|  | His-CM18-PTD4 |  | 0.5 | 5 | 1 | 12.1 ± 1.5 | 98.2 ± 2.4 |
|  |  |  |  |  | 3 | 73.4 ± 1.1 | 84.3 ± 3.8 |
| 35B | No shuttle (Ctrl) | THP-1 | 0 | 5 | 0 | 0.36 ± 0.09 | 97.1 ± 1.2 |
|  | His-CM18-PTD4 |  | 0.8 | 2.5 | 1 | 12.2 ± 0.9 | 92.3 ± 1.9 |
|  |  |  |  |  | 3 | 62.4 ± 3.5 | 68.5 ± 2.2 |
| 35C | No shuttle (Ctrl) | THP-1 | 0 | 5 | 0 | 0.28 ± 0.05 | 96.4 ± 2.0 |
|  | His-CM18-PTD4 |  | 0.8 | 1 | 1 | 1.6 ± 0.2 | 98.4 ± 6.4 |
|  |  |  |  |  | 3 | 6.5 ± 0.9 | 80.6 ± 4.6 |
| 35F | No shuttle (Ctrl) | THP-1 | 0 | 5 | 0 | 0.62 ± 0.11 | 96.3 ± 1.4 |
|  | His-C(LLKK)$_3$C-PTD4 |  | 0.8 | 1 | 1 | 1.8 ± 0.2 | 97.2 ± 2.2 |
|  |  |  |  |  | 3 | 6.6 ± 0.8 | 76.6 ± 3.4 |

The viability of THP-1 cells repeatedly exposed to His-CM18-PTD4 and GFP-NLS was determined as described in Example 3.3a. The results are shown in Tables 11.2 and 11.3 and in FIGS. 35D and 35E. The results in Table 11.2 and FIG. 35D show the metabolic activity index of the THP-1 cells after 1, 2, 4, and 24 h, and the results in Table 11.3 and FIG. 35E show the metabolic activity index of the THP-1 cells after 1 to 4 days.

TABLE 11.2

Figures 35D, 35E, 35F:
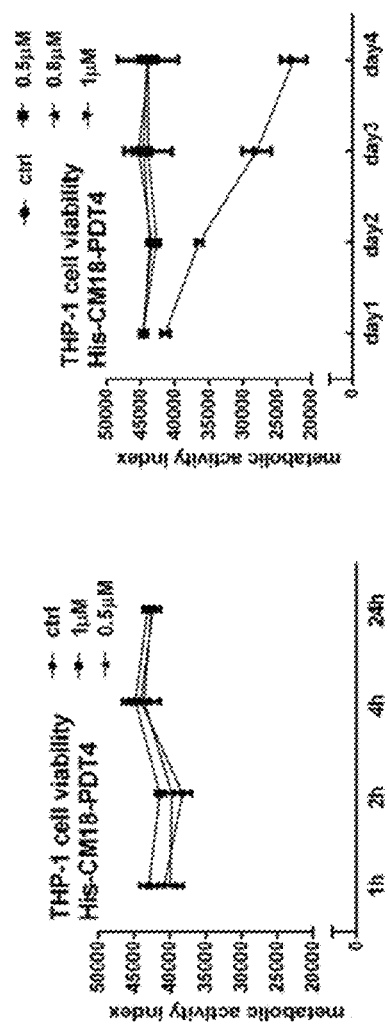

Data from FIG. 35D

| Shuttle agent | Cells | Conc. of shuttle (μM) | Conc. of GFP-NLS (μM) | Mean metabolic activity index (±St. Dev.; n = 3) (Exposure to shuttle/cargo) | | | |
|---|---|---|---|---|---|---|---|
|  |  |  |  | 1 h | 2 h | 4 h | 24 h |
| No shuttle (Ctrl) | THP-1 | 0 | 5 | 40810 ± 757.39 | 38223 ± 238.66 | 44058 ± 320.23 | 42362 ± 333.80 |
| His-CM18-PTD4 | THP-1 | 0.5 | 5 | 9974 ± 1749.85 | 9707 ± 1259.82 | 3619 ± 2247.54 | 2559 ± 528.50 |
|  |  | 1 | 5 | 42915 ± 259.67 | 41386 ± 670.66 | 44806 ± 824.71 | 43112 ± 634.56 |

TABLE 11.3

Data from FIG. 35E

| Shuttle agent | Cells | Conc. of shuttle (μM) | Conc. of GFP-NLS (μM) | Mean metabolic activity index (±St. Dev.; n = 3) (Exposure to shuttle/cargo) | | | |
|---|---|---|---|---|---|---|---|
|  |  |  |  | 1 day | 2 days | 3 days | 4 days |
| No shuttle (Ctrl) | THP-1 | 0 | 5 | 44684 ± 283.27 | 43389 ± 642.47 | 45312 ± 963.40 | 43697 ± 1233 |
| His-CM18-PTD4 | THP-1 | 0.5 | 5 | 44665 ± 310.3 | 42664 ± 398.46 | 43927 ± 3511.54 | 43919 ± 4452.25 |
|  |  | 0.8 | 5 | 44531 ± 176.66 | 43667 ± 421.66 | 44586 ± 383.68 | 44122 ± 239.98 |
|  |  | 1 | 5 | 41386 ± 670.66 | 36422 ± 495.01 | 27965 ± 165.33 | 22564 ± 931.28 |

The results in Example 11 show that repeated daily (or chronic) treatments with relatively low concentrations of His-CM18-PTD4 or His-C(LLKK)$_3$C-PTD4 in the presence of serum result in intracellular delivery of GFP-NLS in THP-1 cells. The results also suggest that the dosages of the shuttle agents and the cargo can be independently adjusted to improve cargo transduction efficiency and/or cell viability.

Example 12

His-CM18-PTD4 Increases Transduction Efficiency and Nuclear Delivery of GFP-NLS in a Plurality of Cell Lines
12.1 GFP-NLS Transduction with His-CM18-PTD4 in Different Adherent & Suspension Cells: Flow Cytometry The ability of the shuttle agent His-CM18-PTD4 to deliver GFP-NLS to the nuclei of different adherent and suspension cells using Protocols B (adherent cells) or C (suspension cells) as described in Example 9.1 was examined. The cell lines tested included: HeLa, Balb3T3, HEK 293T, CHO, NIH3T3, Myoblasts, Jurkat, THP-1, CA46, and HT2 cells, which were cultured as described in Example 1. GFP-NLS (5 μM; see Example 5.1) was co-incubated with 35 μM of His-CM18-PTD4 and exposed to adherent cells for 10 seconds (Protocol B), or was co-incubated with 5 μM of His-CM18-PTD4 and exposed to suspension cells for 15 seconds (Protocol C). Cells were washed and subjected to flow cytometry analysis as described in Example 3.3. Results are shown in Table 12.1 and FIG. 36. "Pos cells (%)" is the mean percentages of all cells that emanate a GFP signal.

TABLE 12.1

Data from FIG. 36

| Shuttle agent | Protocol | Conc. of shuttle (μM) | Conc. of GFP-NLS (μM) | Cells | Mean % cells with GFP signal (±St. Dev.; n = 3) | Cell viability (%) (±St. Dev.; n = 3) |
|---|---|---|---|---|---|---|
| His-CM18-PTD4 | B | 35 | 5 | HeLa | 72.3 ± 5.3 | 94.6 ± 0.4 |
|  |  |  |  | Balb3T3 | 40.2 ± 3.1 | 98.4 ± 0.6 |
|  |  |  |  | HEK 293T | 55.3 ± 0.2 | 95.3 ± 1.2 |
|  |  |  |  | CHO | 53.7 ± 4.6 | 92.8 ± 0.1 |
|  |  |  |  | NIH3T3 | 35.4 ± 3.9 | 3.3 ± 5.4 |
|  |  |  |  | Myoblasts | 25.6 ± 2.6 | 23.5 ± 1.1 |
|  | C | 5 | 5 | Jurkat | 30.7 ± 2.2 | 73.6 ± 0.7 |
|  |  |  |  | THP-1 | 64.1 ± 1.6 | 64.1 ± 4.5 |
|  |  |  |  | CA46 | 24.4 ± 0.6 | 71.6 ± 1.0 |
|  |  |  |  | HT2 | 30.5 ± 2.5 | 90.6 ± 1.5 |

12.2 GFP-NLS Transduction with His-CM18-PTD4 in Several Adherent and Suspension Cells: Visualization by Microscopy GFP-NLS recombinant protein (5 μM; see Example 5.1) was co-incubated with 35 μM of His-CM18-PTD4 and exposed to adherent cells for 10 seconds using Protocol A, or was co-incubated with 5 μM of His-CM18-PTD4 and exposed to suspension cells for 15 seconds using Protocol B, as described in Example 9.1. After washing the cells, GFP fluorescence was visualized by bright field and fluorescence microscopy. Sample images captured at 10× magnifications showing GFP fluorescence are shown in FIGS. 37A-37H for (FIG. 37A) 293T, (FIG. 37B) Balb3T3, (FIG. 37C) CHO, (FIG. 37D) Myoblasts, (FIG. 37E) Jurkat, (FIG. 37F) CA46, (FIG. 37G) HT2, and (FIG. 37H) NIH3T3 cells. The insets show corresponding flow cytometry results performed as described in Example 3.3, indicating the percentage of GFP-NLS-positive cells. No significant cellular GFP fluorescence was observed in negative control samples (i.e., cells exposed to GFP-NLS without any shuttle agent; data not shown).

Nuclear localization of the GFP-NLS was further confirmed in fixed and permeabilized myoblasts using cell immuno-labelling as described in Example 3.2a. GFP-NLS was labeled using a primary mouse monoclonal anti-GFP antibody (Feldan, #A017) and a secondary goat anti-mouse Alexa™-594 antibody (Abcam #150116). Nuclei were labelled with DAPI. Sample results for primary human myoblast cells are shown in FIGS. 38A-38B, in which GFP immuno-labelling is shown in FIG. 38A, and an overlay of the GFP immuno-labelling and DAPI labelling is shown in FIG. 38B. No significant cellular GFP labelling was observed in negative control samples (i.e., cells exposed to GFP-NLS without any shuttle agent; data not shown).

The microscopy results revealed that GFP-NLS is successfully delivered to the nucleus of all the tested cells using the shuttle agent His-CM18-PTD4.

Example 13

His-CM18-PTD4 Enables Transduction of a CRISPR/Cas9-NLS System and Genome Editing in Hela Cells
13.1 Cas9-NLS Recombinant Protein Cas9-NLS recombinant protein was constructed, expressed and purified from a bacterial expression system as described in Example 1.4. The sequence of the Cas9-NLS recombinant protein produced was:

[SEQ ID NO: 74]
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

-continued

```
LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGDGGRSSDDEATADSQHAAPPKKKRKVGGSGGGS

GGGSGGGRHHHHHH
(MW = 162.9 kDa; pI = 9.05)
NLS sequence is underlined
Serine/glycine rich linkers are in bold
```

13.2 Transfection Plasmid Surrogate Assay

This assay enables one to visually identify cells that have been successfully delivered an active CRISPR/Cas9 complex. As shown in FIG. 39A, the assay involves transfecting cells with an expression plasmid DNA encoding the fluorescent proteins mCherry™ and GFP, with a STOP codon separating their two open reading frames. Transfection of the cells with the expression plasmid results in mCherry™ expression, but no GFP expression (FIG. 39B). A CRISPR/Cas9 complex, which has been designed/programmed to cleave the plasmid DNA at the STOP codon, is then delivered intracellularly to the transfected cells expressing mCherry™ (FIG. 39D). Successful transduction of an active CRISPR/Cas9 complex results in the CRISPR/Cas9 complex cleaving the plasmid DNA at the STOP codon (FIG. 39C). In a fraction of the cells, random non-homologous DNA repair of the cleaved plasmid occurs and results in removal of the STOP codon, and thus GFP expression and fluorescence (FIG. 39E).

On Day 1 of the transfection plasmid surrogate assay, DNA plasmids for different experimental conditions (250 ng) are diluted in DMEM (50 μL) in separate sterile 1.5-mL tubes, vortexed and briefly centrifuged. In separate sterile 1.5-mL tubes, Fastfect™ transfection reagent was diluted in DMEM (50 μL) with no serum and no antibiotics at a ratio of 3:1 (3 μL of Fastfect™ transfection reagent for 1 μg of DNA) and then quickly vortexed and briefly centrifuged. The Fastfect™/DMEM mixture was then added to the DNA mix and quickly vortexed and briefly centrifuged. The Fastfect™/DMEM/DNA mixture is then incubated for 15-20 min at room temperature, before being added to the cells (100 μL per well). The cells are then incubated at 37° C. and 5% $CO_2$ for 5 h. The media is then changed for complete medium (with serum) and further incubated at 37° C. and 5% $CO_2$ for 24-48 h. The cells are then visualized under fluorescent microscopy to view the mCherry™ signal.

13.3 His-CM18-PTD4-Mediated CRISPR/Cas9-NLS System Delivery and Cleavage of Plasmid DNA RNAs (crRNA & tracrRNA) were designed to target a nucleotide sequence of the EMX1 gene, containing a STOP codon between the mCherry™ and GFP coding sequences in the plasmid of Example 13.2. The sequences of the crRNA and tracrRNA used were as follows:

```
crRNA [SEQ ID NO: 75]:
5'-GAGUCCGAGCAGAAGAAGAAGUUUUAGAGCUAUGCUGUUUUG-3' tracrRNA [SEQ ID NO: 76]:
5'-AAACAGCAUAGCAAGUUAAAAUAAGGCUAGUCCGUUAUCAACUU
GAAAAAGUGGCACCGAGUCGGUGCU-3'
```

HeLa cells were cultured and subjected to the transfection plasmid surrogate assay as described in Example 13.2). On Day 1, the HeLa cells were transfected with a plasmid surrogate encoding the mCherry™ protein as shown in FIG. 39A. On Day 2, a mix of Cas9-NLS recombinant protein (2 μM; see Example 13.1) and RNAs (crRNA & tracrRNA; 2 μM; see above) were co-incubated with 50 μM of His-CM18-PTD4, and the mixture (CRISPR/Cas9 complex) was exposed to HeLa cells for 10 seconds using Protocol B as described in Example 9.1. Double-stranded plasmid DNA cleavage by the CRISPR/Cas9 complex at the STOP codon between the mCherry™ and GFP coding sequences (FIG. 39B), and subsequent non-homologous repair by the cell in some cases results in removal of the STOP codon (FIG. 39C), thereby allowing expression of both the mCherry™ and GFP fluorescent proteins in the same cell on Day 3 (FIG. 39D-39E). White triangle windows in FIGS. 39D and 39E indicate examples of areas of co-labelling between mCherry™ and GFP.

As a positive control for the CRISPR/Cas9-NLS system, HeLa cells were cultured and co-transfected with three plasmids: the plasmid surrogate (as described in Example 13.2) and other expression plasmids encoding the Cas9-NLS protein (Example 13.1) and the crRNA/tracrRNAs (Example 13.3). Typical fluorescence microscopy results are shown in FIG. 40A to 40D. FIGS. 40A and 40B show cells 24 hours post-transfection, while FIGS. 40C and 40D show cells 72 hours post-transfection.

FIG. 40E-40H shows the results of a parallel transfection plasmid surrogate assay performed using 35 μM of the shuttle His-CM18-PTD4, as described for FIG. 39A-39E. FIGS. 40E and 40F show cells 24 hours post-transduction, while FIGS. 40G and 40H show cells 48 hours post-transduction. FIGS. 40E and 40G show mCherry™ fluorescence, and FIGS. 40F and 40H show GFP fluorescence, the latter resulting from removal of the STOP codon by the transduced CRISPR/Cas9-NLS complex and subsequent non-homologous repair by the cell. No significant cellular GFP fluorescence was observed in negative control samples (i.e., cells exposed to CRISPR/Cas9-NLS complex without any shuttle agent; data not shown).

13.4 T7E1 Assay

The T7E1 assay was performed with the Edit-R™ Synthetic crRNA Positive Controls (Dharmacon #U-007000-05) and the T7 Endonuclease I (NEB, Cat #M03025). After the delivery of the CRISPR/Cas9 complex, cells were lysed in 100 μL of Phusion™ High-Fidelity DNA polymerase (NEB #M0530S) laboratory with additives. The cells were incubated for 15-30 minutes at 56° C., followed by deactivation for 5 minutes at 96° C. The plate was briefly centrifuged to collect the liquid at bottom of the wells. 50-4, PCR samples were set up for each sample to be analyzed. The PCR samples were heated to 95° C. for 10 minutes and then slowly (>15 minutes) cooled to room temperature. PCR product (~5 μL) was then separated on an agarose gel (2%) to confirm amplification. 15 μL of each reaction was incubated with T7E1 nuclease for 25 minutes at 37° C. Immediately, the entire reaction volume was run with the appropriate gel loading buffer on an agarose gel (2%).

13.5 His-CM18-PTD4 and His-C(LLKK)₃C-PTD4-Mediated CRISPR/Cas9-NLS System Delivery and Cleavage of Genomic PPIB Sequence A mix composed of a Cas9-NLS recombinant protein (25 nM; Example 13.1) and crRNA/tracrRNA (50 nM; see below) targeting a nucleotide sequence of the PPIB gene were co-incubated with 10 μM of His-CM18-PTD4 or His-C(LLKK)₃C-PTD4, and incubated with HeLa cells for 16 h in medium without serum using Protocol A as described in Example 9.1.

The sequences of the crRNA and tracrRNAs constructed and their targets were:

```
Feldan tracrRNA [SEQ ID NO: 77]:
5'-AAACAGCAUAGCAAGUUAAAAUAAGGCUAGUCCGUUAUCAACU

UGAAAAAGUGGCACCGAGUCGGUGCU-3'

PPIB crRNA [SEQ ID NO: 78]:
5'-GUGUAUUUUGACCUACGAAUGUUUUAGAGCUAUGCUGUUUUG-3'

Dharmacon tracrRNA [SEQ ID NO: 79]:
5'-AACAGCAUAGCAAGUUAAAAUAAGGCUAGUCCGUUAUCAACUU

GAAAAAGUGGCACCGAGUCGGUGCUUUUUUU-3'
```

After 16 h, HeLa cells were washed with PBS and incubated in medium with serum for 48 h. HeLa cells were harvested to proceed with the T7E1 protocol assay as described in Example 13.4.

FIG. 41A shows an agarose gel with the PPIB DNA sequences after PCR amplification. Lane A shows the amplified PPIB DNA sequence in HeLa cells without any treatment (i.e., no shuttle or Cas9/RNAs complex). Lanes B: The two bands framed in white box #1 are the cleavage product of the PPIB DNA sequence by the CRISPR/Cas9 complex after the delivery of the complex with the shuttle His-C(LLKK)₃C-PTD4. Lane C: These bands show the amplified PPIB DNA sequence after incubation of the HeLa cells with the Cas9/RNAs complex without shuttle (negative control). Lane D: The bands framed in white box #2 show the amplified PPIB DNA sequence after incubation of the HeLa cells with the Cas9/RNAs complex in presence of a lipidic transfection agent (DharmaFect™ transfection reagent #T-20XX-01) (positive control). Similar results were obtained using the shuttle His-CM18-PTD4 (data not shown).

Figure 41B:
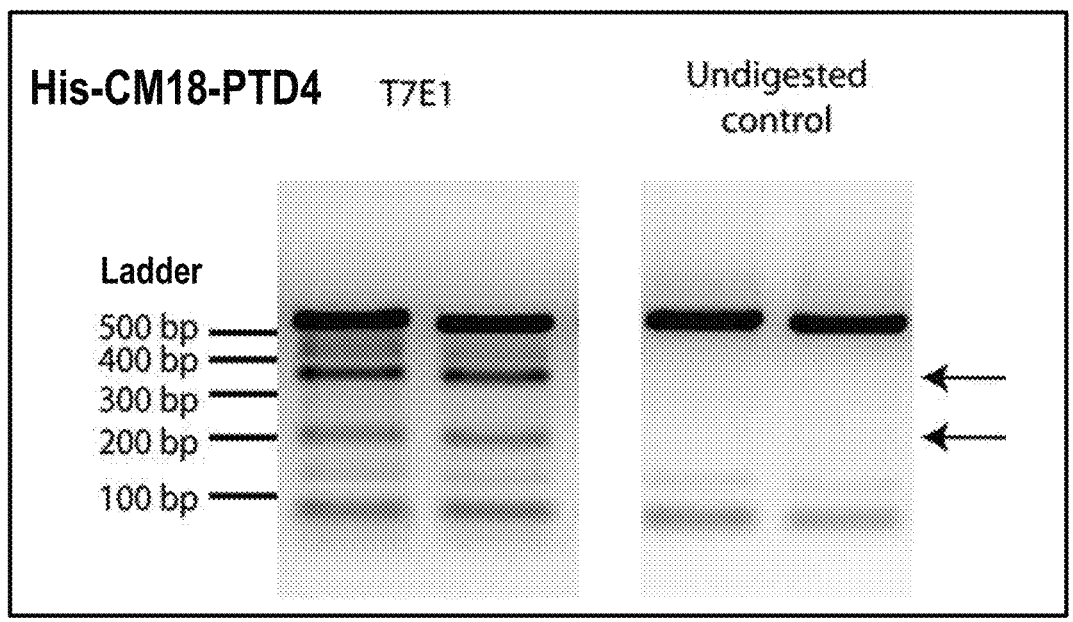
FIG. 41B shows the products of a DNA cleavage assay (T7E1 assay) separated by agarose gel electrophoresis, which is used to measure CRISPR/Cas9-mediated cleavage of cellular genomic DNA (PPIB DNA sequences). The left picture of the FIG. 41B shows the cleavage product of the amplified PPIB DNA sequence by the CRISPR/Cas9 complex after the delivery of the complex with the shuttle agent His-CM18-PTD4 in HeLa cells. The right picture of the FIG. 41B shows amplified DNA sequence before the T7E1 digestion procedure as a negative control.

FIG. 41B shows an agarose gel with the PPIB DNA sequences after PCR amplification. The left panel in FIG. 41B shows the cleavage product of the amplified PPIB DNA sequence by the CRISPR/Cas9 complex after the delivery of the complex with the shuttle agent His-CM18-PTD4 in HeLa cells. The right panel FIG. 41B shows amplified DNA sequence before the T7E1 digestion procedure as a negative control.

Figure 41C:
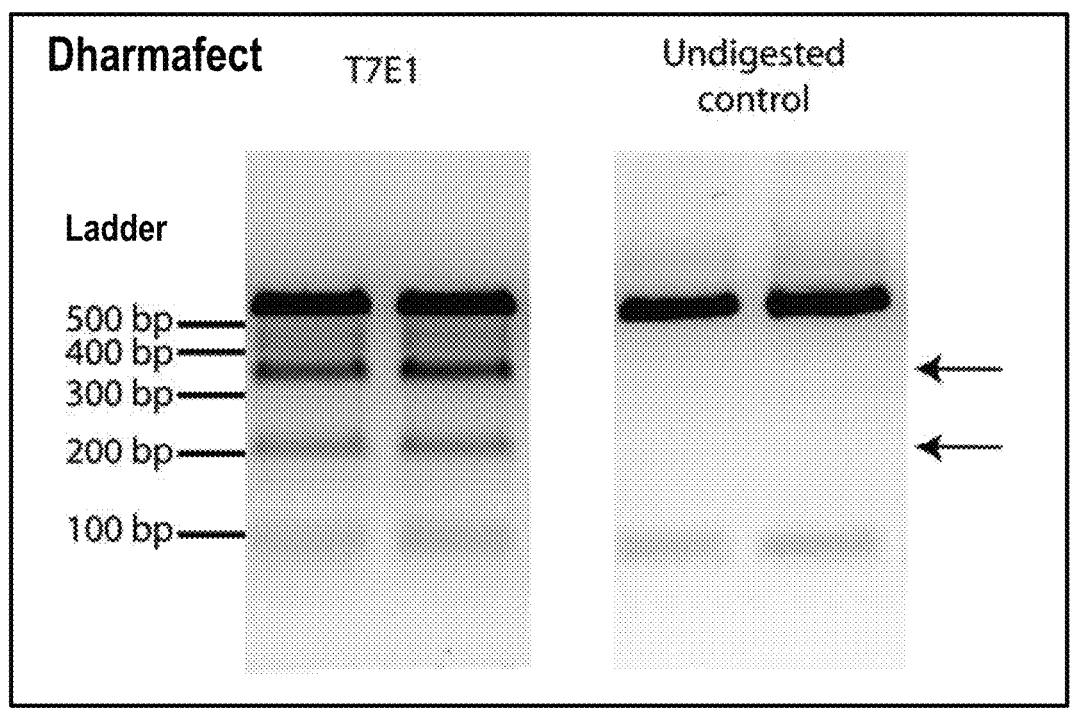
FIG. 41C shows the products of a DNA cleavage assay (T7E1 assay) separated by agarose gel electrophoresis, which is used to measure CRISPR/Cas9-mediated cleavage of cellular genomic DNA (PPIB DNA sequences). The left picture of the FIG. 41C shows the amplified PPIB DNA sequence after incubation of the HeLa cells with the Cas9/RNAs complex in presence of a lipidic transfection agent (DharmaFect™ transfection reagent #T-20XX-01) (positive control). The right picture of the FIG. 41C shows amplified DNA sequence before the T7E1 digestion procedure as a negative control.

FIG. 41C shows an agarose gel with the PPIB DNA sequences after PCR amplification. The left panel FIG. 41C shows the amplified PPIB DNA sequence after incubation of the HeLa cells with the Cas9/RNAs complex in presence of a lipidic transfection agent (DharmaFect™ transfection reagent #T-20XX-01) (positive control). The right panel FIG. 41C shows amplified DNA sequence before the T7E1 digestion procedure as a negative control.

These results show that the shuttle agents His-CM18-PTD4 and His-C(LLKK)₃C-PTD4 successfully deliver a functional CRISPR/Cas9 complex to the nucleus of HeLa cells, and that this delivery results in CRISPR/Cas9-mediated cleavage of genomic DNA.

13.6 CRISPR/Cas9-NLS System Delivery by Different Shuttle Agents, and Cleavage of Genomic HPTR Sequence in HeLa and Jurkat Cells A mix composed of a Cas9-NLS recombinant protein (2.5 μM; Example 13.1) and crRNA/tracrRNA (2 μM; see below) targeting a nucleotide sequence of the HPTR gene were co-incubated with 35 μM of His-CM18-PTD4, His-CM18-PTD4-His, His-C(LLKK)3C-PTD4, or EB1-PTD4, and incubated with HeLa or Jurkat cells for 2 minutes in PBS using Protocol B as described in Example 9.1.

The sequences of the crRNA and tracrRNAs constructed and their targets were:

```
Feldan tracrRNA [SEQ ID NO: 77]:
5'-AAACAGCAUAGCAAGUUAAAAUAAGGCUAGUCCGUUA

UCAACUUGAAAAAGUGGCACCGAGUCGGUGCU-3'

HPRT crRNA [SEQ ID NO: 103]:
5'-AAUUAUGGGGAUUACUAGGAGUUUUAGAGCUAUGCU-3'
```

Figure 46A:
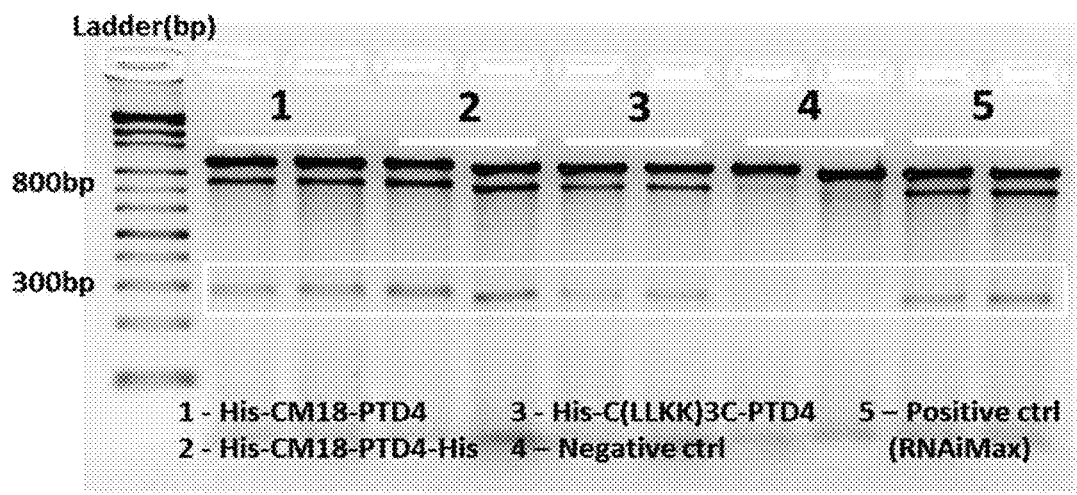
FIGS. 46A-46B show the products of a DNA cleavage assay separated by agarose gel electrophoresis, which is used to measure CRISPR/Cas9-mediated cleavage of cellular genomic DNA (HPTR sequence) after intracellular delivery of the complex with different shuttle agents.
Figure 46B:
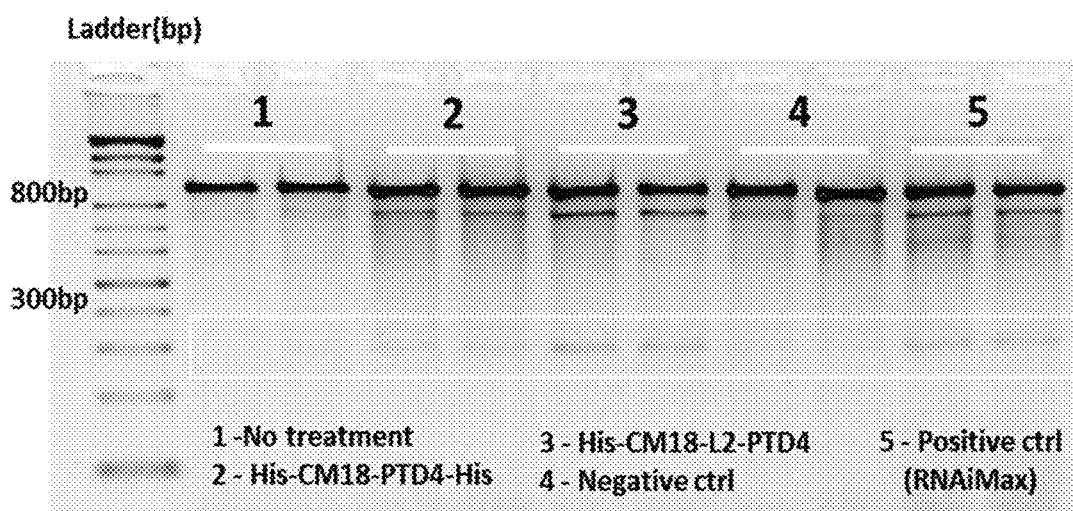

After 2 minutes, cells were washed with PBS and incubated in medium with serum for 48 h. Cells were harvested to proceed with the T7E1 protocol assay as described in Example 13.4. FIGS. 46A-46B shows an agarose gel with the HPTR DNA sequences after PCR amplification and the cleavage product of the amplified HPTR DNA sequence by the CRISPR/Cas9 complex after the delivery of the complex with the different shuttle agents. FIG. 46A shows the results with the shuttle agents: His-CM18-PTD4, His-CM18-PTD4-His, and His-C(LLKK)3C-PTD4 in HeLa cells. FIG. 46B shows the results with His-CM18-PTD4 and His-CM18-L2-PTD4 in Jurkat cells. Negative controls (lanes 4) show amplified HPTR DNA sequence after incubation of the cells with the CRISPR/Cas9 complex without the presence of the shuttle agent. Positive controls (lane 5 in FIGS. 46A and 46B) show the amplified HPTR DNA sequence after incubation of the cells with the Cas9/RNAs complex in presence of a lipidic transfection agent (Lipofectamine® RNAiMAX™ Transfection Reagent ThermoFisher Product No. 13778100). These results show that different polypeptide shuttle agents of the present description may successfully deliver a functional CRISPR/Cas9 complex to the nucleus of HeLa and Jurkat cells, and that this delivery results in CRISPR/Cas9-mediated cleavage of genomic DNA.

Example 14

His-CM18-PTD4 Enables Transduction of the Transcription Factor HOXB4 in THP-1 Cells 14.1 HOXB4-WT Recombinant Protein Human HOXB4 recombinant protein was constructed, expressed and purified from a bacterial expression system as described in Example 1.4. The sequence of the HOXB4-WT recombinant protein produced was:

[SEQ ID NO: 80]
MHHHHHHMAMSSFLINSNYVDPKFPPCEEYSQSDYLPSDHSPGYYAGGQR

RESSFQPEAGFGRRAACTVQRYPPPPPPPPPGLSPRAPAPPPAGALLPE

PGQRCEAVSSSPPPPPCAQNPLHPSPSHSACKEPVVYPWMRKVHVSTVNP

NYAGGEPKRSRTAYTRQQVLELEKEFHYNRYLTRRRRVEIAHALCLSERQ

IKIWFQNRRMKWKKDHKLPNTKIRSGGAAGSAGGPPGRPNGGPRAL
(MW = 28.54 kDa; pI = 9.89)
The initiator methionine and the 6x Histidine tag
are shown in bold.

14.2 Real-Time Polymerase Chain Reaction (rt-PCR)

Control and treated cells are transferred to separate sterile 1.5-mL tubes and centrifuged for 5 minutes at 300 g. The cell pellets are resuspended in appropriate buffer to lyse the cells. RNAase-free 70% ethanol is then added followed by mixing by pipetting. The lysates are transferred to an RNeasy™ Mini spin column and centrifuged 30 seconds at 13000 RPM. After several washes with appropriate buffers and centrifugation steps, the eluates are collected in sterile 1.5-mL tubes on ice, and the RNA quantity in each tube is then quantified with a spectrophotometer. For DNase treatment, 2 μg of RNA is diluted in 15 μL of RNase-free water. 1.75 μL of 10× DNase buffer and 0.75 μL of DNase is then added, followed by incubation at 37° C. for 15 minutes. For reverse transcriptase treatment, 0.88 μL of EDTA (50 nM) is added, followed by incubation at 75° C. for 5 minutes. In a PCR tube, 0.5 μg of DNase-treated RNA is mixed with 4 μL of iScript™ Reverse transcription Supermix (5×) and 20 μL of nuclease-free water. The mix is incubated in a PCR machine with the following program: 5 min at 25° C., 30 min at 42° C. and 5 min at 85° C. Newly synthesized cDNA is transferred in sterile 1.5-mL tubes and diluted in 2 μL of nuclease-free water. 18 μL per well of a qPCR machine (CFX-96™) mix is then added in a PCR plate for analysis.

14.3 HOXB4-WT Transduction by His-CM18-PTD4 in THP-1 Cells: Dose Responses and Viability THP-1 cells were cultured and tested in the protein transduction assay using Protocol A as described in Example 9.1. Briefly, THP-1 cells were plated at 30 000 cells/well one day before transduction. HOXB4-WT recombinant protein (0.3, 0.9, or 1.5 μM; Example 14.1) was co-incubated with different concentrations of His-CM18-PTD4 (0, 0.5, 7.5, 0.8 or 1 μM) and then exposed to THP-1 cells for 2.5 hours in the presence of serum. The cells were subjected to real time-PCR analysis as described in Example 14.2 to measure the mRNA levels of a target gene as a marker for HOXB4 activity, which was then normalized to the target gene mRNA levels detected in the negative control cells (no treatment), to obtain a "Fold over control" value. Total RNA levels (ng/μL) were also measured as a marker for cell viability. Results are shown in Table 14.1 and FIG. 42.

TABLE 14.1

Figure 42:
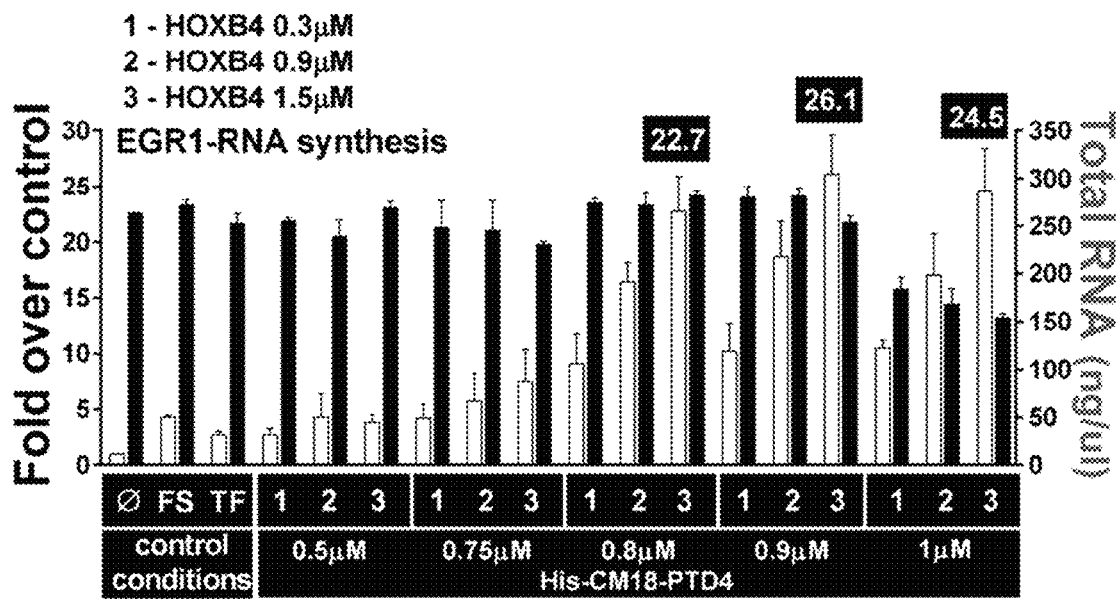

Data from FIG. 42

| Cargo/shuttle agent (FIG. 41) | Cells | Conc. of shuttle (μM) | Conc. of HOXB4-WT (μM) | Fold over control (mean ± St. Dev) | Total RNA in ng/μL (mean ± St. Dev) |
|---|---|---|---|---|---|
| No treatment ("Ø") | THP-1 | 0 | 0 | 1 ± 0.1 | 263 ± 0.4 |
| HOXB4-WT alone ("TF") | THP-1 | 0 | 1.5 | 4.3 ± 0.1 | 271 ± 6.0 |
| His-CM18-PTD4 alone ("FS") | THP-1 | 1 | 0 | 2.7 ± 0.3 | 252 ± 10.7 |
| His-CM18-PTD4 + HOXB4-WT | THP-1 | 0.5 | 0.3 | 2.7 ± 0.6 | 255 ± 3.9 |
| | | | 0.9 | 4.3 ± 2.1 | 239 ± 17.5 |
| | | | 1.5 | 3.8 ± 0.7 | 269 ± 6.4 |
| His-CM18-PTD4 + HOXB4-WT | THP-1 | 0.75 | 0.3 | 4.2 ± 1.2 | 248 ± 28 |
| | | | 0.9 | 5.7 ± 2.5 | 245 ± 31 |
| | | | 1.5 | 7.5 ± 2.8 | 230 ± 3.3 |
| His-CM18-PTD4 + HOXB4-WT | THP-1 | 0.8 | 0.3 | 9.1 ± 2.7 | 274 ± 4.4 |
| | | | 0.9 | 16.4 ± 1.7 | 272 ± 12.5 |
| | | | 1.5 | 22.7 ± 3.2 | 282 ± 4.7 |
| His-CM18-PTD4 + HOXB4-WT | THP-1 | 0.9 | 0.3 | 10.2 ± 2.5 | 280 ± 11.3 |
| | | | 0.9 | 18.7 ± 3.1 | 281 ± 9.2 |
| | | | 1.5 | 26.1 ± 3.5 | 253 ± 7.1 |
| His-CM18-PTD4 + HOXB4-WT | THP-1 | 1 | 0.3 | 10.5 ± 0.7 | 184 ± 12.3 |
| | | | 0.9 | 17 ± 3.7 | 168 ± 16.2 |
| | | | 1.5 | 24.5 ± 3.9 | 154 ± 4.7 |

These results show that exposing THP-1 cells to a mixture of the shuttle agent His-CM18-PTD4 and the transcription factor HOXB4-WT for 2.5 hours in the presence of serum results in a dose-dependent increase in mRNA transcription of the target gene. These results suggest that HOXB4-WT is successfully delivered in an active form to the nucleus of THP-1 cells, where it can mediate transcriptional activation.

14.4 HOXB4-WT Transduction by His-CM18-PTD4 in THP-1 Cells: Time Course and Viability (0 to 48 hours)

THP-1 cells were cultured and tested in the protein transduction assay using Protocol A as described in Example 9.1. Briefly, THP-1 cells were plated at 30 000 cells/well one day before the first time course experiment. HOXB4-WT recombinant protein (1.5 μM; Example 14.1) was co-incubated with His-CM18-PTD4 (0.8 μM) and then exposed to THP-1 cells for 0, 2.5, 4, 24 or 48 hours in presence of serum. The cells were subjected to real time-PCR analysis as described in Example 14.2 to measure mRNA levels of a target gene as a marker for HOXB4 activity, which was then normalized to the target gene mRNA levels detected in the negative control cells (no treatment), to obtain a "Fold over control" value. Total RNA levels (ng/μL) were also measured as a marker for cell viability. Results are shown in Table 14.2 and FIG. 43.

TABLE 14.2

Figure 43:
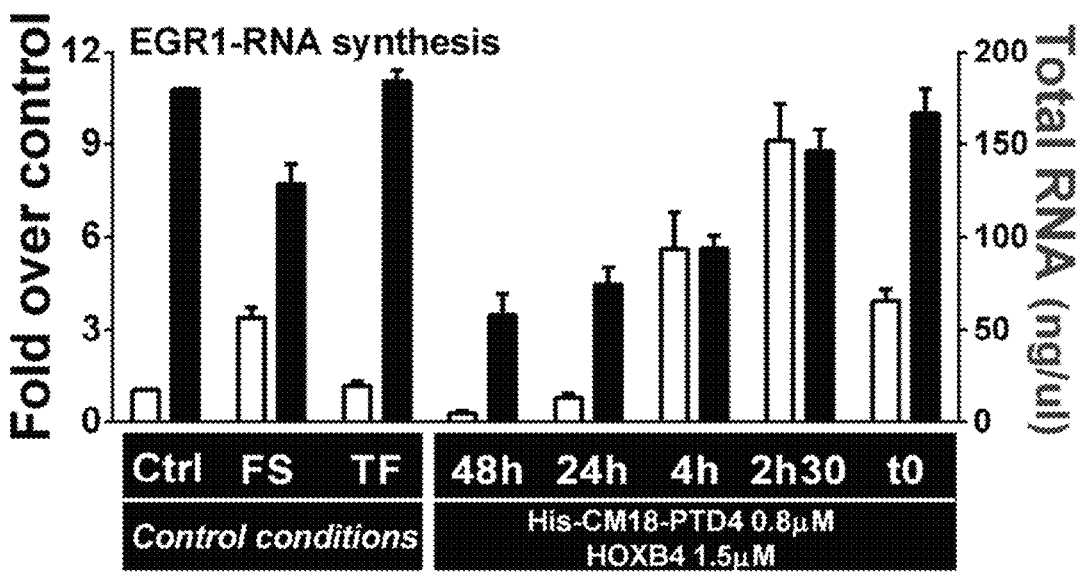

Data from FIG. 43

| Cargo/shuttle agent (FIG. 43) | Cells | Conc. of shuttle (µM) | Conc. of HOXB4-WT (µM) | Exposure time (hours) | Fold over control (mean ± St. Dev) | Total RNA in ng/µL (mean ± St. Dev) |
|---|---|---|---|---|---|---|
| No treatment ("Ctrl") | THP-1 | 0 | 0 | — | 1 ± 0.1 | 180 ± 0.4 |
| HOXB4-WT alone ("TF") | THP-1 | 0 | 1.5 | 2.5 h | 3.4 ± 0.3 | 129 ± 10.7 |
| His-CM18-PTD4 alone ("FS") | THP-1 | 0.8 | 0 | 2.5 h | 1.2 ± 0.14 | 184 ± 6.0 |
| His-CM18-PTD4 + HOXB4-WT | THP-1 | 0.8 | 1.5 | 48 h | 0.27 ± 0.1 | 58 ± 11.2 |
| | | | | 24 h | 0.8 ± 0.14 | 74 ± 9.2 |
| | | | | 4 h | 5.6 ± 1.2 | 94 ± 7.1 |
| | | | | 2.5 h | 9.1 ± 1.2 | 146 ± 11.6 |
| | | | | 0 | 3.9 ± 0.4 | 167 ± 13 |

14.5 HOXB4-WT Transduction by His-CM18-PTD4 in THP-1 Cells: Time Course and Viability (0 to 4 Hours)

THP-1 cells were cultured and tested in the protein transduction assay using Protocol A as described in Example 9.1. Briefly, THP-1 cells were plated at 30 000 cells/well one day before the first time course experiment. HOXB4-WT recombinant protein (0.3 µM; Example 14.1) was co-incubated with His-CM18-PTD4 (0.8 µM) and then exposed to THP-1 cells for 0, 0.5, 1, 2, 2.5, 3 or 4 hours in presence of serum. The cells were subjected to real time-PCR analysis as described in Example 14.2 to measure mRNA levels of a target gene as a marker for HOXB4 activity, which was then normalized to target gene mRNA levels detected in the negative control cells (no treatment), to obtain a "Fold over control" value. Total RNA levels (ng/µL) were also measured as a marker for cell viability. Results are shown in Table 14.3 and FIG. 44.

14.6 HOXB4-WT Transduction by His-CM18-PTD4 in HeLa Cells: Immuno-Labelling and Visualization by Microscopy Recombinant HOXB4-WT transcription factor (25 µM; Example 14.1) was co-incubated with 35 µM of His-CM18-PTD4 and exposed to HeLa cells for 10 seconds using Protocol B as described in Example 9.1. After a 30-minute incubation to allow transduced HOXB4-WT to accumulate in the nucleus, the cells were fixed, permeabilized and immuno-labelled as described in Example 3.2a. HOXB4-WT was labelled using a primary mouse anti-HOXB4 monoclonal antibody (Novus Bio #NBP2-37257) diluted 1/500, and a secondary anti-mouse antibody Alexa™-594 (Abcam #150116) diluted 1/1000. Nuclei were labelled with DAPI. The cells were visualized by bright field and fluorescence microscopy at 20× and 40× magnifications as described in Example 3.2, and sample results are shown in FIGS. 45A-45D. Co-localization was observed between nuclei labelling (FIGS. 45A and 45C) and HOXB4-WT labelling (FIGS. 45B and 45D), indicating that HOXB4-WT was successfully delivered to the nucleus after 30 min in the presence of the shuttle agent His-CM18-PTD4. White triangle windows show examples of areas of co-localization between the nuclei (DAPI) and HOXB4-WT immuno-labels.

TABLE 14.3

Data from FIG. 44

| Cargo/shuttle agent (FIG. 42) | Cells | Conc. of shuttle (µM) | Conc. of HOXB4-WT (µM) | Exposure time (hours) | Fold over control (mean ± St. Dev) | Total RNA in ng/µL (mean ± St. Dev) |
|---|---|---|---|---|---|---|
| No treatment ("Ctrl") | THP-1 | 0 | 0 | — | 1 ± 0.1 | 289 ± 9.2 |
| His-CM18-PTD4 alone ("FS") | THP-1 | 0 | 0.3 | 2.5 h | 2.5 ± 0.2 | 260 ± 7.1 |
| HOXB4-WT alone ("TF") | THP-1 | 0.8 | 0 | 2.5 h | 1 ± 0.14 | 264 ± 12.3 |
| His-CM18-PTD4 + HOXB4-WT | THP-1 | 0.8 | 0.3 | 4 h | 1.2 ± 0.1 | 198 ± 6.0 |
| | | | | 3 h | 1.3 ± 0.21 | 268 ± 12.5 |
| | | | | 2.5 h | 2 ± 0.3 | 275 ± 4.7 |
| | | | | 2 h | 2.2 ± 0.2 | 269 ± 12.5 |
| | | | | 1 | 9.7 ± 2.6 | 268 ± 3.9 |
| | | | | 0.5 | 23.1 ± 2.0 | 266 ± 17.5 |
| | | | | 0 | 4 ± 0.5 | 217 ± 6.4 |

14.7 HOXB4-WT Transduction by Different Shuttle Agents in THP-1 Cells: Dose Responses and Viability THP-1 cells were cultured and tested in the protein transduction assay using Protocol A as described in Example 9.1. Briefly, THP-1 cells were plated at 30 000 cells/well one day before the first time course experiment. HOXB4-WT recombinant protein (1.5 µM; Example 14.1) co-incubated with the shuttle agents His-CM18-PTD4, TAT-KALA, EB1-

PTD4, His-C(LLKK)3C-PTD4 and His-CM18-PTD4-His at 0.8 µM, and then exposed to THP-1 cells for 2.5 hours in presence of serum. The cells were subjected to real time-PCR analysis as described in Example 14.2 to measure mRNA levels of a target gene as a marker for HOXB4 activity, which was then normalized to target gene mRNA levels detected in the negative control cells (no treatment), to obtain a "Fold over control" value. Total RNA levels (ng/µL) were also measured as a marker for cell viability. Results are shown in Table 14.4 and FIG. 47.

TABLE 14.4

Figure 47:
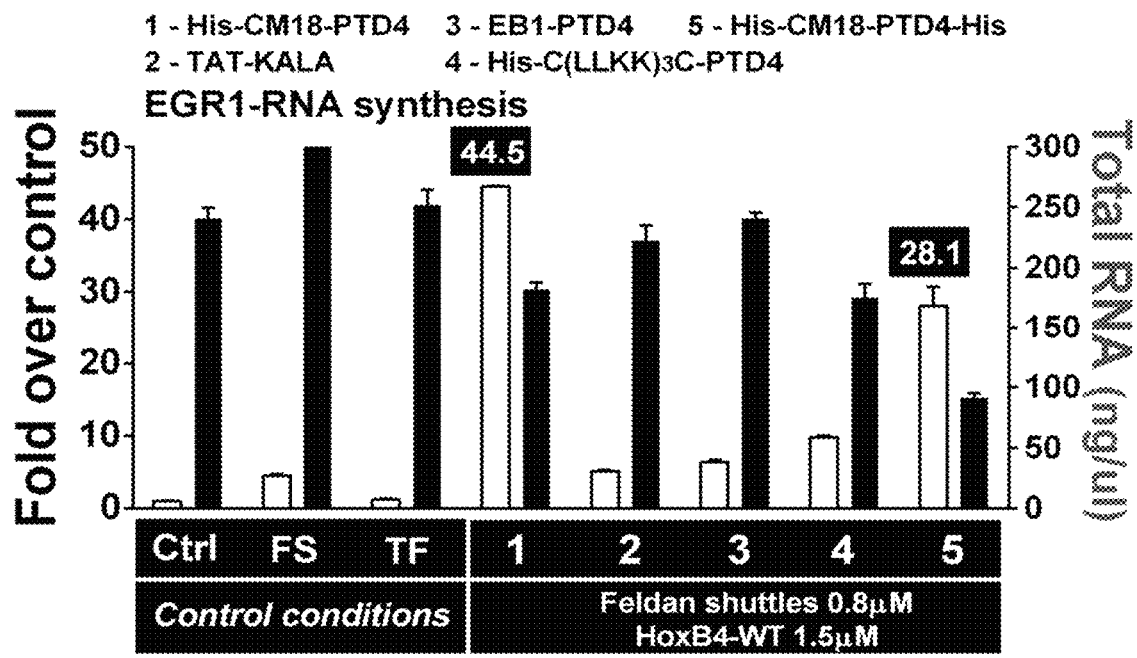
FIG. 47 shows the transcriptional activity of THP-1 cells that have been transduced with the transcription factor HOXB4 using the shuttle agents His-CM18-PTD4, TAT-KALA, EB1-PTD4, His-C(LLKK)3C-PTD4 and His-CM18-PTD4-His. Successful intra-nuclear delivery of HOXB4 was determined by monitoring mRNA levels of a target gene by real-time PCR, and the results were normalized against those in the negative control (HOXB4 without shuttle agent) and expressed as "Fold over control" (left bars). Total cellular RNA (ng/µL) was quantified and used a marker for cell viability (right bars). "Ø" or "Ctrl" means "no treatment"; "TF" means "Transcription Factor alone"; "FS" means "shuttle alone".

Data from FIG. 47

| Cargo/shuttle agent | Shuttle conc. (µM) | HOXB4-WT Conc. (µM) | Exposure time | Fold over control (mean ± St. Dev) | Total RNA in ng/µL (mean ± St. Dev) |
| --- | --- | --- | --- | --- | --- |
| No treatment ("Ctrl") | 0 | 0 | — | 1 ± 0.09 | 240.3 ± 8.9 |
| His-CM18-PTD4 alone ("FS") | 0 | 1.5 | 2.5 h | 2.5 ± 0.3 | 303.9 ± 7.6 |
| HOXB4-WT alone ("TF") | 0.8 | 0 | 2.5 h | 1 ± 0.11 | 251.9 ± 11.9 |
| His-CM18-PTD4 + HOXB4-WT | 0.8 | 1.5 | 2.5 h | 44.5 ± 0.09 | 182 ± 5.97 |
| TAT-KALA + HOXB4-WT | | | | 5.1 ± 0.21 | 222.4 ± 12.5 |
| EB1-PTD4 + HOXB4-WT | | | | 6.4 ± 0.3 | 240.4 ± 4.71 |
| His-C(LLKK)3C-PTD4 + HOXB4-WT | | | | 9.8 ± 0.19 | 175.3 ± 11.25 |
| His-CM18-PTD4-His + HOXB4-WT | | | | 28.1 ± 2.61 | 91.4 ± 3.92 |

Example 15

In Vivo GFP-NLS Delivery in Rat Parietal Cortex by His-CM18-PTD4

The ability of the shuttle agent His-CM18-PTD4 to deliver GFP-NLS in vivo in the nuclei of rat brain cells was tested.

In separate sterile 1.5-mL tubes, shuttle agent His-CM18-PTD4 was diluted in sterile distilled water at room temperature. GFP-NLS, used as cargo protein, was then added to the shuttle agent and, if necessary, sterile PBS was added to obtain the desired concentrations of shuttle agent and cargo in a sufficient final volume for injection in rat brain (e.g., 5 µL per each injection brain site). The shuttle agent/cargo mixture was then immediately used for experiments. One negative control was included for the experiment, which corresponds to the injection of the GFP-NLS alone.

Bilateral injections were performed in the parietal cortex of three rats. In the left parietal cortex (ipsilateral), a mix composed of the shuttle agent (20 µM) and the GFP-NLS (20 µM) was injected, and in the right parietal cortex (contralateral), only the GFP-NLS (20 µM) was injected as a negative control. For surgical procedures, mice were anesthetized with isoflurane. Then the animal was placed in a stereotaxic frame, and the skull surface was exposed. Two holes were drilled at the appropriate sites to allow bilateral infusion of the shuttle/cargo mix or GFP-NLS alone (20 µM) with 5-µL Hamilton syringe. Antero-posterior (AP), lateral (L), and dorso-ventral (DV) coordinates were taken relative to the bregma: (a) AP+0.48 mm, L±3 mm, V−5 mm; (b) AP−2 mm, L±1.3 mm, V−1.5 mm; (c) AP−2.6 mm, L±1.5 mm, V−1.5 mm. The infused volume of the shuttle/cargo mix or cargo alone was 5 µL per injection site and the injection was performed for 10 minutes. After that, experimenter waited 1 min before removing the needle from the brain. All measures were taken before, during, and after surgery to minimize animal pain and discomfort. Animals were sacrificed by perfusion with paraformaldehyde (4%) 2 h after surgery, and brain were collected and prepared for microcopy analysis. Experimental procedures were approved by the Animal Care Committee in line with guidelines from the Canadian Council on Animal Care.

Figure 48A:
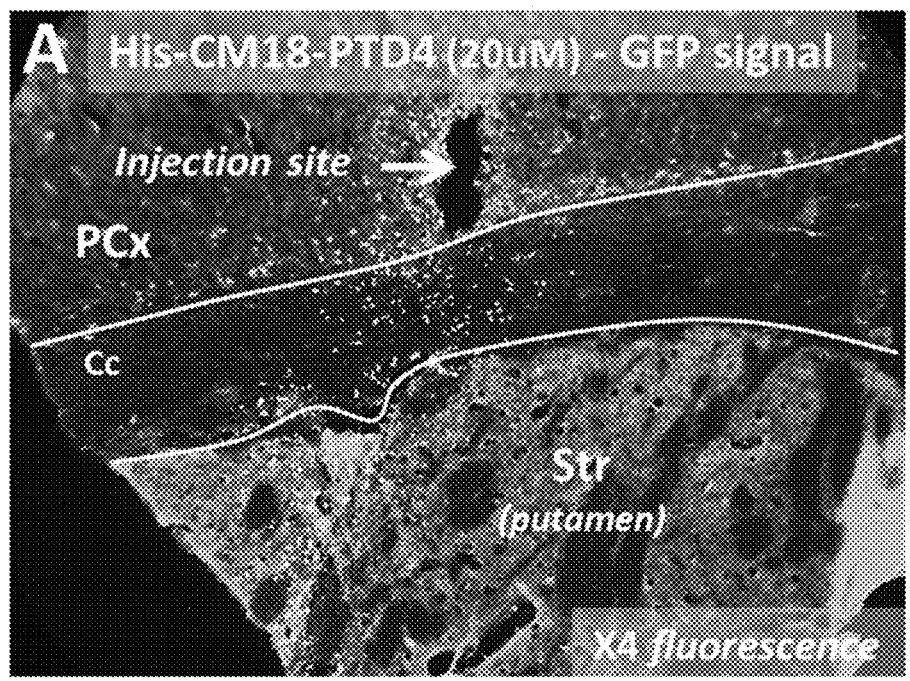
Figure 48B:
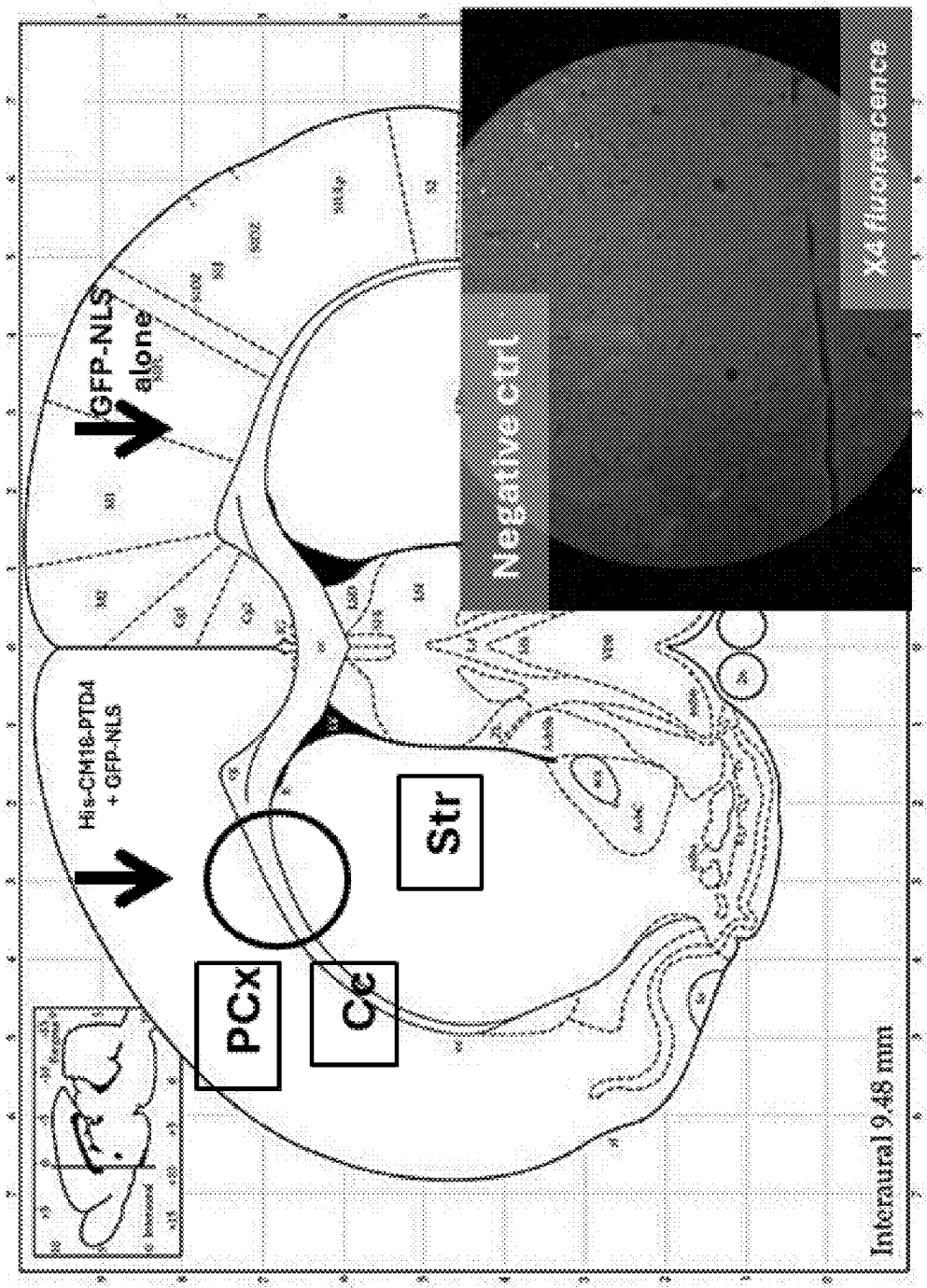

Dorso-ventral rat brain slices were collected and analysed by fluorescence microscopy and results are shown in FIG. 48A-48D at (FIG. 48A) 4×, (FIG. 48C) 10× and (FIG. 48D) 20× magnifications. The injection site is located in the deepest layers of the parietal cortex (PCx). In the presence of the His-CM18-PTD4 shuttle, the GFP-NLS diffused in cell nuclei of the PCx, of the Corpus Callus (Cc) and of the striatum (Str) (White curves mean limitations between brains structures). FIG. 48B shows the stereotaxic coordinates of the injection site (black arrows) from the rat brain atlas of Franklin and Paxinos. The injection of GFP-NLS in presence of His-CM18-PTD4 was performed on the left part of the brain, and the negative control (an injection of GFP-NLS alone), was done on the contralateral site. The black circle and connected black lines in FIG. 48B show the areas observed in the fluorescent pictures (FIGS. 48A, 48C and 48D).

This experiment demonstrated the cell delivery of the cargo GFP-NLS after its stereotaxic injection in the rat parietal cortex in the presence of the shuttle agent His-CM18-PTD4. Results show the delivery of the GFP-NLS in the nucleus of cells from the deeper layers of the parietal cortex (injection site) to the corpus callus and the dorsal level of the striatum (putamen). In contrast, the negative control in which GFP-NLS is only detectable locally around the injection site. This experiment shows that shuttle agent induced nuclear delivery of the cargo in the injection site (parietal cortex) and its diffusion through both neighboring brain areas (corpus callus and striatum rat brain).

What is claimed is:

1. An in vitro or in vivo method for increasing transduction efficiency and decreasing cytosolic delivery time of a polypeptide cargo in eukaryotic cells, the method comprising:
   (a) providing a composition comprising a polypeptide cargo and a shuttle agent, the shuttle agent being a peptide comprising a cationic amphipathic alpha-helical endosome leakage domain (ELD) having endosomolytic activity and a cationic cell penetrating domain (CPD) having cell penetrating activity, wherein the shuttle agent is not bound covalently to the polypeptide cargo; and
   (b) contacting target eukaryotic cells with the composition such that the target eukaryotic cells are exposed simultaneously to the polypeptide cargo and a concentration of the shuttle agent of at least 2.5 µM, thereby increasing transduction efficiency and decreasing cytosolic delivery time of the polypeptide cargo in the target eukaryotic cells as compared to in the absence of the shuttle agent.

2. The method of claim 1, wherein the target eukaryotic cells are contacted with a concentration of the shuttle agent of at least 5 µM.

3. The method of claim 1, wherein the target eukaryotic cells are contacted with a concentration of the shuttle agent of at least 7.5 µM.

4. The method of claim 1, wherein the target eukaryotic cells are contacted with a concentration of the shuttle agent of at least 10 µM.

5. The method of claim 1, wherein the target eukaryotic cells are contacted with a concentration of the shuttle agent of at least 20 µM.

6. The method of claim 1, wherein contacting the target eukaryotic cells with the composition achieves cytosolic delivery of the polypeptide cargo within 5 minutes.

7. The method of claim 1, wherein contacting the target eukaryotic cells with the composition achieves cytosolic delivery of the polypeptide cargo within 2 minutes.

8. The method of claim 1, wherein the shuttle agent has a net charge of at least +5 at physiological pH.

9. The method of claim 1, wherein the shuttle agent is a peptide having a maximum length of 150 amino acids.

10. The method of claim 1, wherein the shuttle agent further comprises a histidine-rich domain.

11. The method of claim 1, wherein the shuttle agent further comprises a linker domain between the ELD and the CPD.

12. The method of claim 1, wherein the polypeptide cargo lacks a CPD.

13. The method of claim 1, wherein said polypeptide cargo is a transcription factor, a nuclease, a cytokine, a hormone, a growth factor, or an antibody.

14. The method of claim 13, wherein said nuclease is a CRISPR endonuclease further comprising a guide RNA, a crRNA, a tracrRNA, or both a crRNA and a tracrRNA.

15. The method of claim 1, which is an in vivo method and wherein the concentration of the shuttle agent in the composition in (a) is at least 10 µM.

16. The method of claim 1, which is an in vivo method and wherein contacting the target eukaryotic cells with the composition comprises parenteral administration or direct injection into a tissue, organ, or system.

17. A pharmaceutical composition comprising a polypeptide cargo for intracellular delivery and a shuttle agent that is not bound covalently to the polypeptide cargo, the shuttle agent being a peptide comprising a cationic amphipathic alpha-helical endosome leakage domain (ELD) having endosomolytic activity and a cationic cell penetrating domain (CPD) having cell penetrating activity, wherein the concentration of the shuttle agent in the composition is at least 10 µM.

18. The pharmaceutical composition of claim 17, wherein the concentration of the shuttle agent in the composition is at least 20 µM.

19. The pharmaceutical composition of claim 17, wherein the concentration of the polypeptide cargo in the composition is at least 5 µM.

* * * * *

SEQUENCE LISTING

<160> NUMBER OF SEQ ID NOS: 105

<210> SEQ ID NO 1
<211> LENGTH: 18
<212> TYPE: PRT
<213> ORGANISM: Artificial sequence
<220> FEATURE:
<223> OTHER INFORMATION: CM18

<400> SEQUENCE: 1

Lys Trp Lys Leu Phe Lys Lys Ile Gly Ala Val Leu Lys Val Leu Thr
1               5                   10                  15

Thr Gly

<210> SEQ ID NO 2
<211> LENGTH: 189
<212> TYPE: PRT
<213> ORGANISM: Artificial sequence
<220> FEATURE:
<223> OTHER INFORMATION: Diphtheria toxin T domain (DT)

<400> SEQUENCE: 2

Val Gly Ser Ser Leu Ser Cys Ile Asn Leu Asp Trp Asp Val Ile Arg
1               5                   10                  15

Asp Lys Thr Lys Thr Lys Ile Glu Ser Leu Lys Glu His Gly Pro Ile
                20                  25                  30

Lys Asn Lys Met Ser Glu Ser Pro Asn Lys Thr Val Ser Glu Glu Lys
        35                  40                  45

Ala Lys Gln Tyr Leu Glu Glu Phe His Gln Thr Ala Leu Glu His Pro
    50                  55                  60

Glu Leu Ser Glu Leu Lys Thr Val Thr Gly Thr Asn Pro Val Phe Ala
65                  70                  75                  80

Gly Ala Asn Tyr Ala Ala Trp Ala Val Asn Val Ala Gln Val Ile Asp
                85                  90                  95

Ser Glu Thr Ala Asp Asn Leu Glu Lys Thr Thr Ala Ala Leu Ser Ile
                100                 105                 110

Leu Pro Gly Ile Gly Ser Val Met Gly Ile Ala Asp Gly Ala Val His
            115                 120                 125

His Asn Thr Glu Glu Ile Val Ala Gln Ser Ile Ala Leu Ser Ser Leu
        130                 135                 140

Met Val Ala Gln Ala Ile Pro Leu Val Gly Glu Leu Val Asp Ile Gly
145                 150                 155                 160

Phe Ala Ala Tyr Asn Phe Val Glu Ser Ile Ile Asn Leu Phe Gln Val
                165                 170                 175

Val His Asn Ser Tyr Asn Arg Pro Ala Tyr Ser Pro Gly
            180                 185

<210> SEQ ID NO 3
<211> LENGTH: 30
<212> TYPE: PRT
<213> ORGANISM: Artificial sequence
<220> FEATURE:
<223> OTHER INFORMATION: GALA

<400> SEQUENCE: 3

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
                20                  25                  30

<210> SEQ ID NO 4
<211> LENGTH: 115
<212> TYPE: PRT
<213> ORGANISM: Artificial sequence
<220> FEATURE:
<223> OTHER INFORMATION: PEA

<400> SEQUENCE: 4

Val Leu Ala Gly Asn Pro Ala Lys His Asp Leu Asp Ile Lys Pro Thr
1               5                   10                  15

Val Ile Ser His Arg Leu His Phe Pro Glu Gly Gly Ser Leu Ala Ala
            20                  25                  30

Leu Thr Ala His Gln Ala Cys His Leu Pro Leu Glu Thr Phe Thr Arg
        35                  40                  45

His Arg Gln Pro Arg Gly Trp Glu Gln Leu Glu Gln Cys Gly Tyr Pro
    50                  55                  60

Val Gln Arg Leu Val Ala Leu Tyr Leu Ala Ala Arg Leu Ser Trp Asn
65                  70                  75                  80

Gln Val Asp Gln Val Ile Arg Asn Ala Leu Ala Ser Pro Gly Ser Gly
                85                  90                  95

Gly Asp Leu Gly Glu Ala Ile Arg Glu Gln Pro Glu Gln Ala Arg Leu
            100                 105                 110

Ala Leu Thr
        115

<210> SEQ ID NO 5
<211> LENGTH: 24
<212> TYPE: PRT
<213> ORGANISM: Artificial sequence
<220> FEATURE:
<223> OTHER INFORMATION: INF-7

<400> SEQUENCE: 5

Gly Leu Phe Glu Ala Ile Glu Gly Phe Ile Glu Asn Gly Trp Glu Gly
1               5                   10                  15

Met Ile Asp Gly Trp Tyr Gly Cys
            20

<210> SEQ ID NO 6
<211> LENGTH: 26
<212> TYPE: PRT
<213> ORGANISM: Artificial sequence
<220> FEATURE:
<223> OTHER INFORMATION: LAH4

<400> SEQUENCE: 6

Lys Lys Ala Leu Leu Ala Leu Ala Leu His His Leu Ala His Leu Ala
1               5                   10                  15

Leu His Leu Ala Leu Ala Leu Lys Lys Ala
            20                  25

<210> SEQ ID NO 7
<211> LENGTH: 24
<212> TYPE: PRT
<213> ORGANISM: Artificial sequence
<220> FEATURE:
<223> OTHER INFORMATION: HGP

<400> SEQUENCE: 7

Leu Leu Gly Arg Arg Gly Trp Glu Val Leu Lys Tyr Trp Trp Asn Leu
1               5                   10                  15

```
Leu Gln Tyr Trp Ser Gln Glu Leu
            20

<210> SEQ ID NO 8
<211> LENGTH: 23
<212> TYPE: PRT
<213> ORGANISM: Artificial sequence
<220> FEATURE:
<223> OTHER INFORMATION: H5WYG

<400> SEQUENCE: 8

Gly Leu Phe His Ala Ile Ala His Phe Ile His Gly Gly Trp His Gly
1               5                   10                  15

Leu Ile His Gly Trp Tyr Gly
            20

<210> SEQ ID NO 9
<211> LENGTH: 23
<212> TYPE: PRT
<213> ORGANISM: Artificial sequence
<220> FEATURE:
<223> OTHER INFORMATION: HA2

<400> SEQUENCE: 9

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 10
<211> LENGTH: 23
<212> TYPE: PRT
<213> ORGANISM: Artificial sequence
<220> FEATURE:
<223> OTHER INFORMATION: EB1

<400> SEQUENCE: 10

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 11
<211> LENGTH: 25
<212> TYPE: PRT
<213> ORGANISM: Artificial sequence
<220> FEATURE:
<223> OTHER INFORMATION: VSVG

<400> SEQUENCE: 11

Lys Phe Thr Ile Val Phe Pro His Asn Gln Lys Gly Asn Trp Lys Asn
1               5                   10                  15

Val Pro Ser Asn Tyr His Tyr Cys Pro
            20                  25

<210> SEQ ID NO 12
<211> LENGTH: 115
<212> TYPE: PRT
<213> ORGANISM: Artificial sequence
<220> FEATURE:
<223> OTHER INFORMATION: Pseudomonas toxin

<400> SEQUENCE: 12

Glu Gly Gly Ser Leu Ala Ala Leu Thr Ala His Gln Ala Cys His Leu
1               5                   10                  15
```

```
Pro Leu Glu Thr Phe Thr Arg His Arg Gln Pro Arg Gly Trp Glu Gln
            20                  25                  30

Leu Glu Gln Cys Gly Tyr Pro Val Gln Arg Leu Val Ala Leu Tyr Leu
            35                  40                  45

Ala Ala Arg Leu Ser Trp Asn Gln Val Asp Val Ile Arg Asn Ala
50                  55                  60

Leu Ala Ser Pro Gly Ser Gly Gly Asp Leu Gly Glu Ala Ile Arg Glu
65                  70                  75                  80

Gln Pro Glu Gln Ala Arg Leu Ala Leu Thr Leu Ala Ala Glu Ser
                85                  90                  95

Glu Arg Phe Val Arg Gln Gly Thr Gly Asn Asp Glu Ala Gly Ala Ala
            100                 105                 110

Asn Ala Asp
        115
```

<210> SEQ ID NO 13
<211> LENGTH: 26
<212> TYPE: PRT
<213> ORGANISM: Artificial sequence
<220> FEATURE:
<223> OTHER INFORMATION: Melittin

<400> SEQUENCE: 13

```
Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

<210> SEQ ID NO 14
<211> LENGTH: 30
<212> TYPE: PRT
<213> ORGANISM: Artificial sequence
<220> FEATURE:
<223> OTHER INFORMATION: KALA

<400> SEQUENCE: 14

```
Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30
```

<210> SEQ ID NO 15
<211> LENGTH: 20
<212> TYPE: PRT
<213> ORGANISM: Artificial sequence
<220> FEATURE:
<223> OTHER INFORMATION: JST-1

<400> SEQUENCE: 15

```
Gly Leu Phe Glu Ala Leu Leu Glu Leu Leu Glu Ser Leu Trp Glu Leu
1               5                   10                  15

Leu Leu Glu Ala
        20
```

<210> SEQ ID NO 16
<211> LENGTH: 16
<212> TYPE: PRT
<213> ORGANISM: Artificial sequence
<220> FEATURE:
<223> OTHER INFORMATION: SP

<400> SEQUENCE: 16

```
Ala Ala Val Ala Leu Leu Pro Ala Val Leu Leu Ala Leu Leu Ala Pro
1               5                   10                  15

<210> SEQ ID NO 17
<211> LENGTH: 11
<212> TYPE: PRT
<213> ORGANISM: Artificial sequence
<220> FEATURE:
<223> OTHER INFORMATION: TAT

<400> SEQUENCE: 17

Tyr Gly Arg Lys Lys Arg Arg Gln Arg Arg
1               5                   10

<210> SEQ ID NO 18
<211> LENGTH: 16
<212> TYPE: PRT
<213> ORGANISM: Artificial sequence
<220> FEATURE:
<223> OTHER INFORMATION: Penetratin (Antennapedia)

<400> SEQUENCE: 18

Arg Gln Ile Lys Ile Trp Phe Gln Asn Arg Arg Met Lys Trp Lys Lys
1               5                   10                  15

<210> SEQ ID NO 19
<211> LENGTH: 18
<212> TYPE: PRT
<213> ORGANISM: Artificial sequence
<220> FEATURE:
<223> OTHER INFORMATION: pVEC

<400> SEQUENCE: 19

Leu Leu Ile Ile Leu Arg Arg Arg Ile Arg Lys Gln Ala His Ala His
1               5                   10                  15

Ser Lys

<210> SEQ ID NO 20
<211> LENGTH: 22
<212> TYPE: PRT
<213> ORGANISM: Artificial sequence
<220> FEATURE:
<223> OTHER INFORMATION: M918

<400> SEQUENCE: 20

Met Val Thr Val Leu Phe Arg Arg Leu Arg Ile Arg Arg Ala Cys Gly
1               5                   10                  15

Pro Pro Arg Val Arg Val
            20

<210> SEQ ID NO 21
<211> LENGTH: 21
<212> TYPE: PRT
<213> ORGANISM: Artificial sequence
<220> FEATURE:
<223> OTHER INFORMATION: Pep-1

<400> SEQUENCE: 21

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 22
```

```
<211> LENGTH: 21
<212> TYPE: PRT
<213> ORGANISM: Artificial sequence
<220> FEATURE:
<223> OTHER INFORMATION: Pep-2

<400> SEQUENCE: 22

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 23
<211> LENGTH: 7
<212> TYPE: PRT
<213> ORGANISM: Artificial sequence
<220> FEATURE:
<223> OTHER INFORMATION: Xentry

<400> SEQUENCE: 23

Leu Cys Leu Arg Pro Val Gly
1               5

<210> SEQ ID NO 24
<211> LENGTH: 9
<212> TYPE: PRT
<213> ORGANISM: Artificial sequence
<220> FEATURE:
<223> OTHER INFORMATION: Arginine stretch

<400> SEQUENCE: 24

Arg Arg Arg Arg Arg Arg Arg Arg Arg
1               5

<210> SEQ ID NO 25
<211> LENGTH: 26
<212> TYPE: PRT
<213> ORGANISM: Artificial sequence
<220> FEATURE:
<223> OTHER INFORMATION: Transportan

<400> SEQUENCE: 25

Trp Thr Leu Asn Ser Ala Gly Tyr Leu Leu Gly Lys Ile Asn Leu Lys
1               5                   10                  15

Ala Leu Ala Ala Leu Ala Lys Lys Ile Leu
            20                  25

<210> SEQ ID NO 26
<211> LENGTH: 18
<212> TYPE: PRT
<213> ORGANISM: Artificial sequence
<220> FEATURE:
<223> OTHER INFORMATION: SynB1

<400> SEQUENCE: 26

Arg Gly Gly Arg Leu Ser Tyr Ser Arg Arg Arg Phe Ser Thr Ser Thr
1               5                   10                  15

Gly Arg

<210> SEQ ID NO 27
<211> LENGTH: 10
<212> TYPE: PRT
<213> ORGANISM: Artificial sequence
<220> FEATURE:
<223> OTHER INFORMATION: SynB3
```

```
<400> SEQUENCE: 27

Arg Arg Leu Ser Tyr Ser Arg Arg Arg Phe
1               5                   10

<210> SEQ ID NO 28
<211> LENGTH: 5
<212> TYPE: PRT
<213> ORGANISM: Artificial sequence
<220> FEATURE:
<223> OTHER INFORMATION: E1a

<400> SEQUENCE: 28

Lys Arg Pro Arg Pro
1               5

<210> SEQ ID NO 29
<211> LENGTH: 7
<212> TYPE: PRT
<213> ORGANISM: Artificial sequence
<220> FEATURE:
<223> OTHER INFORMATION: SV40 T-Ag

<400> SEQUENCE: 29

Pro Lys Lys Lys Arg Lys Val
1               5

<210> SEQ ID NO 30
<211> LENGTH: 9
<212> TYPE: PRT
<213> ORGANISM: Artificial sequence
<220> FEATURE:
<223> OTHER INFORMATION: c-myc

<400> SEQUENCE: 30

Pro Ala Ala Lys Arg Val Lys Leu Asp
1               5

<210> SEQ ID NO 31
<211> LENGTH: 22
<212> TYPE: PRT
<213> ORGANISM: Artificial sequence
<220> FEATURE:
<223> OTHER INFORMATION: Op-T-NLS

<400> SEQUENCE: 31

Ser Ser Asp Asp Glu Ala Thr Ala Asp Ser Gln His Ala Ala Pro Pro
1               5                   10                  15

Lys Lys Lys Arg Lys Val
            20

<210> SEQ ID NO 32
<211> LENGTH: 5
<212> TYPE: PRT
<213> ORGANISM: Artificial sequence
<220> FEATURE:
<223> OTHER INFORMATION: Vp3

<400> SEQUENCE: 32

Lys Lys Lys Arg Lys
1               5

<210> SEQ ID NO 33
<211> LENGTH: 16
<212> TYPE: PRT
<213> ORGANISM: Artificial sequence
<220> FEATURE:
```

<223> OTHER INFORMATION: Nucleoplasmin

<400> SEQUENCE: 33

Lys Arg Pro Ala Ala Thr Lys Lys Ala Gly Gln Ala Lys Lys Lys Lys
1               5                   10                  15

<210> SEQ ID NO 34
<211> LENGTH: 10
<212> TYPE: PRT
<213> ORGANISM: Artificial sequence
<220> FEATURE:
<223> OTHER INFORMATION: Histone 2B NLS

<400> SEQUENCE: 34

Asp Gly Lys Lys Arg Lys Arg Ser Arg Lys
1               5                   10

<210> SEQ ID NO 35
<211> LENGTH: 24
<212> TYPE: PRT
<213> ORGANISM: Artificial sequence
<220> FEATURE:
<223> OTHER INFORMATION: Xenopus N1

<400> SEQUENCE: 35

Val Arg Lys Lys Arg Lys Thr Glu Glu Glu Ser Pro Leu Lys Asp Lys
1               5                   10                  15

Asp Ala Lys Lys Ser Lys Gln Glu
            20

<210> SEQ ID NO 36
<211> LENGTH: 19
<212> TYPE: PRT
<213> ORGANISM: Artificial sequence
<220> FEATURE:
<223> OTHER INFORMATION: PARP

<400> SEQUENCE: 36

Lys Arg Lys Gly Asp Glu Val Asp Gly Val Asp Glu Cys Ala Lys Lys
1               5                   10                  15

Ser Lys Lys

<210> SEQ ID NO 37
<211> LENGTH: 7
<212> TYPE: PRT
<213> ORGANISM: Artificial sequence
<220> FEATURE:
<223> OTHER INFORMATION: PDX-1

<400> SEQUENCE: 37

Arg Arg Met Lys Trp Lys Lys
1               5

<210> SEQ ID NO 38
<211> LENGTH: 7
<212> TYPE: PRT
<213> ORGANISM: Artificial sequence
<220> FEATURE:
<223> OTHER INFORMATION: QKI-5

<400> SEQUENCE: 38

Arg Val His Pro Tyr Gln Arg
1               5

<210> SEQ ID NO 39

```
<211> LENGTH: 24
<212> TYPE: PRT
<213> ORGANISM: Artificial sequence
<220> FEATURE:
<223> OTHER INFORMATION: HCDA

<400> SEQUENCE: 39

Lys Arg Pro Ala Cys Thr Leu Lys Pro Glu Cys Val Gln Gln Leu Leu
1               5                   10                  15

Val Cys Ser Gln Glu Ala Lys Lys
            20

<210> SEQ ID NO 40
<211> LENGTH: 7
<212> TYPE: PRT
<213> ORGANISM: Artificial sequence
<220> FEATURE:
<223> OTHER INFORMATION: H2B

<400> SEQUENCE: 40

Gly Lys Lys Arg Ser Lys Ala
1               5

<210> SEQ ID NO 41
<211> LENGTH: 6
<212> TYPE: PRT
<213> ORGANISM: Artificial sequence
<220> FEATURE:
<223> OTHER INFORMATION: v-Rel

<400> SEQUENCE: 41

Lys Ala Lys Arg Gln Arg
1               5

<210> SEQ ID NO 42
<211> LENGTH: 5
<212> TYPE: PRT
<213> ORGANISM: Artificial sequence
<220> FEATURE:
<223> OTHER INFORMATION: Amida

<400> SEQUENCE: 42

Arg Lys Arg Arg Arg
1               5

<210> SEQ ID NO 43
<211> LENGTH: 9
<212> TYPE: PRT
<213> ORGANISM: Artificial sequence
<220> FEATURE:
<223> OTHER INFORMATION: RanBP3

<400> SEQUENCE: 43

Pro Pro Val Lys Arg Glu Arg Thr Ser
1               5

<210> SEQ ID NO 44
<211> LENGTH: 10
<212> TYPE: PRT
<213> ORGANISM: Artificial sequence
<220> FEATURE:
<223> OTHER INFORMATION: Pho4p

<400> SEQUENCE: 44

Pro Tyr Leu Asn Lys Arg Lys Gly Lys Pro
1               5                   10
```

<210> SEQ ID NO 45
<211> LENGTH: 9
<212> TYPE: PRT
<213> ORGANISM: Artificial sequence
<220> FEATURE:
<223> OTHER INFORMATION: LEF-1

<400> SEQUENCE: 45

Lys Lys Lys Lys Arg Lys Arg Glu Lys
1               5

<210> SEQ ID NO 46
<211> LENGTH: 9
<212> TYPE: PRT
<213> ORGANISM: Artificial sequence
<220> FEATURE:
<223> OTHER INFORMATION: TCF-1

<400> SEQUENCE: 46

Lys Lys Lys Arg Arg Ser Arg Glu Lys
1               5

<210> SEQ ID NO 47
<211> LENGTH: 8
<212> TYPE: PRT
<213> ORGANISM: Artificial sequence
<220> FEATURE:
<223> OTHER INFORMATION: BDV-P

<400> SEQUENCE: 47

Pro Arg Pro Arg Lys Ile Pro Arg
1               5

<210> SEQ ID NO 48
<211> LENGTH: 20
<212> TYPE: PRT
<213> ORGANISM: Artificial sequence
<220> FEATURE:
<223> OTHER INFORMATION: TR2

<400> SEQUENCE: 48

Lys Asp Cys Val Ile Asn Lys His His Arg Asn Arg Cys Gln Tyr Cys
1               5                   10                  15

Arg Leu Gln Arg
            20

<210> SEQ ID NO 49
<211> LENGTH: 5
<212> TYPE: PRT
<213> ORGANISM: Artificial sequence
<220> FEATURE:
<223> OTHER INFORMATION: SOX9

<400> SEQUENCE: 49

Pro Arg Arg Arg Lys
1               5

<210> SEQ ID NO 50
<211> LENGTH: 8
<212> TYPE: PRT
<213> ORGANISM: Artificial sequence
<220> FEATURE:
<223> OTHER INFORMATION: Max

<400> SEQUENCE: 50

Pro Gln Ser Arg Lys Lys Leu Arg

```
1               5

<210> SEQ ID NO 51
<211> LENGTH: 9
<212> TYPE: PRT
<213> ORGANISM: Artificial sequence
<220> FEATURE:
<223> OTHER INFORMATION: Mitochondrial signal sequence from Tim9

<400> SEQUENCE: 51

Asn Leu Val Glu Arg Cys Phe Thr Asp
1               5

<210> SEQ ID NO 52
<211> LENGTH: 12
<212> TYPE: PRT
<213> ORGANISM: Artificial sequence
<220> FEATURE:
<223> OTHER INFORMATION: Mitochondrial signal sequence from Yeast
      cytochrome c oxidase subunit IV

<400> SEQUENCE: 52

Met Leu Ser Leu Arg Gln Ser Ile Arg Phe Phe Lys
1               5                   10

<210> SEQ ID NO 53
<211> LENGTH: 16
<212> TYPE: PRT
<213> ORGANISM: Artificial sequence
<220> FEATURE:
<223> OTHER INFORMATION: Mitochondrial signal sequence from 18S rRNA

<400> SEQUENCE: 53

Met Leu Ile Ser Arg Cys Lys Trp Ser Arg Phe Pro Gly Asn Gln Arg
1               5                   10                  15

<210> SEQ ID NO 54
<211> LENGTH: 3
<212> TYPE: PRT
<213> ORGANISM: Artificial sequence
<220> FEATURE:
<223> OTHER INFORMATION: Peroxisome signal sequence - PTS1

<400> SEQUENCE: 54

Ser Lys Leu
1

<210> SEQ ID NO 55
<211> LENGTH: 17
<212> TYPE: PRT
<213> ORGANISM: Artificial sequence
<220> FEATURE:
<223> OTHER INFORMATION: Nucleolar signal sequence from BIRC5

<400> SEQUENCE: 55

Met Gln Arg Lys Pro Thr Ile Arg Arg Lys Asn Leu Arg Leu Arg Arg
1               5                   10                  15

Lys

<210> SEQ ID NO 56
<211> LENGTH: 11
<212> TYPE: PRT
<213> ORGANISM: Artificial sequence
<220> FEATURE:
<223> OTHER INFORMATION: Nucleolar signal sequence from RECQL4

<400> SEQUENCE: 56
```

```
Lys Gln Ala Trp Lys Gln Lys Trp Arg Lys Lys
1               5                   10
```

<210> SEQ ID NO 57
<211> LENGTH: 29
<212> TYPE: PRT
<213> ORGANISM: Artificial sequence
<220> FEATURE:
<223> OTHER INFORMATION: CM18-TAT

<400> SEQUENCE: 57

```
Lys Trp Lys Leu Phe Lys Lys Ile Gly Ala Val Leu Lys Val Leu Thr
1               5                   10                  15

Thr Gly Tyr Gly Arg Lys Lys Arg Arg Gln Arg Arg Arg
            20                  25
```

<210> SEQ ID NO 58
<211> LENGTH: 34
<212> TYPE: PRT
<213> ORGANISM: Artificial sequence
<220> FEATURE:
<223> OTHER INFORMATION: CM18-Penetratin

<400> SEQUENCE: 58

```
Lys Trp Lys Leu Phe Lys Lys Ile Gly Ala Val Leu Lys Val Leu Thr
1               5                   10                  15

Thr Gly Arg Gln Ile Lys Ile Trp Phe Gln Asn Arg Arg Met Lys Trp
            20                  25                  30

Lys Lys
```

<210> SEQ ID NO 59
<211> LENGTH: 36
<212> TYPE: PRT
<213> ORGANISM: Artificial sequence
<220> FEATURE:
<223> OTHER INFORMATION: His-CM18-TAT

<400> SEQUENCE: 59

```
Met His His His His His His Lys Trp Lys Leu Phe Lys Lys Ile Gly
1               5                   10                  15

Ala Val Leu Lys Val Leu Thr Thr Gly Tyr Gly Arg Lys Lys Arg Arg
            20                  25                  30

Gln Arg Arg Arg
        35
```

<210> SEQ ID NO 60
<211> LENGTH: 290
<212> TYPE: PRT
<213> ORGANISM: Artificial sequence
<220> FEATURE:
<223> OTHER INFORMATION: GFP

<400> SEQUENCE: 60

```
Met His His His His His His Gly Gly Gly Ser Gly Gly Gly Gly
1               5                   10                  15

Ser Gly Gly Ala Ser Thr Gly Thr Gly Ile Arg Met Val Ser Lys Gly
            20                  25                  30

Glu Glu Leu Phe Thr Gly Val Val Pro Ile Leu Val Glu Leu Asp Gly
        35                  40                  45

Asp Val Asn Gly His Lys Phe Ser Val Ser Gly Glu Gly Glu Gly Asp
    50                  55                  60
```

-continued

```
Ala Thr Tyr Gly Lys Leu Thr Leu Lys Phe Ile Cys Thr Thr Gly Lys
 65                  70                  75                  80

Leu Pro Val Pro Trp Pro Thr Leu Val Thr Thr Leu Thr Tyr Gly Val
                 85                  90                  95

Gln Cys Phe Ser Arg Tyr Pro Asp His Met Lys Gln His Asp Phe Phe
            100                 105                 110

Lys Ser Ala Met Pro Glu Gly Tyr Val Gln Glu Arg Thr Ile Phe Phe
        115                 120                 125

Lys Asp Asp Gly Asn Tyr Lys Thr Arg Ala Glu Val Lys Phe Glu Gly
130                 135                 140

Asp Thr Leu Val Asn Arg Ile Glu Leu Lys Gly Ile Asp Phe Lys Glu
145                 150                 155                 160

Asp Gly Asn Ile Leu Gly His Lys Leu Glu Tyr Asn Tyr Asn Ser His
                165                 170                 175

Asn Val Tyr Ile Met Ala Asp Lys Gln Lys Asn Gly Ile Lys Val Asn
            180                 185                 190

Phe Lys Ile Arg His Asn Ile Glu Asp Gly Ser Val Gln Leu Ala Asp
        195                 200                 205

His Tyr Gln Gln Asn Thr Pro Ile Gly Asp Gly Pro Val Leu Leu Pro
210                 215                 220

Asp Asn His Tyr Leu Ser Thr Gln Ser Ala Leu Ser Lys Asp Pro Asn
225                 230                 235                 240

Glu Lys Arg Asp His Met Val Leu Leu Glu Phe Val Thr Ala Ala Gly
                245                 250                 255

Ile Thr Leu Gly Met Asp Glu Leu Tyr Lys Gly Gly Ser Gly Gly Gly
            260                 265                 270

Ser Gly Gly Gly Ser Gly Trp Ile Arg Ala Ser Ser Gly Gly Arg Glu
        275                 280                 285

Ile Ser
290

<210> SEQ ID NO 61
<211> LENGTH: 317
<212> TYPE: PRT
<213> ORGANISM: Artificial sequence
<220> FEATURE:
<223> OTHER INFORMATION: TAT-GFP

<400> SEQUENCE: 61

Met His His His His His Gly Gly Gly Gly Ser Gly Gly Gly Gly
 1               5                  10                  15

Ser Gly Gly Ala Ser Thr Gly Thr Gly Arg Lys Lys Arg Gln Arg
            20                  25                  30

Arg Arg Pro Pro Gln Gly Gly Gly Gly Ser Gly Gly Gly Gly Ser Gly
        35                  40                  45

Gly Gly Thr Gly Ile Arg Met Val Ser Lys Gly Glu Glu Leu Phe Thr
    50                  55                  60

Gly Val Val Pro Ile Leu Val Glu Leu Asp Gly Asp Val Asn Gly His
 65                  70                  75                  80

Lys Phe Ser Val Ser Gly Glu Gly Glu Gly Asp Ala Thr Tyr Gly Lys
                 85                  90                  95

Leu Thr Leu Lys Phe Ile Cys Thr Thr Gly Lys Leu Pro Val Pro Trp
            100                 105                 110

Pro Thr Leu Val Thr Thr Leu Thr Tyr Gly Val Gln Cys Phe Ser Arg
        115                 120                 125
```

```
Tyr Pro Asp His Met Lys Gln His Asp Phe Phe Lys Ser Ala Met Pro
            130                 135                 140

Glu Gly Tyr Val Gln Glu Arg Thr Ile Phe Phe Lys Asp Asp Gly Asn
145                 150                 155                 160

Tyr Lys Thr Arg Ala Glu Val Lys Phe Glu Gly Asp Thr Leu Val Asn
                165                 170                 175

Arg Ile Glu Leu Lys Gly Ile Asp Phe Lys Glu Asp Gly Asn Ile Leu
            180                 185                 190

Gly His Lys Leu Glu Tyr Asn Tyr Asn Ser His Asn Val Tyr Ile Met
            195                 200                 205

Ala Asp Lys Gln Lys Asn Gly Ile Lys Val Asn Phe Lys Ile Arg His
210                 215                 220

Asn Ile Glu Asp Gly Ser Val Gln Leu Ala Asp His Tyr Gln Gln Asn
225                 230                 235                 240

Thr Pro Ile Gly Asp Gly Pro Val Leu Leu Pro Asp Asn His Tyr Leu
                245                 250                 255

Ser Thr Gln Ser Ala Leu Ser Lys Asp Pro Asn Glu Lys Arg Asp His
            260                 265                 270

Met Val Leu Leu Glu Phe Val Thr Ala Ala Gly Ile Thr Leu Gly Met
            275                 280                 285

Asp Glu Leu Tyr Lys Gly Gly Ser Gly Gly Ser Gly Gly Gly Ser
290                 295                 300

Gly Trp Ile Arg Ala Ser Ser Gly Gly Arg Glu Ile Ser
305                 310                 315

<210> SEQ ID NO 62
<211> LENGTH: 327
<212> TYPE: PRT
<213> ORGANISM: Artificial sequence
<220> FEATURE:
<223> OTHER INFORMATION: GFP-NLS

<400> SEQUENCE: 62

Met His His His His His Gly Gly Gly Ser Gly Gly Gly Gly
1               5                   10                  15

Ser Gly Gly Ala Ser Thr Gly Ile Arg Met Val Ser Lys Gly Glu Glu
            20                  25                  30

Leu Phe Thr Gly Val Val Pro Ile Leu Val Glu Leu Asp Gly Asp Val
            35                  40                  45

Asn Gly His Lys Phe Ser Val Ser Gly Glu Gly Glu Gly Asp Ala Thr
50                  55                  60

Tyr Gly Lys Leu Thr Leu Lys Phe Ile Cys Thr Thr Gly Lys Leu Pro
65                  70                  75                  80

Val Pro Trp Pro Thr Leu Val Thr Thr Leu Thr Tyr Gly Val Gln Cys
                85                  90                  95

Phe Ser Arg Tyr Pro Asp His Met Lys Gln His Asp Phe Phe Lys Ser
            100                 105                 110

Ala Met Pro Glu Gly Tyr Val Gln Glu Arg Thr Ile Phe Phe Lys Asp
            115                 120                 125

Asp Gly Asn Tyr Lys Thr Arg Ala Glu Val Lys Phe Glu Gly Asp Thr
130                 135                 140

Leu Val Asn Arg Ile Glu Leu Lys Gly Ile Asp Phe Lys Glu Asp Gly
145                 150                 155                 160

Asn Ile Leu Gly His Lys Leu Glu Tyr Asn Tyr Asn Ser His Asn Val
                165                 170                 175
```

Tyr Ile Met Ala Asp Lys Gln Lys Asn Gly Ile Lys Val Asn Phe Lys
            180                 185                 190

Ile Arg His Asn Ile Glu Asp Gly Ser Val Gln Leu Ala Asp His Tyr
        195                 200                 205

Gln Gln Asn Thr Pro Ile Gly Asp Gly Pro Val Leu Leu Pro Asp Asn
    210                 215                 220

His Tyr Leu Ser Thr Gln Ser Ala Leu Ser Lys Asp Pro Asn Glu Lys
225                 230                 235                 240

Arg Asp His Met Val Leu Leu Glu Phe Val Thr Ala Ala Gly Ile Thr
                245                 250                 255

Leu Gly Met Asp Glu Leu Tyr Lys Gly Gly Ser Gly Gly Gly Ser Gly
            260                 265                 270

Gly Gly Ser Gly Trp Ile Arg Ala Ser Ser Gly Gly Arg Ser Ser Asp
        275                 280                 285

Asp Glu Ala Thr Ala Asp Ser Gln His Ala Ala Pro Pro Lys Lys Lys
    290                 295                 300

Arg Lys Val Gly Gly Ser Gly Gly Gly Ser Gly Gly Ser Gly Gly Gly
305                 310                 315                 320

Gly Arg Gly Thr Glu Ile Ser
            325

<210> SEQ ID NO 63
<211> LENGTH: 14
<212> TYPE: PRT
<213> ORGANISM: Artificial Sequence
<220> FEATURE:
<223> OTHER INFORMATION: C(LLKK)3C

<400> SEQUENCE: 63

Cys Leu Leu Lys Lys Leu Leu Lys Lys Leu Leu Lys Lys Cys
1               5                   10

<210> SEQ ID NO 64
<211> LENGTH: 14
<212> TYPE: PRT
<213> ORGANISM: Artificial Sequence
<220> FEATURE:
<223> OTHER INFORMATION: G(LLKK)3G

<400> SEQUENCE: 64

Gly Leu Leu Lys Lys Leu Leu Lys Lys Leu Leu Lys Lys Gly
1               5                   10

<210> SEQ ID NO 65
<211> LENGTH: 11
<212> TYPE: PRT
<213> ORGANISM: Artificial Sequence
<220> FEATURE:
<223> OTHER INFORMATION: PTD4

<400> SEQUENCE: 65

Tyr Ala Arg Ala Ala Ala Arg Gln Ala Arg Ala
1               5                   10

<210> SEQ ID NO 66
<211> LENGTH: 30
<212> TYPE: PRT
<213> ORGANISM: Artificial Sequence
<220> FEATURE:
<223> OTHER INFORMATION: TAT-CM18

<400> SEQUENCE: 66

```
Tyr Gly Arg Lys Lys Arg Arg Gln Arg Arg Arg Cys Lys Trp Lys Leu
1               5                   10                  15

Phe Lys Lys Ile Gly Ala Val Leu Lys Val Leu Thr Thr Gly
            20                  25                  30
```

<210> SEQ ID NO 67
<211> LENGTH: 42
<212> TYPE: PRT
<213> ORGANISM: Artificial Sequence
<220> FEATURE:
<223> OTHER INFORMATION: TAT-KALA

<400> SEQUENCE: 67

```
Tyr Gly Arg Lys Lys Arg Arg Gln Arg Arg Arg Cys Trp Glu Ala Lys
1               5                   10                  15

Leu Ala Lys Ala Leu Ala Lys Ala Leu Ala Lys His Leu Ala Lys Ala
            20                  25                  30

Leu Ala Lys Ala Leu Lys Ala Cys Glu Ala
        35                  40
```

<210> SEQ ID NO 68
<211> LENGTH: 35
<212> TYPE: PRT
<213> ORGANISM: Artificial Sequence
<220> FEATURE:
<223> OTHER INFORMATION: His-CM18-PTD4

<400> SEQUENCE: 68

```
His His His His His His Lys Trp Lys Leu Phe Lys Lys Ile Gly Ala
1               5                   10                  15

Val Leu Lys Val Leu Thr Thr Gly Tyr Ala Arg Ala Ala Ala Arg Gln
            20                  25                  30

Ala Arg Ala
        35
```

<210> SEQ ID NO 69
<211> LENGTH: 33
<212> TYPE: PRT
<213> ORGANISM: Artificial Sequence
<220> FEATURE:
<223> OTHER INFORMATION: His-CM18-9Arg

<400> SEQUENCE: 69

```
His His His His His His Lys Trp Lys Leu Phe Lys Lys Ile Gly Ala
1               5                   10                  15

Val Leu Lys Val Leu Thr Thr Gly Arg Arg Arg Arg Arg Arg Arg Arg
            20                  25                  30

Arg
```

<210> SEQ ID NO 70
<211> LENGTH: 50
<212> TYPE: PRT
<213> ORGANISM: Artificial Sequence
<220> FEATURE:
<223> OTHER INFORMATION: His-CM18-Transportan

<400> SEQUENCE: 70

```
His His His His His His Lys Trp Lys Leu Phe Lys Lys Ile Gly Ala
1               5                   10                  15

Val Leu Lys Val Leu Thr Thr Gly Gly Trp Thr Leu Asn Ser Ala Gly
            20                  25                  30

Tyr Leu Leu Lys Ile Asn Leu Lys Ala Leu Ala Ala Leu Ala Lys Lys
```

```
                35                  40                  45

Ile Leu
    50

<210> SEQ ID NO 71
<211> LENGTH: 43
<212> TYPE: PRT
<213> ORGANISM: Artificial Sequence
<220> FEATURE:
<223> OTHER INFORMATION: His-LAH4-PDT4

<400> SEQUENCE: 71

His His His His His His Lys Lys Ala Leu Leu Ala Leu Ala Leu His
1               5                   10                  15

His Leu Ala His Leu Ala Leu His Leu Ala Leu Ala Leu Lys Lys Ala
            20                  25                  30

Tyr Ala Arg Ala Ala Ala Arg Gln Ala Arg Ala
        35                  40

<210> SEQ ID NO 72
<211> LENGTH: 31
<212> TYPE: PRT
<213> ORGANISM: Artificial Sequence
<220> FEATURE:
<223> OTHER INFORMATION: His-C(LLKK)3C-PDT4

<400> SEQUENCE: 72

His His His His His His Cys Leu Leu Lys Lys Leu Leu Lys Lys Leu
1               5                   10                  15

Leu Lys Lys Cys Tyr Ala Arg Ala Ala Ala Arg Gln Ala Arg Ala
            20                  25                  30

<210> SEQ ID NO 73
<211> LENGTH: 324
<212> TYPE: PRT
<213> ORGANISM: Artificial Sequence
<220> FEATURE:
<223> OTHER INFORMATION: mCherry-NLS

<400> SEQUENCE: 73

Met His His His His His His Gly Gly Gly Ser Gly Gly Gly Gly
1               5                   10                  15

Ser Gly Gly Ala Ser Thr Gly Ile Arg Met Val Ser Lys Cys Glu Glu
            20                  25                  30

Asp Asn Met Ala Ile Ile Lys Glu Phe Met Arg Phe Lys Val His Met
            35                  40                  45

Glu Gly Ser Val Asn Gly His Glu Phe Glu Ile Glu Gly Glu Gly Glu
    50                  55                  60

Gly Arg Pro Tyr Glu Gly Thr Gln Thr Ala Lys Leu Lys Val Thr Lys
65                  70                  75                  80

Gly Gly Pro Leu Pro Phe Ala Trp Asp Ile Leu Ser Pro Gln Phe Met
                85                  90                  95

Tyr Gly Ser Lys Ala Tyr Val Lys His Pro Ala Asp Ile Pro Asp Tyr
            100                 105                 110

Leu Lys Leu Ser Phe Pro Glu Gly Phe Lys Trp Glu Arg Val Met Asn
        115                 120                 125

Phe Glu Asp Gly Gly Val Val Thr Val Thr Gln Asp Ser Ser Leu Gln
    130                 135                 140

Asp Gly Glu Phe Ile Tyr Lys Val Lys Leu Arg Gly Thr Asn Phe Pro
145                 150                 155                 160
```

```
Ser Asp Gly Gln Val Met Gln Lys Thr Met Gly Trp Glu Ala Ser
                165                 170                 175

Ser Glu Arg Met Tyr Pro Glu Asp Gly Ala Leu Lys Gly Glu Ile Lys
            180                 185                 190

Gln Arg Leu Lys Leu Lys Asp Gly Gly His Tyr Asp Ala Glu Val Lys
        195                 200                 205

Thr Thr Tyr Lys Ala Lys Lys Pro Val Gln Leu Pro Gly Ala Tyr Asn
    210                 215                 220

Val Asn Ile Lys Leu Asp Ile Thr Ser His Asn Glu Asp Tyr Thr Ile
225                 230                 235                 240

Val Glu Gln Tyr Glu Arg Ala Glu Gly Arg His Ser Thr Gly Gly Met
                245                 250                 255

Asp Glu Leu Tyr Lys Gly Gly Ser Gly Gly Ser Gly Gly Gly Ser
            260                 265                 270

Gly Trp Ile Arg Ala Ser Ser Gly Gly Arg Ser Ser Asp Asp Glu Ala
        275                 280                 285

Thr Ala Asp Ser Gln His Ala Ala Pro Pro Lys Lys Lys Arg Lys Val
    290                 295                 300

Gly Gly Ser Gly Gly Gly Ser Gly Gly Gly Ser Gly Gly Gly Arg Gly
305                 310                 315                 320

Thr Glu Ile Ser

<210> SEQ ID NO 74
<211> LENGTH: 1414
<212> TYPE: PRT
<213> ORGANISM: Artificial Sequence
<220> FEATURE:
<223> OTHER INFORMATION: Cas9-NLS

<400> SEQUENCE: 74

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190
```

Asn Gln Leu Phe Glu Glu Asn Pro Ile Asn Ala Ser Gly Val Asp Ala
            195                 200                 205
Lys Ala Ile Leu Ser Ala Arg Leu Ser Lys Ser Arg Arg Leu Glu Asn
210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
            245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
            275                 280                 285
Leu Phe Leu Ala Ala Lys Asn Leu Ser Asp Ala Ile Leu Leu Ser Asp
            290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
            325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
            370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
            405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
            485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
            530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
            565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr

```
                610               615               620
Leu Phe Glu Asp Arg Glu Met Ile Glu Arg Leu Lys Thr Tyr Ala
625               630               635               640

His Leu Phe Asp Asp Lys Val Met Lys Gln Leu Lys Arg Arg Tyr
                  645               650               655

Thr Gly Trp Gly Arg Leu Ser Arg Lys Leu Ile Asn Gly Ile Arg Asp
            660               665               670

Lys Gln Ser Gly Lys Thr Ile Leu Asp Phe Leu Lys Ser Asp Gly Phe
            675               680               685

Ala Asn Arg Asn Phe Met Gln Leu Ile His Asp Asp Ser Leu Thr Phe
690               695               700

Lys Glu Asp Ile Gln Lys Ala Gln Val Ser Gly Gln Gly Asp Ser Leu
705               710               715               720

His Glu His Ile Ala Asn Leu Ala Gly Ser Pro Ala Ile Lys Lys Gly
                  725               730               735

Ile Leu Gln Thr Val Lys Val Val Asp Glu Leu Val Lys Val Met Gly
                  740               745               750

Arg His Lys Pro Glu Asn Ile Val Ile Glu Met Ala Arg Glu Asn Gln
                  755               760               765

Thr Thr Gln Lys Gly Gln Lys Asn Ser Arg Glu Arg Met Lys Arg Ile
770               775               780

Glu Glu Gly Ile Lys Glu Leu Gly Ser Gln Ile Leu Lys Glu His Pro
785               790               795               800

Val Glu Asn Thr Gln Leu Gln Asn Glu Lys Leu Tyr Leu Tyr Tyr Leu
                  805               810               815

Gln Asn Gly Arg Asp Met Tyr Val Asp Gln Glu Leu Asp Ile Asn Arg
                  820               825               830

Leu Ser Asp Tyr Asp Val Asp His Ile Val Pro Gln Ser Phe Leu Lys
                  835               840               845

Asp Asp Ser Ile Asp Asn Lys Val Leu Thr Arg Ser Asp Lys Asn Arg
850               855               860

Gly Lys Ser Asp Asn Val Pro Ser Glu Glu Val Val Lys Lys Met Lys
865               870               875               880

Asn Tyr Trp Arg Gln Leu Leu Asn Ala Lys Leu Ile Thr Gln Arg Lys
                  885               890               895

Phe Asp Asn Leu Thr Lys Ala Glu Arg Gly Gly Leu Ser Glu Leu Asp
                  900               905               910

Lys Ala Gly Phe Ile Lys Arg Gln Leu Val Glu Thr Arg Gln Ile Thr
            915               920               925

Lys His Val Ala Gln Ile Leu Asp Ser Arg Met Asn Thr Lys Tyr Asp
            930               935               940

Glu Asn Asp Lys Leu Ile Arg Glu Val Lys Val Ile Thr Leu Lys Ser
945               950               955               960

Lys Leu Val Ser Asp Phe Arg Lys Asp Phe Gln Phe Tyr Lys Val Arg
                  965               970               975

Glu Ile Asn Asn Tyr His His Ala His Asp Ala Tyr Leu Asn Ala Val
                  980               985               990

Val Gly Thr Ala Leu Ile Lys Lys Tyr Pro Lys Leu Glu Ser Glu Phe
                  995               1000              1005

Val Tyr Gly Asp Tyr Lys Val Tyr Asp Val Arg Lys Met Ile Ala
            1010              1015              1020

Lys Ser Glu Gln Glu Ile Gly Lys Ala Thr Ala Lys Tyr Phe Phe
            1025              1030              1035
```

Tyr Ser Asn Ile Met Asn Phe Phe Lys Thr Glu Ile Thr Leu Ala
    1040            1045            1050

Asn Gly Glu Ile Arg Lys Arg Pro Leu Ile Glu Thr Asn Gly Glu
    1055            1060            1065

Thr Gly Glu Ile Val Trp Asp Lys Gly Arg Asp Phe Ala Thr Val
    1070            1075            1080

Arg Lys Val Leu Ser Met Pro Gln Val Asn Ile Val Lys Lys Thr
    1085            1090            1095

Glu Val Gln Thr Gly Gly Phe Ser Lys Glu Ser Ile Leu Pro Lys
    1100            1105            1110

Arg Asn Ser Asp Lys Leu Ile Ala Arg Lys Lys Asp Trp Asp Pro
    1115            1120            1125

Lys Lys Tyr Gly Gly Phe Asp Ser Pro Thr Val Ala Tyr Ser Val
    1130            1135            1140

Leu Val Val Ala Lys Val Glu Lys Gly Lys Ser Lys Lys Leu Lys
    1145            1150            1155

Ser Val Lys Glu Leu Leu Gly Ile Thr Ile Met Glu Arg Ser Ser
    1160            1165            1170

Phe Glu Lys Asn Pro Ile Asp Phe Leu Glu Ala Lys Gly Tyr Lys
    1175            1180            1185

Glu Val Lys Lys Asp Leu Ile Ile Lys Leu Pro Lys Tyr Ser Leu
    1190            1195            1200

Phe Glu Leu Glu Asn Gly Arg Lys Arg Met Leu Ala Ser Ala Gly
    1205            1210            1215

Glu Leu Gln Lys Gly Asn Glu Leu Ala Leu Pro Ser Lys Tyr Val
    1220            1225            1230

Asn Phe Leu Tyr Leu Ala Ser His Tyr Glu Lys Leu Lys Gly Ser
    1235            1240            1245

Pro Glu Asp Asn Glu Gln Lys Gln Leu Phe Val Glu Gln His Lys
    1250            1255            1260

His Tyr Leu Asp Glu Ile Ile Glu Gln Ile Ser Glu Phe Ser Lys
    1265            1270            1275

Arg Val Ile Leu Ala Asp Ala Asn Leu Asp Lys Val Leu Ser Ala
    1280            1285            1290

Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320

Phe Lys Tyr Phe Asp Thr Thr Ile Asp Arg Lys Arg Tyr Thr Ser
    1325            1330            1335

Thr Lys Glu Val Leu Asp Ala Thr Leu Ile His Gln Ser Ile Thr
    1340            1345            1350

Gly Leu Tyr Glu Thr Arg Ile Asp Leu Ser Gln Leu Gly Gly Asp
    1355            1360            1365

Gly Gly Arg Ser Ser Asp Asp Glu Ala Thr Ala Asp Ser Gln His
    1370            1375            1380

Ala Ala Pro Pro Lys Lys Lys Arg Lys Val Gly Gly Ser Gly Gly
    1385            1390            1395

Gly Ser Gly Gly Gly Ser Gly Gly Arg His His His His His
    1400            1405            1410

His

```
<210> SEQ ID NO 75
<211> LENGTH: 42
<212> TYPE: RNA
<213> ORGANISM: Artificial Sequence
<220> FEATURE:
<223> OTHER INFORMATION: crRNA (Example 13.3)

<400> SEQUENCE: 75
gaguccgagc agaagaagaa guuuuagagc uaugcuguuu ug                        42

<210> SEQ ID NO 76
<211> LENGTH: 69
<212> TYPE: RNA
<213> ORGANISM: Artificial Sequence
<220> FEATURE:
<223> OTHER INFORMATION: tracrRNA (Example 13.3)

<400> SEQUENCE: 76
aaacagcaua gcaaguuaaa auaaggcuag uccguuauca acuugaaaaa guggcaccga     60
gucggugcu                                                            69

<210> SEQ ID NO 77
<211> LENGTH: 69
<212> TYPE: RNA
<213> ORGANISM: Artificial Sequence
<220> FEATURE:
<223> OTHER INFORMATION: tracrRNA (Example 13.5)

<400> SEQUENCE: 77
aaacagcaua gcaaguuaaa auaaggcuag uccguuauca acuugaaaaa guggcaccga     60
gucggugcu                                                            69

<210> SEQ ID NO 78
<211> LENGTH: 42
<212> TYPE: RNA
<213> ORGANISM: Artificial Sequence
<220> FEATURE:
<223> OTHER INFORMATION: PPIB crRNA (Example 13.5)

<400> SEQUENCE: 78
guguauuuug accuacgaau guuuuagagc uaugcuguuu ug                        42

<210> SEQ ID NO 79
<211> LENGTH: 74
<212> TYPE: RNA
<213> ORGANISM: Artificial Sequence
<220> FEATURE:
<223> OTHER INFORMATION: PPIB tracrRNA (Example 13.5)

<400> SEQUENCE: 79
aacagcauag caaguuaaaa uaaggcuagu ccguuaucaa cuugaaaaag uggcaccgag     60
ucggugcuuu uuuu                                                      74

<210> SEQ ID NO 80
<211> LENGTH: 246
<212> TYPE: PRT
<213> ORGANISM: Artificial Sequence
<220> FEATURE:
<223> OTHER INFORMATION: HOXB4-WT

<400> SEQUENCE: 80

Met His His His His His His Met Ala Met Ser Ser Phe Leu Ile Asn
1               5                   10                  15

Ser Asn Tyr Val Asp Pro Lys Phe Pro Pro Cys Glu Glu Tyr Ser Gln
```

```
                20                  25                  30
Ser Asp Tyr Leu Pro Ser Asp His Ser Pro Gly Tyr Tyr Ala Gly Gly
                35                  40                  45

Gln Arg Arg Glu Ser Ser Phe Gln Pro Glu Ala Gly Phe Gly Arg Arg
            50                  55                  60

Ala Ala Cys Thr Val Gln Arg Tyr Pro Pro Pro Pro Pro Pro Pro Pro
 65                 70                  75                  80

Pro Pro Gly Leu Ser Pro Arg Ala Pro Ala Pro Pro Ala Gly Ala
                85                  90                  95

Leu Leu Pro Glu Pro Gly Gln Arg Cys Glu Ala Val Ser Ser Ser Pro
                100                 105                 110

Pro Pro Pro Pro Cys Ala Gln Asn Pro Leu His Pro Ser Pro Ser His
                115                 120                 125

Ser Ala Cys Lys Glu Pro Val Val Tyr Pro Trp Met Arg Lys Val His
            130                 135                 140

Val Ser Thr Val Asn Pro Asn Tyr Ala Gly Gly Glu Pro Lys Arg Ser
145                 150                 155                 160

Arg Thr Ala Tyr Thr Arg Gln Gln Val Leu Glu Leu Glu Lys Glu Phe
                165                 170                 175

His Tyr Asn Arg Tyr Leu Thr Arg Arg Arg Arg Val Glu Ile Ala His
                180                 185                 190

Ala Leu Cys Leu Ser Glu Arg Gln Ile Lys Ile Trp Phe Gln Asn Arg
            195                 200                 205

Arg Met Lys Trp Lys Lys Asp His Lys Leu Pro Asn Thr Lys Ile Arg
        210                 215                 220

Ser Gly Gly Ala Ala Gly Ser Ala Gly Gly Pro Pro Gly Arg Pro Asn
225                 230                 235                 240

Gly Gly Pro Arg Ala Leu
                245

<210> SEQ ID NO 81
<211> LENGTH: 17
<212> TYPE: PRT
<213> ORGANISM: Artificial Sequence
<220> FEATURE:
<223> OTHER INFORMATION: His-PTD4

<400> SEQUENCE: 81

His His His His His His Tyr Ala Arg Ala Ala Ala Arg Gln Ala Arg
1               5                   10                  15

Ala

<210> SEQ ID NO 82
<211> LENGTH: 41
<212> TYPE: PRT
<213> ORGANISM: Artificial Sequence
<220> FEATURE:
<223> OTHER INFORMATION: PTD4-KALA

<400> SEQUENCE: 82

Tyr Ala Arg Ala Ala Ala Arg Gln Ala Arg Ala Trp Glu Ala Lys Leu
1               5                   10                  15

Ala Lys Ala Leu Ala Lys Ala Leu Ala Lys His Leu Ala Lys Ala Leu
            20                  25                  30

Ala Lys Ala Leu Lys Ala Cys Glu Ala
        35                  40
```

```
<210> SEQ ID NO 83
<211> LENGTH: 39
<212> TYPE: PRT
<213> ORGANISM: Artificial Sequence
<220> FEATURE:
<223> OTHER INFORMATION: 9Arg-KALA

<400> SEQUENCE: 83

Arg Arg Arg Arg Arg Arg Arg Arg Arg Trp Glu Ala Lys Leu Ala Lys
1               5                   10                  15

Ala Leu Ala Lys Ala Leu Ala Lys His Leu Ala Lys Ala Leu Ala Lys
            20                  25                  30

Ala Leu Lys Ala Cys Glu Ala
        35

<210> SEQ ID NO 84
<211> LENGTH: 51
<212> TYPE: PRT
<213> ORGANISM: Artificial Sequence
<220> FEATURE:
<223> OTHER INFORMATION: Pep1-KALA

<400> SEQUENCE: 84

Lys Glu Thr Trp Trp Glu Thr Trp Trp Thr Glu Trp Ser Gln Pro Lys
1               5                   10                  15

Lys Lys Arg Lys Val Trp Glu Ala Lys Leu Ala Lys Ala Leu Ala Lys
            20                  25                  30

Ala Leu Ala Lys His Leu Ala Lys Ala Leu Ala Lys Leu Lys Ala
        35                  40                  45

Cys Glu Ala
    50

<210> SEQ ID NO 85
<211> LENGTH: 37
<212> TYPE: PRT
<213> ORGANISM: Artificial Sequence
<220> FEATURE:
<223> OTHER INFORMATION: Xentry-KALA

<400> SEQUENCE: 85

Leu Cys Leu Arg Pro Val Gly Trp Glu Ala Lys Leu Ala Lys Ala Leu
1               5                   10                  15

Ala Lys Ala Leu Ala Lys His Leu Ala Lys Ala Leu Ala Lys Ala Leu
            20                  25                  30

Lys Ala Cys Glu Ala
        35

<210> SEQ ID NO 86
<211> LENGTH: 40
<212> TYPE: PRT
<213> ORGANISM: Artificial Sequence
<220> FEATURE:
<223> OTHER INFORMATION: SynB3-KALA

<400> SEQUENCE: 86

Arg Arg Leu Ser Tyr Ser Arg Arg Arg Phe Trp Glu Ala Lys Leu Ala
1               5                   10                  15

Lys Ala Leu Ala Lys Ala Leu Ala Lys His Leu Ala Lys Ala Leu Ala
            20                  25                  30

Lys Ala Leu Lys Ala Cys Glu Ala
        35                  40
```

<210> SEQ ID NO 87
<211> LENGTH: 36
<212> TYPE: PRT
<213> ORGANISM: Artificial Sequence
<220> FEATURE:
<223> OTHER INFORMATION: VSVG-PTD4

<400> SEQUENCE: 87

Lys Phe Thr Ile Val Phe Pro His Asn Gln Lys Gly Asn Trp Lys Asn
1               5                   10                  15

Val Pro Ser Asn Tyr His Tyr Cys Pro Tyr Ala Arg Ala Ala Ala Arg
            20                  25                  30

Gln Ala Arg Ala
        35

<210> SEQ ID NO 88
<211> LENGTH: 34
<212> TYPE: PRT
<213> ORGANISM: Artificial Sequence
<220> FEATURE:
<223> OTHER INFORMATION: EB1-PTD4

<400> SEQUENCE: 88

Leu Ile Arg Leu Trp Ser His Leu Ile His Ile Trp Phe Gln Asn Arg
1               5                   10                  15

Arg Leu Lys Trp Lys Lys Lys Tyr Ala Arg Ala Ala Ala Arg Gln Ala
            20                  25                  30

Arg Ala

<210> SEQ ID NO 89
<211> LENGTH: 31
<212> TYPE: PRT
<213> ORGANISM: Artificial Sequence
<220> FEATURE:
<223> OTHER INFORMATION: JST-PTD4

<400> SEQUENCE: 89

Gly Leu Phe Glu Ala Leu Leu Glu Leu Leu Glu Ser Leu Trp Glu Leu
1               5                   10                  15

Leu Leu Glu Ala Tyr Ala Arg Ala Ala Ala Arg Gln Ala Arg Ala
            20                  25                  30

<210> SEQ ID NO 90
<211> LENGTH: 29
<212> TYPE: PRT
<213> ORGANISM: Artificial Sequence
<220> FEATURE:
<223> OTHER INFORMATION: CM18-PTD4

<400> SEQUENCE: 90

Lys Trp Lys Leu Phe Lys Lys Ile Gly Ala Val Leu Lys Val Leu Thr
1               5                   10                  15

Thr Gly Tyr Ala Arg Ala Ala Ala Arg Gln Ala Arg Ala
            20                  25

<210> SEQ ID NO 91
<211> LENGTH: 35
<212> TYPE: PRT
<213> ORGANISM: Artificial Sequence
<220> FEATURE:
<223> OTHER INFORMATION: 6Cys-CM18-PTD4

<400> SEQUENCE: 91

Cys Cys Cys Cys Cys Cys Lys Trp Lys Leu Phe Lys Lys Ile Gly Ala

```
                1               5                   10                  15
Val Leu Lys Val Leu Thr Thr Gly Tyr Ala Arg Ala Ala Ala Arg Gln
                20                  25                  30

Ala Arg Ala
        35

<210> SEQ ID NO 92
<211> LENGTH: 32
<212> TYPE: PRT
<213> ORGANISM: Artificial Sequence
<220> FEATURE:
<223> OTHER INFORMATION: CM18-L1-PTD4

<400> SEQUENCE: 92

Lys Trp Lys Leu Phe Lys Lys Ile Gly Ala Val Leu Lys Val Leu Thr
1               5                   10                  15

Thr Gly Gly Gly Ser Tyr Ala Arg Ala Ala Arg Gln Ala Arg Ala
                20                  25                  30

<210> SEQ ID NO 93
<211> LENGTH: 36
<212> TYPE: PRT
<213> ORGANISM: Artificial Sequence
<220> FEATURE:
<223> OTHER INFORMATION: CM18-L2-PTD4

<400> SEQUENCE: 93

Lys Trp Lys Leu Phe Lys Lys Ile Gly Ala Val Leu Lys Val Leu Thr
1               5                   10                  15

Thr Gly Gly Gly Ser Gly Gly Gly Ser Tyr Ala Arg Ala Ala Ala Arg
                20                  25                  30

Gln Ala Arg Ala
        35

<210> SEQ ID NO 94
<211> LENGTH: 41
<212> TYPE: PRT
<213> ORGANISM: Artificial Sequence
<220> FEATURE:
<223> OTHER INFORMATION: CM18-L3-PTD4

<400> SEQUENCE: 94

Lys Trp Lys Leu Phe Lys Lys Ile Gly Ala Val Leu Lys Val Leu Thr
1               5                   10                  15

Thr Gly Gly Gly Ser Gly Gly Gly Ser Gly Gly Gly Ser Gly Tyr Ala
                20                  25                  30

Arg Ala Ala Ala Arg Gln Ala Arg Ala
        35                  40

<210> SEQ ID NO 95
<211> LENGTH: 35
<212> TYPE: PRT
<213> ORGANISM: Artificial Sequence
<220> FEATURE:
<223> OTHER INFORMATION: His-CM18-TAT

<400> SEQUENCE: 95

His His His His His His Lys Trp Lys Leu Phe Lys Lys Ile Gly Ala
1               5                   10                  15

Val Leu Lys Val Leu Thr Thr Gly Tyr Gly Arg Lys Lys Arg Arg Gln
                20                  25                  30

Arg Arg Arg
```

<210> SEQ ID NO 96
<211> LENGTH: 41
<212> TYPE: PRT
<213> ORGANISM: Artificial Sequence
<220> FEATURE:
<223> OTHER INFORMATION: His-CM18-PTD4-6Cys

<400> SEQUENCE: 96

His His His His His His Lys Trp Lys Leu Phe Lys Lys Ile Gly Ala
1               5                   10                  15

Val Leu Lys Val Leu Thr Thr Gly Tyr Ala Arg Ala Ala Ala Arg Gln
            20                  25                  30

Ala Arg Ala Cys Cys Cys Cys Cys Cys
        35                  40

<210> SEQ ID NO 97
<211> LENGTH: 32
<212> TYPE: PRT
<213> ORGANISM: Artificial Sequence
<220> FEATURE:
<223> OTHER INFORMATION: 3His-CM18-PTD4

<400> SEQUENCE: 97

His His His Lys Trp Lys Leu Phe Lys Lys Ile Gly Ala Val Leu Lys
1               5                   10                  15

Val Leu Thr Thr Gly Tyr Ala Arg Ala Ala Ala Arg Gln Ala Arg Ala
            20                  25                  30

<210> SEQ ID NO 98
<211> LENGTH: 41
<212> TYPE: PRT
<213> ORGANISM: Artificial Sequence
<220> FEATURE:
<223> OTHER INFORMATION: 12His-CM18-PTD4

<400> SEQUENCE: 98

His His His His His His His His His His His His Lys Trp Lys Leu
1               5                   10                  15

Phe Lys Lys Ile Gly Ala Val Leu Lys Val Leu Thr Thr Gly Tyr Ala
            20                  25                  30

Arg Ala Ala Ala Arg Gln Ala Arg Ala
        35                  40

<210> SEQ ID NO 99
<211> LENGTH: 36
<212> TYPE: PRT
<213> ORGANISM: Artificial Sequence
<220> FEATURE:
<223> OTHER INFORMATION: HA-CM18-PTD4

<400> SEQUENCE: 99

His His His Ala His His His Lys Trp Lys Leu Phe Lys Lys Ile Gly
1               5                   10                  15

Ala Val Leu Lys Val Leu Thr Thr Gly Tyr Ala Arg Ala Ala Ala Arg
            20                  25                  30

Gln Ala Arg Ala
        35

<210> SEQ ID NO 100
<211> LENGTH: 38
<212> TYPE: PRT

```
<213> ORGANISM: Artificial Sequence
<220> FEATURE:
<223> OTHER INFORMATION: 3HA-CM18-PTD4

<400> SEQUENCE: 100

His Ala His His Ala His His Ala His Lys Trp Lys Leu Phe Lys Lys
1               5                   10                  15

Ile Gly Ala Val Leu Lys Val Leu Thr Thr Gly Tyr Ala Arg Ala Ala
            20                  25                  30

Ala Arg Gln Ala Arg Ala
        35

<210> SEQ ID NO 101
<211> LENGTH: 35
<212> TYPE: PRT
<213> ORGANISM: Artificial Sequence
<220> FEATURE:
<223> OTHER INFORMATION: CM18-His-PTD4

<400> SEQUENCE: 101

Lys Trp Lys Leu Phe Lys Lys Ile Gly Ala Val Leu Lys Val Leu Thr
1               5                   10                  15

Thr Gly His His His His His His Tyr Ala Arg Ala Ala Ala Arg Gln
            20                  25                  30

Ala Arg Ala
        35

<210> SEQ ID NO 102
<211> LENGTH: 41
<212> TYPE: PRT
<213> ORGANISM: Artificial Sequence
<220> FEATURE:
<223> OTHER INFORMATION: His-CM18-PTD4-His

<400> SEQUENCE: 102

His His His His His His Lys Trp Lys Leu Phe Lys Lys Ile Gly Ala
1               5                   10                  15

Val Leu Lys Val Leu Thr Thr Gly Tyr Ala Arg Ala Ala Ala Arg Gln
            20                  25                  30

Ala Arg Ala His His His His His His
        35                  40

<210> SEQ ID NO 103
<211> LENGTH: 36
<212> TYPE: RNA
<213> ORGANISM: Artificial Sequence
<220> FEATURE:
<223> OTHER INFORMATION: HPRT crRNA

<400> SEQUENCE: 103
aauuaugggg auuacuagga guuuuagagc uaugcu                            36

<210> SEQ ID NO 104
<211> LENGTH: 7
<212> TYPE: PRT
<213> ORGANISM: Artificial Sequence
<220> FEATURE:
<223> OTHER INFORMATION: L2

<400> SEQUENCE: 104

Gly Gly Ser Gly Gly Gly Ser
1               5
```

```
<210> SEQ ID NO 105
<211> LENGTH: 11
<212> TYPE: PRT
<213> ORGANISM: Artificial Sequence
<220> FEATURE:
<223> OTHER INFORMATION: L3

<400> SEQUENCE: 105

Gly Gly Ser Gly Gly Gly Ser Gly Gly Gly Ser
1               5                   10
```